(12) United States Patent
Luo et al.

(10) Patent No.: US 8,871,946 B2
(45) Date of Patent: Oct. 28, 2014

(54) BENZIMIDAZOLE-4-CARBOXAMIDE DERIVATIVES, THEIR PREPARATION METHODS, PHARMACEUTICAL COMPOSITIONS AND THEIR USES

(75) Inventors: Xianjin Luo, Shanghai (CN); Fei Xue, Shanghai (CN); Zhonglv Zhang, Shanghai (CN); Naiyun Xiu, Shanghai (CN)

(73) Assignee: Zhejiang Medicine Co., Ltd. Xinchang Pharmaceutical Factory, Xinchang County, Zhejiang Province (CN)

( * ) Notice: Subject to any disclaimer, the term of this patent is extended or adjusted under 35 U.S.C. 154(b) by 0 days.

(21) Appl. No.: 13/143,731

(22) PCT Filed: Jan. 6, 2010

(86) PCT No.: PCT/CN2010/000024
§ 371 (c)(1),
(2), (4) Date: Jul. 8, 2011

(87) PCT Pub. No.: WO2010/078830
PCT Pub. Date: Jul. 15, 2010

(65) Prior Publication Data
US 2011/0269766 A1 Nov. 3, 2011

(30) Foreign Application Priority Data

Jan. 8, 2009 (CN) .......................... 2009 1 0045056
Jan. 5, 2010 (CN) .......................... 2010 1 0000050

(51) Int. Cl.
| | | |
|---|---|---|
| *A61K 31/381* | (2006.01) | |
| *A61K 31/4184* | (2006.01) | |
| *C07D 235/04* | (2006.01) | |
| *C07D 333/10* | (2006.01) | |
| *A61K 31/4439* | (2006.01) | |
| *C07D 405/12* | (2006.01) | |
| *C07D 401/04* | (2006.01) | |
| *C07D 487/04* | (2006.01) | |
| *C07D 473/34* | (2006.01) | |
| *C07D 401/12* | (2006.01) | |
| *C07D 405/04* | (2006.01) | |
| *C07D 417/04* | (2006.01) | |
| *C07D 235/26* | (2006.01) | |
| *C07D 403/12* | (2006.01) | |
| *C07D 417/12* | (2006.01) | |
| *C07D 403/04* | (2006.01) | |

(52) U.S. Cl.
CPC ......... *A61K 31/4184* (2013.01); *A61K 31/4439* (2013.01); *C07D 405/12* (2013.01); *C07D 401/04* (2013.01); *C07D 487/04* (2013.01); *C07D 473/34* (2013.01); *C07D 401/12* (2013.01); *C07D 405/04* (2013.01); *C07D 417/04* (2013.01); *C07D 235/26* (2013.01); *C07D 403/12* (2013.01); *C07D 417/12* (2013.01); *C07D 403/04* (2013.01)
USPC .................. 548/362.5; 548/360.1; 548/361.1; 549/59; 514/394; 514/444

(58) Field of Classification Search
None
See application file for complete search history.

(56) References Cited

U.S. PATENT DOCUMENTS

| 2007/0112047 A1* | 5/2007 | Penning et al. ................ 514/365 |
| 2009/0030016 A1* | 1/2009 | Gandhi et al. ............ 514/255.05 |
| 2011/0190351 A1* | 8/2011 | Ohtani et al. .................. 514/338 |
| 2011/0263566 A1* | 10/2011 | Matsuo et al. ........... 514/210.21 |
| 2011/0301146 A1* | 12/2011 | Matsuo et al. ........... 514/210.21 |

OTHER PUBLICATIONS

"Resistance modifying agents. 3. Novel benzimidazole and quinazolinone inhibitors of the DNA repair enzyme poly(ADP-ribose)polymerase" by Griffin et al., Pharma. Sci. 2, 43-47 (1996) (CAPLUS Abstract).*

* cited by examiner

*Primary Examiner* — Wu-Cheng Winston Shen
*Assistant Examiner* — Theodore R West
(74) *Attorney, Agent, or Firm* — Ash Tankha; Lipton, Weinberger & Husick

(57) ABSTRACT

The present invention relates to the benzimidazole-4-carboxamide derivatives, their preparation methods, pharmaceutical compositions and their uses; wherein X represents monosubstituted or bissubstituted or polysubstitued $C_1$-$C_{14}$ alkoxy, monosubstituted or bisubstituted or polysubstituted $C_1$-$C_{14}$ alkyl, monosubstituted or bisubstituted or polysubstitued $C_2$-$C_{14}$ alkenyl, monosubstituted or bisubstituted or polysubstitued $C_6$-$C_{14}$ aryl, or monosubstituted or bisubstituted or polysubstitued 5 to 6 membered heterocyclic group, or monosubstituted or bisubstituted or polysubstitued fused ring group containing nitrogen heteroatom; Y represents hydrogen, monosubstituted or bisubstituted or polysubstitued $C_1$-$C_{16}$ alkyl, monosubstituted or bisubstituted or polysubstitued $C_6$-$C_{12}$ aryl, or monosubstituted or bisubstituted or polysubstitued 5 to 6 membered heterocyclic group, or monosubstituted or bisubstituted or polysubstitued fused ring group containing nitrogen heteroatom. The derivatives of the present invention have the functions of antiviral medicine.

(I)

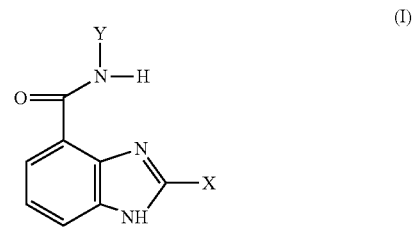

7 Claims, 3 Drawing Sheets

BENZIMIDAZOLE-4-CARBOXAMIDE DERIVATIVES, THEIR PREPARATION METHODS, PHARMACEUTICAL COMPOSITIONS AND THEIR USES

CROSS REFERENCE TO RELATED APPLICATIONS

This application claims the benefit of the following patent applications:
1. Patent application number 200910045056.8 titled "Benzimidazole-4-Carboxamide Derivatives, Their Preparation Methods, Pharmaceutical Compositions And Their Uses", filed on Jan. 8, 2009 in the State Intellectual Property Office of the People's Republic of China.
2. Patent application number 201010000050.1 titled "Benzimidazole-4-Carboxamide Derivatives, Their Preparation Methods, Pharmaceutical Compositions And Their Uses", filed on Jan. 5, 2010 in the State Intellectual Property Office of the People's Republic of China.

The specifications of the above referenced applications are incorporated herein by reference in their entirety.

FIELD OF THE INVENTION

The present invention relates to benzimidazole carboxamide derivatives, in particular, relates to the benzimidazole-4-carboxamide derivatives, their preparation methods, pharmaceutical compositions and their uses.

BACKGROUND OF THE INVENTION

The diseases caused by virus infections severely threaten human health and life and have become major problems in the medical fields. Almost 70% of epidemic diseases are caused by viruses infections statistically. The infectious diseases caused by enteroviruses have often occurred all over the world. The enteroviruses belong to picornaviridae comprising polio viruses, cosxackie viruses, enteric cytopathogenic human orphan virus and new enteroviruses. Each viruses has many serums, at least more than 70 types, which can violate many kinds of tissues, such as nerves, cardiac muscles, muscles, skins and eye conjunctiva etc and can cause lots of infectious diseases all over the world. There are lots of categories of the cosxackie viruses, whose transmission route and pathogenesis are similar to that of poliomyelitis virus, and often occurs latent infections. Their symptom shows slight upper respiratory infections or diarrhea, and occasionally inflects central nervous systems, damages spinal cord anterior horn motor neurons, and causes flaccid paralysis of limbs, however, this symptom is relatively light. The cosxackie viruses can violate many tissues and systems, such as respiratory tracts, intestinal tracts, skins, muscles, hearts, livers, adrenal gland and central nervous systems, Clinical manifestations have various of symptoms such as (1) respiratory tract infection, (2) herpangina, (3) febrile rush, (4) hand-foot-and-mouth disease, (5) diarrhea of children, (6) central nervous system syndrome, (7) myocarditis and pericarditis, (8) epidemic chest pain or epidemic myalgia, (9) epidemic conjunctivitis, (10) coxsackie virus hepatitis and so on.

SUMMARY OF THE INVENTION

The purpose of the present invention is to provide benzimidazole-4-carboxamide derivatives having anti-coxsackie virusesor a pharmaceutically acceptable salts thereof as shown in Formula (I).

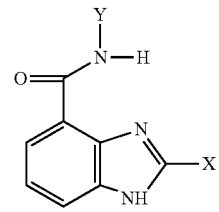

Wherein, X represents monosubstituted or bissubstituted or polysubstitued $C_1$-$C_{14}$ alkoxy, monosubstituted or bisubstituted or polysubstitued $C_1$-$C_{14}$ alkyl, monosubstituted or bisubstituted or polysubstitued $C_2$-$C_{14}$ alkenyl, monosubstituted or bisubstituted or polysubstitued $C_6$-$C_{14}$ aryl, or monosubstituted or bisubstituted or polysubstitued 5 to 6 membered heterocyclic group, or monosubstituted or bisubstituted or polysubstitued fused ring group containing nitrogen heteroatom;

Y represents hydrogen, monosubstituted or bisubstituted or polysubstitued $C_1$-$C_{16}$ alkyl, monosubstituted or bisubstituted or polysubstitued $C_6$-$C_{12}$ aryl, or monosubstituted or bisubstituted or polysubstitued 5 to 6 membered heterocyclic group, or monosubstituted or bisubstituted or polysubstitued fused ring group containing nitrogen heteroatom.

Wherein: X is selected from one of the following groups:

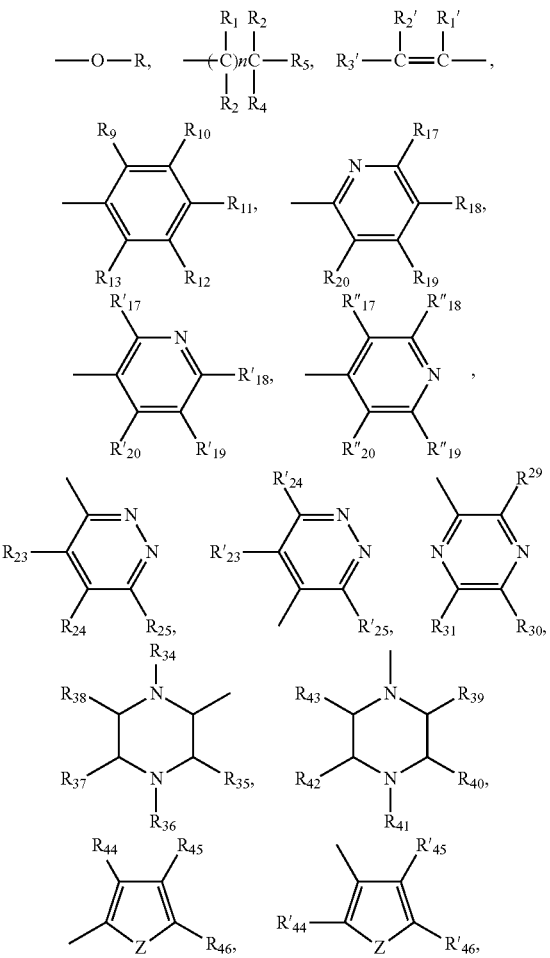

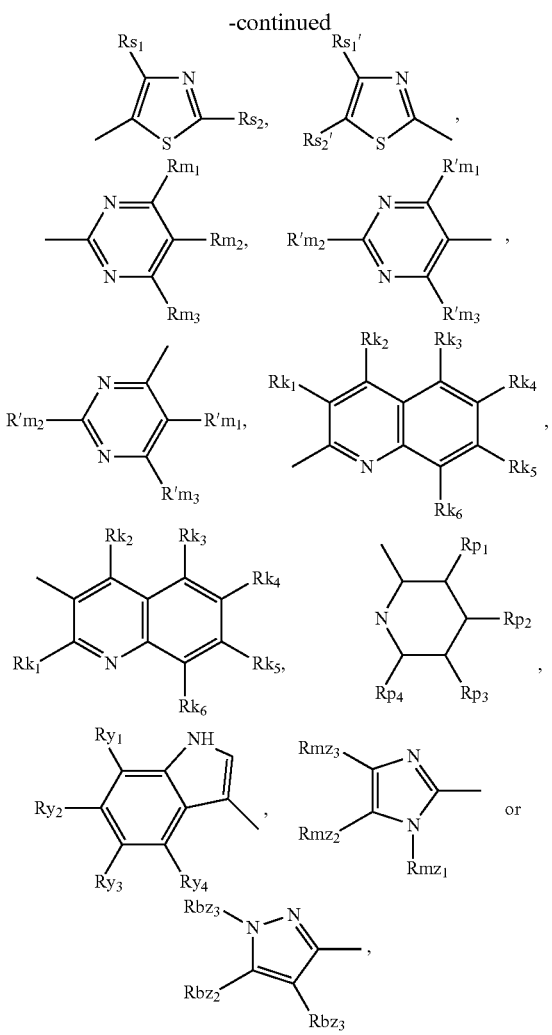

wherein R is selected from —H, or

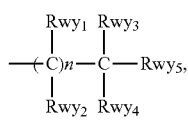

wherein n is selected from 0 to 5, $R_{wy1}$, $R_{wy2}$, $R_{wy3}$, $R_{wy4}$ and $R_{wy5}$ are respectively and independently selected from —H, —CH$_3$, or —CH$_2$CH$_3$;

n=0~5; $R_1$, $R_2$, $R_3$, $R_4$ and $R_5$ are respectively and independently selected from —H, —CH$_3$, —F, —Cl, —Br, —I, —OH, —OCH$_3$, —OCH$_2$CH$_3$, —NO$_2$, —NH—CH$_3$, —NH—CH$_2$CH$_3$, —NH—CH$_2$CH$_2$OH,

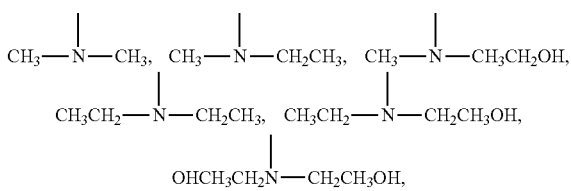

or phenyl substituted by one or several substituents Ra, Ra is selected from —F, —Cl, —Br, —I, —CH$_3$, —CH$_2$CH$_3$, —OH, —OCH$_3$, —OCH$_2$CH$_3$, —CH$_2$CH$_2$OH, —NO$_2$, —NH$_2$, —N(CH$_3$)$_2$, —N(CH$_2$CH$_3$)$_2$, —N(CH$_2$CH$_2$OH)$_2$, —CN, —COOH, —COOCH$_3$, —COOCH$_2$CH$_3$, or —COOC$_6$H$_5$;

$R_1'$, $R_2'$ and $R_3'$ are respectively and independently selected from —H, —CH$_3$, —CH$_2$CH$_3$, or

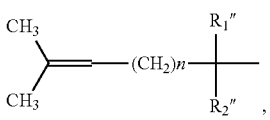

wherein n is an integer between 0 and 5; $R_1''$ and $R_2''$ are respectively and independently selected from —H, —CH$_3$, or —CH$_2$CH$_3$;

$R_9$, $R_{10}$, $R_{11}$, $R_{12}$ and $R_{13}$ are respectively and independently selected from —H, —CH$_3$, —CH$_2$CH$_3$, —COOH, —COOCH$_3$, —COOCH$_2$CH$_3$, —OH, —OCH$_3$, —OCH$_2$CH$_3$, —CN, —F, —Cl, —Br, —I, or —NH$_2$, —N(CH$_3$)$_2$, or —N(CH$_2$CH$_3$)$_2$;

$R_{17}$, $R_{18}$, $R_{19}$, $R_{20}$, $R'_{17}$, $R'_{18}$, $R'_{19}$, $R'_{20}$, $R''_{17}$, $R''_{18}$, $R''_{19}$ and $R''_{20}$ are respectively and independently selected from —H, —CH$_3$, —CH$_2$CH$_3$, —OH, —OCH$_3$, —OCH$_2$CH$_3$, —CF$_3$, —CCl$_3$, —CBr$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —NO or —NO$_2$, which cannot represent H simultaneously;

$R_{23}$, $R_{24}$, $R_{25}$, $R'_{23}$, $R'_{24}$ and $R'_{25}$ are respectively and independently selected from —H, —CH$_3$, —CH$_2$CH$_3$, —F, —Cl, —Br, —I, —OH, —OCH$_3$, —OCH$_2$CH$_3$, —NO$_2$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —COOH, —COOCH$_3$, or —COOCH$_2$CH$_3$;

$R_{29}$, $R_{30}$ and $R_{31}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

$R_{34}$, $R_{36}$ and $R_{41}$ are respectively and independently selected from —H, —(CH$_2$)$_n$CH$_3$, —CH$_2$OH, —CH$_2$CH$_2$OH, —CH(CH$_3$)$_2$ or —CH$_2$CH(OH)CH$_3$, n is an integer between 0 and 5;

$R_{35}$, $R_{37}$, $R_{38}$, $R_{39}$, $R_{40}$, $R_{42}$ and $R_{43}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

Z is selected from N, O or S.

$R_{44}$, $R_{45}$, $R_{46}$, $R'_{44}$, $R'_{45}$ and $R'_{46}$ are respectively and independently selected from —H, —CH$_3$, —CH$_2$CH$_3$, —OH, —OCH$_3$, —OCH$_2$CH$_3$, —NO$_2$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —CN or —COOH, —COOCH$_3$, or —COOCH$_2$CH$_3$;

$R_{s1}$, $R_{s2}$, $R'_{s1}$ and $R'_{s2}$ are respectively and independently selected from —H, —CH$_3$, —CH$_2$CH$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —F, —Cl, —Br, —I, or NHCOCH$_3$, NHCOCH$_2$CH$_3$, or NHCOC$_6$H$_5$;

$R_{m1}$, $R_{m2}$, $R_{m3}$, $R'_{m1}$, $R'_{m2}$ and $R'_{m3}$ are respectively and independently selected from —H, —CH$_3$, —CH$_2$CH$_3$, —F, —Cl, —Br, —I, —OH, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$,

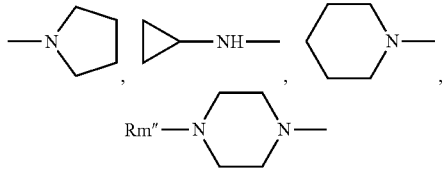

or —NHC$_6$H$_5$;

R$_{k1}$, R$_{k2}$, R$_{k3}$, R$_{k4}$, R$_{k5}$ and R$_{k6}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

R$_{P1}$, R$_{P2}$, R$_{P3}$ and R$_{P4}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

R$_{y1}$, R$_{y2}$, R$_{y3}$ and R$_{y4}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

Rmz1 is selected from —H, —CH$_3$, —CH$_2$CH$_3$, —CH$_2$CH$_2$OH, —C$_6$H$_5$, or —CH$_2$C$_6$H$_5$; Rmz2 and Rmz3 are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

Rbz1 is selected from —H, —CH$_3$, —CH$_2$CH$_3$, —CH$_2$CH$_2$OH, —C$_6$H$_5$, or —CH$_2$C$_6$H$_5$; Rbz2 and Rbz3 are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

Y is selected from one group of the following groups:

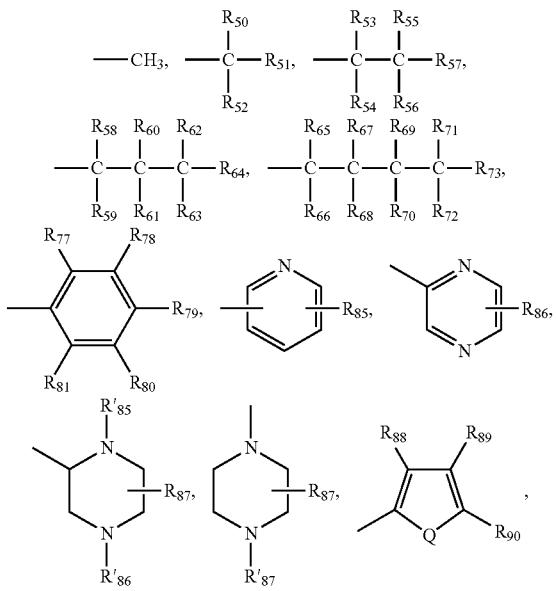

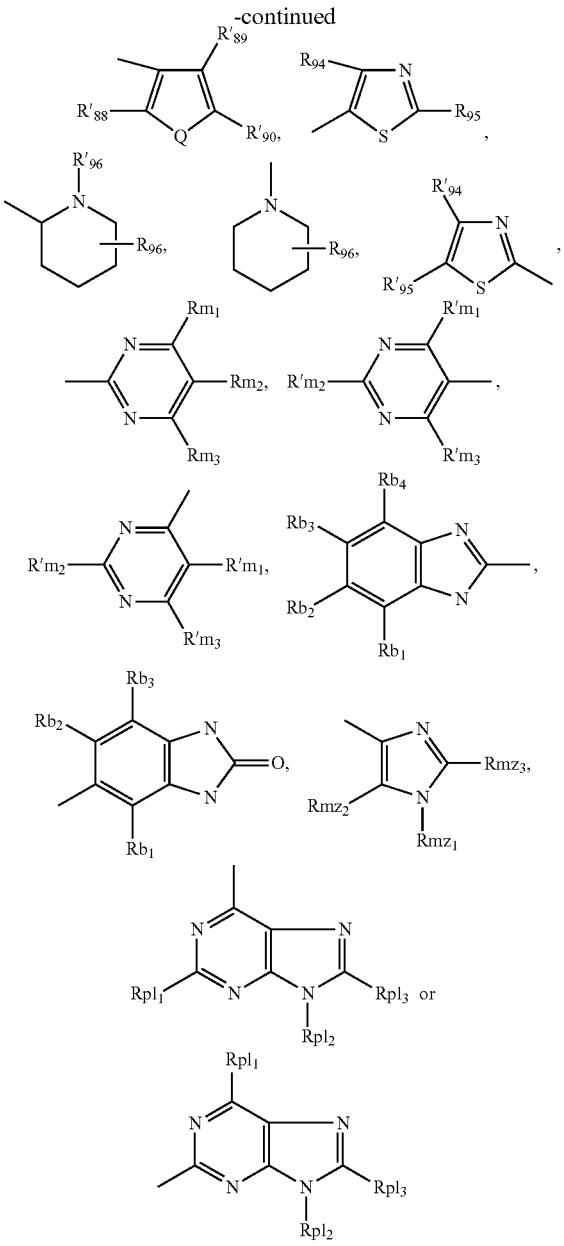

wherein, R$_{50}$, R$_{51}$, R$_{52}$, R$_{53}$, R$_{54}$, R$_{55}$, R$_{56}$, R$_{57}$, R$_{58}$, R$_{59}$, R$_{60}$, R$_{61}$, R$_{62}$, R$_{63}$, R$_{64}$, R$_{65}$, R$_{66}$, R$_{67}$, R$_{68}$, R$_{69}$, R$_{70}$, R$_{71}$, R$_{72}$ and R$_{73}$ are respectively and independently selected from —H, —CH$_3$, —CH$_2$CH$_3$, —CH$_2$OH, —OH, —OCH$_3$, —OCH$_2$CH$_3$, —CN, —NO$_2$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —F, —Cl, —Br, —I, or —C$_6$H$_5$, —C$_6$H$_4$—CH$_3$, —C$_6$H$_4$—OH, —C$_6$H$_4$—NO$_2$, or —C$_6$H$_4$—NH$_2$;

R$_{77}$, R$_{78}$, R$_{79}$, R$_{80}$ and R$_{81}$ are respectively and independently selected from —H, —CH$_3$, —CH$_2$CH$_3$, —OH, —OCH$_3$, —OCH$_2$CH$_3$, —NO$_2$, —CN, —COOH, —COOCH$_3$, —COOCH$_2$CH$_3$, —F, —Cl, —Br, —I, —CF$_3$, —CCl$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$;

R$_{85}$, R$_{86}$ and R$_{87}$ are respectively and independently selected from —H, —CH$_3$, —CH$_2$CH$_3$, —OH or —NH$_2$;

R'$_{85}$, R'$_{86}$ and R'$_{87}$ are respectively and independently selected from —H, —CH$_3$, —CH$_2$CH$_3$, —C$_6$H$_5$, or —CH$_2$C$_6$H$_4$;

Q is selected from N, O or S;

R$_{88}$, R$_{89}$, R$_{90}$, R'$_{88}$, R'$_{89}$ and R'$_{90}$ are respectively and independently selected from —H, —CH$_2$CH$_3$, —OH, —OCH$_3$, —OCH$_2$CH$_3$, —NO$_2$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —CN, —COOH, —COOCH$_3$, or —COOCH$_2$CH$_3$;

R$_{94}$, R$_{95}$, R'$_{94}$ and R'$_{95}$ are respectively and independently selected from —H, —CH$_3$, —CH$_2$CH$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —F, —Cl, —Br, —I, or —NHCOCH$_3$, NHCOCH$_2$CH$_3$, or NHCOC$_6$H$_5$;

R$_{96}$ is selected from —H, —CH$_3$, —CH$_2$CH$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, or —N(CH$_2$CH$_2$OH)$_2$; R'$_{96}$ is selected from —H, —CH$_3$, —CH$_2$CH$_3$, —C$_6$H$_5$, or —CH$_2$C$_6$H$_4$;

R$_{m1}$, R$_{m2}$, R$_{m3}$, R'$_{m1}$, R'$_{m2}$ and R'$_{m3}$ are respectively and independently selected from —H, —CH$_3$, —CH$_2$CH$_3$, —F, —Cl, —Br, —I, —OH, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, or —NHC$_6$H$_5$;

R$_{b1}$, R$_{b2}$, R$_{b3}$ and R$_{b4}$ are respectively and independently selected from —H, —CH$_3$, —CH$_2$CH$_3$, —CH$_2$OH, —OH, —OCH$_3$, —OCH$_2$CH$_3$, —CN, —NO$_2$, —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —F, —Cl, —Br, or —I;

R$_{mz1}$ is selected from —H, —CH$_3$, —CH$_2$CH$_3$, —CH$_2$CH$_2$OH, —C$_6$H$_5$, or —CH$_2$C$_6$H$_5$; R$_{mz2}$ and R$_{mz3}$ are respectively and independently selected from —H, —CH$_3$, —CH$_2$CH$_3$, —OCH$_3$, —CH$_2$OH, —NO$_2$ or —NH$_2$, —NHCH$_3$, —N(CH$_3$)$_2$, —NHCH$_2$CH$_3$, —N(CH$_2$CH$_3$)$_2$, —NHCH$_2$CH$_2$OH, —N(CH$_2$CH$_2$OH)$_2$, —CONH$_2$, or —COOH;

R$_{pl1}$ and R$_{pl2}$ are respectively and independently selected from —H, —CH$_3$, —CH$_2$CH$_3$, —OH, —OCH$_3$, —OCH$_2$CH$_3$, F, Cl, Br, or I; R$_{pl3}$ is selected from —H, —CH$_3$, —CH$_2$CH$_3$, —CH$_2$CH$_2$OH, —C$_6$H$_5$, or —CH$_2$C$_6$H$_5$.

Preferably, X represents monosubstituted or polysubstitued or unsubstituted alkoxy, monosubstituted or polysubstitued or unsubstituted alkyl, monosubstituted or polysubstituted or unsubstituted alkenyl, monosubstituted or bisubstituted or unsubstituted thienyl, monosubstituted or bisubstituted or unsubstituted pyridyl, monosubstituted or bisubstituted or unsubstituted pyridazinyl, monosubstituted or bisubstituted or unsubstituted piperazinyl, monosubstituted or bisubstituted or unsubstituted pyrazinyl, monosubstituted or bisubstituted or unsubstituted thiazolyl, monosubstituted or bisubstituted or trisubstituted or unsubstituted phenyl, monosubstituted or bisubstituted or unsubstituted pyrimidinyl, monosubstituted or bisubstituted or unsubstituted pyrrolyl, monosubstituted or bisubstituted or unsubstituted quinolinyl, monosubstituted or bisubstituted or unsubstituted piperidinyl, monosubstituted or bisubstituted or unsubstituted indolyl, monosubstituted or bisubstituted or trisubstituted or unsubstituted imidazolyl, monosubstituted or bisubstituted or trisubstituted or unsubstituted pyrazolyl.

More preferably, X represents C1-C6 alkyloxy substituted by nitro, amino, hydroxyl or aryl; C1-C6 alkyl substituted by nitro, amino, hydroxyl or aryl; C2-C14 alkenyl substituted by alkyl, hydroxyl or aryl; thienyl monosubstituted by nitro, amino or C1-C6 alkyl; unsubstituted thienyl; pyridyl monosubstituted by nitro, amino or C1-C6 alkyl; unsubstituted pyridyl; quinolinyl monosubstituted by nitro, amino or C1-C6 alkyl; unsubstituted quinolinyl; indolyl monosubstituted by nitro, amino or C1-C6 alkyl; unsubstituted indolyl; pyridyl monosubstituted or bisubstituted by C1-C6 alkoxy; pyridyl monosubstituted or bisubstituted by C1-C3 dialkylamino; pyridyl monosubstituted or bisubstituted by C1-C6 alkyl; unsubstituted pyridyl; pyridazinyl monosubstituted by C1-C6 alkoxy; pyridazinyl monosubstituted by C1-C6 alkyl; unsubstituted pyridazinyl; unsubstituted piperazinyl; piperazinyl bisubstituted by C1-C6 alkyl; unsubstituted piperidinyl; unsubstituted pyrazinyl; unsubstituted thiazolyl; imidazolyl monosubstituted by nitro, amino or C1-C6 alkyl; unsubstituted imidazolyl; thiazolyl bisubstituted by C1-C6 alkyl and nitro; unsubstituted pyrimidinyl; pyrimidinyl monosubstituted by phenyl; pyrimidinyl bisubstituted by amino and a group selected from nitro, —F, —Cl, —Br or —I; phenyl trisubstituted by trihydroxyl; phenyl trisubstituted by trimethoxyl; phenyl bisubstituted by hydroxyl and methoxyl; imidazolyl substituted by a group selected from methyl, ethyl, carboxyl or amido; pyrazolyl bisubstituted or trisubstituted by a group selected from C1-C6 alkyl or aryl and a group selected from —F, —Cl, —Br or —I.

Preferably, Y represents hydroxyl, C$_1$-C$_6$ alkyl, monosubstituted or bisubstituted or trisubstituted phenyl, monosubstituted or bisubstituted or trisubstituted or unsubstituted pyridyl, monosubstituted or bisubstituted or unsubstituted pyrazinyl, monosubstituted or bisubstituted or trisubstituted or unsubstituted piperazinyl, monosubstituted or bisubstituted or trisubstituted or unsubstituted pyrrolyl, monosubstituted or bisubstituted or trisubstituted or unsubstituted piperidinyl, monosubstituted or bisubstituted or trisubstituted or unsubstituted thiazolyl, monosubstituted or bisubstituted or trisubstituted or unsubstituted benzpyrimidinyl, monosubstituted or bisubstituted or trisubstituted or tetrasubstituted or unsubstituted benzimidazolyl, monosubstituted or bisubstituted or trisubstituted or unsubstituted benzimidazolonyl, monosubstituted or bisubstituted or trisubstituted or unsubstituted imidazolyl, monosubstituted or bisubstituted or trisubstituted or unsubstituted purinyl.

More preferably, Y represents hydroxymethyl, hydroxyethyl, aminophenyl, hydroxyphenyl, C$_1$-C$_6$ alkylphenyl, phenyl monosubstituted by —F, —Cl, —Br or —I, phenyl bisubstituted by hydroxyl and carboxyl, hydroxyethyl bisubstituted by hydroxylmethyl or C$_1$-C$_6$ alkyl and monosubstituted phenyl, piperazinyl monosubstituted or bisubstituted or trisubstituted or unsubstituted by C$_1$-C$_6$ alkyl, pyridyl monosubstituted or bisubstituted or trisubstituted or unsubstituted by C$_1$-C$_6$ alkyl, pyrazinyl monosubstituted or bisubstituted or unsubstituted, by C$_1$-C$_6$ alkyl, piperazinyl monosubstituted or bisubstituted or trisubstituted or unsubstituted by C$_1$-C$_6$ alkyl, pyrrolyl monosubstituted or bisubstituted or trisubstituted or unsubstituted by C$_1$-C$_6$ alkyl, thiazolyl monosubstituted by C$_1$-C$_6$ alkyl, pyrimidinyl monosubstituted or bisubstituted or unsubstituted by C$_1$-C$_6$ alkyl, pyrimidinyl monosubstituted by C$_1$-C$_6$ alkyl and bisubstituted by hydroxyl, pyrimidinyl monosubstituted C$_1$-C$_6$ alkyl and bisubstituted or trisubstituted by —F, —Cl, —Br or —I, purinyl monosubstituted or bisubstituted or unsubstituted by C$_1$-C$_6$ alkyl, purinyl monosubstituted by C$_1$-C$_6$ alkyl and substituted or trisuvstituted by hydroxyl.

Most preferably, the benzimidazole-4-carboxamide derivatives as shown in Formula (1) includes the following compounds:
(1) (L)-2-(5-nitro-2-thienyl)-1H-benzimidazole-4-[N-(1-hydroxymethyl-2-p-nitrophenylhydroxyethyl)]amide
(2) (L)-2-(5-amino-2-thienyl)-1H-benzimidazole-4-[N-(1-hydroxymethyl-2-p-nitrophenylhydroxyethyl)]amide (3) (L)-2-(5-amino-2-thienyl)-1H-benzimidazole-4-[N-(1-hydroxymethyl-2-p-aminophenyl hydroxyethyl)]amide
(4) 2-(5-amino-2-thienyl)-1H-benzimidazole-4-[N-(1-methyl-2-p-chlorophenylhydroxyethyl)]amide
(5) 2-(5-amino-2-thienyl)-1H-benzimidazole-4-(N-o-fluorophenyl)amide
(6) 2-(5-amino-2-thienyl)-1H-benzimidazole-4-(N-o-chlorophenyl)amide
(7) 2-(5-amino-2-thienyl)-1H-benzimidazole-4-(N-o-bromophenyl)amide
(8) 2-(5-amino-2-thienyl)-1H-benzimidazole-4-(N-m-fluorophenyl)amide
(9) 2-(5-amino-2-thienyl)-1H-benzimidazole-4-(N-m-chlorophenyl)amide
(10) 2-(5-amino-2-thienyl)-1H-benzimidazole-4-(N-m-bromophenyl)amide
(11) 2-(5-amino-2-thienyl)-1H-benzimidazole-4-(N-p-fluorophenyl)amide
(12) 2-(5-amino-2-thienyl)-1H-benzimidazole-4-(N-p-chlorophenyl)amide
(13) 2-(5-amino-2-thienyl)-1H-benzimidazole-4-(N-p-bromophenyl)amide
(14) 2-(5-amino-2-thienyl)-1H-benzimidazole-4-(N-o-methylphenyl)amide
(15) 2-(5-amino-2-thienyl)-1H-benzimidazole-4-(N-o-hydroxylphenyl)amide
(16) 2-(5-amino-2-thienyl)-1H-benzimidazole-4-(N-o-aminophenyl)amide
(17) 2-(5-amino-2-thienyl)-1H-benzimidazole-4-(N-m-methylphenyl)amide
(18) 2-(5-amino-2-thienyl)-1H-benzimidazole-4-(N-m-hydroxylphenyl)amide
(19) 2-(5-amino-2-thienyl)-1H-benzimidazole-4-(N-m-aminophenyl)amide
(20) 2-(5-amino-2-thienyl)-1H-benzimidazole-4-(N-p-methylphenyl)amide
(21) 2-(5-amino-2-thienyl)-1H-benzimidazole-4-(N-p-hydroxylphenyl)amide
(22) 2-(5-amino-2-thienyl)-1H-benzimidazole-4-(N-p-aminophenyl)amide
(23) (L)-2-(4-methoxypyridyl)-1H-benzimidazole-4-[N-(1-hydroxymethyl-2-p-nitrophenylhydroxyethyl)]amide
(24) (L)-2-(4-methoxypyridyl)-1H-benzimidazole-4-[N-(1-hydroxymethyl-2-p-aminophenylhydroxyethyl)]amide
(25) 2-(4-methoxypyridyl)-1H-benzimidazole-4-[N-(1-methyl-2-p-chlorophenylhydroxyethyl)]amide
(26) 2-(4-methoxypyridyl)-1H-benzimidazole-4-(N-o-fluorophenyl)amide
(27) 2-(4-methoxypyridyl)-1H-benzimidazole-4-(N-o-chlorophenyl)amide
(28) 2-(4-methoxypyridyl)-1H-benzimidazole-4-(N-o-bromophenyl)amide
(29) 2-(4-methoxypyridyl)-1H-benzimidazole-4-(N-m-fluorophenyl)amide
(30) 2-(4-methoxypyridyl)-1H-benzimidazole-4-(N-p-fluorophenyl)amide
(31) 2-(4-methoxypyridyl)-1H-benzimidazole-4-(N-o-hydroxyphenyl)amide
(32) 2-(4-methoxypyridyl)-1H-benzimidazole-4-(N-o-aminophenyl)amide
(33) 2-(4-methoxypyridyl)-1H-benzimidazole-4-(N-m-hydroxyphenyl)amide
(34) 2-(4-methoxypyridyl)-1H-benzimidazole-4-(N-m-aminophenyl)amide
(35) 2-(4-methoxypyridyl)-1H-benzimidazole-4-(N-p-hydroxyphenyl)amide
(36) 2-(4-methoxypyridyl)-1H-benzimidazole-4-(N-p-aminophenyl)amide
(37) (L)-2-(6-methoxypyridyl)-1H-benzimidazole-4-[N-(1-hydroxymethyl-2-p-nitrophenylhydroxyethyl)]amide
(38) (L)-2-(6-methoxypyridyl)-1H-benzimidazole-4-[N-(1-hydroxymethyl-2-p-aminophenylhydroxyethyl)]amide
(39) 2-(6-methoxypyridyl)-1H-benzimidazole-4-[N-(1-methyl-2-p-chlorophenylhydroxyethyl)]amide
(40) 2-(6-methoxypyridyl)-1H-benzimidazole-4-(N-o-fluorophenyl)amide
(41) 2-(6-methoxypyridyl)-1H-benzimidazole-4-(N-m-fluorophenyl)amide
(42) 2-(6-methoxypyridyl)-1H-benzimidazole-4-(N-p-fluorophenyl)amide
(43) 2-(6-methoxypyridyl)-1H-benzimidazole-4-(N-o-hydroxyphenyl)amide
(44) 2-(6-methoxypyridyl)-1H-benzimidazole-4-(N-o-aminophenyl)amide
(45) 2-(6-methoxypyridyl)-1H-benzimidazole-4-(N-m-hydroxyphenyl)amide
(46) 2-(6-methoxypyridyl)-1H-benzimidazole-4-(N-m-aminophenyl)amide
(47) 2-(6-methoxypyridyl)-1H-benzimidazole-4-(N-p-hydroxyphenyl)amide
(48) 2-(6-methoxypyridyl)-1H-benzimidazole-4-(N-p-aminophenyl)amide
(49) (L)-2-(4-dimethylaminopyridyl)-1H-benzimidazole-4-[N-(1-hydroxymethyl-2-p-nitrophenylhydroxyethyl)]amide
(50) (L)-2-(4-dimethylaminopyridyl)-1H-benzimidazole-4-[N-(1-hydroxymethyl-2-p-aminophenylhydroxyethyl)]amide
(51) 2-(4-dimethylaminopyridyl)-1H-benzimidazole-4-[N-(1-methyl-2-p-chlorophenylhydroxyethyl)]amide
(52) 2-(4-dimethylaminopyridyl)-1H-benzimidazole-4-(N-o-fluorophenyl)amide
(53) 2-(4-dimethylaminopyridyl)-1H-benzimidazole-4-(N-m-fluorophenyl)amide
(54) 2-(4-dimethylaminopyridyl)-1H-benzimidazole-4-(N-p-fluorophenyl)amide
(55) 2-(4-dimethylaminopyridyl)-1H-benzimidazole-4-(N-o-hydroxyphenyl)amide
(56) 2-(4-dimethylaminopyridyl)-1H-benzimidazole-4-(N-o-aminophenyl)amide
(57) 2-(4-dimethylaminopyridyl)-1H-benzimidazole-4-(N-m-hydroxyphenyl)amide
(58) 2-(4-dimethylaminopyridyl)-1H-benzimidazole-4-(N-m-aminophenyl)amide
(59) 2-(4-dimethylaminopyridyl)-1H-benzimidazole-4-(N-p-hydroxyphenyl)amide
(60) 2-(4-dimethylaminopyridyl)-1H-benzimidazole-4-(N-p-aminophenyl)amide
(61) (L)-2-(3-pyridazinyl)-1H-benzimidazole-4-[N-(1-hydroxymethyl-2-p-nitrophenylhydroxyethyl)]amide
(62) (L)-2-(3-pyridazinyl)-1H-benzimidazole-4-[N-(1-hydroxymethyl-2-p-aminophenylhydroxyethyl)]amide
(63) 2-(3-pyridazinyl)-1H-benzimidazole-4-[N-(1-methyl-2-p-chlorophenylhydroxyethyl)]amide
(64) 2-(3-pyridazinyl)-1H-benzimidazole-4-(N-o-fluorophenyl)amide
(65) 2-(3-pyridazinyl)-1H-benzimidazole-4-(N-m-fluorophenyl)amide
(66) 2-(3-pyridazinyl)-1H-benzimidazole-4-(N-p-fluorophenyl)amide
(67) 2-(3-pyridazinyl)-1H-benzimidazole-4-(N-o-hydroxyphenyl)amide

(68) 2-(3-pyridazinyl)-1H-benzimidazole-4-(N-o-aminophenyl)amide
(69) 2-(3-pyridazinyl)-1H-benzimidazole-4-(N-m-hydroxyphenyl)amide
(70) 2-(3-pyridazinyl)-1H-benzimidazole-4-(N-m-aminophenyl)amide
(71) 2-(3-pyridazinyl)-1H-benzimidazole-4-(N-p-hydroxyphenyl)amide
(72) 2-(3-pyridazinyl)-1H-benzimidazole-4-(N-p-aminophenyl)amide
(73) (L)-2-(2-N-methyl-4-N-methylpiperazinyl)-1H-benzimidazole-4-[N-(1-hydroxymethyl-2-p-nitrophenylhydroxyethyl)]amide
(74) (L)-2-(2-N-methyl-4-N-methylpiperazinyl)-1H-benzimidazole-4-[N-(1-hydroxymethyl-2-p-aminophenylhydroxyethyl)]amide
(75) 2-(2-N-methyl-4-N-methylpiperazinyl)-1H-benzimidazole-4-[N-(1-methyl-2-p-chlorophenylhydroxyethyl)]amide
(76) 2-(2-N-methyl-4-N-methylpiperazinyl)-1H-benzimidazole-4-(N-o-fluorophenyl)amide
(77) 2-(2-N-methyl-4-N-methylpiperazinyl)-1H-benzimidazole-4-(N-m-fluorophenyl)amide
(78) 2-(2-N-methyl-4-N-methylpiperazinyl)-1H-benzimidazole-4-(N-p-fluorophenyl)amide
(79) 2-(2-N-methyl-4-N-methylpiperazinyl)-1H-benzimidazole-4-(N-o-hydroxyphenyl)amide
(80) 2-(2-N-methyl-4-N-methylpiperazinyl)-1H-benzimidazole-4-(N-o-aminophenyl)amide
(81) 2-(2-N-methyl-4-N-methylpiperazinyl)-1H-benzimidazole-4-(N-m-hydroxyphenyl)amide
(82) 2-(2-N-methyl-4-N-methylpiperazinyl)-1H-benzimidazole-4-(N-m-aminophenyl)amide
(83) 2-(2-N-methyl-4-N-methylpiperazinyl)-1H-benzimidazole-4-(N-p-hydroxyphenyl)amide
(84) 2-(2-N-methyl-4-N-methylpiperazinyl)-1H-benzimidazole-4-(N-p-aminophenyl)amide
(85) (L)-2-(2-pyrazinyl)-1H-benzimidazole-4-[N-(1-hydroxymethyl-2-p-nitrophenylhydroxyethyl)]amide
(86) (L)-2-(2-pyrazinyl)-1H-benzimidazole-4-[N-(1-hydroxymethyl-2-p-aminophenylhydroxyethyl)]amide
(87) 2-(2-pyrazinyl)-1H-benzimidazole-4-[N-(1-methyl-2-p-chlorophenylhydroxyethyl)]amide
(88) 2-(2-pyrazinyl)-1H-benzimidazole-4-(N-o-fluorophenyl)amide
(89) 2-(2-pyrazinyl)-1H-benzimidazole-4-(N-m-fluorophenyl)amide
(90) 2-(2-pyrazinyl)-1H-benzimidazole-4-(N-p-fluorophenyl)amide
(91) 2-(2-pyrazinyl)-1H-benzimidazole-4-(N-o-hydroxyphenyl)amide
(92) 2-(2-pyrazinyl)-1H-benzimidazole-4-(N-o-aminophenyl)amide
(93) 2-(2-pyrazinyl)-1H-benzimidazole-4-(N-m-hydroxyphenyl)amide
(94) 2-(2-pyrazinyl)-1H-benzimidazole-4-(N-m-aminophenyl)amide
(95) 2-(2-pyrazinyl)-1H-benzimidazole-4-(N-p-hydroxyphenyl)amide
(96) 2-(2-pyrazinyl)-1H-benzimidazole-4-(N-p-aminophenyl)amide
(97) (L)-2-N-piperazinyl-1H-benzimidazole-4-[N-(1-hydroxymethyl-2-p-nitrophenylhydroxyethyl)]amide
(98) (L)-2-N-piperazinyl-1H-benzimidazole-4-[N-(1-hydroxymethyl-2-p-aminophenylhydroxyethyl)]amide
(99) 2-N-piperazinyl-1H-benzimidazole-4-[N-(1-methyl-2-p-chlorophenylhydroxyethyl)]amide
(100) 2-N-piperazinyl-1H-benzimidazole-4-(N-o-fluorophenyl)amide
(101) 2-N-piperazinyl-1H-benzimidazole-4-(N-m-fluorophenyl)amide
(102) 2-N-piperazinyl-1H-benzimidazole-4-(N-p-fluorophenyl)amide
(103) 2-N-piperazinyl-1H-benzimidazole-4-(N-o-hydroxyphenyl)amide
(104) 2-N-piperazinyl-1H-benzimidazole-4-(N-o-aminophenyl)amide
(105) 2-N-piperazinyl-1H-benzimidazole-4-(N-m-hydroxyphenyl)amide
(106) 2-N-piperazinyl-1H-benzimidazole-4-(N-m-aminophenyl)amide
(107) 2-N-piperazinyl-1H-benzimidazole-4-(N-p-hydroxyphenyl)amide
(108) 2-N-piperazinyl-1H-benzimidazole-4-(N-p-aminophenyl)amide
(109) (L)-2-(4-methyl-5-aminothiazolyl)-1H-benzimidazole-4-[N-(1-hydroxymethyl-2-p-nitrophenylhydroxyethyl)]amide
(110) (L)-2-(4-methyl-5-aminothiazolyl)-1H-benzimidazole-4-[N-(1-hydroxymethyl-2-p-aminophenylhydroxyethyl)]amide
(111) 2-(4-methyl-5-aminothiazolyl)-1H-benzimidazole-4-[N-(1-methyl-2-p-chlorophenylhydroxyethyl)]amide
(112) 2-(4-methyl-5-aminothiazolyl)-1H-benzimidazole-4-(N-o-fluorophenyl)amide
(113) 2-(4-methyl-5-aminothiazolyl)-1H-benzimidazole-4-(N-m-fluorophenyl)amide
(114) 2-(4-methyl-5-aminothiazolyl)-1H-benzimidazole-4-(N-p-fluorophenyl)amide
(115) 2-(4-methyl-5-aminothiazolyl)-1H-benzimidazole-4-(N-o-hydroxyphenyl)amide
(116) 2-(4-methyl-5-aminothiazolyl)-1H-benzimidazole-4-(N-o-aminophenyl)amide
(117) 2-(4-methyl-5-aminothiazolyl)-1H-benzimidazole-4-(N-m-hydroxyphenyl)amide
(118) 2-(4-methyl-5-aminothiazolyl)-1H-benzimidazole-4-(N-m-aminophenyl)amide
(119) 2-(4-methyl-5-aminothiazolyl)-1H-benzimidazole-4-(N-p-hydroxyphenyl)amide
(120) 2-(4-methyl-5-aminothiazolyl)-1H-benzimidazole-4-(N-p-aminophenyl)amide
(121) (L)-2-thiazolyl-1H-benzimidazole-4-[N-(1-hydroxymethyl-2-p-nitrophenylhydroxyethyl)]amide
(122) (L)-2-thiazolyl-1H-benzimidazole-4-[N-(1-hydroxymethyl-2-p-aminophenylhydroxyethyl)]amide
(123) 2-thiazolyl-1H-benzimidazole-4-[N-(1-methyl-2-p-chlorophenylhydroxyethyl)]amide
(124) 2-thiazolyl-1H-benzimidazole-4-(N-o-fluorophenyl)amide
(125) 2-thiazolyl-1H-benzimidazole-4-(N-m-fluorophenyl)amide
(126) 2-thiazolyl-1H-benzimidazole-4-(N-p-fluorophenyl)amide
(127) 2-thiazolyl-1H-benzimidazole-4-(N-o-hydroxyphenyl)amide
(128) 2-thiazolyl-1H-benzimidazole-4-(N-o-aminophenyl)amide
(129) 2-thiazolyl-1H-benzimidazole-4-(N-m-hydroxyphenyl)amide
(130) 2-thiazolyl-1H-benzimidazole-4-(N-m-aminophenyl)amide
(131) 2-thiazolyl-1H-benzimidazole-4-(N-p-hydroxyphenyl)amide (132) 2-thiazolyl-1H-benzimidazole-4-(N-p-aminophenyl)amide
(133) (L)-5-thiazolyl-1H-benzimidazole-4-[N-(1-hydroxymethyl-2-p-nitrophenylhydroxyethyl)]amide
(134) (L)-5-thiazolyl-1H-benzimidazole-4-[N-(1-hydroxymethyl-2-p-aminophenylhydroxyethyl)]amide
(135) 5-thiazolyl-1H-benzimidazole-4-[N-(1-methyl-2-p-chlorophenylhydroxyethyl)]amide
(136) 5-thiazolyl-1H-benzimidazole-4-(N-o-fluorophenyl)amide
(137) 5-thiazolyl-1H-benzimidazole-4-(N-m-fluorophenyl)amide
(138) 5-thiazolyl-1H-benzimidazole-4-(N-p-fluorophenyl)amide
(139) 5-thiazolyl-1H-benzimidazole-4-(N-o-hydroxyphenyl)amide
(140) 5-thiazolyl-1H-benzimidazole-4-(N-o-aminophenyl)amide
(141) 5-thiazolyl-1H-benzimidazole-4-(N-m-hydroxyphenyl)amide
(142) 5-thiazolyl-1H-benzimidazole-4-(N-m-aminophenyl)amide
(143) 5-thiazolyl-1H-benzimidazole-4-(N-p-hydroxyphenyl)amide
(144) 5-thiazolyl-1H-benzimidazole-4-(N-p-aminophenyl)amide
(145) (L)-2-(3,4,5-trihydroxyphenyl)-1H-benzimidazole-4-[N-(1-hydroxymethyl-2-p-nitrophenylhydroxyethyl)]amide
(146) (L)-2-(3,4,5-trihydroxyphenyl)-1H-benzimidazole-4-[N-(1-hydroxymethyl-2-p-aminophenylhydroxyethyl)]amide
(147) 2-(3,4,5-trihydroxyphenyl)-1H-benzimidazole-4-[N-(1-methyl-2-p-chlorophenylhydroxyethyl)]amide
(148) 2-(3,4,5-trihydroxyphenyl)-1H-benzimidazole-4-(N-o-fluorophenyl)amide
(149) 2-(3,4,5-trihydroxyphenyl)-1H-benzimidazole-4-(N-m-fluorophenyl)amide
(150) 2-(3,4,5-trihydroxyphenyl)-1H-benzimidazole-4-(N-p-fluorophenyl)amide
(151) 2-(3,4,5-trihydroxyphenyl)-1H-benzimidazole-4-(N-o-hydroxyphenyl)amide
(152) 2-(3,4,5-trihydroxyphenyl)-1H-benzimidazole-4-(N-o-aminophenyl)amide
(153) 2-(3,4,5-trihydroxyphenyl)-1H-benzimidazole-4-(N-m-hydroxyphenyl)amide
(154) 2-(3,4,5-trihydroxyphenyl)-1H-benzimidazole-4-(N-m-aminophenyl)amide
(155) 2-(3,4,5-trihydroxyphenyl)-1H-benzimidazole-4-(N-p-hydroxyphenyl)amide
(156) 2-(3,4,5-trihydroxyphenyl)-1H-benzimidazole-4-(N-p-aminophenyl)amide
(157) (L)-2-(2,3,4-trihydroxyphenyl)-1H-benzimidazole-4-[N-(1-hydroxymethyl-2-p-nitrophenylhydroxyethyl)]amide
(158) (L)-2-(2,3,4-trihydroxyphenyl)-1H-benzimidazole-4-[N-(1-hydroxymethyl-2-p-aminophenylhydroxyethyl)]amide
(159) 2-(2,3,4-trihydroxyphenyl)-1H-benzimidazole-4-[N-(1-methyl-2-p-chlorophenylhydroxyethyl)]amide
(160) 2-(2,3,4-trihydroxyphenyl)-1H-benzimidazole-4-(N-o-fluorophenyl)amide
(161) 2-(2,3,4-trihydroxyphenyl)-1H-benzimidazole-4-(N-m-fluorophenyl)amide
(162) 2-(2,3,4-trihydroxyphenyl)-1H-benzimidazole-4-(N-p-fluorophenyl)amide
(163) 2-(2,3,4-trihydroxyphenyl)-1H-benzimidazole-4-(N-o-hydroxyphenyl)amide
(164) 2-(2,3,4-trihydroxyphenyl)-1H-benzimidazole-4-(N-o-aminophenyl)amide
(165) 2-(2,3,4-trihydroxyphenyl)-1H-benzimidazole-4-(N-m-hydroxyphenyl)amide
(166) 2-(2,3,4-trihydroxyphenyl)-1H-benzimidazole-4-(N-m-aminophenyl)amide
(167) 2-(2,3,4-trihydroxyphenyl)-1H-benzimidazole-4-(N-p-hydroxyphenyl)amide
(168) 2-(2,3,4-trihydroxyphenyl)-1H-benzimidazole-4-(N-p-aminophenyl)amide
(169) (L)-2-(2-pyrimidinyl)-1H-benzimidazole-4-[N-(1-hydroxymethyl-2-p-nitrophenylhydroxyethyl)]amide
(170) (L)-2-(2-pyrimidinyl)-1H-benzimidazole-4-[N-(1-hydroxymethyl-2-p-aminophenylhydroxyethyl)]amide
(171) 2-(2-pyrimidinyl)-1H-benzimidazole-4-[N-(1-methyl-2-p-chlorophenylhydroxyethyl)]amide
(172) 2-(2-pyrimidinyl)-1H-benzimidazole-4-(N-o-fluorophenyl)amide
(173) 2-(2-pyrimidinyl)-1H-benzimidazole-4-(N-m-fluorophenyl)amide
(174) 2-(2-pyrimidinyl)-1H-benzimidazole-4-(N-p-fluorophenyl)amide
(175) 2-(2-pyrimidinyl)-1H-benzimidazole-4-(N-o-hydroxyphenyl)amide
(176) 2-(2-pyrimidinyl)-1H-benzimidazole-4-(N-o-aminophenyl)amide
(177) 2-(2-pyrimidinyl)-1H-benzimidazole-4-(N-m-hydroxyphenyl)amide
(178) 2-(2-pyrimidinyl)-1H-benzimidazole-4-(N-m-aminophenyl)amide
(179) 2-(2-pyrimidinyl)-1H-benzimidazole-4-(N-p-hydroxyphenyl)amide
(180) 2-(2-pyrimidinyl)-1H-benzimidazole-4-(N-p-aminophenyl)amide
(181) (L)-2-(2-phenyl-5-pyrimidinyl)-1H-benzimidazole-4-[N-(1-hydroxymethyl-2-p-nitrophenylhydroxyethyl)]amide
(182) (L)-2-(2-phenyl-5-pyrimidinyl)-1H-benzimidazole-4-[N-(1-hydroxymethyl-2-p-aminophenylhydroxyethyl)]amide
(183) 2-(2-phenyl-5-pyrimidinyl)-1H-benzimidazole-4-[N-(1-methyl-2-p-chlorophenylhydroxyethyl)]amide
(184) 2-(2-phenyl-5-pyrimidinyl)-1H-benzimidazole-4-(N-o-fluorophenyl)amide
(185) 2-(2-phenyl-5-pyrimidinyl)-1H-benzimidazole-4-(N-m-fluorophenyl)amide
(186) 2-(2-phenyl-5-pyrimidinyl)-1H-benzimidazole-4-(N-p-fluorophenyl)amide
(187) 2-(2-phenyl-5-pyrimidinyl)-1H-benzimidazole-4-(N-o-hydroxyphenyl)amide
(188) 2-(2-phenyl-5-pyrimidinyl)-1H-benzimidazole-4-(N-o-aminophenyl)amide
(189) 2-(2-phenyl-5-pyrimidinyl)-1H-benzimidazole-4-(N-m-hydroxyphenyl)amide
(190) 2-(2-phenyl-5-pyrimidinyl)-1H-benzimidazole-4-(N-m-aminophenyl)amide
(191) 2-(2-phenyl-5-pyrimidinyl)-1H-benzimidazole-4-(N-p-hydroxyphenyl)amide
(192) 2-(2-phenyl-5-pyrimidinyl)-1H-benzimidazole-4-(N-p-aminophenyl)amide
(193) (L)-2-(4-amino-6-chloro-5-pyrimidinyl)-1H-benzimidazole-4-[N-(1-hydroxymethyl-2-p-nitrophenylhydroxyethyl)]amide (194) (L)-2-(4-amino-6-chloro-5-pyrimidinyl)-1H-benzimidazole-4-[N-(1-hydroxymethyl-2-p-aminophenylhydroxyethyl)]amide
(195) 2-(4-amino-6-chloro-5-pyrimidinyl)-1H-benzimidazole-4-[N-(1-methyl-2-p-chlorophenylhydroxyethyl)]amide
(196) 2-(4-amino-6-chloro-5-pyrimidinyl)-1H-benzimidazole-4-(N-o-fluorophenyl)amide
(197) 2-(4-amino-6-chloro-5-pyrimidinyl)-1H-benzimidazole-4-(N-m-fluorophenyl)amide
(198) 2-(4-amino-6-chloro-5-pyrimidinyl)-1H-benzimidazole-4-(N-p-fluorophenyl)amide
(199) 2-(4-amino-6-chloro-5-pyrimidinyl)-1H-benzimidazole-4-(N-o-hydroxyphenyl)amide
(200) 2-(4-amino-6-chloro-5-pyrimidinyl)-1H-benzimidazole-4-(N-o-aminophenyl)amide
(201) 2-(4-amino-6-chloro-5-pyrimidinyl)-1H-benzimidazole-4-(N-m-hydroxyphenyl)amide
(202) 2-(4-amino-6-chloro-5-pyrimidinyl)-1H-benzimidazole-4-(N-m-aminophenyl)amide
(203) 2-(4-amino-6-chloro-5-pyrimidinyl)-1H-benzimidazole-4-(N-p-hydroxyphenyl)amide
(204) 2-(4-amino-6-chloro-5-pyrimidinyl)-1H-benzimidazole-4-(N-p-aminophenyl)amide
(205) (L)-2-(2-pyrrolyl)-1H-benzimidazole-4-[N-(1-hydroxymethyl-2-p-nitrophenylhydroxyethyl)]amide
(206) (L)-2-(2-pyrrolyl)-1H-benzimidazole-4-[N-(1-hydroxymethyl-2-p-aminophenylhydroxyethyl)]amide
(207) 2-(2-pyrrolyl)-1H-benzimidazole-4-[N-(1-methyl-2-p-chlorophenylhydroxyethyl)]amide
(208) 2-(2-pyrrolyl)-1H-benzimidazole-4-(N-o-fluorophenyl)amide
(209) 2-(2-pyrrolyl)-1H-benzimidazole-4-(N-m-fluorophenyl)amide
(210) 2-(2-pyrrolyl)-1H-benzimidazole-4-(N-p-fluorophenyl)amide
(211) 2-(2-pyrrolyl)-1H-benzimidazole-4-(N-o-hydroxyphenyl)amide
(212) 2-(2-pyrrolyl)-1H-benzimidazole-4-(N-o-aminophenyl)amide
(213) 2-(2-pyrrolyl)-1H-benzimidazole-4-(N-m-hydroxyphenyl)amide
(214) 2-(2-pyrrolyl)-1H-benzimidazole-4-(N-m-aminophenyl)amide
(215) 2-(2-pyrrolyl)-1H-benzimidazole-4-(N-p-hydroxyphenyl)amide
(216) (L)-2-(N-methyl-2-pyrrolyl)-1H-benzimidazole-4-[N-(1-hydroxymethyl-2-p-nitrophenylhydroxyethyl)]amide
(217) (L)-2-(N-methyl-2-pyrrolyl)-1H-benzimidazole-4-[N-(1-hydroxymethyl-2-p-aminophenylhydroxyethyl)]amide
(218) 2-(N-methyl-2-pyrrolyl)-1H-benzimidazole-4-[N-(1-methyl-2-p-chlorophenylhydroxyethyl)]amide
(219) 2-(N-methyl-2-pyrrolyl)-1H-benzimidazole-4-(N-o-fluorophenyl)amide
(220) 2-(N-methyl-2-pyrrolyl)-1H-benzimidazole-4-(N-m-fluorophenyl)amide
(221) 2-(N-methyl-2-pyrrolyl)-1H-benzimidazole-4-(N-p-fluorophenyl)amide
(222) 2-(N-methyl-2-pyrrolyl)-1H-benzimidazole-4-(N-o-hydroxyphenyl)amide
(223) 2-(N-methyl-2-pyrrolyl)-1H-benzimidazole-4-(N-o-aminophenyl)amide
(224) 2-(N-methyl-2-pyrrolyl)-1H-benzimidazole-4-(N-m-hydroxyphenyl)amide
(225) 2-(N-methyl-2-pyrrolyl)-1H-benzimidazole-4-(N-m-aminophenyl)amide
(226) 2-(N-methyl-2-pyrrolyl)-1H-benzimidazole-4-(N-p-hydroxyphenyl)amide
(227) (L)-2-(3,5-dimethyl-2-pyrrolyl)-1H-benzimidazole-4-[N-(1-hydroxymethyl-2-p-nitrophenylhydroxyethyl)]amide
(228) (L)-2-(3,5-dimethyl-2-pyrrolyl)-1H-benzimidazole-4-[N-(1-hydroxymethyl-2-p-aminophenylhydroxyethyl)]amide
(229) 2-(3,5-dimethyl-2-pyrrolyl)-1H-benzimidazole-4-[N-(1-methyl-2-p-chlorophenylhydroxyethyl)]amide
(230) 2-(3,5-dimethyl-2-pyrrolyl)-1H-benzimidazole-4-(N-o-fluorophenyl)amide
(231) 2-(3,5-dimethyl-2-pyrrolyl)-1H-benzimidazole-4-(N-m-fluorophenyl)amide
(232) 2-(3,5-dimethyl-2-pyrrolyl)-1H-benzimidazole-4-(N-p-fluorophenyl)amide
(233) 2-(3,5-dimethyl-2-pyrrolyl)-1H-benzimidazole-4-(N-o-hydroxyphenyl)amide
(234) 2-(3,5-dimethyl-2-pyrrolyl)-1H-benzimidazole-4-(N-o-aminophenyl)amide
(235) 2-(3,5-dimethyl-2-pyrrolyl)-1H-benzimidazole-4-(N-m-hydroxyphenyl)amide
(236) 2-(3,5-dimethyl-2-pyrrolyl)-1H-benzimidazole-4-(N-m-aminophenyl)amide
(237) 2-(3,5-dimethyl-2-pyrrolyl)-1H-benzimidazole-4-(N-p-hydroxyphenyl)amide
(238) (L)-2-(2-quinolinyl)-1H-benzimidazole-4-[N-(1-hydroxymethyl-2-p-nitrophenylhydroxyethyl)]amide
(239) (L)-2-(2-quinolinyl)-1H-benzimidazole-4-[N-(1-hydroxymethyl-2-p-aminophenylhydroxyethyl)]amide
(240) 2-(2-quinolinyl)-1H-benzimidazole-4-[N-(1-methyl-2-p-chlorophenylhydroxyethyl)]amide
(241) 2-(2-quinolinyl)-1H-benzimidazole-4-(N-o-fluorophenyl)amide
(242) 2-(2-quinolinyl)-1H-benzimidazole-4-(N-m-fluorophenyl)amide
(243) 2-(2-quinolinyl)-1H-benzimidazole-4-(N-p-fluorophenyl)amide
(244) 2-(2-quinolinyl)-1H-benzimidazole-4-(N-o-hydroxyphenyl)amide
(245) 2-(2-quinolinyl)-1H-benzimidazole-4-(N-o-aminophenyl)amide
(246) 2-(2-quinolinyl)-1H-benzimidazole-4-(N-m-hydroxyphenyl)amide
(247) 2-(2-quinolinyl)-1H-benzimidazole-4-(N-m-aminophenyl)amide
(248) 2-(2-quinolinyl)-1H-benzimidazole-4-(N-p-hydroxyphenyl)amide
(249) (L)-2-(3-quinolinyl)-1H-benzimidazole-4-[N-(1-hydroxymethyl-2-p-nitrophenylhydroxyethyl)]amide
(250) (L)-2-(3-quinolinyl)-1H-benzimidazole-4-[N-(1-hydroxymethyl-2-p-aminophenylhydroxyethyl)]amide
(251) 2-(3-quinolinyl)-1H-benzimidazole-4-[N-(1-methyl-2-p-chlorophenylhydroxyethyl)]amide
(252) 2-(3-quinolinyl)-1H-benzimidazole-4-(N-o-fluorophenyl)amide
(253) 2-(3-quinolinyl)-1H-benzimidazole-4-(N-m-fluorophenyl)amide
(254) 2-(3-quinolinyl)-1H-benzimidazole-4-(N-p-fluorophenyl)amide
(255) 2-(3-quinolinyl)-1H-benzimidazole-4-(N-o-hydroxyphenyl)amide
(256) 2-(3-quinolinyl)-1H-benzimidazole-4-(N-o-aminophenyl)amide
(257) 2-(3-quinolinyl)-1H-benzimidazole-4-(N-m-hydroxyphenyl)amide (258) 2-(3-quinolinyl)-1H-benzimidazole-4-(N-m-aminophenyl)amide
(259) 2-(3-quinolinyl)-1H-benzimidazole-4-(N-p-hydroxyphenyl)amide
(260) (L)-2-(2-piperidinyl)-1H-benzimidazole-4-[N-(1-hydroxymethyl-2-p-nitrophenylhydroxyethyl)]amide
(261) (L)-2-(2-piperidinyl)-1H-benzimidazole-4-[N-(1-hydroxymethyl-2-p-aminophenylhydroxyethyl)]amide
(262) 2-(2-piperidinyl)-1H-benzimidazole-4-[N-(1-methyl-2-p-chlorophenylhydroxyethyl)]amide
(263) 2-(2-piperidinyl)-1H-benzimidazole-4-(N-o-fluorophenyl)amide
(264) 2-(2-piperidinyl)-1H-benzimidazole-4-(N-m-fluorophenyl)amide
(265) 2-(2-piperidinyl)-1H-benzimidazole-4-(N-p-fluorophenyl)amide
(266) 2-(2-piperidinyl)-1H-benzimidazole-4-(N-o-hydroxyphenyl)amide
(267) 2-(2-piperidinyl)-1H-benzimidazole-4-(N-o-aminophenyl)amide
(268) 2-(2-piperidinyl)-1H-benzimidazole-4-(N-m-hydroxyphenyl)amide
(269) 2-(2-piperidinyl)-1H-benzimidazole-4-(N-m-aminophenyl)amide
(270) 2-(2-piperidinyl)-1H-benzimidazole-4-(N-p-hydroxyphenyl)amide
(271) (L)-2-(3-piperidinyl)-1H-benzimidazole-4-[N-(1-hydroxymethyl-2-p-nitrophenylhydroxyethyl)]amide
(272) (L)-2-(3-piperidinyl)-1H-benzimidazole-4-[N-(1-hydroxymethyl-2-p-aminophenylhydroxyethyl)]amide
(273) 2-(3-piperidinyl)-1H-benzimidazole-4-[N-(1-methyl-2-p-chlorophenylhydroxyethyl)]amide
(274) 2-(3-piperidinyl)-1H-benzimidazole-4-(N-o-fluorophenyl)amide
(275) 2-(3-piperidinyl)-1H-benzimidazole-4-(N-m-fluorophenyl)amide
(276) 2-(3-piperidinyl)-1H-benzimidazole-4-(N-p-fluorophenyl)amide
(277) 2-(3-piperidinyl)-1H-benzimidazole-4-(N-o-hydroxyphenyl)amide
(278) 2-(3-piperidinyl)-1H-benzimidazole-4-(N-o-aminophenyl)amide
(279) 2-(3-piperidinyl)-1H-benzimidazole-4-(N-m-hydroxyphenyl)amide
(280) 2-(3-piperidinyl)-1H-benzimidazole-4-(N-m-aminophenyl)amide
(281) 2-(3-piperidinyl)-1H-benzimidazole-4-(N-p-hydroxyphenyl)amide
(282) (L)-2-(4-piperidinyl)-1H-benzimidazole-4-[N-(1-hydroxymethyl-2-p-nitrophenylhydroxyethyl)]amide
(283) (L)-2-(4-piperidinyl)-1H-benzimidazole-4-[N-(1-hydroxymethyl-2-p-aminophenylhydroxyethyl)]amide
(284) 2-(4-piperidinyl)-1H-benzimidazole-4-[N-(1-methyl-2-p-chlorophenylhydroxyethyl)]amide
(285) 2-(4-piperidinyl)-1H-benzimidazole-4-(N-o-fluorophenyl)amide
(286) 2-(4-piperidinyl)-1H-benzimidazole-4-(N-m-fluorophenyl)amide
(287) 2-(4-piperidinyl)-1H-benzimidazole-4-(N-p-fluorophenyl)amide
(288) 2-(4-piperidinyl)-1H-benzimidazole-4-(N-o-hydroxyphenyl)amide
(289) 2-(4-piperidinyl)-1H-benzimidazole-4-(N-o-aminophenyl)amide
(290) 2-(4-piperidinyl)-1H-benzimidazole-4-(N-m-hydroxyphenyl)amide
(291) 2-(4-piperidinyl)-1H-benzimidazole-4-(N-m-aminophenyl)amide
(292) 2-(4-piperidinyl)-1H-benzimidazole-4-(N-p-hydroxyphenyl)amide
(293) (L)-2-(3-indolyl)-1H-benzimidazole-4-[N-(1-hydroxymethyl-2-p-nitrophenylhydroxyethyl)]amide
(294) (L)-2-(3-indolyl)-1H-benzimidazole-4-[N-(1-hydroxymethyl-2-p-aminophenylhydroxyethyl)]amide
(295) 2-(3-indolyl)-1H-benzimidazole-4-[N-(1-methyl-2-p-chlorophenylhydroxyethyl)]amide
(296) 2-(3-indolyl)-1H-benzimidazole-4-(N-o-fluorophenyl)amide
(297) 2-(3-indolyl)-1H-benzimidazole-4-(N-m-fluorophenyl)amide
(298) 2-(3-indolyl)-1H-benzimidazole-4-(N-p-fluorophenyl)amide
(299) 2-(3-indolyl)-1H-benzimidazole-4-(N-o-hydroxyphenyl)amide
(300) 2-(3-indolyl)-1H-benzimidazole-4-(N-o-aminophenyl)amide
(301) 2-(3-indolyl)-1H-benzimidazole-4-(N-m-hydroxyphenyl)amide
(302) 2-(3-indolyl)-1H-benzimidazole-4-(N-m-aminophenyl)amide
(303) 2-(3-indolyl)-1H-benzimidazole-4-(N-p-hydroxyphenyl)amide
(304) (L)-2-(2,3,4-trimethoxyphenyl)-1H-benzimidazole-4-[N-(1-hydroxymethyl-2-p-nitrophenylhydroxyethyl)]amide
(305) (L)-2-(2,3,4-trimethoxyphenyl)-1H-benzimidazole-4-[N-(1-hydroxymethyl-2-p-aminophenylhydroxyethyl)]amide
(306) 2-(2,3,4-trimethoxyphenyl)-1H-benzimidazole-4-[N-(1-methyl-2-p-chlorophenylhydroxyethyl)]amide
(307) 2-(2,3,4-trimethoxyphenyl)-1H-benzimidazole-4-(N-o-fluorophenyl)amide
(308) 2-(2,3,4-trimethoxyphenyl)-1H-benzimidazole-4-(N-m-fluorophenyl)amide
(309) 2-(2,3,4-trimethoxyphenyl)-1H-benzimidazole-4-(N-p-fluorophenyl)amide
(310) 2-(2,3,4-trimethoxyphenyl)-1H-benzimidazole-4-(N-o-hydroxyphenyl)amide
(311) 2-(2,3,4-trimethoxyphenyl)-1H-benzimidazole-4-(N-o-aminophenyl)amide
(312) 2-(2,3,4-trimethoxyphenyl)-1H-benzimidazole-4-(N-m-hydroxyphenyl)amide
(313) 2-(2,3,4-trimethoxyphenyl)-1H-benzimidazole-4-(N-m-aminophenyl)amide
(314) 2-(2,3,4-trimethoxyphenyl)-1H-benzimidazole-4-(N-p-hydroxyphenyl)amide
(315) (L)-2-(3-hydroxyl-4-methoxyphenyl)-1H-benzimidazole-4-[N-(1-hydroxymethyl-2-p-nitrophenylhydroxyethyl)]amide
(316) (L)-2-(3-hydroxyl-4-methoxyphenyl)-1H-benzimidazole-4-[N-(1-hydroxymethyl-2-p-aminophenylhydroxyethyl)]amide
(317) 2-(3-hydroxyl-4-methoxyphenyl)-1H-benzimidazole-4-[N-(1-methyl-2-p-chlorophenylhydroxyethyl)]amide
(318) 2-(3-hydroxyl-4-methoxyphenyl)-1H-benzimidazole-4-(N-o-fluorophenyl)amide
(319) 2-(3-hydroxyl-4-methoxyphenyl)-1H-benzimidazole-4-(N-m-fluorophenyl)amide
(320) 2-(3-hydroxyl-4-methoxyphenyl)-1H-benzimidazole-4-(N-p-fluorophenyl)amide
(321) 2-(3-hydroxyl-4-methoxyphenyl)-1H-benzimidazole-4-(N-o-hydroxyphenyl)amide (322) 2-(3-hydroxyl-4-methoxyphenyl)-1H-benzimidazole-4-(N-o-aminophenyl)amide
(323) 2-(3-hydroxyl-4-methoxyphenyl)-1H-benzimidazole-4-(N-m-hydroxyphenyl)amide
(324) 2-(3-hydroxyl-4-methoxyphenyl)-1H-benzimidazole-4-(N-m-aminophenyl)amide
(325) 2-(3-hydroxyl-4-methoxyphenyl)-1H-benzimidazole-4-(N-p-hydroxyphenyl)amide
(326) (L)-2-methoxy-1H-benzimidazole-4-[N-(1-hydroxymethyl-2-p-nitrophenylhydroxyethyl)]amide
(327) (L)-2-methoxy-1H-benzimidazole-4-[N-(1-hydroxymethyl-2-p-aminophenylhydroxyethyl)]amide
(328) 2-methoxy-1H-benzimidazole-4-[N-(1-methyl-2-p-chlorophenylhydroxyethyl)]amide
(329) 2-methoxy-1H-benzimidazole-4-(N—N'-piperidinyl)amide
(330) 2-methoxy-1H-benzimidazole-4-(N-2-piperazinyl)amide
(331) 2-methoxy-1H-benzimidazole-4-(N-2'-benzimidazolyl)amide
(332) 2-methoxy-1H-benzimidazole-4-(N-o-hydroxyphenyl)amide
(333) 2-methoxy-1H-benzimidazole-4-(N-o-aminophenyl)amide
(334) 2-methoxy-1H-benzimidazole-4-(N-5-benzimidazolonyl)amide
(335) 2-methoxy-1H-benzimidazole-4-(N-4'-carbonamido-5'-imidazolyl)amide
(336) 2-methoxy-1H-benzimidazole-4-(N-4'-carboxyl-5'-imidazolyl)amide
(337) 2-methoxy-1H-benzimidazole-4-(N-2-imidazolyl)amide
(338) 2-methoxy-1H-benzimidazole-4-(N-4'-pyrazolyl)amide
(339) 2-methoxy-1H-benzimidazole-4-(N—(N'-piperazinyl))amide
(340) 2-methoxy-1H-benzimidazole-4-(N'-ethyl-N-piperazinyl)amide
(341) 2-methoxy-1H-benzimidazole-4-(N-2-pyrazinyl)amide
(342) 2-methoxy-1H-benzimidazole-4-(N-2-pyrimidinyl)amide
(343) 2-methoxy-1H-benzimidazole-4-(N-4-pyrimidinyl)amide
(344) 2-methoxy-1H-benzimidazole-4-(N-5-pyrimidinyl)amide
(345) 2-methoxy-1H-benzimidazole-4-(N-2-pyridyl)amide
(346) 2-methoxy-1H-benzimidazole-4-(N-3-pyridyl)amide
(347) 2-methoxy-1H-benzimidazole-4-(N-4-pyridyl)amide
(348) 2-methoxy-1H-benzimidazole-4-(N-4-methyl-5-thiazolyl)amide
(349) 2-methoxy-1H-benzimidazole-4-(N-5-thiazolyl)amide
(350) 2-methoxy-1H-benzimidazole-4-(N-2,4-dihydroxyl-5-pyrimidinyl)amide
(351) 2-methoxy-1H-benzimidazole-4-(N-4,6-dimethoxy-2-pyrimidinyl)amide
(352) 2-methoxy-1H-benzimidazole-4-(N-4-chloro-6-amino-2-pyrimidinyl)amide
(353) 2-methoxy-1H-benzimidazole-4-(N-4,6-dichloro-5-pyrimidinyl)amide
(354) (L)-2-ethoxy-1H-benzimidazole-4-[N-(1-hydroxymethyl-2-p-nitrophenylhydroxyethyl)]amide
(355) (L)-2-ethoxy-1H-benzimidazole-4-[N-(1-hydroxymethyl-2-p-aminophenylhydroxyethyl)]amide
(356) 2-ethoxy-1H-benzimidazole-4-[N-(1-methyl-2-p-chlorophenylhydroxyethyl)]amide
(357) 2-ethoxy-1H-benzimidazole-4-(N—N'-piperidinyl)amide
(358) 2-ethoxy-1H-benzimidazole-4-(N-2-piperazinyl)amide
(359) 2-ethoxy-1H-benzimidazole-4-(N-2'-benzimidazolyl)amide
(360) 2-ethoxy-1H-benzimidazole-4-(N-o-hydroxyphenyl)amide
(361) 2-ethoxy-1H-benzimidazole-4-(N-o-aminophenyl)amide
(362) 2-ethoxy-1H-benzimidazole-4-(N-5-benzimidazolonyl)amide
(363) 2-ethoxy-1H-benzimidazole-4-(N-4'-carbonamido-5'-imidazolyl)amide
(364) 2-ethoxy-1H-benzimidazole-4-(N-4'-carboxyl-5'-imidazolyl)amide
(365) 2-ethoxy-1H-benzimidazole-4-(N-2-imidazolyl)amide
(366) 2-ethoxy-1H-benzimidazole-4-(N-4'-pyrazolyl)amide
(367) 2-ethoxy-1H-benzimidazole-4-(N—(N'-piperazinyl))amide
(368) 2-ethoxy-1H-benzimidazole-4-(N'-ethyl-N-piperazinyl)amide
(369) 2-ethoxy-1H-benzimidazole-4-(N-2-pyrazinyl)amide
(370) 2-ethoxy-1H-benzimidazole-4-(N-2-pyrimidinyl)amide
(371) 2-ethoxy-1H-benzimidazole-4-(N-4-pyrimidinyl)amide
(372) 2-ethoxy-1H-benzimidazole-4-(N-5-pyrimidinyl)amide
(373) 2-ethoxy-1H-benzimidazole-4-(N-2-pyridyl)amide
(374) 2-ethoxy-1H-benzimidazole-4-(N-3-pyridyl)amide
(375) 2-ethoxy-1H-benzimidazole-4-(N-4-pyridyl)amide
(376) 2-ethoxy-1H-benzimidazole-4-(N-4-methyl-5-thiazolyl)amide
(377) 2-ethoxy-1H-benzimidazole-4-(N-5-thiazolyl)amide
(378) 2-ethoxy-1H-benzimidazole-4-(N-2,4-dihydroxyl-5-pyrimidinyl)amide
(379) 2-ethoxy-1H-benzimidazole-4-(N-4,6-dimethoxy-2-pyrimidinyl)amide
(380) 2-ethoxy-1H-benzimidazole-4-(N-4-chloro-6-amino-2-pyrimidinyl)amide
(381) 2-ethoxy-1H-benzimidazole-4-(N-4,6-dichloro-5-pyrimidinyl)amide
(382) (L)-2-(2,6-dimethyl-2,6-octadienyl)-1H-benzimidazole-4-[N-(1-hydroxymethyl-2-p-nitrophenylhydroxyethyl)]amide
(383) (L)-2-(2,6-dimethyl-2,6-octadienyl)-1H-benzimidazole-4-[N-(1-hydroxymethyl-2-p-aminophenylhydroxyethyl)]amide
(384) 2-(2,6-dimethyl-2,6-octadienyl)-1H-benzimidazole-4-[N-(1-methyl-2-p-chlorophenylhydroxyethyl)]amide
(385) 2-(2,6-dimethyl-2,6-octadienyl)-1H-benzimidazole-4-(N—N'-piperidinyl)amide
(386) 2-(2,6-dimethyl-2,6-octadienyl)-1H-benzimidazole-4-(N-2-piperazinyl)amide
(387) 2-(2,6-dimethyl-2,6-octadienyl)-1H-benzimidazole-4-(N-2'-benzimidazolyl)amide
(388) 2-(2,6-dimethyl-2,6-octadienyl)-1H-benzimidazole-4-(N-o-hydroxyphenyl)amide
(389) 2-(2,6-dimethyl-2,6-octadienyl)-1H-benzimidazole-4-(N-o-aminophenyl)amide
(390) 2-(2,6-dimethyl-2,6-octadienyl)-1H-benzimidazole-4-(N-5-benzimidazolonyl)amide
(391) 2-(2,6-dimethyl-2,6-octadienyl)-1H-benzimidazole-4-(N-4'-carbonamido-5'-imidazolyl)amide (392) 2-(2,6-dimethyl-2,6-octadienyl)-1H-benzimidazole-4-(N-4'-carboxyl-5'-imidazolyl)amide
(393) 2-(2,6-dimethyl-2,6-octadienyl)-1H-benzimidazole-4-(N-2-imidazolyl)amide
(394) 2-(2,6-dimethyl-2,6-octadienyl)-1H-benzimidazole-4-(N-4'-pyrazolyl)amide
(395) 2-(2,6-dimethyl-2,6-octadienyl)-1H-benzimidazole-4-(N—(N'-piperazinyl))amide
(396) 2-(2,6-dimethyl-2,6-octadienyl)-1H-benzimidazole-4-(N'-ethyl-N-piperazinyl)amide
(397) 2-(2,6-dimethyl-2,6-octadienyl)-1H-benzimidazole-4-(N-2-pyrazinyl)amide
(398) 2-(2,6-dimethyl-2,6-octadienyl)-1H-benzimidazole-4-(N-2-pyrimidinyl)amide
(399) 2-(2,6-dimethyl-2,6-octadienyl)-1H-benzimidazole-4-(N-4-pyrimidinyl)amide
(400) 2-(2,6-dimethyl-2,6-octadienyl)-1H-benzimidazole-4-(N-5-pyrimidinyl)amide
(401) 2-(2,6-dimethyl-2,6-octadienyl)-1H-benzimidazole-4-(N-2-pyridyl)amide
(402) 2-(2,6-dimethyl-2,6-octadienyl)-1H-benzimidazole-4-(N-3-pyridyl)amide
(403) 2-(2,6-dimethyl-2,6-octadienyl)-1H-benzimidazole-4-(N-4-pyridyl)amide
(404) 2-(2,6-dimethyl-2,6-octadienyl)-1H-benzimidazole-4-(N-4-methyl-5-thiazolyl)amide
(405) 2-(2,6-dimethyl-2,6-octadienyl)-1H-benzimidazole-4-(N-5-thiazolyl)amide
(406) 2-(2,6-dimethyl-2,6-octadienyl)-1H-benzimidazole-4-(N-2,4-dihydroxyl-5-pyrimidinyl)amide
(407) 2-(2,6-dimethyl-2,6-octadienyl)-1H-benzimidazole-4-(N-4,6-dimethoxy-2-pyrimidinyl)amide
(408) 2-(2,6-dimethyl-2,6-octadienyl)-1H-benzimidazole-4-(N-4-chloro-6-amino-2-pyrimidinyl)amide
(409) 2-(2,6-dimethyl-2,6-octadienyl)-1H-benzimidazole-4-(N-4,6-dichloro-5-pyrimidinyl)amide
(410) (L)-2-pyrazolyl-1H-benzimidazole-4-[N-(1-hydroxymethyl-2-p-nitrophenylhydroxyethyl)]amide
(411) (L)-2-pyrazolyl-1H-benzimidazole-4-[N-(1-hydroxymethyl-2-p-aminophenylhydroxyethyl)]amide
(412) 2-pyrazolyl-1H-benzimidazole-4-[N-(1-methyl-2-p-chlorophenylhydroxyethyl)]amide
(413) 2-pyrazolyl-1H-benzimidazole-4-(N—N'-piperidinyl)amide
(414) 2-pyrazolyl-1H-benzimidazole-4-(N-2-piperazinyl)amide
(415) 2-pyrazolyl-1H-benzimidazole-4-(N-2'-benzimidazolyl)amide
(416) 2-pyrazolyl-1H-benzimidazole-4-(N-o-hydroxyphenyl)amide
(417) 2-pyrazolyl-1H-benzimidazole-4-(N-o-aminophenyl)amide
(418) 2-pyrazolyl-1H-benzimidazole-4-(N-5-benzimidazolonyl)amide
(419) 2-pyrazolyl-1H-benzimidazole-4-(N-4'-carbonamido-5'-imidazolyl)amide
(420) 2-pyrazolyl-1H-benzimidazole-4-(N-4'-carboxyl-5'-imidazolyl)amide
(421) 2-pyrazolyl-1H-benzimidazole-4-(N-2-imidazolyl)amide
(422) 2-pyrazolyl-1H-benzimidazole-4-(N-4'-pyrazolyl)amide
(423) 2-pyrazolyl-1H-benzimidazole-4-(N—(N'-piperazinyl))amide
(424) 2-pyrazolyl-1H-benzimidazole-4-(N'-ethyl-N-piperazinyl)amide
(425) 2-pyrazolyl-1H-benzimidazole-4-(N-2-pyrazinyl)amide
(426) 2-pyrazolyl-1H-benzimidazole-4-(N-2-pyrimidinyl)amide
(427) 2-pyrazolyl-1H-benzimidazole-4-(N-4-pyrimidinyl)amide
(428) 2-pyrazolyl-1H-benzimidazole-4-(N-5-pyrimidinyl)amide
(429) 2-pyrazolyl-1H-benzimidazole-4-(N-2-pyridyl)amide
(430) 2-pyrazolyl-1H-benzimidazole-4-(N-3-pyridyl)amide
(431) 2-pyrazolyl-1H-benzimidazole-4-(N-4-pyridyl)amide
(432) 2-pyrazolyl-1H-benzimidazole-4-(N-4-methyl-5-thiazolyl)amide
(433) 2-pyrazolyl-1H-benzimidazole-4-(N-5-thiazolyl)amide
(434) 2-pyrazolyl-1H-benzimidazole-4-(N-2,4-dihydroxyl-5-pyrimidinyl)amide
(435) 2-pyrazolyl-1H-benzimidazole-4-(N-4,6-dimethoxy-2-pyrimidinyl)amide
(436) 2-pyrazolyl-1H-benzimidazole-4-(N-4-chloro-6-amino-2-pyrimidinyl)amide
(437) 2-pyrazolyl-1H-benzimidazole-4-(N-4,6-dichloro-5-pyrimidinyl)amide
(438) (L)-2-(2'-pyridyl)-1H-benzimidazole-4-[N-(1-hydroxymethyl-2-p-nitrophenylhydroxyethyl)]amide
(439) (L)-2-(2'-pyridyl)-1H-benzimidazole-4-[N-(1-hydroxymethyl-2-p-aminophenylhydroxyethyl)]amide
(440) 2-(2'-pyridyl)-1H-benzimidazole-4-[N-(1-methyl-2-p-chlorophenylhydroxyethyl)]amide
(441) 2-(2'-pyridyl)-1H-benzimidazole-4-(N—N'-piperidinyl)amide
(442) 2-(2'-pyridyl)-1H-benzimidazole-4-(N-2-piperazinyl)amide
(443) 2-(2'-pyridyl)-1H-benzimidazole-4-(N-2'-benzimidazolyl)amide
(444) 2-(2'-pyridyl)-1H-benzimidazole-4-(N-o-hydroxyphenyl)amide
(445) 2-(2'-pyridyl)-1H-benzimidazole-4-(N-o-aminophenyl)amide
(446) 2-(2'-pyridyl)-1H-benzimidazole-4-(N-5-benzimidazolonyl)amide
(447) 2-(2'-pyridyl)-1H-benzimidazole-4-(N-4'-carbonamido-5'-imidazolyl)amide
(448) 2-(2'-pyridyl)-1H-benzimidazole-4-(N-4'-carboxyl-5'-imidazolyl)amide
(449) 2-(2'-pyridyl)-1H-benzimidazole-4-(N-2-imidazolyl)amide
(450) 2-(2'-pyridyl)-1H-benzimidazole-4-(N-4'-pyrazolyl)amide
(451) 2-(2'-pyridyl)-1H-benzimidazole-4-(N—(N'-piperazinyl))amide
(452) 2-(2'-pyridyl)-1H-benzimidazole-4-(N'-ethyl-N-piperazinyl)amide
(453) 2-(2'-pyridyl)-1H-benzimidazole-4-(N-2-pyrazinyl)amide
(454) 2-(2'-pyridyl)-1H-benzimidazole-4-(N-2-pyrimidinyl)amide
(455) 2-(2'-pyridyl)-1H-benzimidazole-4-(N-4-pyrimidinyl)amide
(456) 2-(2'-pyridyl)-1H-benzimidazole-4-(N-5-pyrimidinyl)amide
(457) 2-(2'-pyridyl)-1H-benzimidazole-4-(N-2-pyridyl)amide
(458) 2-(2'-pyridyl)-1H-benzimidazole-4-(N-3-pyridyl)amide
(459) 2-(2'-pyridyl)-1H-benzimidazole-4-(N-4-pyridyl)amide (460) 2-(2'-pyridyl)-1H-benzimidazole-4-(N-4-methyl-5-thiazolyl)amide
(461) 2-(2'-pyridyl)-1H-benzimidazole-4-(N-5-thiazolyl)amide
(462) 2-(2'-pyridyl)-1H-benzimidazole-4-(N-2,4-dihydroxyl-5-pyrimidinyl)amide
(463) 2-(2'-pyridyl)-1H-benzimidazole-4-(N-4,6-dimethoxy-2-pyrimidinyl)amide
(464) 2-(2'-pyridyl)-1H-benzimidazole-4-(N-4-chloro-6-amino-2-pyrimidinyl)amide
(465) 2-(2'-pyridyl)-1H-benzimidazole-4-(N-4,6-dichloro-5-pyrimidinyl)amide
(466) (L)-2-(3'-pyridyl)-1H-benzimidazole-4-[N-(1-hydroxymethyl-2-p-nitrophenylhydroxyethyl)]amide
(467) (L)-2-(3'-pyridyl)-1H-benzimidazole-4-[N-(1-hydroxymethyl-2-p-aminophenylhydroxyethyl)]amide
(468) 2-(3'-pyridyl)-1H-benzimidazole-4-[N-(1-methyl-2-p-chlorophenylhydroxyethyl)]amide
(469) 2-(3'-pyridyl)-1H-benzimidazole-4-(N—N'-piperidinyl)amide
(470) 2-(3'-pyridyl)-1H-benzimidazole-4-(N-2-piperazinyl)amide
(471) 2-(3'-pyridyl)-1H-benzimidazole-4-(N-2'-benzimidazolyl)amide
(472) 2-(3'-pyridyl)-1H-benzimidazole-4-(N-o-hydroxyphenyl)amide
(473) 2-(3'-pyridyl)-1H-benzimidazole-4-(N-o-aminophenyl)amide
(474) 2-(3'-pyridyl)-1H-benzimidazole-4-(N-5-benzimidazolonyl)amide
(475) 2-(3'-pyridyl)-1H-benzimidazole-4-(N-4'-carbonamido-5'-imidazolyl)amide
(476) 2-(3'-pyridyl)-1H-benzimidazole-4-(N-4'-carboxyl-5'-imidazolyl)amide
(477) 2-(3'-pyridyl)-1H-benzimidazole-4-(N-2-imidazolyl)amide
(478) 2-(3'-pyridyl)-1H-benzimidazole-4-(N-4'-pyrazolyl)amide
(479) 2-(3'-pyridyl)-1H-benzimidazole-4-(N—(N'-piperazinyl))amide
(480) 2-(3'-pyridyl)-1H-benzimidazole-4-(N'-ethyl-N-piperazinyl)amide
(481) 2-(3'-pyridyl)-1H-benzimidazole-4-(N-2-pyrazinyl)amide
(482) 2-(3'-pyridyl)-1H-benzimidazole-4-(N-2-pyrimidinyl)amide
(483) 2-(3'-pyridyl)-1H-benzimidazole-4-(N-4-pyrimidinyl)amide
(484) 2-(3'-pyridyl)-1H-benzimidazole-4-(N-5-pyrimidinyl)amide
(485) 2-(3'-pyridyl)-1H-benzimidazole-4-(N-2-pyridyl)amide
(486) 2-(3'-pyridyl)-1H-benzimidazole-4-(N-3-pyridyl)amide
(487) 2-(3'-pyridyl)-1H-benzimidazole-4-(N-4-pyridyl)amide
(488) 2-(3'-pyridyl)-1H-benzimidazole-4-(N-4-methyl-5-thiazolyl)amide
(489) 2-(3'-pyridyl)-1H-benzimidazole-4-(N-5-thiazolyl)amide
(490) 2-(3'-pyridyl)-1H-benzimidazole-4-(N-2,4-dihydroxyl-5-pyrimidinyl)amide
(491) 2-(3'-pyridyl)-1H-benzimidazole-4-(N-4,6-dimethoxy-2-pyrimidinyl)amide
(492) 2-(3'-pyridyl)-1H-benzimidazole-4-(N-4-chloro-6-amino-2-pyrimidinyl)amide
(493) 2-(3'-pyridyl)-1H-benzimidazole-4-(N-4,6-dichloro-5-pyrimidinyl)amide
(494) (L)-2-(4'-pyridyl)-1H-benzimidazole-4-[N-(1-hydroxymethyl-2-p-nitrophenylhydroxyethyl)]amide
(495) (L)-2-(4'-pyridyl)-1H-benzimidazole-4-[N-(1-hydroxymethyl-2-p-aminophenylhydroxyethyl)]amide
(496) 2-(4'-pyridyl)-1H-benzimidazole-4-[N-(1-methyl-2-p-chlorophenylhydroxyethyl)]amide
(497) 2-(4'-pyridyl)-1H-benzimidazole-4-(N—N'-piperidinyl)amide
(498) 2-(4'-pyridyl)-1H-benzimidazole-4-(N-2-piperazinyl)amide
(499) 2-(4'-pyridyl)-1H-benzimidazole-4-(N-2'-benzimidazolyl)amide
(500) 2-(4'-pyridyl)-1H-benzimidazole-4-(N-o-hydroxyphenyl)amide
(501) 2-(4'-pyridyl)-1H-benzimidazole-4-(N-o-aminophenyl)amide
(502) 2-(4'-pyridyl)-1H-benzimidazole-4-(N-5-benzimidazolonyl)amide
(503) 2-(4'-pyridyl)-1H-benzimidazole-4-(N-4'-carbonamido-5'-imidazolyl)amide
(504) 2-(4'-pyridyl)-1H-benzimidazole-4-(N-4'-carboxyl-5'-imidazolyl)amide
(505) 2-(4'-pyridyl)-1H-benzimidazole-4-(N-2-imidazolyl)amide
(506) 2-(4'-pyridyl)-1H-benzimidazole-4-(N-4'-pyrazolyl)amide
(507) 2-(4'-pyridyl)-1H-benzimidazole-4-(N—(N'-piperazinyl))amide
(508) 2-(4'-pyridyl)-1H-benzimidazole-4-(N'-ethyl-N-piperazinyl)amide
(509) 2-(4'-pyridyl)-1H-benzimidazole-4-(N-2-pyrazinyl)amide
(510) 2-(4'-pyridyl)-1H-benzimidazole-4-(N-2-pyrimidinyl)amide
(511) 2-(4'-pyridyl)-1H-benzimidazole-4-(N-4-pyrimidinyl)amide
(512) 2-(4'-pyridyl)-1H-benzimidazole-4-(N-5-pyrimidinyl)amide
(513) 2-(4'-pyridyl)-1H-benzimidazole-4-(N-2-pyridyl)amide
(514) 2-(4'-pyridyl)-1H-benzimidazole-4-(N-3-pyridyl)amide
(515) 2-(4'-pyridyl)-1H-benzimidazole-4-(N-4-pyridyl)amide
(516) 2-(4'-pyridyl)-1H-benzimidazole-4-(N-4-methyl-5-thiazolyl)amide
(517) 2-(4'-pyridyl)-1H-benzimidazole-4-(N-5-thiazolyl)amide
(518) 2-(4'-pyridyl)-1H-benzimidazole-4-(N-2,4-dihydroxyl-5-pyrimidinyl)amide
(519) 2-(4'-pyridyl)-1H-benzimidazole-4-(N-4,6-dimethoxy-2-pyrimidinyl)amide
(520) 2-(4'-pyridyl)-1H-benzimidazole-4-(N-4-chloro-6-amino-2-pyrimidinyl)amide
(521) 2-(4'-pyridyl)-1H-benzimidazole-4-(N-4,6-dichloro-5-pyrimidinyl)amide
(522) (L)-2-(2'-imidazolyl)-1H-benzimidazole-4-[N-(1-hydroxymethyl-2-p-nitrophenylhydroxyethyl)]amide
(523) (L)-2-(2'-imidazolyl)-1H-benzimidazole-4-[N-(1-hydroxymethyl-2-p-aminophenylhydroxyethyl)]amide
(524) 2-(2'-imidazolyl)-1H-benzimidazole-4-[N-(1-methyl-2-p-chlorophenylhydroxyethyl)]amide
(525) 2-(2'-imidazolyl)-1H-benzimidazole-4-(N—N'-piperidinyl)amide (526) 2-(2'-imidazolyl)-1H-benzimidazole-4-(N-2-piperazinyl)amide
(527) 2-(2'-imidazolyl)-1H-benzimidazole-4-(N-2'-benzimidazolyl)amide
(528) 2-(2'-imidazolyl)-1H-benzimidazole-4-(N-o-hydroxyphenyl)amide
(529) 2-(2'-imidazolyl)-1H-benzimidazole-4-(N-o-aminophenyl)amide
(530) 2-(2'-imidazolyl)-1H-benzimidazole-4-(N-5-benzimidazolonyl)amide
(531) 2-(2'-imidazolyl)-1H-benzimidazole-4-(N-4'-carbonamido-5'-imidazolyl)amide
(532) 2-(2'-imidazolyl)-1H-benzimidazole-4-(N-4'-carboxyl-5'-imidazolyl)amide
(533) 2-(2'-imidazolyl)-1H-benzimidazole-4-(N-2-imidazolyl)amide
(534) 2-(2'-imidazolyl)-1H-benzimidazole-4-(N-4'-pyrazolyl)amide
(535) 2-(2'-imidazolyl)-1H-benzimidazole-4-(N—(N'-piperazinyl))amide
(536) 2-(2'-imidazolyl)-1H-benzimidazole-4-(N'-ethyl-N-piperazinyl)amide
(537) 2-(2'-imidazolyl)-1H-benzimidazole-4-(N-2-pyrazinyl)amide
(538) 2-(2'-imidazolyl)-1H-benzimidazole-4-(N-2-pyrimidinyl)amide
(539) 2-(2'-imidazolyl)-1H-benzimidazole-4-(N-4-pyrimidinyl)amide
(540) 2-(2'-imidazolyl)-1H-benzimidazole-4-(N-5-pyrimidinyl)amide
(541) 2-(2'-imidazolyl)-1H-benzimidazole-4-(N-2-pyridyl)amide
(542) 2-(2'-imidazolyl)-1H-benzimidazole-4-(N-3-pyridyl)amide
(543) 2-(2'-imidazolyl)-1H-benzimidazole-4-(N-4-pyridyl)amide
(544) 2-(2'-imidazolyl)-1H-benzimidazole-4-(N-4-methyl-5-thiazolyl)amide
(545) 2-(2'-imidazolyl)-1H-benzimidazole-4-(N-5-thiazolyl)amide
(546) 2-(2'-imidazolyl)-1H-benzimidazole-4-(N-2,4-dihydroxyl-5-pyrimidinyl)amide
(547) 2-(2'-imidazolyl)-1H-benzimidazole-4-(N-4,6-dimethoxy-2-pyrimidinyl)amide
(548) 2-(2'-imidazolyl)-1H-benzimidazole-4-(N-4-chloro-6-amino-2-pyrimidinyl)amide
(549) 2-(2'-imidazolyl)-1H-benzimidazole-4-(N-4,6-dichloro-5-pyrimidinyl)amide
(550) 2-(4-methoxypyridyl)-1H-benzimidazole-4-(N—N'-piperidinyl)amide
(551) 2-(4-methoxypyridyl)-1H-benzimidazole-4-(N-2-piperazinyl)amide
(552) 2-(4-methoxypyridyl)-1H-benzimidazole-4-(N-2'-benzimidazolyl)amide
(553) 2-(4-methoxypyridyl)-1H-benzimidazole-4-(N-5-benzimidazolonyl)amide
(554) 2-(4-methoxypyridyl)-1H-benzimidazole-4-(N-4'-carbonamido-5'-imidazolyl)amide
(555) 2-(4-methoxypyridyl)-1H-benzimidazole-4-(N-4'-carboxyl-5'-imidazolyl)amide
(556) 2-(4-methoxypyridyl)-1H-benzimidazole-4-(N-2-imidazolyl)amide
(557) 2-(4-methoxypyridyl)-1H-benzimidazole-4-(N-4'-pyrazolyl)amide
(558) 2-(4-methoxypyridyl)-1H-benzimidazole-4-(N—(N'-piperazinyl))amide
(559) 2-(4-methoxypyridyl)-1H-benzimidazole-4-(N'-ethyl-N-piperazinyl)amide
(560) 2-(4-methoxypyridyl)-1H-benzimidazole-4-(N-2-pyrazinyl)amide
(561) 2-(4-methoxypyridyl)-1H-benzimidazole-4-(N-2-pyrimidinyl)amide
(562) 2-(4-methoxypyridyl)-1H-benzimidazole-4-(N-4-pyrimidinyl)amide
(563) 2-(4-methoxypyridyl)-1H-benzimidazole-4-(N-5-pyrimidinyl)amide
(564) 2-(4-methoxypyridyl)-1H-benzimidazole-4-(N-2-pyridyl)amide
(565) 2-(4-methoxypyridyl)-1H-benzimidazole-4-(N-3-pyridyl)amide
(566) 2-(4-methoxypyridyl)-1H-benzimidazole-4-(N-4-pyridyl)amide
(567) 2-(4-methoxypyridyl)-1H-benzimidazole-4-(N-4-methyl-5-thiazolyl)amide
(568) 2-(4-methoxypyridyl)-1H-benzimidazole-4-(N-5-thiazolyl)amide
(569) 2-(4-methoxypyridyl)-1H-benzimidazole-4-(N-2,4-dihydroxyl-5-pyrimidinyl)amide
(570) 2-(4-methoxypyridyl)-1H-benzimidazole-4-(N-4,6-dimethoxy-2-pyrimidinyl)amide
(571) 2-(4-methoxypyridyl)-1H-benzimidazole-4-(N-4-chloro-6-amino-2-pyrimidinyl)amide
(572) 2-(4-methoxypyridyl)-1H-benzimidazole-4-(N-4,6-dichloro-5-pyrimidinyl)amide
(573) 2-(6-methoxypyridyl)-1H-benzimidazole-4-(N—N'-piperidinyl)amide
(574) 2-(6-methoxypyridyl)-1H-benzimidazole-4-(N-2-piperazinyl)amide
(575) 2-(6-methoxypyridyl)-1H-benzimidazole-4-(N-2'-benzimidazolyl)amide
(576) 2-(6-methoxypyridyl)-1H-benzimidazole-4-(N-5-benzimidazolonyl)amide
(577) 2-(6-methoxypyridyl)-1H-benzimidazole-4-(N-4'-carbonamido-5'-imidazolyl)amide
(578) 2-(6-methoxypyridyl)-1H-benzimidazole-4-(N-4'-carboxyl-5'-imidazolyl)amide
(579) 2-(6-methoxypyridyl)-1H-benzimidazole-4-(N-2-imidazolyl)amide
(580) 2-(6-methoxypyridyl)-1H-benzimidazole-4-(N-4'-pyrazolyl)amide
(581) 2-(6-methoxypyridyl)-1H-benzimidazole-4-(N—(N'-piperazinyl))amide
(582) 2-(6-methoxypyridyl)-1H-benzimidazole-4-(N'-ethyl-N-piperazinyl)amide
(583) 2-(6-methoxypyridyl)-1H-benzimidazole-4-(N-2-pyrazinyl)amide
(584) 2-(6-methoxypyridyl)-1H-benzimidazole-4-(N-2-pyrimidinyl)amide
(585) 2-(6-methoxypyridyl)-1H-benzimidazole-4-(N-4-pyrimidinyl)amide
(586) 2-(6-methoxypyridyl)-1H-benzimidazole-4-(N-5-pyrimidinyl)amide
(587) 2-(6-methoxypyridyl)-1H-benzimidazole-4-(N-2-pyridyl)amide
(588) 2-(6-methoxypyridyl)-1H-benzimidazole-4-(N-3-pyridyl)amide
(589) 2-(6-methoxypyridyl)-1H-benzimidazole-4-(N-4-pyridyl)amide
(590) 2-(6-methoxypyridyl)-1H-benzimidazole-4-(N-4-methyl-5-thiazolyl)amide
(591) 2-(6-methoxypyridyl)-1H-benzimidazole-4-(N-5-thiazolyl)amide (592) 2-(6-methoxypyridyl)-1H-benzimidazole-4-(N-2,4-dihydroxyl-5-pyrimidinyl)amide
(593) 2-(6-methoxypyridyl)-1H-benzimidazole-4-(N-4,6-dimethoxy-2-pyrimidinyl)amide
(594) 2-(6-methoxypyridyl)-1H-benzimidazole-4-(N-4-chloro-6-amino-2-pyrimidinyl)amide
(595) 2-(6-methoxypyridyl)-1H-benzimidazole-4-(N-4,6-dichloro-5-pyrimidinyl)amide
(596) 2-(4-dimethylaminopyridyl)-1H-benzimidazole-4-(N—N'-piperidinyl)amide
(597) 2-(4-dimethylaminopyridyl)-1H-benzimidazole-4-(N-2-piperazinyl))amide
(598) 2-(4-dimethylaminopyridyl)-1H-benzimidazole-4-(N-2'-benzimidazolyl)amide
(599) 2-(4-dimethylaminopyridyl)-1H-benzimidazole-4-(N-5-benzimidazolonyl)amide
(600) 2-(4-dimethylaminopyridyl)-1H-benzimidazole-4-(N-4'-carbonamido-5'-imidazolyl)amide
(601) 2-(4-dimethylaminopyridyl)-1H-benzimidazole-4-(N-4'-carboxyl-5'-imidazolyl)amide
(602) 2-(4-dimethylaminopyridyl)-1H-benzimidazole-4-(N-2-imidazolyl)amide
(603) 2-(4-dimethylaminopyridyl)-1H-benzimidazole-4-(N-4'-pyrazolyl)amide
(604) 2-(4-dimethylaminopyridyl)-1H-benzimidazole-4-(N—(N'-piperazinyl))amide
(605) 2-(4-dimethylaminopyridyl)-1H-benzimidazole-4-(N'-ethyl-N-piperazinyl)amide
(606) 2-(4-dimethylaminopyridyl)-1H-benzimidazole-4-(N-2-pyrazinyl)amide
(607) 2-(4-dimethylaminopyridyl)-1H-benzimidazole-4-(N-2-pyrimidinyl)amide
(608) 2-(4-dimethylaminopyridyl)-1H-benzimidazole-4-(N-4-pyrimidinyl)amide
(609) 2-(4-dimethylaminopyridyl)-1H-benzimidazole-4-(N-5-pyrimidinyl)amide
(610) 2-(4-dimethylaminopyridyl)-1H-benzimidazole-4-(N-2-pyridyl)amide
(611) 2-(4-dimethylaminopyridyl)-1H-benzimidazole-4-(N-3-pyridyl)amide
(612) 2-(4-dimethylaminopyridyl)-1H-benzimidazole-4-(N-4-pyridyl)amide
(613) 2-(4-dimethylaminopyridyl)-1H-benzimidazole-4-(N-4-methyl-5-thiazolyl)amide
(614) 2-(4-dimethylaminopyridyl)-1H-benzimidazole-4-(N-5-thiazolyl)amide
(615) 2-(4-dimethylaminopyridyl)-1H-benzimidazole-4-(N-2,4-dihydroxyl-5-pyrimidinyl)amide
(616) 2-(4-dimethylaminopyridyl)-1H-benzimidazole-4-(N-4,6-dimethoxy-2-pyrimidinyl)amide
(617) 2-(4-dimethylaminopyridyl)-1H-benzimidazole-4-(N-4-chloro-6-amino-2-pyrimidinyl)amide
(618) 2-(4-dimethylaminopyridyl)-1H-benzimidazole-4-(N-4,6-dichloro-5-pyrimidinyl)amide
(619) 2-(3-pyridazinyl)-1H-benzimidazole-4-(N—N'-piperidinyl)amide
(620) 2-(3-pyridazinyl)-1H-benzimidazole-4-(N-2-piperazinyl))amide
(621) 2-(3-pyridazinyl)-1H-benzimidazole-4-(N-2'-benzimidazolyl)amide
(622) 2-(3-pyridazinyl)-1H-benzimidazole-4-(N-5-benzimidazolonyl)amide
(623) 2-(3-pyridazinyl)-1H-benzimidazole-4-(N-4'-carbonamido-5'-imidazolyl)amide
(624) 2-(3-pyridazinyl)-1H-benzimidazole-4-(N-4'-carboxyl-5'-imidazolyl)amide
(625) 2-(3-pyridazinyl)-1H-benzimidazole-4-(N-2-imidazolyl)amide
(626) 2-(3-pyridazinyl)-1H-benzimidazole-4-(N-4'-pyrazolyl)amide
(627) 2-(3-pyridazinyl)-1H-benzimidazole-4-(N—(N'-piperazinyl))amide
(628) 2-(3-pyridazinyl)-1H-benzimidazole-4-(N'-ethyl-N-piperazinyl)amide
(629) 2-(3-pyridazinyl)-1H-benzimidazole-4-(N-2-pyrazinyl)amide
(630) 2-(3-pyridazinyl)-1H-benzimidazole-4-(N-2-pyrimidinyl)amide
(631) 2-(3-pyridazinyl)-1H-benzimidazole-4-(N-4-pyrimidinyl)amide
(632) 2-(3-pyridazinyl)-1H-benzimidazole-4-(N-5-pyrimidinyl)amide
(633) 2-(3-pyridazinyl)-1H-benzimidazole-4-(N-2-pyridyl)amide
(634) 2-(3-pyridazinyl)-1H-benzimidazole-4-(N-3-pyridyl)amide
(635) 2-(3-pyridazinyl)-1H-benzimidazole-4-(N-4-pyridyl)amide
(636) 2-(3-pyridazinyl)-1H-benzimidazole-4-(N-4-methyl-5-thiazolyl)amide
(637) 2-(3-pyridazinyl)-1H-benzimidazole-4-(N-5-thiazolyl)amide
(638) 2-(3-pyridazinyl)-1H-benzimidazole-4-(N-2,4-dihydroxyl-5-pyrimidinyl)amide
(639) 2-(3-pyridazinyl)-1H-benzimidazole-4-(N-4,6-dimethoxy-2-pyrimidinyl)amide
(640) 2-(3-pyridazinyl)-1H-benzimidazole-4-(N-4-chloro-6-amino-2-pyrimidinyl)amide
(641) 2-(3-pyridazinyl)-1H-benzimidazole-4-(N-4,6-dichloro-5-pyrimidinyl)amide
(642) 2-(2-N-methyl-4-N-methylpiperazinyl)-1H-benzimidazole-4-(N—N'-piperidinyl)amide
(643) 2-(2-N-methyl-4-N-methylpiperazinyl)-1H-benzimidazole-4-(N-2-piperazinyl))amide
(644) 2-(2-N-methyl-4-N-methylpiperazinyl)-1H-benzimidazole-4-(N-2'-benzimidazolyl)amide
(645) 2-(2-N-methyl-4-N-methylpiperazinyl)-1H-benzimidazole-4-(N-5-benzimidazolonyl)amide
(646) 2-(2-N-methyl-4-N-methylpiperazinyl)-1H-benzimidazole-4-(N-4'-carbonamido-5'-imidazolyl)amide
(647) 2-(2-N-methyl-4-N-methylpiperazinyl)-1H-benzimidazole-4-(N-4'-carboxyl-5'-imidazolyl)amide
(648) 2-(2-N-methyl-4-N-methylpiperazinyl)-1H-benzimidazole-4-(N-2-imidazolyl)amide
(649) 2-(2-N-methyl-4-N-methylpiperazinyl)-1H-benzimidazole-4-(N-4'-pyrazolyl)amide
(650) 2-(2-N-methyl-4-N-methylpiperazinyl)-1H-benzimidazole-4-(N—(N'-piperazinyl))amide
(651) 2-(2-N-methyl-4-N-methylpiperazinyl)-1H-benzimidazole-4-(N'-ethyl-N-piperazinyl)amide
(652) 2-(2-N-methyl-4-N-methylpiperazinyl)-1H-benzimidazole-4-(N-2-pyrazinyl)amide
(653) 2-(2-N-methyl-4-N-methylpiperazinyl)-1H-benzimidazole-4-(N-2-pyrimidinyl)amide
(654) 2-(2-N-methyl-4-N-methylpiperazinyl)-1H-benzimidazole-4-(N-4-pyrimidinyl)amide
(655) 2-(2-N-methyl-4-N-methylpiperazinyl)-1H-benzimidazole-4-(N-5-pyrimidinyl)amide
(656) 2-(2-N-methyl-4-N-methylpiperazinyl)-1H-benzimidazole-4-(N-2-pyridyl)amide
(657) 2-(2-N-methyl-4-N-methylpiperazinyl)-1H-benzimidazole-4-(N-3-pyridyl)amide (658) 2-(2-N-methyl-4-N-methylpiperazinyl)-1H-benzimidazole-4-(N-4-pyridyl)amide
(659) 2-(2-N-methyl-4-N-methylpiperazinyl)-1H-benzimidazole-4-(N-4-methyl-5-thiazolyl)amide
(660) 2-(2-N-methyl-4-N-methylpiperazinyl)-1H-benzimidazole-4-(N-5-thiazolyl)amide
(661) 2-(2-N-methyl-4-N-methylpiperazinyl)-1H-benzimidazole-4-(N-2,4-dihydroxyl-5-pyrimidinyl)amide
(662) 2-(2-N-methyl-4-N-methylpiperazinyl)-1H-benzimidazole-4-(N-4,6-dimethoxy-2-pyrimidinyl)amide
(663) 2-(2-N-methyl-4-N-methylpiperazinyl)-1H-benzimidazole-4-(N-4-chloro-6-amino-2-pyrimidinyl)amide
(664) 2-(2-N-methyl-4-N-methylpiperazinyl)-1H-benzimidazole-4-(N-4,6-dichloro-5-pyrimidinyl)amide
(665) 2-(2-pyrazinyl)-1H-benzimidazole-4-(N—N'-piperidinyl)amide
(666) 2-(2-pyrazinyl)-1H-benzimidazole-4-(N-2-piperazinyl))amide
(667) 2-(2-pyrazinyl)-1H-benzimidazole-4-(N-2'-benzimidazolyl)amide
(668) 2-(2-pyrazinyl)-1H-benzimidazole-4-(N-5-benzimidazolonyl)amide
(669) 2-(2-pyrazinyl)-1H-benzimidazole-4-(N-4'-carbonamido-5'-imidazolyl)amide
(670) 2-(2-pyrazinyl)-1H-benzimidazole-4-(N-4'-carboxyl-5'-imidazolyl)amide
(671) 2-(2-pyrazinyl)-1H-benzimidazole-4-(N-2-imidazolyl)amide
(672) 2-(2-pyrazinyl)-1H-benzimidazole-4-(N-4'-pyrazolyl)amide
(673) 2-(2-pyrazinyl)-1H-benzimidazole-4-(N—(N'-piperazinyl))amide
(674) 2-(2-pyrazinyl)-1H-benzimidazole-4-(N'-ethyl-N-piperazinyl)amide
(675) 2-(2-pyrazinyl)-1H-benzimidazole-4-(N-2-pyrazinyl)amide
(676) 2-(2-pyrazinyl)-1H-benzimidazole-4-(N-2-pyrimidinyl)amide
(677) 2-(2-pyrazinyl)-1H-benzimidazole-4-(N-4-pyrimidinyl)amide
(678) 2-(2-pyrazinyl)-1H-benzimidazole-4-(N-5-pyrimidinyl)amide
(679) 2-(2-pyrazinyl)-1H-benzimidazole-4-(N-2-pyridyl)amide
(680) 2-(2-pyrazinyl)-1H-benzimidazole-4-(N-3-pyridyl)amide
(681) 2-(2-pyrazinyl)-1H-benzimidazole-4-(N-4-pyridyl)amide
(682) 2-(2-pyrazinyl)-1H-benzimidazole-4-(N-4-methyl-5-thiazolyl)amide
(683) 2-(2-pyrazinyl)-1H-benzimidazole-4-(N-5-thiazolyl)amide
(684) 2-(2-pyrazinyl)-1H-benzimidazole-4-(N-2,4-dihydroxyl-5-pyrimidinyl)amide
(685) 2-(2-pyrazinyl)-1H-benzimidazole-4-(N-4,6-dimethoxy-2-pyrimidinyl)amide
(686) 2-(2-pyrazinyl)-1H-benzimidazole-4-(N-4-chloro-6-amino-2-pyrimidinyl)amide
(687) 2-(2-pyrazinyl)-1H-benzimidazole-4-(N-4,6-dichloro-5-pyrimidinyl)amide
(688) 2-(2-piperazinyl)-1H-benzimidazole-4-(N—N'-piperidinyl)amide
(689) 2-(2-piperazinyl)-1H-benzimidazole-4-(N-2-piperazinyl))amide
(690) 2-(2-piperazinyl)-1H-benzimidazole-4-(N-2'-benzimidazolyl)amide
(691) 2-(2-piperazinyl)-1H-benzimidazole-4-(N-5-benzimidazolonyl)amide
(692) 2-(2-piperazinyl)-1H-benzimidazole-4-(N-4'-carbonamido-5'-imidazolyl)amide
(693) 2-(2-piperazinyl)-1H-benzimidazole-4-(N-4'-carboxyl-5'-imidazolyl)amide
(694) 2-(2-piperazinyl)-1H-benzimidazole-4-(N-2-imidazolyl)amide
(695) 2-(2-piperazinyl)-1H-benzimidazole-4-(N-4'-pyrazolyl)amide
(696) 2-(2-piperazinyl)-1H-benzimidazole-4-(N—(N'-piperazinyl))amide
(697) 2-(2-piperazinyl)-1H-benzimidazole-4-(N'-ethyl-N-piperazinyl)amide
(698) 2-(2-piperazinyl)-1H-benzimidazole-4-(N-2-pyrazinyl)amide
(699) 2-(2-piperazinyl)-1H-benzimidazole-4-(N-2-pyrimidinyl)amide
(700) 2-(2-piperazinyl)-1H-benzimidazole-4-(N-4-pyrimidinyl)amide
(701) 2-(2-piperazinyl)-1H-benzimidazole-4-(N-5-pyrimidinyl)amide
(702) 2-(2-piperazinyl)-1H-benzimidazole-4-(N-2-pyridyl)amide
(703) 2-(2-piperazinyl)-1H-benzimidazole-4-(N-3-pyridyl)amide
(704) 2-(2-piperazinyl)-1H-benzimidazole-4-(N-4-pyridyl)amide
(705) 2-(2-piperazinyl)-1H-benzimidazole-4-(N-4-methyl-5-thiazolyl)amide
(706) 2-(2-piperazinyl)-1H-benzimidazole-4-(N-5-thiazolyl)amide
(707) 2-(2-piperazinyl)-1H-benzimidazole-4-(N-2,4-dihydroxyl-5-pyrimidinyl)amide
(708) 2-(2-piperazinyl)-1H-benzimidazole-4-(N-4,6-dimethoxy-2-pyrimidinyl)amide
(709) 2-(2-piperazinyl)-1H-benzimidazole-4-(N-4-chloro-6-amino-2-pyrimidinyl)amide
(710) 2-(2-piperazinyl)-1H-benzimidazole-4-(N-4,6-dichloro-5-pyrimidinyl)amide
(711) 2-(4-methyl-5-aminothiazolyl)-1H-benzimidazole-4-(N—N'-piperidinyl)amide
(712) 2-(4-methyl-5-aminothiazolyl)-1H-benzimidazole-4-(N-2-piperazinyl))amide
(713) 2-(4-methyl-5-aminothiazolyl)-1H-benzimidazole-4-(N-2'-benzimidazolyl)amide
(714) 2-(4-methyl-5-aminothiazolyl)-1H-benzimidazole-4-(N-5-benzimidazolonyl)amide
(715) 2-(4-methyl-5-aminothiazolyl)-1H-benzimidazole-4-(N-4'-carbonamido-5'-imidazolyl)amide
(716) 2-(4-methyl-5-aminothiazolyl)-1H-benzimidazole-4-(N-4'-carboxyl-5'-imidazolyl)amide
(717) 2-(4-methyl-5-aminothiazolyl)-1H-benzimidazole-4-(N-2-imidazolyl)amide
(718) 2-(4-methyl-5-aminothiazolyl)-1H-benzimidazole-4-(N-4'-pyrazolyl)amide
(719) 2-(4-methyl-5-aminothiazolyl)-1H-benzimidazole-4-(N—(N'-piperazinyl))amide
(720) 2-(4-methyl-5-aminothiazolyl)-1H-benzimidazole-4-(N'-ethyl-N-piperazinyl)amide
(721) 2-(4-methyl-5-aminothiazolyl)-1H-benzimidazole-4-(N-2-pyrazinyl)amide
(722) 2-(4-methyl-5-aminothiazolyl)-1H-benzimidazole-4-(N-2-pyrimidinyl)amide
(723) 2-(4-methyl-5-aminothiazolyl)-1H-benzimidazole-4-(N-4-pyrimidinyl)amide (724) 2-(4-methyl-5-aminothiazolyl)-1H-benzimidazole-4-(N-5-pyrimidinyl)amide
(725) 2-(4-methyl-5-aminothiazolyl)-1H-benzimidazole-4-(N-2-pyridyl)amide
(726) 2-(4-methyl-5-aminothiazolyl)-1H-benzimidazole-4-(N-3-pyridyl)amide
(727) 2-(4-methyl-5-aminothiazolyl)-1H-benzimidazole-4-(N-4-pyridyl)amide
(728) 2-(4-methyl-5-aminothiazolyl)-1H-benzimidazole-4-(N-4-methyl-5-thiazolyl)amide
(729) 2-(4-methyl-5-aminothiazolyl)-1H-benzimidazole-4-(N-5-thiazolyl)amide
(730) 2-(4-methyl-5-aminothiazolyl)-1H-benzimidazole-4-(N-2,4-dihydroxyl-5-pyrimidinyl)amide
(731) 2-(4-methyl-5-aminothiazolyl)-1H-benzimidazole-4-(N-4,6-dimethoxy-2-pyrimidinyl)amide
(732) 2-(4-methyl-5-aminothiazolyl)-1H-benzimidazole-4-(N-4-chloro-6-amino-2-pyrimidinyl)amide
(733) 2-(4-methyl-5-aminothiazolyl)-1H-benzimidazole-4-(N-4,6-dichloro-5-pyrimidinyl)amide
(734) 2-(2-thiazolyl)-1H-benzimidazole-4-(N—N'-piperidinyl)amide
(735) 2-(2-thiazolyl)-1H-benzimidazole-4-(N-2-piperazinyl))amide
(736) 2-(2-thiazolyl)-1H-benzimidazole-4-(N-2'-benzimidazolyl)amide
(737) 2-(2-thiazolyl)-1H-benzimidazole-4-(N-5-benzimidazolonyl)amide
(738) 2-(2-thiazolyl)-1H-benzimidazole-4-(N-4'-carbonamido-5'-imidazolyl)amide
(739) 2-(2-thiazolyl)-1H-benzimidazole-4-(N-4'-carboxyl-5'-imidazolyl)amide
(740) 2-(2-thiazolyl)-1H-benzimidazole-4-(N-2-imidazolyl)amide
(741) 2-(2-thiazolyl)-1H-benzimidazole-4-(N-4'-pyrazolyl)amide
(742) 2-(2-thiazolyl)-1H-benzimidazole-4-(N—(N'-piperazinyl))amide
(743) 2-(2-thiazolyl)-1H-benzimidazole-4-(N'-ethyl-N-piperazinyl)amide
(744) 2-(2-thiazolyl)-1H-benzimidazole-4-(N-2-pyrazinyl)amide
(745) 2-(2-thiazolyl)-1H-benzimidazole-4-(N-2-pyrimidinyl)amide
(746) 2-(2-thiazolyl)-1H-benzimidazole-4-(N-4-pyrimidinyl)amide
(747) 2-(2-thiazolyl)-1H-benzimidazole-4-(N-5-pyrimidinyl)amide
(748) 2-(2-thiazolyl)-1H-benzimidazole-4-(N-2-pyridyl)amide
(749) 2-(2-thiazolyl)-1H-benzimidazole-4-(N-3-pyridyl)amide
(750) 2-(2-thiazolyl)-1H-benzimidazole-4-(N-4-pyridyl)amide
(751) 2-(2-thiazolyl)-1H-benzimidazole-4-(N-4-methyl-5-thiazolyl)amide
(752) 2-(2-thiazolyl)-1H-benzimidazole-4-(N-5-thiazolyl)amide
(753) 2-(2-thiazolyl)-1H-benzimidazole-4-(N-2,4-dihydroxyl-5-pyrimidinyl)amide
(754) 2-(2-thiazolyl)-1H-benzimidazole-4-(N-4,6-dimethoxy-2-pyrimidinyl)amide
(755) 2-(2-thiazolyl)-1H-benzimidazole-4-(N-4-chloro-6-amino-2-pyrimidinyl)amide
(756) 2-(2-thiazolyl)-1H-benzimidazole-4-(N-4,6-dichloro-5-pyrimidinyl)amide
(757) 2-(5-thiazolyl)-1H-benzimidazole-4-(N—N'-piperidinyl)amide
(758) 2-(5-thiazolyl)-1H-benzimidazole-4-(N-2-piperazinyl))amide
(759) 2-(5-thiazolyl)-1H-benzimidazole-4-(N-2'-benzimidazolyl)amide
(760) 2-(5-thiazolyl)-1H-benzimidazole-4-(N-5-benzimidazolonyl)amide
(761) 2-(5-thiazolyl)-1H-benzimidazole-4-(N-4'-carbonamido-5'-imidazolyl)amide
(762) 2-(5-thiazolyl)-1H-benzimidazole-4-(N-4'-carboxyl-5'-imidazolyl)amide
(763) 2-(5-thiazolyl)-1H-benzimidazole-4-(N-2-imidazolyl)amide
(764) 2-(5-thiazolyl)-1H-benzimidazole-4-(N-4'-pyrazolyl)amide
(765) 2-(5-thiazolyl)-1H-benzimidazole-4-(N—(N'-piperazinyl))amide
(766) 2-(5-thiazolyl)-1H-benzimidazole-4-(N'-ethyl-N-piperazinyl)amide
(767) 2-(5-thiazolyl)-1H-benzimidazole-4-(N-2-pyrazinyl)amide
(768) 2-(5-thiazolyl)-1H-benzimidazole-4-(N-2-pyrimidinyl)amide
(769) 2-(5-thiazolyl)-1H-benzimidazole-4-(N-4-pyrimidinyl)amide
(770) 2-(5-thiazolyl)-1H-benzimidazole-4-(N-5-pyrimidinyl)amide
(771) 2-(5-thiazolyl)-1H-benzimidazole-4-(N-2-pyridyl)amide
(772) 2-(5-thiazolyl)-1H-benzimidazole-4-(N-3-pyridyl)amide
(773) 2-(2-thiazolyl)-1H-benzimidazole-4-(N-4-pyridyl)amide
(774) 2-(5-thiazolyl)-1H-benzimidazole-4-(N-4-methyl-5-thiazolyl)amide
(775) 2-(5-thiazolyl)-1H-benzimidazole-4-(N-5-thiazolyl)amide
(776) 2-(5-thiazolyl)-1H-benzimidazole-4-(N-2,4-dihydroxyl-5-pyrimidinyl)amide
(777) 2-(5-thiazolyl)-1H-benzimidazole-4-(N-4,6-dimethoxy-2-pyrimidinyl)amide
(778) 2-(5-thiazolyl)-1H-benzimidazole-4-(N-4-chloro-6-amino-2-pyrimidinyl)amide
(779) 2-(5-thiazolyl)-1H-benzimidazole-4-(N-4,6-dichloro-5-pyrimidinyl)amide
(780) 2-(2-pyrimidinyl)-1H-benzimidazole-4-(N—N'-piperidinyl)amide
(781) 2-(2-pyrimidinyl)-1H-benzimidazole-4-(N-2-piperazinyl))amide
(782) 2-(2-pyrimidinyl)-1H-benzimidazole-4-(N-2'-benzimidazolyl)amide
(783) 2-(2-pyrimidinyl)-1H-benzimidazole-4-(N-5-benzimidazolonyl)amide
(784) 2-(2-pyrimidinyl)-1H-benzimidazole-4-(N-4'-carbonamido-5'-imidazolyl)amide
(785) 2-(2-pyrimidinyl)-1H-benzimidazole-4-(N-4'-carboxyl-5'-imidazolyl)amide
(786) 2-(2-pyrimidinyl)-1H-benzimidazole-4-(N-2-imidazolyl)amide
(787) 2-(2-pyrimidinyl)-1H-benzimidazole-4-(N-4'-pyrazolyl)amide
(788) 2-(2-pyrimidinyl)-1H-benzimidazole-4-(N—(N'-piperazinyl))amide
(789) 2-(2-pyrimidinyl)-1H-benzimidazole-4-(N'-ethyl-N-piperazinyl)amide (790) 2-(2-pyrimidinyl)-1H-benzimidazole-4-(N-2-pyrazinyl)amide
(791) 2-(2-pyrimidinyl)-1H-benzimidazole-4-(N-2-pyrimidinyl)amide
(792) 2-(2-pyrimidinyl)-1H-benzimidazole-4-(N-4-pyrimidinyl)amide
(793) 2-(2-pyrimidinyl)-1H-benzimidazole-4-(N-5-pyrimidinyl)amide
(794) 2-(2-pyrimidinyl)-1H-benzimidazole-4-(N-2-pyridyl)amide
(795) 2-(2-pyrimidinyl)-1H-benzimidazole-4-(N-3-pyridyl)amide
(796) 2-(2-pyrimidinyl)-1H-benzimidazole-4-(N-4-pyridyl)amide
(797) 2-(2-pyrimidinyl)-1H-benzimidazole-4-(N-4-methyl-5-thiazolyl)amide
(798) 2-(2-pyrimidinyl)-1H-benzimidazole-4-(N-5-thiazolyl)amide
(799) 2-(2-pyrimidinyl)-1H-benzimidazole-4-(N-2,4-dihydroxyl-5-pyrimidinyl)amide
(800) 2-(2-pyrimidinyl)-1H-benzimidazole-4-(N-4,6-dimethoxy-2-pyrimidinyl)amide
(801) 2-(2-pyrimidinyl)-1H-benzimidazole-4-(N-4-chloro-6-amino-2-pyrimidinyl)amide
(802) 2-(2-pyrimidinyl)-1H-benzimidazole-4-(N-4,6-dichloro-5-pyrimidinyl)amide
(803) 2-(2-phenyl-5-pyrimidinyl)-1H-benzimidazole-4-(N—N'-piperidinyl)amide
(804) 2-(2-phenyl-5-pyrimidinyl)-1H-benzimidazole-4-(N-2-piperazinyl))amide
(805) 2-(2-phenyl-5-pyrimidinyl)-1H-benzimidazole-4-(N-2'-benzimidazolyl)amide
(806) 2-(2-phenyl-5-pyrimidinyl)-1H-benzimidazole-4-(N-5-benzimidazolonyl)amide
(807) 2-(2-phenyl-5-pyrimidinyl)-1H-benzimidazole-4-(N-4'-carbonamido-5'-imidazolyl)amide
(808) 2-(2-phenyl-5-pyrimidinyl)-1H-benzimidazole-4-(N-4'-carboxyl-5'-imidazolyl)amide
(809) 242-phenyl-5-pyrimidinyl)-1H-benzimidazole-4-(N-2-imidazolyl)amide
(810) 2-(2-phenyl-5-pyrimidinyl)-1H-benzimidazole-4-(N-4'-pyrazolyl)amide
(811) 2-(2-phenyl-5-pyrimidinyl)-1H-benzimidazole-4-(N—(N'-piperazinyl))amide
(812) 2-(2-phenyl-5-pyrimidinyl)-1H-benzimidazole-4-(N'-ethyl-N-piperazinyl)amide
(813) 2-(2-phenyl-5-pyrimidinyl)-1H-benzimidazole-4-(N-2-pyrazinyl)amide
(814) 2-(2-phenyl-5-pyrimidinyl)-1H-benzimidazole-4-(N-2-pyrimidinyl)amide
(815) 2-(2-phenyl-5-pyrimidinyl)-1H-benzimidazole-4-(N-4-pyrimidinyl)amide
(816) 2-(2-phenyl-5-pyrimidinyl)-1H-benzimidazole-4-(N-5-pyrimidinyl)amide
(817) 2-(2-phenyl-5-pyrimidinyl)-1H-benzimidazole-4-(N-2-pyridyl)amide
(818) 2-(2-phenyl-5-pyrimidinyl)-1H-benzimidazole-4-(N-3-pyridyl)amide
(819) 2-(2-phenyl-5-pyrimidinyl)-1H-benzimidazole-4-(N-4-pyridyl)amide
(820) 2-(2-phenyl-5-pyrimidinyl)-1H-benzimidazole-4-(N-4-methyl-5-thiazolyl)amide
(821) 2-(2-phenyl-5-pyrimidinyl)-1H-benzimidazole-4-(N-5-thiazolyl)amide
(822) 2-(2-phenyl-5-pyrimidinyl)-1H-benzimidazole-4-(N-2,4-dihydroxyl-5-pyrimidinyl)amide
(823) 2-(2-phenyl-5-pyrimidinyl)-1H-benzimidazole-4-(N-4,6-dimethoxy-2-pyrimidinyl)amide
(824) 2-(2-phenyl-5-pyrimidinyl)-1H-benzimidazole-4-(N-4-chloro-6-amino-2-pyrimidinyl)amide
(825) 2-(2-phenyl-5-pyrimidinyl)-1H-benzimidazole-4-(N-4,6-dichloro-5-pyrimidinyl)amide
(826) 2-(4-amino-6-chloro-5-pyrimidinyl)-1H-benzimidazole-4-(N—N'-piperidinyl)amide
(827) 2-(4-amino-6-chloro-5-pyrimidinyl)-1H-benzimidazole-4-(N-2-piperazinyl))amide
(828) 2-(4-amino-6-chloro-5-pyrimidinyl)-1H-benzimidazole-4-(N-2'-benzimidazolyl)amide
(829) 2-(4-amino-6-chloro-5-pyrimidinyl)-1H-benzimidazole-4-(N-5-benzimidazolonyl)amide
(830) 2-(4-amino-6-chloro-5-pyrimidinyl)-1H-benzimidazole-4-(N-4'-carbonamido-5'-imidazolyl)amide
(831) 2-(4-amino-6-chloro-5-pyrimidinyl)-1H-benzimidazole-4-(N-4'-carboxyl-5'-imidazolyl)amide
(832) 2-(4-amino-6-chloro-5-pyrimidinyl)-1H-benzimidazole-4-(N-2-imidazolyl)amide
(833) 2-(4-amino-6-chloro-5-pyrimidinyl)-1H-benzimidazole-4-(N-4'-pyrazolyl)amide
(834) 2-(4-amino-6-chloro-5-pyrimidinyl)-1H-benzimidazole-4-(N—(N'-piperazinyl))amide
(835) 2-(4-amino-6-chloro-5-pyrimidinyl)-1H-benzimidazole-4-(N'-ethyl-N-piperazinyl)amide
(836) 2-(4-amino-6-chloro-5-pyrimidinyl)-1H-benzimidazole-4-(N-2-pyrazinyl)amide
(837) 2-(4-amino-6-chloro-5-pyrimidinyl)-1H-benzimidazole-4-(N-2-pyrimidinyl)amide
(838) 2-(4-amino-6-chloro-5-pyrimidinyl)-1H-benzimidazole-4-(N-4-pyrimidinyl)amide
(839) 2-(4-amino-6-chloro-5-pyrimidinyl)-1H-benzimidazole-4-(N-5-pyrimidinyl)amide
(840) 2-(4-amino-6-chloro-5-pyrimidinyl)-1H-benzimidazole-4-(N-2-pyridyl)amide
(841) 2-(4-amino-6-chloro-5-pyrimidinyl)-1H-benzimidazole-4-(N-3-pyridyl)amide
(842) 2-(4-amino-6-chloro-5-pyrimidinyl)-1H-benzimidazole-4-(N-4-pyridyl)amide
(843) 2-(4-amino-6-chloro-5-pyrimidinyl)-1H-benzimidazole-4-(N-4-methyl-5-thiazolyl)amide
(844) 2-(4-amino-6-chloro-5-pyrimidinyl)-1H-benzimidazole-4-(N-5-thiazolyl)amide
(845) 2-(4-amino-6-chloro-5-pyrimidinyl)-1H-benzimidazole-4-(N-2,4-dihydroxyl-5-pyrimidinyl)amide
(846) 2-(4-amino-6-chloro-5-pyrimidinyl)-1H-benzimidazole-4-(N-4,6-dimethoxy-2-pyrimidinyl)amide
(847) 2-(4-amino-6-chloro-5-pyrimidinyl)-1H-benzimidazole-4-(N-4-chloro-6-amino-2-pyrimidinyl)amide
(848) 2-(4-amino-6-chloro-5-pyrimidinyl)-1H-benzimidazole-4-(N-4,6-dichloro-5-pyrimidinyl)amide
(849) 2-(2-pyrrolyl)-1H-benzimidazole-4-(N—N'-piperidinyl)amide
(850) 2-(2-pyrrolyl)-1H-benzimidazole-4-(N-2-piperazinyl))amide
(851) 2-(2-pyrrolyl)-1H-benzimidazole-4-(N-2'-benzimidazolyl)amide
(852) 2-(2-pyrrolyl)-1H-benzimidazole-4-(N-5-benzimidazolonyl)amide
(853) 2-(2-pyrrolyl)-1H-benzimidazole-4-(N-4'-carbonamido-5'-imidazolyl)amide
(854) 2-(2-pyrrolyl)-1H-benzimidazole-4-(N-4'-carboxyl-5'-imidazolyl)amide
(855) 2-(2-pyrrolyl)-1H-benzimidazole-4-(N-2-imidazolyl)amide (856) 2-(2-pyrrolyl)-1H-benzimidazole-4-(N-4'-pyrazolyl)amide
(857) 2-(2-pyrrolyl)-1H-benzimidazole-4-(N—(N'-piperazinyl))amide
(858) 2-(2-pyrrolyl)-1H-benzimidazole-4-(N'-ethyl-N-piperazinyl)amide
(859) 2-(2-pyrrolyl)-1H-benzimidazole-4-(N-2-pyrazinyl)amide
(860) 2-(2-pyrrolyl)-1H-benzimidazole-4-(N-2-pyrimidinyl)amide
(861) 2-(2-pyrrolyl)-1H-benzimidazole-4-(N-4-pyrimidinyl)amide
(862) 2-(2-pyrrolyl)-1H-benzimidazole-4-(N-5-pyrimidinyl)amide
(863) 2-(2-pyrrolyl)-1H-benzimidazole-4-(N-2-pyridyl)amide
(864) 2-(2-pyrrolyl)-1H-benzimidazole-4-(N-3-pyridyl)amide
(865) 2-(2-pyrrolyl)-1H-benzimidazole-4-(N-4-pyridyl)amide
(866) 2-(2-pyrrolyl)-1H-benzimidazole-4-(N-4-methyl-5-thiazolyl)amide
(867) 2-(2-pyrrolyl)-1H-benzimidazole-4-(N-5-thiazolyl)amide
(868) 2-(2-pyrrolyl)-1H-benzimidazole-4-(N-2,4-dihydroxyl-5-pyrimidinyl)amide
(869) 2-(2-pyrrolyl)-1H-benzimidazole-4-(N-4,6-dimethoxy-2-pyrimidinyl)amide
(870) 2-(2-pyrrolyl)-1H-benzimidazole-4-(N-4-chloro-6-amino-2-pyrimidinyl)amide
(871) 2-(2-pyrrolyl)-1H-benzimidazole-4-(N-4,6-dichloro-5-pyrimidinyl)amide
(872) 2-(N-methyl-2-pyrrolyl)-1H-benzimidazole-4-(N—N'-piperidinyl)amide
(873) 2-(N-methyl-2-pyrrolyl)-1H-benzimidazole-4-(N-2-piperazinyl))amide
(874) 2-(N-methyl-2-pyrrolyl)-1H-benzimidazole-4-(N-2'-benzimidazolyl)amide
(875) 2-(N-methyl-2-pyrrolyl)-1H-benzimidazole-4-(N-5-benzimidazolonyl)amide
(876) 2-(N-methyl-2-pyrrolyl)-1H-benzimidazole-4-(N-4'-carbonamido-5'-imidazolyl)amide
(877) 2-(N-methyl-2-pyrrolyl)-1H-benzimidazole-4-(N-4'-carboxyl-5'-imidazolyl)amide
(878) 2-(N-methyl-2-pyrrolyl)-1H-benzimidazole-4-(N-2-imidazolyl)amide
(879) 2-(N-methyl-2-pyrrolyl)-1H-benzimidazole-4-(N-4'-pyrazolyl)amide
(880) 2-(N-methyl-2-pyrrolyl)-1H-benzimidazole-4-(N—(N'-piperazinyl))amide
(881) 2-(N-methyl-2-pyrrolyl)-1H-benzimidazole-4-(N'-ethyl-N-piperazinyl)amide
(882) 2-(N-methyl-2-pyrrolyl)-1H-benzimidazole-4-(N-2-pyrazinyl)amide
(883) 2-(N-methyl-2-pyrrolyl)-1H-benzimidazole-4-(N-2-pyrimidinyl)amide
(884) 2-(N-methyl-2-pyrrolyl)-1H-benzimidazole-4-(N-4-pyrimidinyl)amide
(885) 2-(N-methyl-2-pyrrolyl)-1H-benzimidazole-4-(N-5-pyrimidinyl)amide
(886) 2-(N-methyl-2-pyrrolyl)-1H-benzimidazole-4-(N-2-pyridyl)amide
(887) 2-(N-methyl-2-pyrrolyl)-1H-benzimidazole-4-(N-3-pyridyl)amide
(888) 2-(N-methyl-2-pyrrolyl)-1H-benzimidazole-4-(N-4-pyridyl)amide
(889) 2-(N-methyl-2-pyrrolyl)-1H-benzimidazole-4-(N-4-methyl-5-thiazolyl)amide
(890) 2-(N-methyl-2-pyrrolyl)-1H-benzimidazole-4-(N-5-thiazolyl)amide
(891) 2-(N-methyl-2-pyrrolyl)-1H-benzimidazole-4-(N-2,4-dihydroxyl-5-pyrimidinyl)amide
(892) 2-(N-methyl-2-pyrrolyl)-1H-benzimidazole-4-(N-4,6-dimethoxy-2-pyrimidinyl)amide
(893) 2-(N-methyl-2-pyrrolyl)-1H-benzimidazole-4-(N-4-chloro-6-amino-2-pyrimidinyl)amide
(894) 2-(N-methyl-2-pyrrolyl)-1H-benzimidazole-4-(N-4,6-dichloro-5-pyrimidinyl)amide
(895) 2-(3,5-dimethyl-2-pyrrolyl)-1H-benzimidazole-4-(N—N'-piperidinyl)amide
(896) 2-(3,5-dimethyl-2-pyrrolyl)-1H-benzimidazole-4-(N-2-piperazinyl))amide
(897) 2-(3,5-dimethyl-2-pyrrolyl)-1H-benzimidazole-4-(N-2'-benzimidazolyl)amide
(898) 2-(3,5-dimethyl-2-pyrrolyl)-1H-benzimidazole-4-(N-5-benzimidazolonyl)amide
(899) 2-(3,5-dimethyl-2-pyrrolyl)-1H-benzimidazole-4-(N-4'-carbonamido-5'-imidazolyl)amide
(900) 2-(3,5-dimethyl-2-pyrrolyl)-1H-benzimidazole-4-(N-4'-carboxyl-5'-imidazolyl)amide
(901) 2-(3,5-dimethyl-2-pyrrolyl)-1H-benzimidazole-4-(N-2-imidazolyl)amide
(902) 2-(3,5-dimethyl-2-pyrrolyl)-1H-benzimidazole-4-(N-4'-pyrazolyl)amide
(903) 2-(3,5-dimethyl-2-pyrrolyl)-1H-benzimidazole-4-(N—(N'-piperazinyl))amide
(904) 2-(3,5-dimethyl-2-pyrrolyl)-1H-benzimidazole-4-(N'-ethyl-N-piperazinyl)amide
(905) 2-(3,5-dimethyl-2-pyrrolyl)-1H-benzimidazole-4-(N-2-pyrazinyl)amide
(906) 2-(3,5-dimethyl-2-pyrrolyl)-1H-benzimidazole-4-(N-2-pyrimidinyl)amide
(907) 2-(3,5-dimethyl-2-pyrrolyl)-1H-benzimidazole-4-(N-4-pyrimidinyl)amide
(908) 2-(3,5-dimethyl-2-pyrrolyl)-1H-benzimidazole-4-(N-5-pyrimidinyl)amide
(909) 2-(3,5-dimethyl-2-pyrrolyl)-1H-benzimidazole-4-(N-2-pyridyl)amide
(910) 2-(3,5-dimethyl-2-pyrrolyl)-1H-benzimidazole-4-(N-3-pyridyl)amide
(911) 2-(3,5-dimethyl-2-pyrrolyl)-1H-benzimidazole-4-(N-4-pyridyl)amide
(912) 2-(3,5-dimethyl-2-pyrrolyl)-1H-benzimidazole-4-(N-4-methyl-5-thiazolyl)amide
(913) 2-(3,5-dimethyl-2-pyrrolyl)-1H-benzimidazole-4-(N-5-thiazolyl)amide
(914) 2-(3,5-dimethyl-2-pyrrolyl)-1H-benzimidazole-4-(N-2,4-dihydroxyl-5-pyrimidinyl)amide
(915) 2-(3,5-dimethyl-2-pyrrolyl)-1H-benzimidazole-4-(N-4,6-dimethoxy-2-pyrimidinyl)amide
(916) 2-(3,5-dimethyl-2-pyrrolyl)-1H-benzimidazole-4-(N-4-chloro-6-amino-2-pyrimidinyl)amide
(917) 2-(3,5-dimethyl-2-pyrrolyl)-1H-benzimidazole-4-(N-4,6-dichloro-5-pyrimidinyl)amide
(918) 2-(2-quinolinyl)-1H-benzimidazole-4-(N—N'-piperidinyl)amide
(919) 2-(2-quinolinyl)-1H-benzimidazole-4-(N-2-piperazinyl))amide
(920) 2-(2-quinolinyl)-1H-benzimidazole-4-(N-2'-benzimidazolyl)amide
(921) 2-(2-quinolinyl)-1H-benzimidazole-4-(N-5-benzimidazolonyl)amide (922) 2-(2-quinolinyl)-1H-benzimidazole-4-(N-4'-carbonamido-5'-imidazolyl)amide
(923) 2-(2-quinolinyl)-1H-benzimidazole-4-(N-4'-carboxyl-5'-imidazolyl)amide
(924) 2-(2-quinolinyl)-1H-benzimidazole-4-(N-2-imidazolyl)amide
(925) 2-(2-quinolinyl)-1H-benzimidazole-4-(N-4'-pyrazolyl)amide
(926) 2-(2-quinolinyl)-1H-benzimidazole-4-(N—(N'-piperazinyl))amide
(927) 2-(2-quinolinyl)-1H-benzimidazole-4-(N'-ethyl-N-piperazinyl)amide
(928) 2-(2-quinolinyl)-1H-benzimidazole-4-(N-2-pyrazinyl)amide
(929) 2-(2-quinolinyl)-1H-benzimidazole-4-(N-2-pyrimidinyl)amide
(930) 2-(2-quinolinyl)-1H-benzimidazole-4-(N-4-pyrimidinyl)amide
(931) 2-(2-quinolinyl)-1H-benzimidazole-4-(N-5-pyrimidinyl)amide
(932) 2-(2-quinolinyl)-1H-benzimidazole-4-(N-2-pyridyl)amide
(933) 2-(2-quinolinyl)-1H-benzimidazole-4-(N-3-pyridyl)amide
(934) 2-(2-quinolinyl)-1H-benzimidazole-4-(N-4-pyridyl)amide
(935) 2-(2-quinolinyl)-1H-benzimidazole-4-(N-4-methyl-5-thiazolyl)amide
(936) 2-(2-quinolinyl)-1H-benzimidazole-4-(N-5-thiazolyl)amide
(937) 2-(2-quinolinyl)-1H-benzimidazole-4-(N-2,4-dihydroxyl-5-pyrimidinyl)amide
(938) 2-(2-quinolinyl)-1H-benzimidazole-4-(N-4,6-dimethoxy-2-pyrimidinyl)amide
(939) 2-(2-quinolinyl)-1H-benzimidazole-4-(N-4-chloro-6-amino-2-pyrimidinyl)amide
(940) 2-(2-quinolinyl)-1H-benzimidazole-4-(N-4,6-dichloro-5-pyrimidinyl)amide
(941) 2-(2-piperidinyl)-1H-benzimidazole-4-(N—N'-piperidinyl)amide
(942) 2-(2-piperidinyl)-1H-benzimidazole-4-(N-2-piperazinyl))amide
(943) 2-(2-piperidinyl)-1H-benzimidazole-4-(N-2'-benzimidazolyl)amide
(944) 2-(2-piperidinyl)-1H-benzimidazole-4-(N-5-benzimidazolonyl)amide
(945) 2-(2-piperidinyl)-1H-benzimidazole-4-(N-4'-carbonamido-5'-imidazolyl)amide
(946) 2-(2-piperidinyl)-1H-benzimidazole-4-(N-4'-carboxyl-5'-imidazolyl)amide
(947) 2-(2-piperidinyl)-1H-benzimidazole-4-(N-2-imidazolyl)amide
(948) 2-(2-piperidinyl)-1H-benzimidazole-4-(N-4'-pyrazolyl)amide
(949) 2-(2-piperidinyl)-1H-benzimidazole-4-(N—(N'-piperazinyl))amide
(950) 2-(2-piperidinyl)-1H-benzimidazole-4-(N'-ethyl-N-piperazinyl)amide
(951) 2-(2-piperidinyl)-1H-benzimidazole-4-(N-2-pyrazinyl)amide
(952) 2-(2-piperidinyl)-1H-benzimidazole-4-(N-2-pyrimidinyl)amide
(953) 2-(2-piperidinyl)-1H-benzimidazole-4-(N-4-pyrimidinyl)amide
(954) 2-(2-piperidinyl)-1H-benzimidazole-4-(N-5-pyrimidinyl)amide
(955) 2-(2-piperidinyl)-1H-benzimidazole-4-(N-2-pyridyl)amide
(956) 2-(2-piperidinyl)-1H-benzimidazole-4-(N-3-pyridyl)amide
(957) 2-(2-piperidinyl)-1H-benzimidazole-4-(N-4-pyridyl)amide
(958) 2-(2-piperidinyl)-1H-benzimidazole-4-(N-4-methyl-5-thiazolyl)amide
(959) 2-(2-piperidinyl)-1H-benzimidazole-4-(N-5-thiazolyl)amide
(960) 2-(2-piperidinyl)-1H-benzimidazole-4-(N-2,4-dihydroxyl-5-pyrimidinyl)amide
(961) 2-(2-piperidinyl)-1H-benzimidazole-4-(N-4,6-dimethoxy-2-pyrimidinyl)amide
(962) 2-(2-piperidinyl)-1H-benzimidazole-4-(N-4-chloro-6-amino-2-pyrimidinyl)amide
(963) 2-(2-piperidinyl)-1H-benzimidazole-4-(N-4,6-dichloro-5-pyrimidinyl)amide
(964) 2-(3-piperidinyl)-1H-benzimidazole-4-(N—N'-piperidinyl)amide
(965) 2-(3-piperidinyl)-1H-benzimidazole-4-(N-2-piperazinyl))amide
(966) 2-(3-piperidinyl)-1H-benzimidazole-4-(N-2'-benzimidazolyl)amide
(967) 2-(3-piperidinyl)-1H-benzimidazole-4-(N-5-benzimidazolonyl)amide
(968) 2-(3-piperidinyl)-1H-benzimidazole-4-(N-4'-carbonamido-5'-imidazolyl)amide
(969) 2-(3-piperidinyl)-1H-benzimidazole-4-(N-4'-carboxyl-5'-imidazolyl)amide
(970) 2-(3-piperidinyl)-1H-benzimidazole-4-(N-2-imidazolyl)amide
(971) 2-(3-piperidinyl)-1H-benzimidazole-4-(N-4'-pyrazolyl)amide
(972) 2-(3-piperidinyl)-1H-benzimidazole-4-(N—(N'-piperazinyl))amide
(973) 2-(3-piperidinyl)-1H-benzimidazole-4-(N'-ethyl-N-piperazinyl)amide
(974) 2-(3-piperidinyl)-1H-benzimidazole-4-(N-2-pyrazinyl)amide
(975) 2-(3-piperidinyl)-1H-benzimidazole-4-(N-2-pyrimidinyl)amide
(976) 2-(3-piperidinyl)-1H-benzimidazole-4-(N-4-pyrimidinyl)amide
(977) 2-(3-piperidinyl)-1H-benzimidazole-4-(N-5-pyrimidinyl)amide
(978) 2-(3-piperidinyl)-1H-benzimidazole-4-(N-2-pyridyl)amide
(979) 2-(3-piperidinyl)-1H-benzimidazole-4-(N-3-pyridyl)amide
(980) 2-(3-piperidinyl)-1H-benzimidazole-4-(N-4-pyridyl)amide
(981) 2-(3-piperidinyl)-1H-benzimidazole-4-(N-4-methyl-5-thiazolyl)amide
(982) 2-(3-piperidinyl)-1H-benzimidazole-4-(N-5-thiazolyl)amide
(983) 2-(3-piperidinyl)-1H-benzimidazole-4-(N-2,4-dihydroxyl-5-pyrimidinyl)amide
(984) 2-(3-piperidinyl)-1H-benzimidazole-4-(N-4,6-dimethoxy-2-pyrimidinyl)amide
(985) 2-(3-piperidinyl)-1H-benzimidazole-4-(N-4-chloro-6-amino-2-pyrimidinyl)amide
(986) 2-(3-piperidinyl)-1H-benzimidazole-4-(N-4,6-dichloro-5-pyrimidinyl)amide
(987) 2-(4-piperidinyl)-1H-benzimidazole-4-(N—N'-piperidinyl)amide (988) 2-(4-piperidinyl)-1H-benzimidazole-4-(N-2-piperazinyl))amide
(989) 2-(4-piperidinyl)-1H-benzimidazole-4-(N-2'-benzimidazolyl)amide
(990) 2-(4-piperidinyl)-1H-benzimidazole-4-(N-5-benzimidazolonyl)amide
(991) 2-(4-piperidinyl)-1H-benzimidazole-4-(N-4'-carbonamido-5'-imidazolyl)amide
(992) 2-(4-piperidinyl)-1H-benzimidazole-4-(N-4'-carboxyl-5'-imidazolyl)amide
(993) 2-(4-piperidinyl)-1H-benzimidazole-4-(N-2-imidazolyl)amide
(994) 2-(4-piperidinyl)-1H-benzimidazole-4-(N-4'-pyrazolyl)amide
(995) 2-(4-piperidinyl)-1H-benzimidazole-4-(N—(N'-piperazinyl))amide
(996) 2-(4-piperidinyl)-1H-benzimidazole-4-(N'-ethyl-N-piperazinyl)amide
(997) 2-(4-piperidinyl)-1H-benzimidazole-4-(N-2-pyrazinyl)amide
(998) 2-(4-piperidinyl)-1H-benzimidazole-4-(N-2-pyrimidinyl)amide
(999) 2-(4-piperidinyl)-1H-benzimidazole-4-(N-4-pyrimidinyl)amide
(1000) 2-(4-piperidinyl)-1H-benzimidazole-4-(N-5-pyrimidinyl)amide
(1001) 2-(4-piperidinyl)-1H-benzimidazole-4-(N-2-pyridyl)amide
(1002) 2-(4-piperidinyl)-1H-benzimidazole-4-(N-3-pyridyl)amide
(1003) 2-(4-piperidinyl)-1H-benzimidazole-4-(N-4-pyridyl)amide
(1004) 2-(4-piperidinyl)-1H-benzimidazole-4-(N-4-methyl-5-thiazolyl)amide
(1005) 2-(4-piperidinyl)-1H-benzimidazole-4-(N-5-thiazolyl)amide
(1006) 2-(4-piperidinyl)-1H-benzimidazole-4-(N-2,4-dihydroxyl-5-pyrimidinyl)amide
(1007) 2-(4-piperidinyl)-1H-benzimidazole-4-(N-4,6-dimethoxy-2-pyrimidinyl)amide
(1008) 2-(4-piperidinyl)-1H-benzimidazole-4-(N-4-chloro-6-amino-2-pyrimidinyl)amide
(1009) 2-(4-piperidinyl)-1H-benzimidazole-4-(N-4,6-dichloro-5-pyrimidinyl)amide
(1010) 2-(3-indolyl)-1H-benzimidazole-4-(N—N'-piperidinyl)amide
(1011) 2-(3-indolyl)-1H-benzimidazole-4-(N-2-piperazinyl))amide
(1012) 2-(3-indolyl)-1H-benzimidazole-4-(N-2'-benzimidazolyl)amide
(1013) 2-(3-indolyl)-1H-benzimidazole-4-(N-5-benzimidazolonyl)amide
(1014) 2-(3-indolyl)-1H-benzimidazole-4-(N-4'-carbonamido-5'-imidazolyl)amide
(1015) 2-(3-indolyl)-1H-benzimidazole-4-(N-4'-carboxyl-5'-imidazolyl)amide
(1016) 2-(3-indolyl)-1H-benzimidazole-4-(N-2-imidazolyl)amide
(1017) 2-(3-indolyl)-1H-benzimidazole-4-(N-4'-pyrazolyl)amide
(1018) 2-(3-indolyl)-1H-benzimidazole-4-(N—(N'-piperazinyl))amide
(1019) 2-(3-indolyl)-1H-benzimidazole-4-(N'-ethyl-N-piperazinyl)amide
(1020) 2-(3-indolyl)-1H-benzimidazole-4-(N-2-pyrazinyl)amide
(1021) 2-(3-indolyl)-1H-benzimidazole-4-(N-2-pyrimidinyl)amide
(1022) 2-(3-indolyl)-1H-benzimidazole-4-(N-4-pyrimidinyl)amide
(1023) 2-(3-indolyl)-1H-benzimidazole-4-(N-5-pyrimidinyl)amide
(1024) 2-(3-indolyl)-1H-benzimidazole-4-(N-2-pyridyl)amide
(1025) 2-(3-indolyl)-1H-benzimidazole-4-(N-3-pyridyl)amide
(1026) 2-(3-indolyl)-1H-benzimidazole-4-(N-4-pyridyl)amide
(1027) 2-(3-indolyl)-1H-benzimidazole-4-(N-4-methyl-5-thiazolyl)amide
(1028) 2-(3-indolyl)-1H-benzimidazole-4-(N-5-thiazolyl)amide
(1029) 2-(3-indolyl)-1H-benzimidazole-4-(N-2,4-dihydroxyl-5-pyrimidinyl)amide
(1030) 2-(3-indolyl)-1H-benzimidazole-4-(N-4,6-dimethoxy-2-pyrimidinyl)amide
(1031) 2-(3-indolyl)-1H-benzimidazole-4-(N-4-chloro-6-amino-2-pyrimidinyl)amide
(1032) 2-(3-indolyl)-1H-benzimidazole-4-(N-4,6-dichloro-5-pyrimidinyl)amide
(1033) 2-(2,3,4-trimethoxyphenyl)-1H-benzimidazole-4-(N—N'-piperidinyl)amide
(1034) 2-(2,3,4-trimethoxyphenyl)-1H-benzimidazole-4-(N-2-piperazinyl))amide
(1035) 2-(2,3,4-trimethoxyphenyl)-1H-benzimidazole-4-(N-2'-benzimidazolyl)amide
(1036) 2-(2,3,4-trimethoxyphenyl)-1H-benzimidazole-4-(N-5-benzimidazolonyl)amide
(1037) 2-(2,3,4-trimethoxyphenyl)-1H-benzimidazole-4-(N-4'-carbonamido-5'-imidazolyl)amide
(1038) 2-(2,3,4-trimethoxyphenyl)-1H-benzimidazole-4-(N-4'-carboxyl-5'-imidazolyl)amide
(1039) 2-(2,3,4-trimethoxyphenyl)-1H-benzimidazole-4-(N-2-imidazolyl)amide
(1040) 2-(2,3,4-trimethoxyphenyl)-1H-benzimidazole-4-(N-4'-pyrazolyl)amide
(1041) 2-(2,3,4-trimethoxyphenyl)-1H-benzimidazole-4-(N—(N'-piperazinyl))amide
(1042) 2-(2,3,4-trimethoxyphenyl)-1H-benzimidazole-4-(N'-ethyl-N-piperazinyl)amide
(1043) 2-(2,3,4-trimethoxyphenyl)-1H-benzimidazole-4-(N-2-pyrazinyl)amide
(1044) 2-(2,3,4-trimethoxyphenyl)-1H-benzimidazole-4-(N-2-pyrimidinyl)amide
(1045) 2-(2,3,4-trimethoxyphenyl)-1H-benzimidazole-4-(N-4-pyrimidinyl)amide
(1046) 2-(2,3,4-trimethoxyphenyl)-1H-benzimidazole-4-(N-5-pyrimidinyl)amide
(1047) 2-(2,3,4-trimethoxyphenyl)-1H-benzimidazole-4-(N-2-pyridyl)amide
(1048) 2-(2,3,4-trimethoxyphenyl)-1H-benzimidazole-4-(N-3-pyridyl)amide
(1049) 2-(2,3,4-trimethoxyphenyl)-1H-benzimidazole-4-(N-4-pyridyl)amide
(1050) 2-(2,3,4-trimethoxyphenyl)-1H-benzimidazole-4-(N-4-methyl-5-thiazolyl)amide
(1051) 2-(2,3,4-trimethoxyphenyl)-1H-benzimidazole-4-(N-5-thiazolyl)amide
(1052) 2-(2,3,4-trimethoxyphenyl)-1H-benzimidazole-4-(N-2,4-dihydroxyl-5-pyrimidinyl)amide
(1053) 2-(2,3,4-trimethoxyphenyl)-1H-benzimidazole-4-(N-4,6-dimethoxy-2-pyrimidinyl)amide (1054) 2-(2,3,4-trimethoxyphenyl)-1H-benzimidazole-4-(N-4-chloro-6-amino-2-pyrimidinyl)amide
(1055) 2-(2,3,4-trimethoxyphenyl)-1H-benzimidazole-4-(N-4,6-dichloro-5-pyrimidinyl)amide
(1056) 2-(3-hydroxyl-4-methoxyphenyl)-1H-benzimidazole-4-(N—N'-piperidinyl)amide
(1057) 2-(3-hydroxyl-4-methoxyphenyl)-1H-benzimidazole-4-(N-2-piperazinyl))amide
(1058) 2-(3-hydroxyl-4-methoxyphenyl)-1H-benzimidazole-4-(N-2'-benzimidazolyl)amide
(1059) 2-(3-hydroxyl-4-methoxyphenyl)-1H-benzimidazole-4-(N-5-benzimidazolonyl)amide
(1060) 2-(3-hydroxyl-4-methoxyphenyl)-1H-benzimidazole-4-(N-4'-carbonamido-5'-imidazolyl)amide
(1061) 2-(3-hydroxyl-4-methoxyphenyl)-1H-benzimidazole-4-(N-4'-carboxyl-5'-imidazolyl)amide
(1062) 2-(3-hydroxyl-4-methoxyphenyl)-1H-benzimidazole-4-(N-2-imidazolyl)amide
(1063) 2-(3-hydroxyl-4-methoxyphenyl)-1H-benzimidazole-4-(N-4'-pyrazolyl)amide
(1064) 2-(3-hydroxyl-4-methoxyphenyl)-1H-benzimidazole-4-(N—(N'-piperazinyl))amide
(1065) 2-(3-hydroxyl-4-methoxyphenyl)-1H-benzimidazole-4-(N'-ethyl-N-piperazinyl)amide
(1066) 2-(3-hydroxyl-4-methoxyphenyl)-1H-benzimidazole-4-(N-2-pyrazinyl)amide
(1067) 2-(3-hydroxyl-4-methoxyphenyl)-1H-benzimidazole-4-(N-2-pyrimidinyl)amide
(1068) 2-(3-hydroxyl-4-methoxyphenyl)-1H-benzimidazole-4-(N-4-pyrimidinyl)amide
(1069) 2-(3-hydroxyl-4-methoxyphenyl)-1H-benzimidazole-4-(N-5-pyrimidinyl)amide
(1070) 2-(3-hydroxyl-4-methoxyphenyl)-1H-benzimidazole-4-(N-2-pyridyl)amide
(1071) 2-(3-hydroxyl-4-methoxyphenyl)-1H-benzimidazole-4-(N-3-pyridyl)amide
(1072) 2-(3-hydroxyl-4-methoxyphenyl)-1H-benzimidazole-4-(N-4-pyridyl)amide
(1073) 2-(3-hydroxyl-4-methoxyphenyl)-1H-benzimidazole-4-(N-4-methyl-5-thiazolyl)amide
(1074) 2-(3-hydroxyl-4-methoxyphenyl)-1H-benzimidazole-4-(N-5-thiazolyl)amide
(1075) 2-(3-hydroxyl-4-methoxyphenyl)-1H-benzimidazole-4-(N-2,4-dihydroxyl-5-pyrimidinyl)amide
(1076) 2-(3-hydroxyl-4-methoxyphenyl)-1H-benzimidazole-4-(N-4,6-dimethoxy-2-pyrimidinyl)amide
(1077) 2-(3-hydroxyl-4-methoxyphenyl)-1H-benzimidazole-4-(N-4-chloro-6-amino-2-pyrimidinyl)amide
(1078) 2-(3-hydroxyl-4-methoxyphenyl)-1H-benzimidazole-4-(N-4,6-dichloro-5-pyrimidinyl)amide
(1079) (L)-2-(2-bromo-5-pyridine)-1H-benzimidazole-4-[N-(1-hydroxymethyl-2-p-nitrophenylhydroxyethyl)]amide
(1080) (L)-2-(2-bromo-5-pyridine)-1H-benzimidazole-44N-(1-hydroxymethyl-2-p-aminophenylhydroxyethyl)]amide
(1081) 2-(2-bromo-5-pyridine)-1H-benzimidazole-4-[N-(1-methyl-2-p-chlorophenylhydroxyethyl)]amide
(1082) 2-(2-bromo-5-pyridine)-1H-benzimidazole-4-(N—N'-piperidinyl)amide
(1083) 2-(2-bromo-5-pyridine)-1H-benzimidazole-4-(N-2-piperazinyl))amide
(1084) 2-(2-bromo-5-pyridine)-1H-benzimidazole-4-(N-2'-benzimidazolyl)amide
(1085) 2-(2-bromo-5-pyridine)-1H-benzimidazole-4-(N-o-hydroxyphenyl)amide
(1086) 2-(2-bromo-5-pyridine)-1H-benzimidazole-4-(N-o-aminophenyl)amide
(1087) 2-(2-bromo-5-pyridine)-1H-benzimidazole-4-(N-5-benzimidazolonyl)amide
(1088) 2-(2-bromo-5-pyridine)-1H-benzimidazole-4-(N-4'-carbonamido-5'-imidazolyl)amide
(1089) 2-(2-bromo-5-pyridine)-1H-benzimidazole-4-(N-4'-carboxyl-5'-imidazolyl)amide
(1090) 2-(2-bromo-5-pyridine)-1H-benzimidazole-4-(N-2-imidazolyl)amide
(1091) 2-(2-bromo-5-pyridine)-1H-benzimidazole-4-(N-4'-pyrazolyl)amide
(1092) 2-(2-bromo-5-pyridine)-1H-benzimidazole-4-(N—(N'-piperazinyl))amide
(1093) 2-(2-bromo-5-pyridine)-1H-benzimidazole-4-(N'-ethyl-N-piperazinyl)amide
(1094) 2-(2-bromo-5-pyridine)-1H-benzimidazole-4-(N-2-pyrazinyl)amide
(1095) 2-(2-bromo-5-pyridine)-1H-benzimidazole-4-(N-2-pyrimidinyl)amide
(1096) 2-(2-bromo-5-pyridine)-1H-benzimidazole-4-(N-4-pyrimidinyl)amide
(1097) 2-(2-bromo-5-pyridine)-1H-benzimidazole-4-(N-5-pyrimidinyl)amide
(1098) 2-(2-bromo-5-pyridine)-1H-benzimidazole-4-(N-2-pyridyl)amide
(1099) 2-(2-bromo-5-pyridine)-1H-benzimidazole-4-(N-3-pyridyl)amide
(1100) 2-(2-bromo-5-pyridine)-1H-benzimidazole-4-(N-4-pyridyl)amide
(1101) 2-(2-bromo-5-pyridine)-1H-benzimidazole-4-(N-4-methyl-5-thiazolyl)amide
(1102) 2-(2-bromo-5-pyridine)-1H-benzimidazole-4-(N-5-thiazolyl)amide
(1103) 2-(2-bromo-5-pyridine)-1H-benzimidazole-4-(N-2,4-dihydroxyl-5-pyrimidinyl)amide
(1104) 2-(2-bromo-5-pyridine)-1H-benzimidazole-4-(N-4,6-di(2-bromo-5-pyridine)-2-pyrimidinyl)amide
(1105) 2-(2-bromo-5-pyridine)-1H-benzimidazole-4-(N-4-chloro-6-amino-2-pyrimidinyl)amide
(1106) 2-(2-bromo-5-pyridine)-1H-benzimidazole-4-(N-4,6-dichloro-5-pyrimidinyl)amide
(1107) (L)-2-(2-amino-3-pyridine)-1H-benzimidazole-4-[N-(1-hydroxymethyl-2-p-nitrophenylhydroxyethyl)]amide
(1108) (L)-2-(2-amino-3-pyridine)-1H-benzimidazole-44N-(1-hydroxymethyl-2-p-aminophenylhydroxyethyl)]amide
(1109) 2-(2-amino-3-pyridine)-1H-benzimidazole-4-[N-(1-methyl-2-p-chlorophenylhydroxyethyl)]amide
(1110) 2-(2-amino-3-pyridine)-1H-benzimidazole-4-(N—N'-piperidinyl)amide
(1111) 2-(2-amino-3-pyridine)-1H-benzimidazole-4-(N-2-piperazinyl))amide
(1112) 2-(2-amino-3-pyridine)-1H-benzimidazole-4-(N-2'-benzimidazolyl)amide
(1113) 2-(2-amino-3-pyridine)-1H-benzimidazole-4-(N-o-hydroxyphenyl)amide
(1114) 2-(2-amino-3-pyridine)-1H-benzimidazole-4-(N-o-aminophenyl)amide
(1115) 2-(2-amino-3-pyridine)-1H-benzimidazole-4-(N-5-benzimidazolonyl)amide
(1116) 2-(2-amino-3-pyridine)-1H-benzimidazole-4-(N-4'-carbonamido-5'-imidazolyl)amide
(1117) 2-(2-amino-3-pyridine)-1H-benzimidazole-4-(N-4'-carboxyl-5'-imidazolyl)amide
(1118) 2-(2-amino-3-pyridine)-1H-benzimidazole-4-(N-2-imidazolyl)amide
(1119) 2-(2-amino-3-pyridine)-1H-benzimidazole-4-(N-4'-pyrazolyl)amide (1120) 2-(2-amino-3-pyridine)-1H-benzimidazole-4-(N—(N'-piperazinyl))amide
(1121) 2-(2-amino-3-pyridine)-1H-benzimidazole-4-(N'-ethyl-N-piperazinyl)amide
(1122) 2-(2-amino-3-pyridine)-1H-benzimidazole-4-(N-2-pyrazinyl)amide
(1123) 2-(2-amino-3-pyridine)-1H-benzimidazole-4-(N-2-pyrimidinyl)amide
(1124) 2-(2-amino-3-pyridine)-1H-benzimidazole-4-(N-4-pyrimidinyl)amide
(1125) 2-(2-amino-3-pyridine)-1H-benzimidazole-4-(N-5-pyrimidinyl)amide
(1126) 2-(2-amino-3-pyridine)-1H-benzimidazole-4-(N-2-pyridyl)amide
(1127) 2-(2-amino-3-pyridine)-1H-benzimidazole-4-(N-3-pyridyl)amide
(1128) 2-(2-amino-3-pyridine)-1H-benzimidazole-4-(N-4-pyridyl)amide
(1129) 2-(2-amino-3-pyridine)-1H-benzimidazole-4-(N-4-methyl-5-thiazolyl)amide
(1130) 2-(2-amino-3-pyridine)-1H-benzimidazole-4-(N-5-thiazolyl)amide
(1131) 2-(2-amino-3-pyridine)-1H-benzimidazole-4-(N-2,4-dihydroxyl-5-pyrimidinyl)amide
(1132) 2-(2-amino-3-pyridine)-1H-benzimidazole-4-(N-4,6-di(2-amino-3-pyridine)-2-pyrimidinyl)amide
(1133) 2-(2-amino-3-pyridine)-1H-benzimidazole-4-(N-4-chloro-6-amino-2-pyrimidinyl)amide
(1134) 2-(2-amino-3-pyridine)-1H-benzimidazole-4-(N-4,6-dichloro-5-pyrimidinyl)amide
(1135) (L)-2-(2-pyrrolidine-1-yl-5-pyrimidinyl)-1H-benzimidazole-4-[N-(1-hydroxymethyl-2-p-nitrophenylhydroxyethyl)]amide
(1136) (L)-2-(2-pyrrolidine-1-yl-5-pyrimidinyl)-1H-benzimidazole-4-[N-(1-hydroxymethyl-2-p-aminophenylhydroxyethyl)]amide
(1137) 2-(2-pyrrolidine-1-yl-5-pyrimidinyl)-1H-benzimidazole-4-[N-(1-methyl-2-p-chlorophenylhydroxyethyl)]amide
(1138) 2-(2-pyrrolidine-1-yl-5-pyrimidinyl)-1H-benzimidazole-4-(N—N'-piperidinyl)amide
(1139) 2-(2-pyrrolidine-1-yl-5-pyrimidinyl)-1H-benzimidazole-4-(N-2-piperazinyl)amide
(1140) 2-(2-pyrrolidine-1-yl-5-pyrimidinyl)-1H-benzimidazole-4-(N-2'-benzimidazolyl)amide
(1141) 2-(2-pyrrolidine-1-yl-5-pyrimidinyl)-1H-benzimidazole-4-(N-o-hydroxyphenyl)amide
(1142) 2-(2-pyrrolidine-1-yl-5-pyrimidinyl)-1H-benzimidazole-4-(N-o-aminophenyl)amide
(1143) 2-(2-pyrrolidine-1-yl-5-pyrimidinyl)-1H-benzimidazole-4-(N-5-benzimidazolonyl)amide
(1144) 2-(2-pyrrolidine-1-yl-5-pyrimidinyl)-1H-benzimidazole-4-(N-4'-carbonamido-5'-imidazolyl)amide
(1145) 2-(2-pyrrolidine-1-yl-5-pyrimidinyl)-1H-benzimidazole-4-(N-4'-carboxyl-5'-imidazolyl)amide
(1146) 2-(2-pyrrolidine-1-yl-5-pyrimidinyl)-1H-benzimidazole-4-(N-2-imidazolyl)amide
(1147) 2-(2-pyrrolidine-1-yl-5-pyrimidinyl)-1H-benzimidazole-4-(N-4'-pyrazolyl)amide
(1148) 2-(2-pyrrolidine-1-yl-5-pyrimidinyl)-1H-benzimidazole-4-(N—(N'-piperazinyl))amide
(1149) 2-(2-pyrrolidine-1-yl-5-pyrimidinyl)-1H-benzimidazole-4-(N'-ethyl-N-piperazinyl)amide
(1150) 2-(2-pyrrolidine-1-yl-5-pyrimidinyl)-1H-benzimidazole-4-(N-2-pyrazinyl)amide
(1151) 2-(2-pyrrolidine-1-yl-5-pyrimidinyl)-1H-benzimidazole-4-(N-2-pyrimidinyl)amide
(1152) 2-(2-pyrrolidine-1-yl-5-pyrimidinyl)-1H-benzimidazole-4-(N-4-pyrimidinyl)amide
(1153) 2-(2-pyrrolidine-1-yl-5-pyrimidinyl)-1H-benzimidazole-4-(N-5-pyrimidinyl)amide
(1154) 2-(2-pyrrolidine-1-yl-5-pyrimidinyl)-1H-benzimidazole-4-(N-2-pyridyl)amide
(1155) 2-(2-pyrrolidine-1-yl-5-pyrimidinyl)-1H-benzimidazole-4-(N-3-pyridyl)amide
(1156) 2-(2-pyrrolidine-1-yl-5-pyrimidinyl)-1H-benzimidazole-4-(N-5-pyridyl)amide
(1157) 2-(2-pyrrolidine-1-yl-5-pyrimidinyl)-1H-benzimidazole-4-(N-4-methyl-5-thiazolyl)amide
(1158) 2-(2-pyrrolidine-1-yl-5-pyrimidinyl)-1H-benzimidazole-4-(N-5-thiazolyl)amide
(1159) 2-(2-pyrrolidine-1-yl-5-pyrimidinyl)-1H-benzimidazole-4-(N-2,4-dihydroxyl-5-pyrimidinyl)amide
(1160) 2-(2-pyrrolidine-1-yl-5-pyrimidinyl)-1H-benzimidazole-4-(N-4,6-di(2-pyrrolidine-1-yl-5-pyrimidinyl)-2-pyrimidinyl)amide
(1161) 2-(2-pyrrolidine-1-yl-5-pyrimidinyl)-1H-benzimidazole-4-(N-4-chloro-6-amino-2-pyrimidinyl)amide
(1162) 2-(2-pyrrolidine-1-yl-5-pyrimidinyl)-1H-benzimidazole-4-(N-4,6-dichloro-5-pyrimidinyl)amide
(1163) (L)-2-(2-piperidine-1-yl-5-pyrimidinyl)-1H-benzimidazole-4-[N-(1-hydroxymethyl-2-p-nitrophenylhydroxyethyl)]amide
(1164) (L)-2-(2-piperidine-1-yl-5-pyrimidinyl)-1H-benzimidazole-4-[N-(1-hydroxymethyl-2-p-aminophenylhydroxyethyl)]amide
(1165) 2-(2-piperidine-1-yl-5-pyrimidinyl)-1H-benzimidazole-4-[N-(1-methyl-2-p-chlorophenylhydroxyethyl)]amide
(1166) 2-(2-piperidine-1-yl-5-pyrimidinyl)-1H-benzimidazole-4-(N—N'-piperidinyl)amide
(1167) 2-(2-piperidine-1-yl-5-pyrimidinyl)-1H-benzimidazole-4-(N-2-piperazinyl)amide
(1168) 2-(2-piperidine-1-yl-5-pyrimidinyl)-1H-benzimidazole-4-(N-2'-benzimidazolyl)amide
(1169) 2-(2-piperidine-1-yl-5-pyrimidinyl)-1H-benzimidazole-4-(N-o-hydroxyphenyl)amide
(1170) 2-(2-piperidine-1-yl-5-pyrimidinyl)-1H-benzimidazole-4-(N-o-aminophenyl)amide
(1171) 2-(2-piperidine-1-yl-5-pyrimidinyl)-1H-benzimidazole-4-(N-5-benzimidazolonyl)amide
(1172) 2-(2-piperidine-1-yl-5-pyrimidinyl)-1H-benzimidazole-4-(N-4'-carbonamido-5'-imidazolyl)amide
(1173) 2-(2-piperidine-1-yl-5-pyrimidinyl)-1H-benzimidazole-4-(N-4'-carboxyl-5'-imidazolyl)amide
(1174) 2-(2-piperidine-1-yl-5-pyrimidinyl)-1H-benzimidazole-4-(N-2-imidazolyl)amide
(1175) 2-(2-piperidine-1-yl-5-pyrimidinyl)-1H-benzimidazole-4-(N-4'-pyrazolyl)amide
(1176) 2-(2-piperidine-1-yl-5-pyrimidinyl)-1H-benzimidazole-4-(N—(N'-piperazinyl))amide
(1177) 2-(2-piperidine-1-yl-5-pyrimidinyl)-1H-benzimidazole-4-(N'-ethyl-N-piperazinyl)amide
(1178) 2-(2-piperidine-1-yl-5-pyrimidinyl)-1H-benzimidazole-4-(N-2-pyrazinyl)amide
(1179) 2-(2-piperidine-1-yl-5-pyrimidinyl)-1H-benzimidazole-4-(N-2-pyrimidinyl)amide
(1180) 2-(2-piperidine-1-yl-5-pyrimidinyl)-1H-benzimidazole-4-(N-4-pyrimidinyl)amide
(1181) 2-(2-piperidine-1-yl-5-pyrimidinyl)-1H-benzimidazole-4-(N-5-pyrimidinyl)amide
(1182) 2-(2-piperidine-1-yl-5-pyrimidinyl)-1H-benzimidazole-4-(N-2-pyridyl)amide (1183) 2-(2-piperidine-1-yl-5-pyrimidinyl)-1H-benzimidazole-4-(N-3-pyridyl)amide
(1184) 2-(2-piperidine-1-yl-5-pyrimidinyl)-1H-benzimidazole-4-(N-4-pyridyl)amide
(1185) 2-(2-piperidine-1-yl-5-pyrimidinyl)-1H-benzimidazole-4-(N-4-methyl-5-thiazolyl)amide
(1186) 2-(2-piperidine-1-yl-5-pyrimidinyl)-1H-benzimidazole-4-(5-thiazolyl)amide
(1187) 2-(2-piperidine-1-yl-5-pyrimidinyl)-1H-benzimidazole-4-(N-2,4-dihydroxyl-5-pyrimidinyl)amide
(1188) 2-(2-piperidine-1-yl-5-pyrimidinyl)-1H-benzimidazole-4-(N-4,6-di(2-piperidine-1-yl-5-pyrimidinyl)-2-pyrimidinyl)amide
(1189) 2-(2-piperidine-1-yl-5-pyrimidinyl)-1H-benzimidazole-4-(N-4-chloro-6-amino-2-pyrimidinyl)amide
(1190) 2-(2-piperidine-1-yl-5-pyrimidinyl)-1H-benzimidazole-4-(N-4,6-dichloro-5-pyrimidinyl)amide
(1191) (L)-2-(2-cyclopropylamino-5-pyrimidinyl)-1H-benzimidazole-4-[N-(1-hydroxymethyl-2-p-nitrophenylhydroxyethyl)]amide
(1192) (L)-2-(2-cyclopropylamino-5-pyrimidinyl)-1H-benzimidazole-4-[N-(1-hydroxymethyl-2-p-aminophenylhydroxyethyl)]amide
(1193) 2-(2-cyclopropylamino-5-pyrimidinyl)-1H-benzimidazole-4-[N-(1-methyl-2-p-chlorophenylhydroxyethyl)]amide
(1194) 2-(2-cyclopropylamino-5-pyrimidinyl)-1H-benzimidazole-4-(N—N'-piperidinyl)amide
(1195) 2-(2-cyclopropylamino-5-pyrimidinyl)-1H-benzimidazole-4-(N-2-piperazinyl)amide
(1196) 2-(2-cyclopropylamino-5-pyrimidinyl)-1H-benzimidazole-4-(N-2'-benzimidazolyl)amide
(1197) 2-(2-cyclopropylamino-5-pyrimidinyl)-1H-benzimidazole-4-(N-o-hydroxyphenyl)amide
(1198) 2-(2-cyclopropylamino-5-pyrimidinyl)-1H-benzimidazole-4-(N-o-aminophenyl)amide
(1199) 2-(2-cyclopropylamino-5-pyrimidinyl)-1H-benzimidazole-4-(N-5-benzimidazolonyl)amide
(1200) 2-(2-cyclopropylamino-5-pyrimidinyl)-1H-benzimidazole-4-(N-4'-carbonamido-5'-imidazolyl)amide
(1201) 2-(2-cyclopropylamino-5-pyrimidinyl)-1H-benzimidazole-4-(N-4'-carboxyl-5'-imidazolyl)amide
(1202) 2-(2-cyclopropylamino-5-pyrimidinyl)-1H-benzimidazole-4-(N-2-imidazolyl)amide
(1203) 2-(2-cyclopropylamino-5-pyrimidinyl)-1H-benzimidazole-4-(N-4'-pyrazolyl)amide
(1204) 2-(2-cyclopropylamino-5-pyrimidinyl)-1H-benzimidazole-4-(N—(N'-piperazinyl))amide
(1205) 2-(2-cyclopropylamino-5-pyrimidinyl)-1H-benzimidazole-4-(N'-ethyl-N-piperazinyl)amide
(1206) 2-(2-cyclopropylamino-5-pyrimidinyl)-1H-benzimidazole-4-(N-2-pyrazinyl)amide
(1207) 2-(2-cyclopropylamino-5-pyrimidinyl)-1H-benzimidazole-4-(N-2-pyrimidinyl)amide
(1208) 2-(2-cyclopropylamino-5-pyrimidinyl)-1H-benzimidazole-4-(N-4-pyrimidinyl)amide
(1209) 2-(2-cyclopropylamino-5-pyrimidinyl)-1H-benzimidazole-4-(N-5-pyrimidinyl)amide
(1210) 2-(2-cyclopropylamino-5-pyrimidinyl)-1H-benzimidazole-4-(N-2-pyridyl)amide
(1211) 2-(2-cyclopropylamino-5-pyrimidinyl)-1H-benzimidazole-4-(N-3-pyridyl)amide
(1212) 2-(2-cyclopropylamino-5-pyrimidinyl)-1H-benzimidazole-4-(N-4-pyridyl)amide
(1213) 2-(2-cyclopropylamino-5-pyrimidinyl)-1H-benzimidazole-4-(N-4-methyl-5-thiazolyl)amide
(1214) 2-(2-cyclopropylamino-5-pyrimidinyl)-1H-benzimidazole-4-(5-thiazolyl)amide
(1215) 2-(2-cyclopropylamino-5-pyrimidinyl)-1H-benzimidazole-4-(N-2,4-dihydroxyl-5-pyrimidinyl)amide
(1216) 2-(2-cyclopropylamino-5-pyrimidinyl)-1H-benzimidazole-4-(N-4,6-di(2-cyclopropylamino-5-pyrimidinyl)-2-pyrimidinyl)amide
(1217) 2-(2-cyclopropylamino-5-pyrimidinyl)-1H-benzimidazole-4-(N-4-chloro-6-amino-2-pyrimidinyl)amide
(1218) 2-(2-cyclopropylamino-5-pyrimidinyl)-1H-benzimidazole-4-(N-4,6-dichloro-5-pyrimidinyl)amide
(1219) (L)-2-(1,3-dimethyl-5-chloro-4-pyrazolyl)-1H-benzimidazole-4-[N-(1-hydroxymethyl-2-p-nitrophenylhydroxyethyl)]amide
(1220) (L)-2-(1,3-dimethyl-5-chloro-4-pyrazolyl)-1H-benzimidazole-4-[N-(1-hydroxymethyl-2-p-aminophenylhydroxyethyl)]amide
(1221) 2-(1,3-dimethyl-5-chloro-4-pyrazolyl)-1H-benzimidazole-4-[N-(1-methyl-2-p-chlorophenylhydroxyethyl)]amide
(1222) 2-(1,3-dimethyl-5-chloro-4-pyrazolyl)-1H-benzimidazole-4-(N—N'-piperidinyl)amide
(1223) 2-(1,3-dimethyl-5-chloro-4-pyrazolyl)-1H-benzimidazole-4-(N-2-piperazinyl)amide
(1224) 2-(1,3-dimethyl-5-chloro-4-pyrazolyl)-1H-benzimidazole-4-(N-2'-benzimidazolyl)amide
(1225) 2-(1,3-dimethyl-5-chloro-4-pyrazolyl)-1H-benzimidazole-4-(N-o-hydroxyphenyl)amide
(1226) 2-(1,3-dimethyl-5-chloro-4-pyrazolyl)-1H-benzimidazole-4-(N-o-aminophenyl)amide
(1227) 2-(1,3-dimethyl-5-chloro-4-pyrazolyl)-1H-benzimidazole-4-(N-5-benzimidazolonyl)amide
(1228) 2-(1,3-dimethyl-5-chloro-4-pyrazolyl)-1H-benzimidazole-4-(N-4'-carbonamido-5'-imidazolyl)amide
(1229) 2-(1,3-dimethyl-5-chloro-4-pyrazolyl)-1H-benzimidazole-4-(N-4'-carboxyl-5'-imidazolyl)amide
(1230) 2-(1,3-dimethyl-5-chloro-4-pyrazolyl)-1H-benzimidazole-4-(N-2-imidazolyl)amide
(1231) 2-(1,3-dimethyl-5-chloro-4-pyrazolyl)-1H-benzimidazole-4-(N-4'-pyrazolyl)amide
(1232) 2-(1,3-dimethyl-5-chloro-4-pyrazolyl)-1H-benzimidazole-4-(N—(N'-piperazinyl))amide
(1233) 2-(1,3-dimethyl-5-chloro-4-pyrazolyl)-1H-benzimidazole-4-(N'-ethyl-N-piperazinyl)amide
(1234) 2-(1,3-dimethyl-5-chloro-4-pyrazolyl)-1H-benzimidazole-4-(N-2-pyrazinyl)amide
(1235) 2-(1,3-dimethyl-5-chloro-4-pyrazolyl)-1H-benzimidazole-4-(N-2-pyrimidinyl)amide
(1236) 2-(1,3-dimethyl-5-chloro-4-pyrazolyl)-1H-benzimidazole-4-(N-4-pyrimidinyl)amide
(1237) 2-(1,3-dimethyl-5-chloro-4-pyrazolyl)-1H-benzimidazole-4-(N-5-pyrimidinyl)amide
(1238) 2-(1,3-dimethyl-5-chloro-4-pyrazolyl)-1H-benzimidazole-4-(N-2-pyridyl)amide
(1239) 2-(1,3-dimethyl-5-chloro-4-pyrazolyl)-1H-benzimidazole-4-(N-3-pyridyl)amide
(1240) 2-(1,3-dimethyl-5-chloro-4-pyrazolyl)-1H-benzimidazole-4-(N-4-pyridyl)amide
(1241) 2-(1,3-dimethyl-5-chloro-4-pyrazolyl)-1H-benzimidazole-4-(N-4-methyl-5-thiazolyl)amide
(1242) 2-(1,3-dimethyl-5-chloro-4-pyrazolyl)-1H-benzimidazole-4-(5-thiazolyl)amide
(1243) 2-(1,3-dimethyl-5-chloro-4-pyrazolyl)-1H-benzimidazole-4-(N-2,4-dihydroxyl-5-pyrimidinyl)amide
(1244) 2-(1,3-dimethyl-5-chloro-4-pyrazolyl)-1H-benzimidazole-4-(N-4,6-dimethoxy-2-pyrimidinyl)amide (1245) 2-(1,3-dimethyl-5-chloro-4-pyrazolyl)-1H-benzimidazole-4-(N-4-chloro-6-amino-2-pyrimidinyl)amide
(1246) 2-(1,3-dimethyl-5-chloro-4-pyrazolyl)-1H-benzimidazole-4-(N-4,6-dichloro-5-pyrimidinyl)amide
(1247) 2-(4-methoxypyridyl)-1H-benzimidazole-4-(N-2-hydroxyl-4-pyrimidinyl)amide
(1248) 2-(4-methoxypyridyl)-1H-benzimidazole-4-(N-6-purinyl)amide
(1249) 2-(4-methoxypyridyl)-1H-benzimidazole-4-(N-6-hydroxyl-2-purinyl)amide
(1250) 2-(5-amino-2-thienyl)-1H-benzimidazole-4-(N-2-hydroxyl-4-pyrimidinyl)amide
(1251) 2-(5-amino-2-thienyl)-1H-benzimidazole-4-(N-6-purinyl)amide
(1252) 2-(5-amino-2-thienyl)-1H-benzimidazole-4-(N-6-hydroxyl-2-purinyl)amide
(1253) 2-(6-methoxypyridyl)-1H-benzimidazole-4-(N-2-hydroxyl-4-pyrimidinyl)amide
(1254) 2-(6-methoxypyridyl)-1H-benzimidazole-4-(N-6-purinyl)amide
(1255) 2-(6-methoxypyridyl)-1H-benzimidazole-4-(N-6-hydroxyl-2-purinyl)amide
(1256) 2-(4-dimethylaminopyridyl)-1H-benzimidazole-4-(N-2-hydroxyl-4-pyrimidinyl)amide
(1257) 2-(4-dimethylaminopyridyl)-1H-benzimidazole-4-(N-6-purinyl)amide
(1258) 2-(4-dimethylaminopyridyl)-1H-benzimidazole-4-(N-6-hydroxyl-2-purinyl)amide
(1259) 2-(3-pyridazinyl)-1H-benzimidazole-4-(N-2-hydroxyl-4-pyrimidinyl)amide
(1260) 2-(3-pyridazinyl)-1H-benzimidazole-4-(N-6-purinyl)amide
(1261) 2-(3-pyridazinyl)-1H-benzimidazole-4-(N-6-hydroxyl-2-purinyl)amide
(1262) 2-(2-N-methyl-4-N-methylpiperazinyl)-1H-benzimidazole-4-(N-2-hydroxyl-4-pyrimidinyl)amide
(1263) 2-(2-N-methyl-4-N-methylpiperazinyl)-1H-benzimidazole-4-(N-6-purinyl)amide
(1264) 2-(2-N-methyl-4-N-methylpiperazinyl)-1H-benzimidazole-4-(N-6-hydroxyl-2-purinyl)amide
(1265) 2-(2-pyrazinyl)-1H-benzimidazole-4-(N-2-hydroxyl-4-pyrimidinyl)amide
(1266) 2-(2-pyrazinyl)-1H-benzimidazole-4-(N-6-purinyl)amide
(1267) 2-(2-pyrazinyl)-1H-benzimidazole-4-(N-6-hydroxyl-2-purinyl)amide
(1268) 2-N-piperazinyl-1H-benzimidazole-4-(N-2-hydroxyl-4-pyrimidinyl)amide
(1269) 2-N-piperazinyl-1H-benzimidazole-4-(N-6-purinyl)amide
(1270) 2-N-piperazinyl-1H-benzimidazole-4-(N-6-hydroxyl-2-purinyl)amide
(1271) 2-(4-methyl-5-aminothiazolyl)-1H-benzimidazole-4-(N-2-hydroxyl-4-pyrimidinyl)amide
(1272) 2-(4-methyl-5-aminothiazolyl)-1H-benzimidazole-4-(N-6-purinyl)amide
(1273) 2-(4-methyl-5-aminothiazolyl)-1H-benzimidazole-4-(N-6-hydroxyl-2-purinyl)amide
(1274) 2-thiazolyl-1H-benzimidazole-4-(N-2-hydroxyl-4-pyrimidinyl)amide
(1275) 2-thiazolyl-1H-benzimidazole-4-(N-6-purinyl)amide
(1276) 2-thiazolyl-1H-benzimidazole-4-(N-6-hydroxyl-2-purinyl)amide
(1277) 5-thiazolyl-1H-benzimidazole-4-(N-2-hydroxyl-4-pyrimidinyl)amide
(1278) 5-thiazolyl-1H-benzimidazole-4-(N-6-purinyl)amide
(1279) 5-thiazolyl-1H-benzimidazole-4-(N-6-hydroxyl-2-purinyl)amide
(1280) 2-(2-pyrimidinyl)-1H-benzimidazole-4-(N-2-hydroxyl-4-pyrimidinyl)amide
(1281) 2-(2-pyrimidinyl)-1H-benzimidazole-4-(N-6-purinyl)amide
(1282) 2-(2-pyrimidinyl)-1H-benzimidazole-4-(N-6-hydroxyl-2-purinyl)amide
(1283) 2-(2-phenyl-5-pyrimidinyl)-1H-benzimidazole-4-(N-2-hydroxyl-4-pyrimidinyl)amide
(1284) 2-(2-phenyl-5-pyrimidinyl)-1H-benzimidazole-4-(N-6-purinyl)amide
(1285) 2-(2-phenyl-5-pyrimidinyl)-1H-benzimidazole-4-(N-6-hydroxyl-2-purinyl)amide
(1286) 2-(4-amino-6-chloro-5-pyrimidinyl)-1H-benzimidazole-4-(N-2-hydroxyl-4-pyrimidinyl)amide
(1287) 2-(4-amino-6-chloro-5-pyrimidinyl)-1H-benzimidazole-4-(N-6-purinyl)amide
(1288) 2-(4-amino-6-chloro-5-pyrimidinyl)-1H-benzimidazole-4-(N-6-hydroxyl-2-purinyl)amide
(1289) 2-(2-pyrrolyl)-1H-benzimidazole-4-(N-2-hydroxyl-4-pyrimidinyl)amide
(1290) 2-(2-pyrrolyl)-1H-benzimidazole-4-(N-6-purinyl)amide
(1291) 2-(2-pyrrolyl)-1H-benzimidazole-4-(N-6-hydroxyl-2-purinyl)amide
(1292) 2-(N-methyl-2-pyrrolyl)-1H-benzimidazole-4-(N-2-hydroxyl-4-pyrimidinyl)amide
(1293) 2-(N-methyl-2-pyrrolyl)-1H-benzimidazole-4-(N-6-purinyl)amide
(1294) 2-(N-methyl-2-pyrrolyl)-1H-benzimidazole-4-(N-6-hydroxyl-2-purinyl)amide
(1295) 2-(3,5-dimethyl-2-pyrrolyl)-1H-benzimidazole-4-(N-2-hydroxyl-4-pyrimidinyl)amide
(1296) 2-(3,5-dimethyl-2-pyrrolyl)-1H-benzimidazole-4-(N-6-purinyl)amide
(1297) 2-(3,5-dimethyl-2-pyrrolyl)-1H-benzimidazole-4-(N-6-hydroxyl-2-purinyl)amide
(1298) 2-(2-quinolinyl)-1H-benzimidazole-4-(N-2-hydroxyl-4-pyrimidinyl)amide
(1299) 2-(2-quinolinyl)-1H-benzimidazole-4-(N-6-purinyl)amide
(1300) 2-(2-quinolinyl)-1H-benzimidazole-4-(N-6-hydroxyl-2-purinyl)amide
(1301) 2-(3-quinolinyl)-1H-benzimidazole-4-(N-2-hydroxyl-4-pyrimidinyl)amide
(1302) 2-(3-quinolinyl)-1H-benzimidazole-4-(N-6-purinyl)amide
(1303) 2-(3-quinolinyl)-1H-benzimidazole-4-(N-6-hydroxyl-2-purinyl)amide
(1304) 2-(2-piperidinyl)-1H-benzimidazole-4-(N-2-hydroxyl-4-pyrimidinyl)amide
(1305) 2-(2-piperidinyl)-1H-benzimidazole-4-(N-6-purinyl)amide
(1306) 2-(2-piperidinyl)-1H-benzimidazole-4-(N-6-hydroxyl-2-purinyl)amide
(1307) 2-(3-piperidinyl)-1H-benzimidazole-4-(N-2-hydroxyl-4-pyrimidinyl)amide
(1308) 2-(3-piperidinyl)-1H-benzimidazole-4-(N-6-purinyl)amide
(1309) 2-(3-piperidinyl)-1H-benzimidazole-4-(N-6-hydroxyl-2-purinyl)amide
(1310) 2-(4-piperidinyl)-1H-benzimidazole-4-(N-2-hydroxyl-4-pyrimidinyl)amide
(1311) 2-(4-piperidinyl)-1H-benzimidazole-4-(N-6-purinyl)amide (1312) 2-(4-piperidinyl)-1H-benzimidazole-4-(N-6-hydroxyl-2-purinyl)amide
(1313) 2-(3-indolyl)-1H-benzimidazole-4-(N-2-hydroxyl-4-pyrimidinyl)amide
(1314) 2-(3-indolyl)-1H-benzimidazole-4-(N-6-purinyl)amide
(1315) 2-(3-indolyl)-1H-benzimidazole-4-(N-6-hydroxyl-2-purinyl)amide
(1316) 2-(2,3,4-trimethoxyphenyl)-1H-benzimidazole-4-(N-2-hydroxyl-4-pyrimidinyl)amide
(1317) 2-(2,3,4-trimethoxyphenyl)-1H-benzimidazole-4-(N-6-purinyl)amide
(1318) 2-(2,3,4-trimethoxyphenyl)-1H-benzimidazole-4-(N-6-hydroxyl-2-purinyl)amide
(1319) 2-(3-hydroxyl-4-methoxyphenyl)-1H-benzimidazole-4-(N-2-hydroxyl-4-pyrimidinyl)amide
(1320) 2-(3-hydroxyl-4-methoxyphenyl)-1H-benzimidazole-4-(N-6-purinyl)amide
(1321) 2-(3-hydroxyl-4-methoxyphenyl)-1H-benzimidazole-4-(N-6-hydroxyl-2-purinyl)amide
(1322) 2-methoxy-1H-benzimidazole-4-(N-2-hydroxyl-4-pyrimidinyl)amide
(1323) 2-methoxy-1H-benzimidazole-4-(N-6-purinyl)amide
(1324) 2-methoxy-1H-benzimidazole-4-(N-6-hydroxyl-2-purinyl)amide
(1325) 2-ethoxy-1H-benzimidazole-4-(N-2-hydroxyl-4-pyrimidinyl)amide
(1326) 2-ethoxy-1H-benzimidazole-4-(N-6-purinyl)amide
(1327) 2-ethoxy-1H-benzimidazole-4-(N-6-hydroxyl-2-purinyl)amide
(1328) 2-(2,6-dimethyl-2,6-octadienyl)-1H-benzimidazole-4-(N-2-hydroxyl-4-pyrimidinyl)amide
(1329) 2-(2,6-dimethyl-2,6-octadienyl)-1H-benzimidazole-4-(N-6-purinyl)amide
(1330) 2-(2,6-dimethyl-2,6-octadienyl)-1H-benzimidazole-4-(N-6-hydroxyl-2-purinyl)amide
(1331) 2-pyrazolyl-1H-benzimidazole-4-(N-2-hydroxyl-4-pyrimidinyl)amide
(1332) 2-pyrazolyl-1H-benzimidazole-4-(N-6-purinyl)amide
(1333) 2-pyrazolyl-1H-benzimidazole-4-(N-6-hydroxyl-2-purinyl)amide
(1334) 2-(2'-pyridyl)-1H-benzimidazole-4-(N-2-hydroxyl-4-pyrimidinyl)amide
(1335) 2-(2'-pyridyl)-1H-benzimidazole-4-(N-6-purinyl)amide
(1336) 2-(2'-pyridyl)-1H-benzimidazole-4-(N-6-hydroxyl-2-purinyl)amide
(1337) 2-(3'-pyridyl)-1H-benzimidazole-4-(N-2-hydroxyl-4-pyrimidinyl)amide
(1338) 2-(3'-pyridyl)-1H-benzimidazole-4-(N-6-purinyl)amide
(1339) 2-(3'-pyridyl)-1H-benzimidazole-4-(N-6-hydroxyl-2-purinyl)amide
(1340) 2-(4'-pyridyl)-1H-benzimidazole-4-(N-2-hydroxyl-4-pyrimidinyl)amide
(1341) 2-(4'-pyridyl)-1H-benzimidazole-4-(N-6-purinyl)amide
(1342) 2-(4'-pyridyl)-1H-benzimidazole-4-(N-6-hydroxyl-2-purinyl)amide
(1343) 2-(2'-imidazolyl)-1H-benzimidazole-4-(N-2-hydroxyl-4-pyrimidinyl)amide
(1344) 2-(2'-imidazolyl)-1H-benzimidazole-4-(N-6-purinyl)amide
(1345) 2-(2'-imidazolyl)-1H-benzimidazole-4-(N-6-hydroxyl-2-purinyl)amide
(1346) 2-(4-methoxypyridyl)-1H-benzimidazole-4-(N-2-hydroxyl-4-pyrimidinyl)amide
(1347) 2-(4-methoxypyridyl)-1H-benzimidazole-4-(N-6-purinyl)amide
(1348) 2-(4-methoxypyridyl)-1H-benzimidazole-4-(N-6-hydroxyl-2-purinyl)amide
(1349) 2-(4-dimethylaminopyridyl)-1H-benzimidazole-4-(N-2-hydroxyl-4-pyrimidinyl)amide
(1350) 2-(4-dimethylaminopyridyl)-1H-benzimidazole-4-(N-6-purinyl)amide;
(1351) 2-(4-dimethylaminopyridyl)-1H-benzimidazole-4-(N-6-hydroxyl-2-purinyl)amide
(1352) 2-(3-pyridazinyl)-1H-benzimidazole-4-(N-2-hydroxyl-4-pyrimidinyl)amide
(1353) 2-(3-pyridazinyl)-1H-benzimidazole-4-(N-6-purinyl)amide
(1354) 2-(3-pyridazinyl)-1H-benzimidazole-4-(N-6-hydroxyl-2-purinyl)amide
(1355) 2-(2-N-methyl-4-N-methylpiperazinyl)-1H-benzimidazole-4-(N-2-hydroxyl-4-pyrimidinyl)amide
(1356) 2-(2-N-methyl-4-N-methylpiperazinyl)-1H-benzimidazole-4-(N-6-purinyl)amide
(1357) 2-(2-N-methyl-4-N-methylpiperazinyl)-1H-benzimidazole-4-(N-6-hydroxyl-2-purinyl)amide
(1358) 2-(2-pyrazinyl)-1H-benzimidazole-4-(N-2-hydroxyl-4-pyrimidinyl)amide
(1359) 2-(2-pyrazinyl)-1H-benzimidazole-4-(N-6-purinyl)amide
(1360) 2-(2-pyrazinyl)-1H-benzimidazole-4-(N-6-hydroxyl-2-purinyl)amide
(1361) 2-(4-methyl-5-aminothiazolyl)-1H-benzimidazole-4-(N-2-hydroxyl-4-pyrimidinyl)amide
(1362) 2-(4-methyl-5-aminothiazolyl)-1H-benzimidazole-4-(N-6-purinyl)amide
(1363) 2-(4-methyl-5-aminothiazolyl)-1H-benzimidazole-4-(N-6-hydroxyl-2-purinyl)amide
(1364) 2-(2-thiazolyl)-1H-benzimidazole-4-(N-2-hydroxyl-4-pyrimidinyl)amide
(1365) 2-(2-thiazolyl)-1H-benzimidazole-4-(N-6-purinyl)amide
(1366) 2-(2-thiazolyl)-1H-benzimidazole-4-(N-6-hydroxyl-2-purinyl)amide
(1367) 2-(5-thiazolyl)-1H-benzimidazole-4-(N-2-hydroxyl-4-pyrimidinyl)amide
(1368) 2-(5-thiazolyl)-1H-benzimidazole-4-(N-6-purinyl)amide
(1369) 2-(5-thiazolyl)-1H-benzimidazole-4-(N-6-hydroxyl-2-purinyl)amide
(1370) 2-(2-pyridyl)-1H-benzimidazole-4-(N-2-hydroxyl-4-pyrimidinyl)amide
(1371) 2-(2-pyridyl)-1H-benzimidazole-4-(N-6-purinyl)amide
(1372) 2-(2-pyridyl)-1H-benzimidazole-4-(N-6-hydroxyl-2-purinyl)amide
(1373) 2-(2-phenyl-5-pyrimidinyl)-1H-benzimidazole-4-(N-2-hydroxyl-4-pyrimidinyl)amide
(1374) 2-(2-phenyl-5-pyrimidinyl)-1H-benzimidazole-4-(N-6-purinyl)amide
(1375) 2-(2-phenyl-5-pyrimidinyl)-1H-benzimidazole-4-(N-6-hydroxyl-2-purinyl)amide
(1376) 2-(4-amino-6-chloro-5-pyrimidinyl)-1H-benzimidazole-4-(N-2-hydroxyl-4-pyrimidinyl)amide
(1377) 2-(4-amino-6-chloro-5-pyrimidinyl)-1H-benzimidazole-4-(N-6-purinyl)amide
(1378) 2-(4-amino-6-chloro-5-pyrimidinyl)-1H-benzimidazole-4-(N-6-hydroxyl-2-purinyl)amide (1379) 2-(2-pyrrolyl)-1H-benzimidazole-4-(N-2-hydroxyl-4-pyrimidinyl)amide
(1380) 2-(2-pyrrolyl)-1H-benzimidazole-4-(N-6-purinyl)amide
(1381) 2-(2-pyrrolyl)-1H-benzimidazole-4-(N-6-hydroxyl-2-purinyl)amide
(1382) 2-(N-methyl-2-pyrrolyl)-1H-benzimidazole-4-(N-2-hydroxyl-4-pyrimidinyl)amide
(1383) 2-(N-methyl-2-pyrrolyl)-1H-benzimidazole-4-(N-6-purinyl)amide
(1384) 2-(N-methyl-2-pyrrolyl)-1H-benzimidazole-4-(N-6-hydroxyl-2-purinyl)amide
(1385) 2-(3,5-dimethyl-2-pyrrolyl)-1H-benzimidazole-4-(N-2-hydroxyl-4-pyrimidinyl)amide
(1386) 2-(3,5-dimethyl-2-pyrrolyl)-1H-benzimidazole-4-(N-6-purinyl)amide
(1387) 2-(3,5-dimethyl-2-pyrrolyl)-1H-benzimidazole-4-(N-6-hydroxyl-2-purinyl)amide
(1388) 2-(2-quinolinyl)-1H-benzimidazole-4-(N-2-hydroxyl-4-pyrimidinyl)amide
(1389) 2-(2-quinolinyl)-1H-benzimidazole-4-(N-6-purinyl)amide
(1390) 2-(2-quinolinyl)-1H-benzimidazole-4-(N-6-hydroxyl-2-purinyl)amide
(1391) 2-(2-piperidinyl)-1H-benzimidazole-4-(N-2-hydroxyl-4-pyrimidinyl)amide
(1392) 2-(2-piperidinyl)-1H-benzimidazole-4-(N-6-purinyl)amide
(1393) 2-(2-piperidinyl)-1H-benzimidazole-4-(N-6-hydroxyl-2-purinyl)amide
(1394) 2-(4-piperidinyl)-1H-benzimidazole-4-(N-2-hydroxyl-4-pyrimidinyl)amide
(1395) 2-(4-piperidinyl)-1H-benzimidazole-4-(N-6-purinyl)amide
(1396) 2-(4-piperidinyl)-1H-benzimidazole-4-(N-6-hydroxyl-2-purinyl)amide
(1397) 2-(3-indolyl)-1H-benzimidazole-4-(N-2-hydroxyl-4-pyrimidinyl)amide
(1398) 2-(3-indolyl)-1H-benzimidazole-4-(N-6-purinyl)amide
(1399) 2-(3-indolyl)-1H-benzimidazole-4-(N-6-hydroxyl-2-purinyl)amide
(1400) 2-(2,3,4-trimethoxyphenyl)-1H-benzimidazole-4-(N-2-hydroxyl-4-pyrimidinyl)amide
(1401) 2-(2,3,4-trimethoxyphenyl)-1H-benzimidazole-4-(N-6-purinyl)amide
(1402) 2-(2,3,4-trimethoxyphenyl)-1H-benzimidazole-4-(N-6-hydroxyl-2-purinyl)amide
(1403) 2-(3-hydroxyl-4-methoxyphenyl)-1H-benzimidazole-4-(N-2-hydroxyl-4-pyrimidinyl)amide
(1404) 2-(3-hydroxyl-4-methoxyphenyl)-1H-benzimidazole-4-(N-6-purinyl)amide
(1405) 2-(3-hydroxyl-4-methoxyphenyl)-1H-benzimidazole-4-(N-6-hydroxyl-2-purinyl)amide
(1406) 2-(2-bromo-5-pyridine)-1H-benzimidazole-4-(N-2-hydroxyl-4-pyrimidinyl)amide
(1407) 2-(2-bromo-5-pyridine)-1H-benzimidazole-4-(N-6-purinyl)amide
(1408) 2-(2-bromo-5-pyridine)-1H-benzimidazole-4-(N-6-hydroxyl-2-purinyl)amide
(1409) 2-(2-amino-3-pyridine)-1H-benzimidazole-4-(N-2-hydroxyl-4-pyrimidinyl)amide
(1410) 2-(2-amino-3-pyridine)-1H-benzimidazole-4-(N-6-purinyl)amide
(1411) 2-(2-amino-3-pyridine)-1H-benzimidazole-4-(N-6-hydroxyl-2-purinyl)amide
(1412) 2-(2-pyrrolidine-1-yl-5-pyrimidinyl)-1H-benzimidazole-4-(N-2-hydroxyl-4-pyrimidinyl)amide
(1413) 2-(2-pyrrolidine-1-yl-5-pyrimidinyl)-1H-benzimidazole-4-(N-6-purinyl)amide
(1414) 2-(2-pyrrolidine-1-yl-5-pyrimidinyl)-1H-benzimidazole-4-(N-6-hydroxyl-2-purinyl)amide
(1415) 2-(2-piperidine-1-yl-5-pyrimidinyl)-1H-benzimidazole-4-(N-2-hydroxyl-4-pyrimidinyl)amide
(1416) 2-(2-piperidine-1-yl-5-pyrimidinyl)-1H-benzimidazole-4-(N-6-purinyl)amide
(1417) 2-(2-piperidine-1-yl-5-pyrimidinyl)-1H-benzimidazole-4-(N-6-hydroxyl-2-purinyl)amide
(1418) 2-(2-cyclopropylamino)-1H-benzimidazole-4-(N-2-hydroxyl-4-pyrimidinyl)amide
(1419) 2-(2-cyclopropylamino-5-pyrimidinyl)-1H-benzimidazole-4-(N-6-purinyl)amide
(1420) 2-(2-cyclopropylamino-5-pyrimidinyl)-1H-benzimidazole-4-(N-6-hydroxyl-2-purinyl)amide
(1421) 2-(1,3-dimethyl-5-chloro-4-pyrazolyl)-1H-benzimidazole-4-(N-2-hydroxyl-4-pyrimidinyl)amide
(1422) 2-(1,3-dimethyl-5-chloro-4-pyrazolyl)-1H-benzimidazole-4-(N-6-purinyl)amide
(1423) 2-(1,3-dimethyl-5-chloro-4-pyrazolyl)-1H-benzimidazole-4-(N-6-hydroxyl-2-purinyl)amide
(1424) 2-(1,3-dimethyl-5-chloro-4-pyrazolyl)-1H-benzimidazole-4-(N-6-hydroxyl-2-purinyl)amide.

Preferably, the pharmaceutically acceptable salts of benzimidazole-4-carboxamide derivatives are inorganic acid salts thereof selected from sulfate, hydrochloride, nitrate, phosphate or boratethe, or organic acid salts thereof selected from citrate, succinate, tartrate, lactate or mesylate.

Another purpose of the present invention is to provide anti-cosxackie-viruses pharmaceutical compositions. The pharmaceutical compositions comprise a therapeutically effective amount of the benzimidazole-4-carboxamide derivatives or a pharmaceutically acceptable salts thereof according to any one of claims 1~7, and one or more pharmaceutically acceptable thinner, excipient and/or inert carrier.

A further purpose of the present invention is to provide uses of the benzimidazole-4-carboxamide derivatives or a pharmaceutically acceptable salts for for preparation of antivirus medications, wherein the viruses are Coxsackie Virus, echovirus and enterovirus which belong to picornaviridae.

Another purpose of the present invention is to provide a method of the benzimidazole-4-carboxamide derivatives or a pharmaceutically acceptable salt thereof as shown in Formula (I), comprising the following steps:

(1) 2-aminoacetyl-3-nitrobenzoic acid is Undergoing Reactions of Ammonolysis, Hoffman Degradation and Reduction in Turn, to Produce 2,3-diamino benzoic acid (2) 2,3-diamino benzoic acid is Condensed with Aldehydes X—CHO in the Presence of Catalyst of Cupric Acetate, to Produce benzimidazole-4-carboxylic acid of Formula (II)

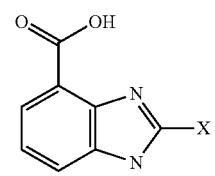

(II)

(3) benzimidazole-4-carboxylic acid is Reacted with thionyl chloride to Produce acyl chloride, and then Condensing the acyl chloride and an amine NH$_2$—Y, to Produce the benzimidazole-4-carboxamide Derivative of Formula (I)

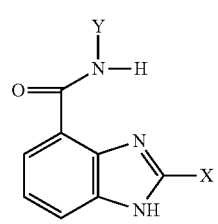

(I)

The above reaction conditions are as follows: benzimidazole-4-carboxylic acid is reated with thionyl chloride at temperature of 0~80° C. in a molar molecular ratio of thionyl chloride to benzimidazole-4-carboxylic acid is 1~20 times, to produce benzimidazole-4-carbonyl chloride, and then benzimidazole-4-carbonyl chloride is reacted with an amine in an organic solvent at temperature of 0~100° C. to produce benzimidazole-4-carboxamide derivatives. Wherein the organic solvent comprises dichloroethane, 1,1,2-trichloroethane, chloroform, tetrachloroethylene, benzene, toluene, xylene, chlorobenzene or dichlorobenzene, and so on.

The benzimidazole-4-carboxamide derivatives or a pharmaceutically acceptable salt thereof of the present invention may be administered orally or not. The dosage varies with different drugs, the dosage is 10~300 mg per day in general conditions.

DETAILED DESCRIPTION OF THE INVENTION

Figure 1:
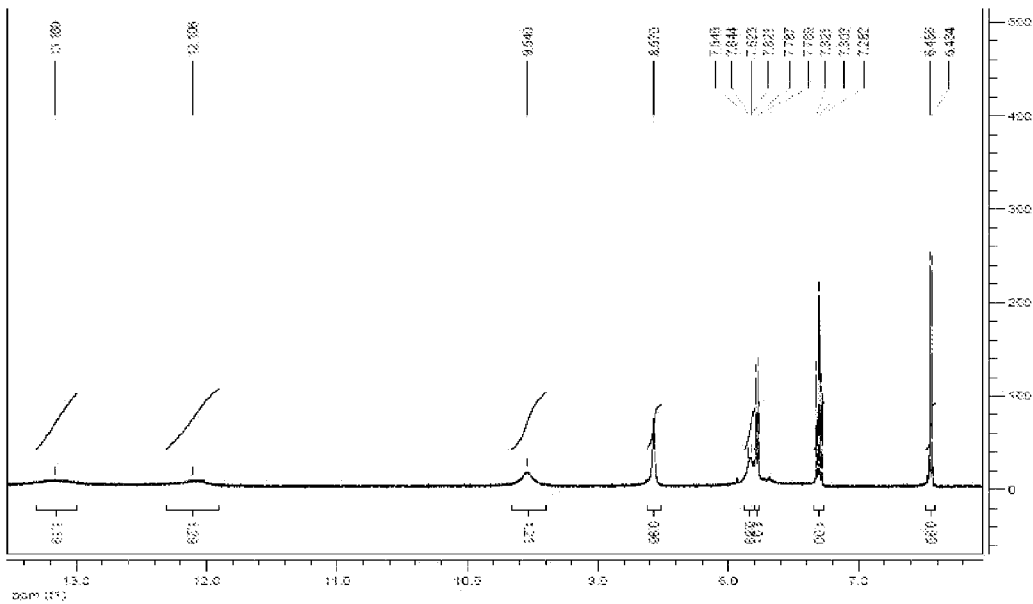
FIG. 1 shows $^1$HNMR spectrogram of 2-(2,3,4-trihydroxyphenyl)-1H-benzimidazole-4-carboxylic acid in Example 9.

Hereafter, the present invention will be described specifically with reference to examples. The examples are given only for illustration of the technical solution of the present invention and should not be construed to limit the present invention.

The method of preparing for benzimidazole-4-amide derivatives of the present invention is as follows: using 2-aminoacetyl-3-nitrobenzoic acid as an initiating raw material, 2-aminoacetyl-3-nitrobenzoic acid in turn is undergoing ammonolysis, Hoffman degradation and reduction, to produce 2,3-diamino benzoic acid; and then condensing 2,3-diamino benzoic acid and aldehydes X—CHO in the presence of catalyst of cupric acetate, to produce benzimidazole-4-carboxylic acid; and then reacting benzimidazole-4-carboxylic acid with thionyl chloride to produce acyl chloride, and then condensing the acyl chloride and an amine NH$_2$—Y, to produce the benzimidazole-4-carboxamide derivative.

EXAMPLE 1

Synthesis of 2.3-diamino benzoic acid

Step 1: Synthesis of 2-aminoacetyl-3-nitrobenzoic acid 30 g of 3-nitro phthalic anhydride is added into 45 ml of concentrated ammonia with 28 g/g % concentration; and heat it to 60° C. under stiffing for 30 minutes; and then to cool it to 10° C. till precipitate needle shape crystals; and to acidize the needle shape crystals with concentrated chlorhydric acid to produce white solids; and then to filter and dry it to obtain 29.4 g of 2-aminoacetyl-3-nitrobenzoic acid.

Step 2: Synthesis of 2-amino-3-nitrobenzoic acid 13.9 g of bromine is dropped into 100 ml of sodium hydroxide aqueous-solution containing 7.3 g of sodium hydroxide to a solution. Then 17 g of 2-aminoacetyl-3-nitrobenzoic acid is added into the above solution; and to heat it to 80° C. to precipitate a large amount of red solids; to filter and then acidize it with the concentrated chlorhydric acid to produce yellow solid products; to dry it to obtain 13.7 g of 2-amino-3-nitrobenzoic acid; and then recrystallize the yellow solid products by adding hot water to obtain the yellow needle shape crystals.

Step 3: Synthesis of 2,3-diaminobenzoic acid 3 g of the above mentioned 2-amino-3-nitrobenzoic acid is added into 30 ml of methanol, 20% sodium hydroxide aqueous solution with the same molar as 2-amino-3-nitrobenzoic acid is dropped into the above methanol solution till dissolve completely. 0.2 g of Raney nickel at the moment is added in to the methanol solution, and to heat it to 65° C. and reflux it at the temperature; and then drop 80 g/g % hydrazine hydrate (about 1.5 equivalent weight×1.1) till the yellow disappears completely. Hot Raney nickel is filtered; and then heat and concentrate the mother liquid and acidize it with the concentrated chlorhydric acid to produce 2.3 g of red 2,3-diaminobenzoic acid; afterwards isolate and purify the crude product of red 2,3-diaminobenzoic acid by column chromatography.

EXAMPLE 2

Synthesis of 2-(5-nitro-2-thienyl)-1H-benzimidazole-4-carboxylic acid 2.0 g of 2,3-diaminobenzoic acid is dissolved into 60 ml of methanol, and methanol solution of 5-nitrofurfural is added into the methanol under stirring. Then 0.5 g of cupric acetate (Cu(Ac)$_2$.H$_2$O) is added into the above methanol, and then to heat and reflux it; and then to filter hot solution after 2,3-diaminobenzoic acid disappears. 20% sodium sulfide aqueous solution is added into the filtrate and heat it till boiling; and then filtrate the copper sulfide deposition while it is hot;

and then to evaporate the filtrate to dry, purify it through column chromatography to obtain 2-(5-nitro-2-thienyl)-1H-benzimidazole-4-carboxylic acid. The yield is about 65%.

EXAMPLES 3-20

Synthesis of Intermediates of benzimidazole-4-carboxylic acid

Synthesize the benzimidazole-4-carboxylic acid as shown in Formula (II) according to the method of Example 2. The difference is to use aldehydes with different X group as listed in Table 1.

TABLE 1

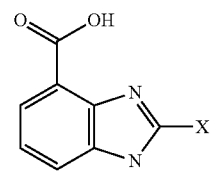

(II)

| No. of products | Compounds | X | Yield % |
|---|---|---|---|
| 4 | 2-(2-pyrimidinyl)-1H-benzimidazole-4-carboxylic acid | pyrimidin-2-yl | 75 |
| 5 | 2-(2-thienyl)-1H-benzimidazole-4-carboxylic acid | thien-2-yl | 76 |
| 6 | 2-methyl-1H-benzimidazole-4-carboxylic acid | —CH3 | 72 |
| 7 | 2-phenyl-1H-benzimidazole-4-carboxylic acid | phenyl | 80 |
| 8 | 2-(4-(dimethylamino)-phenyl)-1H-benzimidazole-4-carboxylic acid | 4-(dimethylamino)phenyl | 75 |
| 9 | 2-(2,3,4-trihydroxyphenyl)-1H-benzimidazole-4-carboxylic acid | 2,3,4-trihydroxyphenyl | 65 |
| 10 | 2-(4-methoxy-2-pyridyl)-1H-benzimidazole-4-carboxylic acid | 4-methoxy-pyridin-2-yl | 68 |

TABLE 1-continued (II)

| No. of products | Compounds | X | Yield % |
|---|---|---|---|
| 11 | 2-(6-methoxy-2-pyridyl)-1H-benzimidazole-4-carboxylic acid | 6-methoxy-pyridin-2-yl | 70 |
| 12 | 2-(4-(dimethylamino)-2-pyridyl)-1H-benzimidazole-4-carboxylic acid | 4-(dimethylamino)pyridin-2-yl | 75 |
| 13 | 2-(3-pyridazinyl)-1H-benzimidazole-4-carboxylic acid | pyridazin-3-yl | 60 |
| 14 | 2-(2-piperazinyl)-1H-benzimidazole-4-carboxylic acid | piperazin-2-yl | 61 |
| 15 | 2-(5-amino-4-methyl-2-thiazolyl)-1H-benzimidazole-4-carboxylic acid | 5-amino-4-methyl-thiazol-2-yl | 70 |
| 16 | 2-(3-quinolinyl)-1H-benzimidazole-4-carboxylic acid | quinolin-3-yl | 63 |
| 17 | 2-(2-pyrrolyl)-1H-benzimidazole-4-carboxylic acid | pyrrol-2-yl | 75 |
| 18 | 2-(3-indolyl)-1H-benzimidazole-4-carboxylic acid | indol-3-yl | 71 |
| 19 | 2-(2-piperidinyl)-1H-benzimidazole-4-carboxylic acid | piperidin-2-yl | 68 |

TABLE 1-continued (II)

[Structure: benzimidazole-4-carboxylic acid with 2-X substituent]

| No. of products | Compounds | X | Yield % |
|---|---|---|---|
| 20 | 2-(2-quinolinyl)-1H-benzimidazole-4-carboxylic acid | [2-methylquinolinyl group] | 70 |

Structure Identification of Products:

(4)
2-(2-pyrimidinyl)-1H-benzimidazole-4-carboxylic acid $^1$HNMR (DMSO, 400 MHz) δ: 7.43-7.45(t,1H), 7.67-7.80 (t,1H), 7.90-7.91(d,1H), 7.93-7.94(d,1H), 9.08-9.09(d,1H), 9.10-9.12(d,1H);

(5) 2-(2-thienyl)-1H-benzimidazole-4-carboxylic acid $^1$HNMR (DMSO, 400 MHz) δ: 7.15-7.18(t,1H), 7.41-7.45 (t,1H), 7.68-7.70(d,1H), 7.85(d,1H), 7.89-7.91(d,1H), 7.93-7.94(d,1H);

(6) 2-methyl-1H-benzimidazole-4-carboxylic acid $^1$HNMR (DMSO, 400 MHz) δ: 2.51(s,3H), 7.41-7.45(t, 1H), 7.89-7.91(d,1H), 7.93-7.94(d,1H);

(7) 2-phenyl-1H-benzimidazole-4-carboxylic acid $^1$HNMR (DMSO, 400 MHz) δ: 7.41-7.45(t,1H), 7.38-7.42 (t,1H) 7.50-7.53(t,2H), 7.89-7.91(d,1H), 7.93-7.94(d,1H), 8.28-8.30(d,2H);

(8) 2-(4-(dimethylamino)-phenyl)-1H-benzimidazole-4-carboxylic acid $^1$HNMR (DMSO, 400 MHz) δ: 3.06(s,6H) 6.82-6.84(d, 2H), 7.41-7.45(t,1H), 7.89-7.91(d,1H), 7.93-7.94(d,1H), 7.97-7.99(d,2H);

(9) 2-(2,3,4-trihydroxyphenyl)-1H-benzimidazole-4-carboxylic acid (Refer to FIG. 1)

$^1$HNMR (DMSO, 400 MHz) δ: 6.43-6.46 (d, 1H), 7.28-7.32 (t, 1H), 7.77-7.79 (d, 1H), 7.82-7.85 (m, 1H), 8.57(s, 1H), 9.54 (s, 1H), 12.11(s, 1H), 13.16(s, 1H);

(10) 2-(4-(methoxy)-2-pyridyl)-1H-benzimidazole-4-carboxylic acid $^1$HNMR (DMSO, 400 MHz) δ: 3.83(s,3H), 7.31(s,1H), 7.41-7.45(t,1H), 7.59-7.61(d,1H), 7.89-7.91(d,1H), 7.93-7.94(d,1H), 8.48-8.49(d,1H);

(11) 2-(6-methoxy-2-pyridyl)-1H-benzimidazole-4-carboxylic acid $^1$HNMR (DMSO, 400 MHz) δ: 3.80(s,3H), 6.50-6.51(d, 1H), 7.38-7.39(d,1H), 7.41-7.45(t,1H), 7.72-7.75(t,1H), 7.89-7.91(d,1H), 7.93-7.94(d,1H);

(12) 2-(4-(dimethylamino)-2-pyridyl)-1H-benzimidazole-4-carboxylic acid $^1$HNMR (DMSO, 400 MHz) δ: 2.68(s,6H), 7.16-7.18(d, 1H), 7.41-7.45(t,1H), 7.71(s,1H), 7.89-7.91(d,1H), 7.93-7.94 (d,1H), 8.05-8.07(d,1H);

(13)
2-(3-pyridazinyl)-1H-benzimidazole-4-carboxylic acid $^1$HNMR (DMSO, 400 MHz) δ: 7.41-7.45(t,1H), 7.61-7.63 (t,1H), 7.89-7.91(d,1H), 7.93-7.94(d,1H), 8.06-8.08(d,1H), 9.34-9.37(d,1H);

(14)
2-(2-piperazinyl)-1H-benzimidazole-4-carboxylic acid $^1$HNMR (DMSO, 400 MHz) δ: 1.91-1.95(m,2H), 2.60-2.62(m,1H), 2.65-2.66(m,1H), 2.67-2.70(m,1H), 2.72-2.75 (m,1H), 2.84-2.88(m,1H), 3.09-3.14(m,1H), 4.14-4.19(m, 1H), 7.41-7.45(t,1H), 7.89-7.91(d,1H), 7.93-7.94(d,1H);

(15) 2-(5-amino-4-methyl-2-thiazolyl)-1H-benzimidazole-4-carboxylic acid $^1$HNMR (DMSO, 400 MHz) δ: 1.03-1.09(d,3H), 3.70-3.73 (m,1H), 4.17-4.22(m,1H), 5.11-5.13(d,2H), 7.41-7.45(t,1H), 7.89-7.91(d,1H), 7.93-7.94(d,1H);

(16)
2-(3-quinolinyl)-1H-benzimidazole-4-carboxylic acid $^1$HNMR (DMSO, 400 MHz) δ: 7.41-7.45(t,1H), 7.60-7.65 (t,1H), 7.78-7.80(t,1H), 7.89-7.91(d,1H), 7.93-7.94(d,1H), 7.97-7.99(d,1H), 8.06-8.09(d,1H), 8.22(s,1H), 8.57(s,1H);

(17) 2-(2-pyrrolyl)-1H-benzimidazole-4-carboxylic acid $^1$HNMR (DMSO, 400 MHz) δ: 6.15-6.17(t,1H), 6.39-6.40 (d,1H), 6.95-6.98(t,1H), 7.41-7.45(t,1H), 7.89-7.91(d,1H), 7.93-7.94(d,1H);

(18) 2-(3-indolyl)-1H-benzimidazole-4-carboxylic acid $^1$HNMR (DMSO, 400 MHz) δ: 7.01-7.05(t,1H), 7.31-7.34 (t,1H), 7.41-7.45(t,1H), 7.54-7.56(d,1H), 7.89-7.91(d,1H), 7.93-7.94(d,1H), 8.14-8.16(d,1H), 8.60(s,1H);

(19)
2-(2-piperidinyl)-1H-benzimidazole-4-carboxylic acid $^1$HNMR (DMSO, 400 MHz) δ: 1.47-1.49(m,2H), 1.50-1.55(m,2H), 1.67-1.92(m,2H), 4.01-4.03(m,1H), 7.41-7.45 (t,1H), 7.89-7.91(d,1H), 7.93-7.94(d,1H);

(20)
2-(2-quinolinyl)-1H-benzimidazole-4-carboxylic acid

¹HNMR (DMSO, 400 MHz) δ: 1.43-1.45(m,1H), 1.46-1.47(m,1H), 1.49-1.51(m,1H), 1.53-1.55(m,1H), 1.67-1.70 (m,1H), 1.92-1.96(m,1H), 2.69-2.71(m,1H), 2.78-2.80(m, 1H), 4.01-4.03(m,1H), 7.41-7.45(t,1H), 7.89-7.91(d,1H), 7.93-7.94(d,1H)

EXAMPLE 21

Figure 2:
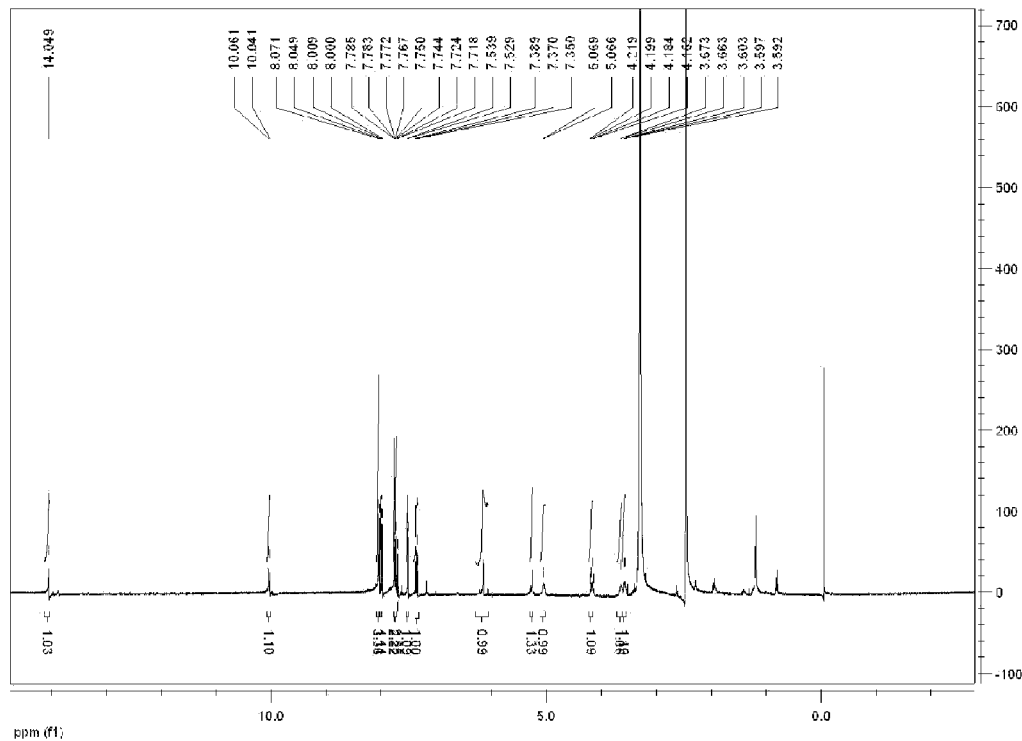
FIG. 2 shows $^1$HNMR spectrogram of 2-(5-nitro-2-thienyl)-1H-benzimidazole-4-(N-(1-hydroxymethyl-2-p-nitrophenylhydroxyethyl))amide in Example 21.

Synthesis of (L)-2-(5-nitro-2-thienyl)-1H-benzimidazole-4-(N-(1-hydroxymethyl-2-p-nitrophenylhydroxyethyl)amide 1.0 g of 2-(5-nitro-2-thienyl)-1H-benzimidazole-4-carboxylic acid in Example 2 is added into 15 ml of thionyl chloride and is reacted for 60 minutes, after end of the reaction completely, (L)-2-amino-1-p-nitrophenyl-1,3-propylene glycol (1.1 eq.) is added into the reaction mixture under stirring for 2 hours at the room temperature; and then filter the inorganic salt, evaporate the solvent to dry and obtain the final product of 2-(5-nitro-2-thienyl)-1H-benzimidazole-4-(N-(1-hydroxymethyl-2-p-nitrophenylhydroxyethyl)amide. The yield is about 93%. ¹HNMR spectrum is shown in FIG. 2.
Structure Identification of Product:
¹HNMR(DMSO,400 MHz) δ: 3.59-3.60(m,1H),3.65-3.67 (t,1H),4.16-4.22(q,1H),5.07-5.08(t,1H),5.27-5.28(t,1H), 6.16-6.17(d,1H),7.35-7.39(t,1H),7.53-7.54(d,1H),7.72-7.75 (m,2H),7.77-7.79(m,2H),8.00-8.01(d,1H),8.05-8.07(d,3H), 10.04-10.06(d,2H),14.05(s,1H).

EXAMPLE 22

Synthesis of 2-(5-nitro-2-thienyl)-1H-benzimidazole-4-(N-(1-methyl-2-p-chlorophenylhydroxyethyl)amide 1.0 g of 2-(5-nitro-2-thienyl)-1H-benzimidazole-4-carboxylic acid is added into 15 ml of thionyl chloride; and to heat and reflux it for 60 minutes. After end of the reaction, 2-amino-1-p-chlorophenyl-1-propanol (1.1 eq) is dissolved into tetrahydrofuran, and then drop acyl chloride to the above tetrahydrofuran mixture under stirring at the room temperature and then filter inorganic salt, evaporate the solvent to dry, and then isolate the mixture through column chromatography to obtain 2-(5-nitro-2-thienyl)-1H-benzimidazole-4-(N-(1-hydroxymethyl-2-p-nitrophenylhydroxyethyl)amide. The yield is about 92%.
Structure Identification of Product:
¹HNMR (DMSO, 400 MHz) δ: 1.10-1.16(d,3H), 3.26-3.28 (m,1H), 3.64-3.66(d,1H), 4.71-4.74(m,1H), 7.28-7.30(d, 2H), 7.35-7.38(d,2H), 7.41-7.45(t,1H), 7.56-7.58(d,1H), 7.62-7.68(d,1H), 7.89-7.91(d,1H), 7.93-7.94(d,1H).

EXAMPLES 23-67

Use the same process as Example 22 to synthesize the compound as shown in Table 2.

TABLE 2

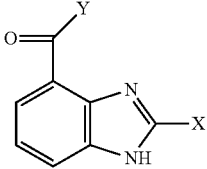

| No. | Compounds | X | Y | Field % |
|---|---|---|---|---|
| 23 | 2-(2-pyridyl)-1H-benzimidazole-4-N-hydroxyethylamide | 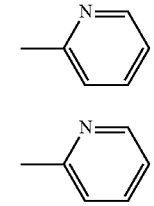 | —NHCH2CH2OH | 88 |
| 24 | 2-(2-pyridyl)-1H-benzimidazole-4-N-o-hydroxyphenylcarboxylamide | 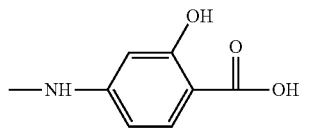 | 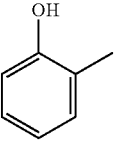 | 80 |
| 25 | 2-(2-hydroxyphenyl)-1H-benzimidazole-4-(N-o-fluorophenyl)amide | 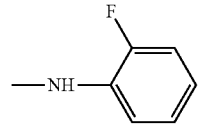 | 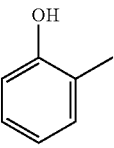 | 82 |
| 26 | (L)-2-(2-hydroxyphenyl)-1H-benzimidazole-4-[N-(1-hydroxyl-2-p-nitrophenylhydroxyethyl)]amide | 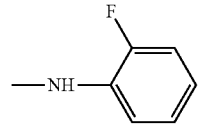 | 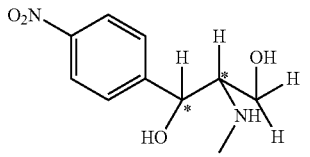 | 91 |

TABLE 2-continued

| No. | Compounds | X | Y | Field % |
|---|---|---|---|---|
| 27 | 2-(5-nitro-2-thienyl)-1H-benzimidazole-4-(N-6-hydroxyl-2-purinyl)amide | 5-nitro-2-thienyl | 6-hydroxy-2-purinylamino | 90 |
| 28 | 2-(5-nitro-2-thienyl)-1H-benzimidazole-4-(N-o-fluorophenyl)amide | 5-nitro-2-thienyl | o-fluorophenylamino | 89 |
| 29 | 2-(3,4,5-trihydroxyphenyl)-1H-benzimidazole-4-(N-o-fluorophenyl)amide | 3,4,5-trihydroxyphenyl | o-fluorophenylamino | 93 |
| 30 | 2-(3,4,5-trihydroxyphenyl)-1H-benzimidazole-4-(N-hydroxyethyl)amide | 3,4,5-trihydroxyphenyl | —NHCH2CH2OH | 86 |
| 31 | 2-(2-piperidinyl)-1H-benzimidazole-4-(4-N'-ethyl-N-piperazinyl)amide | 2-piperidinyl | 4-N'-ethyl-N-piperazinyl | 95 |
| 32 | 2-(2-pyridyl)-1H-benzimidazole-4-(4-N'-ethyl-N-piperazinyl)amide | 2-pyridyl | 4-N'-ethyl-N-piperazinyl | 94 |
| 33 | (L)-2-(2,6-dimethyl-2,6-octadienyl)-1H-benzimidazole-4-[N-(1-hydroxymethyl-2-p-nitrophenylhydroxyethyl)]amide | 2,6-dimethyl-2,6-octadienyl | 1-hydroxymethyl-2-p-nitrophenylhydroxyethylamino | 90 |
| 34 | (L)-2-(2,6-dimethyl-2,6-octadienyl)-1H-benzimidazole-4-[N-(1-hydroxymethyl-2-p-aminophenylhydroxyethyl)]amide | 2,6-dimethyl-2,6-octadienyl | 1-hydroxymethyl-2-p-aminophenylhydroxyethylamino | 89 |

TABLE 2-continued

| No. | Compounds | X | Y | Field % |
|---|---|---|---|---|
| 35 | 2-(2,6-dimethyl-2,6-octadienyl)-1H-benzimidazole-4-[N-(1-methyl-2-p-chlorophenylhydroxyethyl)]amide | 2,6-dimethyl-2,6-octadienyl | 1-methyl-2-(p-chlorophenyl)-2-hydroxyethylamino | 90 |
| 36 | 2-(2,6-dimethyl-2,6-octadienyl)-1H-benzimidazole-4-(N-N'-piperidinyl)amide | 2,6-dimethyl-2,6-octadienyl | N'-piperidinylamino | 90 |
| 37 | 2-(2,6-dimethyl-2,6-octadienyl)-1H-benzimidazole-4-(N-2-piperazinyl)amide | 2,6-dimethyl-2,6-octadienyl | 2-piperazinylamino | 89 |
| 38 | 2-(2,6-dimethyl-2,6-octadienyl)-1H-benzimidazole-4-(N-2'-benzimidazolyl)amide | 2,6-dimethyl-2,6-octadienyl | 2'-benzimidazolylamino | 91 |
| 39 | 2-(2,6-dimethyl-2,6-octadienyl)-1H-benzimidazole-4-(N-o-aminophenyl)amide | 2,6-dimethyl-2,6-octadienyl | o-aminophenylamino | 88 |
| 40 | 2-(2,6-dimethyl-2,6-octadienyl)-1H-benzimidazole-4-(N-5-benzimidazolonyl)amide | 2,6-dimethyl-2,6-octadienyl | 5-benzimidazolonylamino | 87 |

TABLE 2-continued

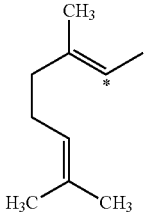

| No. | Compounds | X | Y | Field % |
|---|---|---|---|---|
| 41 | 2-(2,6-dimethyl-2,6-octadienyl)-1H-benzimidazole-4-(N-4'-carbonamido-5'-imidazolyl)amide | 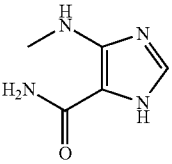 | 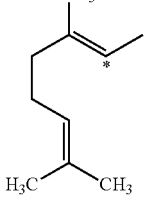 | 90 |
| 42 | 2-(2,6-dimethyl-2,6-octadienyl)-1H-benzimidazole-4-(N-4'-pyrazolyl)amide | 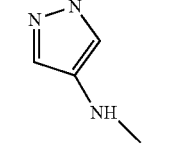 | 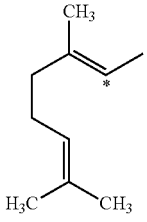 | 87 |
| 43 | 2-(2,6-dimethyl-2,6-octadienyl)-1H-benzimidazole-4-(N-(N'-piperazinyl))amide | 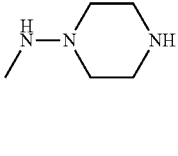 | 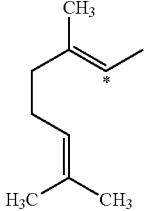 | 87 |
| 44 | 2-(2,6-dimethyl-2,6-octadienyl)-1H-benzimidazole-4-(N-2-pyrazinyl)amide | 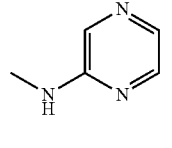 | 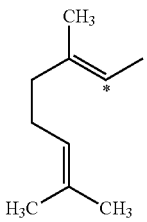 | 90 |
| 45 | 2-(2,6-dimethyl-2,6-octadienyl)-1H-benzimidazole-4-(N-2-pyrimidinyl)amide | 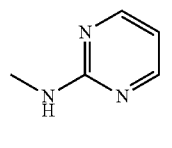 | 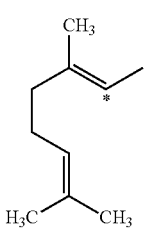 | 91 |
| 46 | 2-(2,6-dimethyl-2,6-octadienyl)-1H-benzimidazole-4-(N-2-pyridyl)amide | 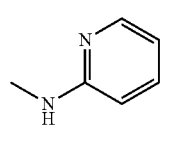 | | 93 |

TABLE 2-continued

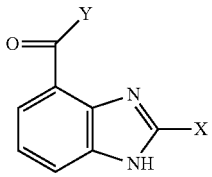

| No. | Compounds | X | Y | Field % |
|---|---|---|---|---|
| 47 | 2-(2,6-dimethyl-2,6-octadienyl)-1H-benzimidazole-4-(N-4-methyl-5-thiazolyl)amide | 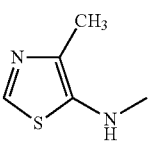 | 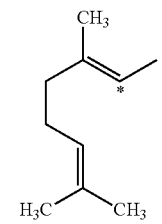 | 90 |
| 48 | 2-(2,6-dimethyl-2,6-octadienyl)-1H-benzimidazole-4-(N-2,4-dihydroxyl-5-pyrimidinyl)amide | 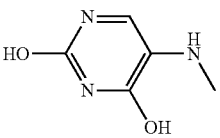 | 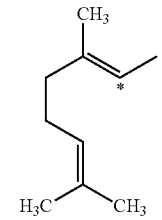 | 85 |
| 49 | 2-(2,6-dimethyl-2,6-octadienyl)-1H-benzimidazole-4-(N-4,6-dimethoxy-2-pyrimidinyl)amide | 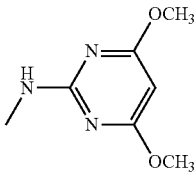 | 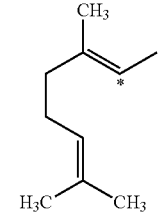 | 94 |
| 50 | 2-(2,6-dimethyl-2,6-octadienyl)-1H-benzimidazole-4-(N-4-chloro-6-amino-2-pyrimidinyl)amide | 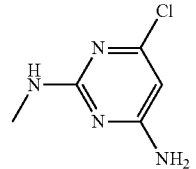 | 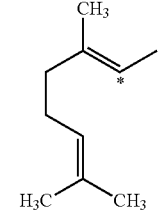 | 88 |
| 51 | 2-(2,6-dimethyl-2,6-octadienyl)-1H-benzimidazole-4-(N-4,6-dichloro-5-pyrimidinyl)amide | 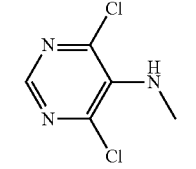 | 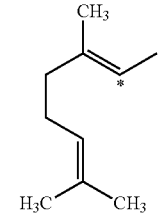 | 90 |
| 52 | 2-(2,6-dimethyl-2,6-octadienyl)-1H-benzimidazole-4-(N-o-fluorophenyl)amide | | 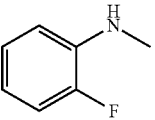 | 93 |

TABLE 2-continued

| No. | Compounds | X | Y | Field % |
|---|---|---|---|---|
| 53 | 2-(2,6-dimethyl-2,6-octadienyl)-1H-benzimidazole-4-(N-2-hydroxyl-4-pyrimidinyl)amide | 2,6-dimethyl-2,6-octadienyl | 2-hydroxy-4-pyrimidinylamino | 86 |
| 54 | 2-(2,6-dimethyl-2,6-octadienyl)-1H-benzimidazole-4-(N-6-purinyl)amide | 2,6-dimethyl-2,6-octadienyl | 6-purinylamino | 90 |
| 55 | 2-(2,6-dimethyl-2,6-octadienyl)-1H-benzimidazole-4-(N-6-hydroxy-2-purinyl)amide | 2,6-dimethyl-2,6-octadienyl | 6-hydroxy-2-purinylamino | 91 |
| 56 | (L)-2-(2-thienyl)-1H-benzimidazole-4-[N-(1-hydroxymethyl-2-p-nitrophenylhydroxyethyl)]amide | 2-thienyl | 1-hydroxymethyl-2-p-nitrophenylhydroxyethylamino | 90 |
| 57 | (L)-2-(2-thienyl)-1H-benzimidazole-4-[N-(1-hydroxymethyl-2-p-aminophenylhydroxyethyl)]amide | 2-thienyl | 1-hydroxymethyl-2-p-aminophenylhydroxyethylamino | 92 |
| 58 | 2-(2-thienyl)-1H-benzimidazole-4-[N-(1-methyl-2-p-chlorophenylhydroxyethyl)]amide | 2-thienyl | 1-methyl-2-p-chlorophenylhydroxyethylamino | 92 |
| 59 | 2-(2-thienyl)-1H-benzimidazole-4-(N-N'-piperidinyl)amide | 2-thienyl | N'-methyl-piperidinylamino | 91 |

TABLE 2-continued

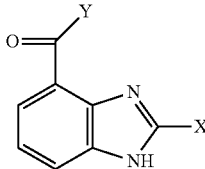

| No. | Compounds | X | Y | Field % |
|---|---|---|---|---|
| 60 | 2-(2-thienyl)-1H-benzimidazole-4-(N-2-piperazinyl)amide | 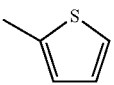 | 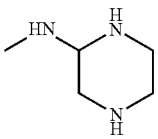 | 88 |
| 61 | 2-(2-thienyl)-1H-benzimidazole-4-(N-2'-benzimidazolyl)amide | 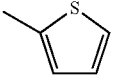 | 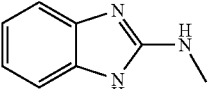 | 93 |
| 62 | 2-(2-thienyl)-1H-benzimidazole-4-(N-o-aminophenyl)amide | 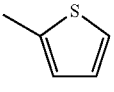 | 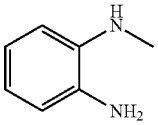 | 94 |
| 63 | 2-(2-thienyl)-1H-benzimidazole-4-(N-5-benzimidazolonyl)amide | 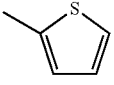 | 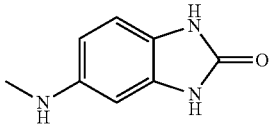 | 90 |
| 64 | 2-(2-thienyl)-1H-benzimidazole-4-(N-4'-carbonamido-5'-imidazolyl)amide | 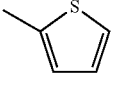 | 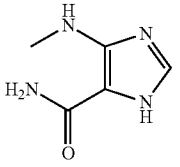 | 94 |
| 65 | 2-(2-thienyl)-1H-benzimidazole-4-(N-4'-pyrazolyl)amide | 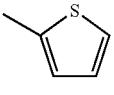 | 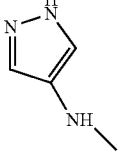 | 92 |
| 66 | 2-(2-thienyl)-1H-benzimidazole-4-(N-(N'-piperazinyl))amide | 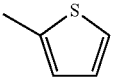 | 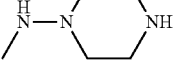 | 94 |
| 67 | 2-(2-thienyl)-1H-benzimidazole-4-(N-2-pyrazinyl)amide | 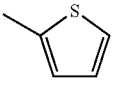 | 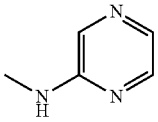 | 94 |
| 68 | 2-(2-thienyl)-1H-benzimidazole-4-(N-2-pyrimidinyl)amide | 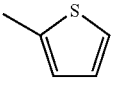 | 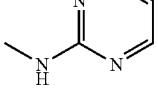 | 93 |
| 69 | 2-(2-thienyl)-1H-benzimidazole-4-(N-2-pyridyl)amide | 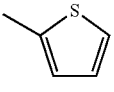 | 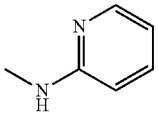 | 90 |

TABLE 2-continued

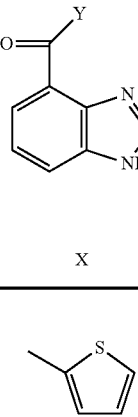

| No. Compounds | X | Y | Field % |
|---|---|---|---|
| 70 2-(2-thienyl)-1H-benzimidazole-4-(N-4-methyl-5-thiazolyl)amide | 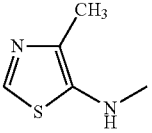 | 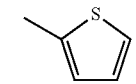 | 91 |
| 71 2-(2-thienyl)-1H-benzimidazole-4-(N-2,4-dihydroxyl-5-pyrimidinyl)amide | 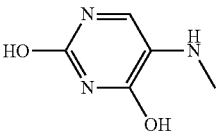 | 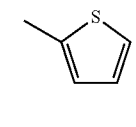 | 93 |
| 72 2-(2-thienyl)-1H-benzimidazole-4-(N-4,6-dimethoxy-2-pyrimidinyl)amide | 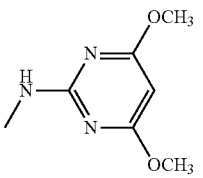 | 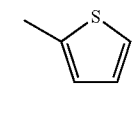 | 93 |
| 73 2-(2-thienyl)-1H-benzimidazole-4-(N-4-chloro-6-amino-2-pyrimidinyl)amide | 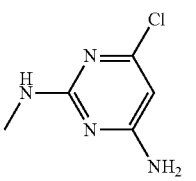 | 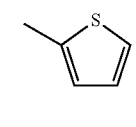 | 88 |
| 74 2-(2-thienyl)-1H-benzimidazole-4-(N-4,6-dichloro-5-pyrimidinyl)amide | 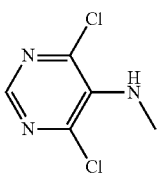 | 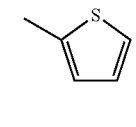 | 89 |
| 75 2-(2-thienyl)-1H-benzimidazole-4-(N-o-fluorophenyl)amide | 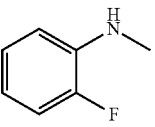 | 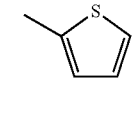 | 87 |
| 76 2-(2-thienyl)-1H-benzimidazole-4-(N-2-hydroxyl-4-pyrimidinyl)amide | 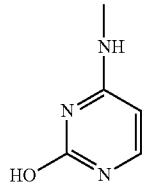 | | 92 |

TABLE 2-continued

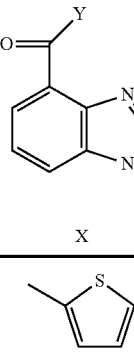

| No. | Compounds | X | Y | Field % |
|---|---|---|---|---|
| 77 | 2-(2-thienyl)-1H-benzimidazole-4-(N-6-purinyl)amide | 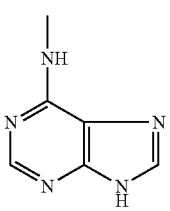 | 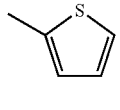 | 90 |
| 78 | 2-(2-thienyl)-1H-benzimidazole-4-(N-6-hydroxyl-2-purinyl)amide | 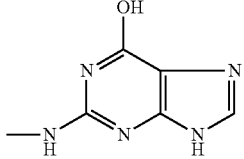 | 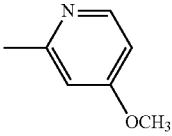 | 91 |
| 79 | (L)-2-(4-methoxypyridyl)-1H-benzimidazole-4-[N-(1-hydroxymethyl-2-p-nitrophenylhydroxyethyl)]amide | 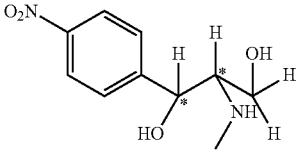 | 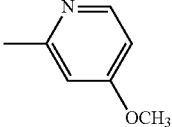 | 93 |
| 80 | (L)-2-(4-methoxypyridyl)-1H-benzimidazole-4-[N-(1-hydroxymethyl-2-p-aminophenylhydroxyethyl)]amide | 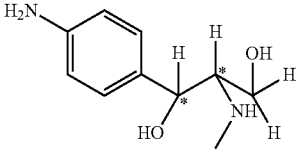 | 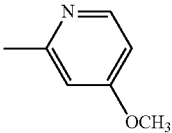 | 93 |
| 81 | 2-(4-methoxypyridyl)-1H-benzimidazole-4-[N-(1-methyl-2-p-chlorophenylhydroxyethyl)]amide | 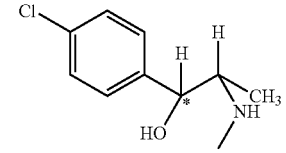 | 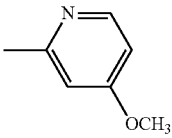 | 94 |
| 82 | 2-(4-methoxypyridyl)-1H-benzimidazole-4-(N-N'-piperidinyl)amide | 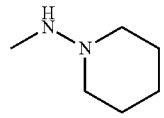 | 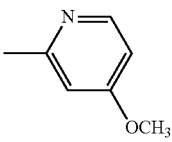 | 90 |
| 83 | 2-(4-methoxypyridyl)-1H-benzimidazole-4-(N-2-piperazinyl)amide | 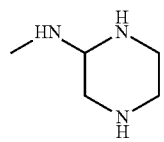 | 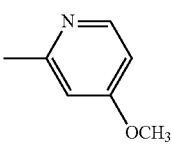 | 93 |
| 84 | 2-(4-methoxypyridyl)-1H-benzimidazole-4-(N-2'-benzimidazolyl)amide | | 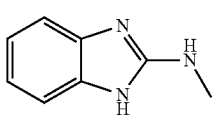 | 92 |

TABLE 2-continued

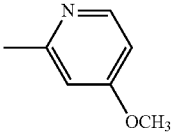

| No. | Compounds | X | Y | Field % |
|-----|-----------|---|---|---------|
| 85 | 2-(4-methoxypyridyl)-1H-benzimidazole-4-(N-o-aminophenyl)amide | 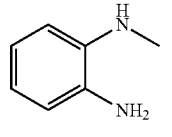 | 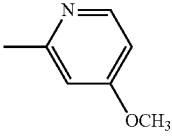 | 91 |
| 86 | 2-(4-methoxypyridyl)-1H-benzimidazole-4-(N-5-benzimidazolonyl)amide | 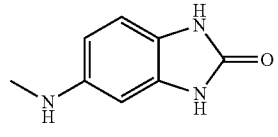 | 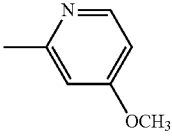 | 91 |
| 87 | 2-(4-methoxypyridyl)-1H-benzimidazole-4-(N-4'-carbonamido-5'-imidazolyl)amide | 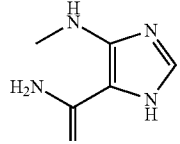 | 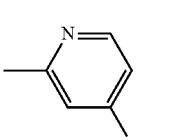 | 93 |
| 88 | 2-(4-methoxypyridyl)-1H-benzimidazole-4-(N-4'-pyrazolyl)amide | 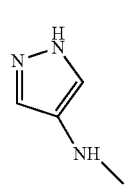 | 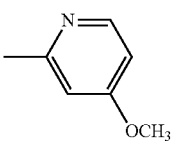 | 92 |
| 89 | 2-(4-methoxypyridyl)-1H-benzimidazole-4-(N-(N'-piperazinyl))amide | 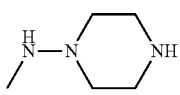 | 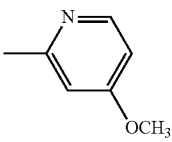 | 93 |
| 90 | 2-(4-methoxypyridyl)-1H-benzimidazole-4-(N-2-pyrazinyl)amide | 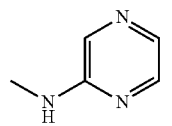 | 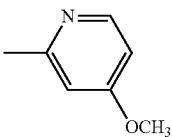 | 94 |
| 91 | 2-(4-methoxypyridyl)-1H-benzimidazole-4-(N-2-pyrimidinyl)amide | 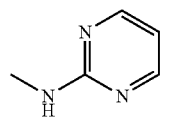 | 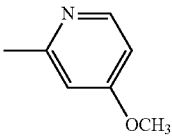 | 92 |
| 92 | 2-(4-methoxypyridyl)-1H-benzimidazole-4-(N-2-pyridyl)amide | 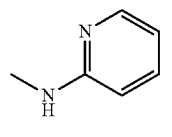 | 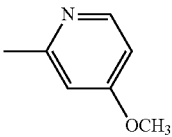 | 92 |
| 93 | 2-(4-methoxypyridyl)-1H-benzimidazole-4-(N-4-methyl-5-thiazolyl)amide | 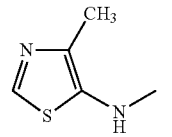 | | 93 |

TABLE 2-continued

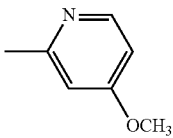

| No. Compounds | X | Y | Field % |
|---|---|---|---|
| 94 2-(4-methoxypyridyl)-1H-benzimidazole-4-(N-2,4-dihydroxyl-5-pyrimidinyl)amide | 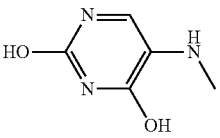 | 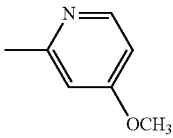 | 94 |
| 95 2-(4-methoxypyridyl)-1H-benzimidazole-4-(N-4,6-dimethoxy-2-pyrimidinyl)amide | 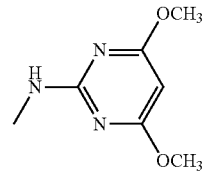 | 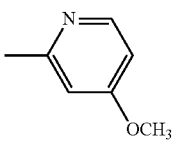 | 90 |
| 96 2-(4-methoxypyridyl)-1H-benzimidazole-4-(N-4-chloro-6-amino-2-pyrimidinyl)amide | 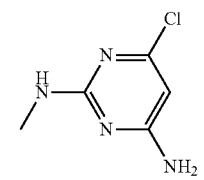 | 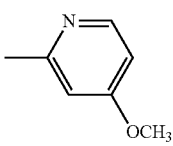 | 94 |
| 97 2-(4-methoxypyridyl)-1H-benzimidazole-4-(N-4,6-dichloro-5-pyrimidinyl)amide | 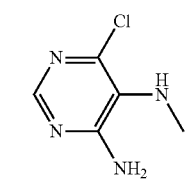 | 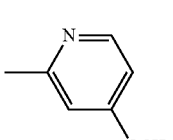 | 92 |
| 98 2-(4-methoxypyridyl)-1H-benzimidazole-4-(N-o-fluorophenyl)amide | 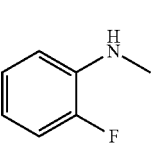 | 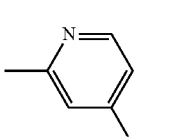 | 94 |
| 99 2-(4-methoxypyridyl)-1H-benzimidazole-4-(N-2-hydroxyl-4-pyrimidinyl)amide | 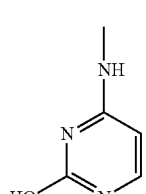 | 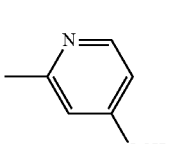 | 94 |
| 100 2-(4-methoxypyridyl)-1H-benzimidazole-4-(N-6-purinyl)amide | 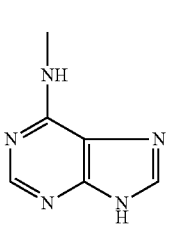 |  | 93 |

TABLE 2-continued

| No. | Compounds | X | Y | Field % |
|---|---|---|---|---|
| 101 | 2-(4-methoxypyridyl)-1H-benzimidazole-4-(N-6-hydroxyl-2-purinyl)amide | 4-methoxy-2-pyridyl | 6-hydroxy-2-purinyl (via NH) | 90 |
| 102 | (L)-2-(6-methoxypyridyl)-1H-benzimidazole-4-[N-(1-hydroxymethyl-2-p-nitrophenylhydroxyethyl)]amide | 6-methoxy-2-pyridyl | 1-hydroxymethyl-2-p-nitrophenylhydroxyethyl (N-methyl) | 91 |
| 103 | (L)-2-(6-methoxypyridyl)-1H-benzimidazole-4-[N-(1-hydroxymethyl-2-p-aminophenylhydroxyethyl)]amide | 6-methoxy-2-pyridyl | 1-hydroxymethyl-2-p-aminophenylhydroxyethyl (N-methyl) | 93 |
| 104 | 2-(6-methoxypyridyl)-1H-benzimidazole-4-[N-(1-methyl-2-p-chlorophenylhydroxyethyl)]amide | 6-methoxy-2-pyridyl | 1-methyl-2-p-chlorophenylhydroxyethyl (N-methyl) | 93 |
| 105 | 2-(6-methoxypyridyl)-1H-benzimidazole-4-(N-N'-piperdinyl)amide | 6-methoxy-2-pyridyl | N'-piperidinyl (via NH) | 94 |
| 106 | 2-(6-methoxypyridyl)-1H-benzimidazole-4-(N-2-piperazinyl)amide | 6-methoxy-2-pyridyl | 2-piperazinyl | 89 |
| 107 | 2-(6-methoxypyridyl)-1H-benzimidazole-4-(N-2'-benzimidazolyl)amide | 6-methoxy-2-pyridyl | 2'-benzimidazolyl | 93 |
| 108 | 2-(6-methoxypyridyl)-1H-benzimidazole-4-(N-o-aminophenyl)amide | 6-methoxy-2-pyridyl | o-aminophenyl | 92 |

TABLE 2-continued

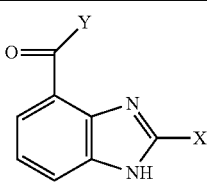

| No. | Compounds | X | Y | Field % |
|---|---|---|---|---|
| 109 | 2-(6-methoxypyridyl)-1H-benzimidazole-4-(N-5-benzimidazolonyl)amide | 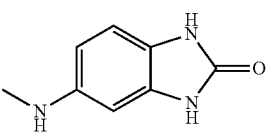 | 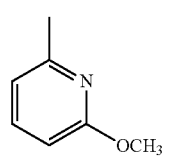 | 90 |
| 110 | 2-(6-methoxypyridyl)-1H-benzimidazole-4-(N-4'-carbonamido-5'-imidazolyl)amide |  | 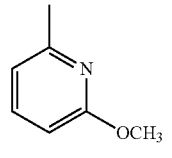 | 89 |
| 111 | 2-(6-methoxypyridyl)-1H-benzimidazole-4-(N-4'-pyrazolyl)amide | 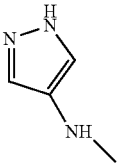 | 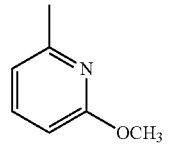 | 93 |
| 112 | 2-(6-methoxypyridyl)-1H-benzimidazole-4-(N-(N'-piperazinyl))amide | 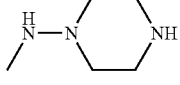 | 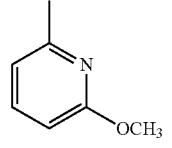 | 93 |
| 113 | 2-(6-methoxypyridyl)-1H-benzimidazole-4-(N-2-pyrazinyl)amide | 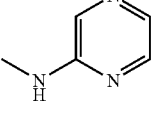 | 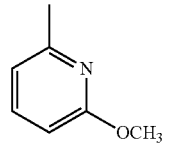 | 94 |
| 114 | 2-(6-methoxypyridyl)-1H-benzimidazole-4-(N-2-pyrimidinyl)amide | 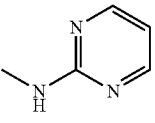 | 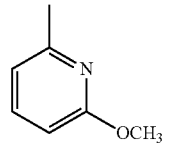 | 90 |
| 115 | 2-(6-methoxypyridyl)-1H-benzimidazole-4-(N-2-pyridyl)amide | 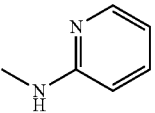 | 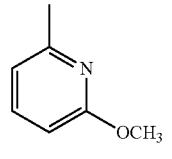 | 93 |
| 116 | 2-(6-methoxypyridyl)-1H-benzimidazole-4-(N-4-methyl-5-thiazolyl)amide | 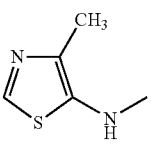 | | 92 |

TABLE 2-continued

| No. Compounds | X | Y | Field % |
|---|---|---|---|
| 117 2-(6-methoxypyridyl)-1H-benzimidazole-4-(N-2,4-dihydroxyl-5-pyrimidinyl)amide | 6-methoxypyridyl | 2,4-dihydroxy-5-pyrimidinyl-NH- | 86 |
| 118 2-(6-methoxypyridyl)-1H-benzimidazole-4-(N-4,6-dimethoxy-2-pyrimidinyl)amide | 6-methoxypyridyl | 4,6-dimethoxy-2-pyrimidinyl-NH- | 91 |
| 119 2-(6-methoxypyridyl)-1H-benzimidazole-4-(N-4-chloro-6-amino-2-pyrimidinyl)amide | 6-methoxypyridyl | 4-chloro-6-amino-2-pyrimidinyl-NH- | 90 |
| 120 2-(6-methoxypyridyl)-1H-benzimidazole-4-(N-4,6-dichloro-5-pyrimidinyl)amide | 6-methoxypyridyl | 4,6-dichloro-5-pyrimidinyl-NH- | 92 |
| 121 2-(6-methoxypyridyl)-1H-benzimidazole-4-(N-o-fluorophenyl)amide | 6-methoxypyridyl | o-fluorophenyl-NH- | 93 |
| 122 2-(6-methoxypyridyl)-1H-benzimidazole-4-(N-2-hydroxyl-4-pyrimidinyl)amide | 6-methoxypyridyl | 2-hydroxyl-4-pyrimidinyl-NH- | 87 |
| 123 2-(6-methoxypyridyl)-1H-benzimidazole-4-(N-6-purinyl)amide | 6-methoxypyridyl | 6-purinyl-NH- | 92 |

TABLE 2-continued

| No. Compounds | X | Y | Field % |
|---|---|---|---|
| 124 2-(6-methoxypyridyl)-1H-benzimidazole-4-(N-6-hydroxyl-2-purinyl)amide | 6-methoxypyridyl | 6-hydroxy-2-purinyl-NH- | 88 |
| 125 (L)-2-(4-dimethylaminopyridyl)-1H-benzimidazole-4-[N-(1-hydroxymethyl-2-p-nitrophenylhydroxyethyl)]amide | 4-dimethylaminopyridyl | 1-hydroxymethyl-2-(p-nitrophenyl)-2-hydroxyethyl | 93 |
| 126 (L)-2-(4-dimethylaminopyridyl)-1H-benzimidazole-4-[N-(1-hydroxymethyl-2-p-aminophenylhydroxyethyl)]amide | 4-dimethylaminopyridyl | 1-hydroxymethyl-2-(p-aminophenyl)-2-hydroxyethyl | 94 |
| 127 2-(4-dimethylaminopyridyl)-1H-benzimidazole-4-[N-(1-methyl-2-p-chlorophenylhydroxyethyl)]amide | 4-dimethylaminopyridyl | 1-methyl-2-(p-chlorophenyl)-2-hydroxyethyl | 90 |
| 128 2-(4-dimethylaminopyridyl)-1H-benzimidazole-(N-N'-piperidinyl)amide | 4-dimethylaminopyridyl | N'-piperidinyl | 94 |
| 129 2-(4-dimethylaminopyridyl)-1H-benzimidazole-4-(N-2-piperazinyl)amide | 4-dimethylaminopyridyl | 2-piperazinyl | 92 |
| 130 2-(4-dimethylaminopyridyl)-1H-benzimidazole-4-(N-2'-benzimidazolyl)amide | 4-dimethylaminopyridyl | 2'-benzimidazolyl | 94 |

TABLE 2-continued

| No. | Compounds | X | Y | Field % |
|---|---|---|---|---|
| 131 | 2-(4-dimethylaminopyridyl)-1H-benzimidazole-4-(N-o-aminophenyl)amide | 4-dimethylaminopyridyl | o-aminophenyl | 94 |
| 132 | 2-(4-dimethylaminopyridyl)-1H-benzimidazole-4-(N-5-benzimidazolonyl)amide | 4-dimethylaminopyridyl | 5-benzimidazolonyl | 93 |
| 133 | 2-(4-dimethylaminopyridyl)-1H-benzimidazole-4-(N-4'-carbonamido-5'-imidazolyl)amide | 4-dimethylaminopyridyl | 4'-carbonamido-5'-imidazolyl | 86 |
| 134 | 2-(4-dimethylaminopyridyl)-1H-benzimidazole-4-(N-4'-pyrazolyl)amide | 4-dimethylaminopyridyl | 4'-pyrazolyl | 91 |
| 135 | 2-(4-dimethylaminopyridyl)-1H-benzimidazole-4-(N-(N'-piperazinyl))amide | 4-dimethylaminopyridyl | N'-piperazinyl | 93 |
| 136 | 2-(4-dimethylaminopyridyl)-1H-benzimidazole-4-(N-2-pyrazinyl)amide | 4-dimethylaminopyridyl | 2-pyrazinyl | 93 |

TABLE 2-continued

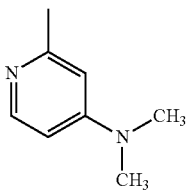

| No. Compounds | X | Y | Field % |
|---|---|---|---|
| 137 2-(4-dimethylaminopyridyl)-1H-benzimidazole-4-(N-2-pyrimidinyl)amide | 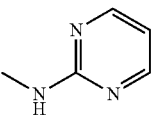 | 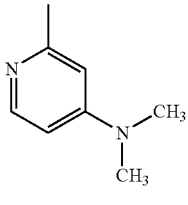 | 88 |
| 138 2-(4-dimethylaminopyridyl)-1H-benzimidazole-4-(N-2-pyridyl)amide | 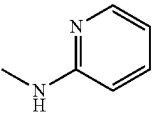 | 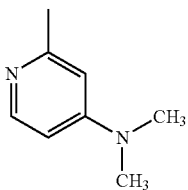 | 89 |
| 139 2-(4-dimethylaminopyridyl)-1H-benzimidazole-4-(N-4-methyl-5-thiazolyl)amide | 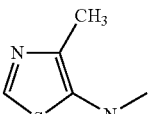 | 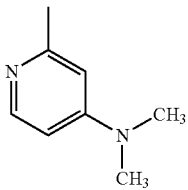 | 87 |
| 140 2-(4-dimethylaminopyridyl)-1H-benzimidazole-4-(N-2,4-dihydroxyl-5-pyrimidinyl)amide | 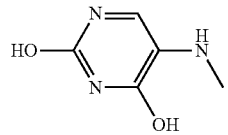 | 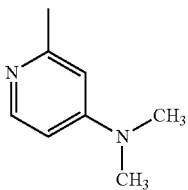 | 88 |
| 141 2-(4-dimethylaminopyridyl)-1H-benzimidazole-4-(N-4,6-dimethoxy-2-pyrimidinyl)amide | 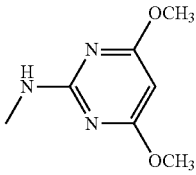 | 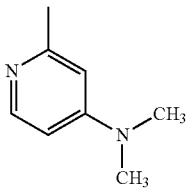 | 90 |
| 142 2-(4-dimethylaminopyridyl)-1H-benzimidazole-4-(N-4-chloro-6-amino-2-pyrimidinyl)amide | | 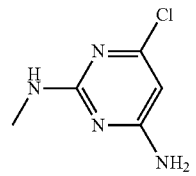 | 89 |

TABLE 2-continued

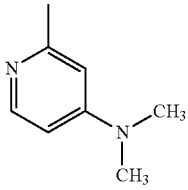

| No. | Compounds | X | Y | Field % |
|---|---|---|---|---|
| 143 | 2-(4-dimethylaminopyridyl)-1H-benzimidazole-4-(N-4,6-dichloro-5-pyrimidinyl)amide | 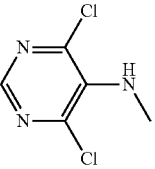 | 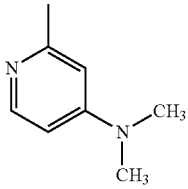 | 93 |
| 144 | 2-(4-dimethylaminopyridyl)-1H-benzimidazole-4-(N-o-fluorophenyl)amide | 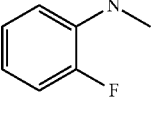 | 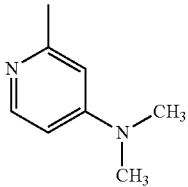 | 93 |
| 145 | 2-(4-dimethylaminopyridyl)-1H-benzimidazole-4-(N-2-hydroxyl-4-pyrimidinyl)amide | 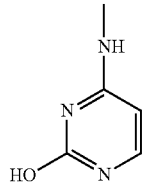 | 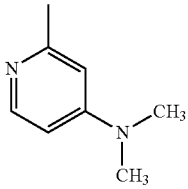 | 88 |
| 146 | 2-(4-dimethylaminopyridyl)-1H-benzimidazole-4-(N-6-purinyl)amide | 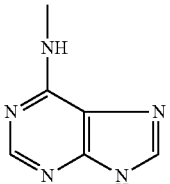 | 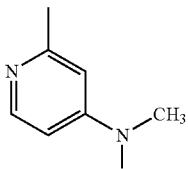 | 90 |
| 147 | 2-(4-dimethylaminopyridyl)-1H-benzimidazole-4-(N-6-hydroxyl-2-purinyl)amide | 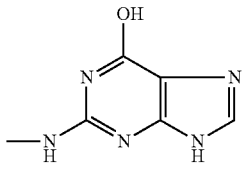 | 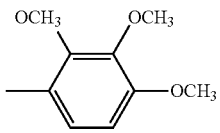 | 93 |
| 148 | (L)-2-(2,3,4-trimethoxyphenyl)-1H-benzimidazole-4-[N-(1-hydroxymethyl-2-p-nitrophenylhydroxyethyl)]amide | 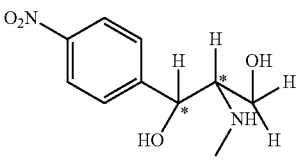 | 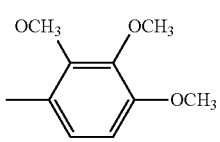 | 92 |
| 149 | (L)-2-(2,3,4-trimethoxyphenyl)-1H-benzimidazole-4-[N-(1-hydroxymethyl-2-p-aminophenylhydroxyethyl)]amide | 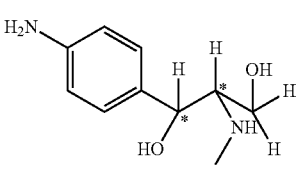 | | 91 |

TABLE 2-continued

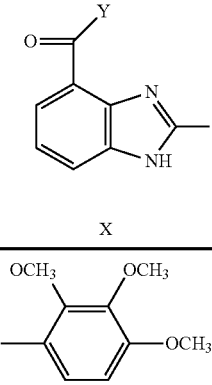

| No. | Compounds | X | Y | Field % |
|---|---|---|---|---|
| 150 | 2-(2,3,4-trimethoxyphenyl)-1H-benzimidazole-4-[N-(1-methyl-2-p-chlorophenylhydroxyethyl)]amide | 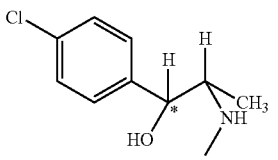 | 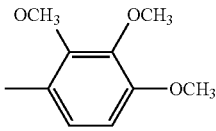 | 91 |
| 151 | 2-(2,3,4-trimethoxyphenyl)-1H-benzimidazole-4-(N-N'-piperidinyl)amide | 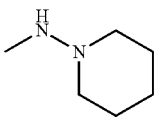 | 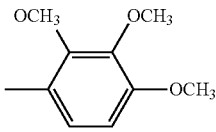 | 93 |
| 152 | 2-(2,3,4-trimethoxyphenyl)-1H-benzimidazole-4-(N-2-piperazinyl)amide | 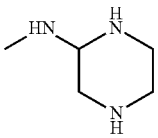 | 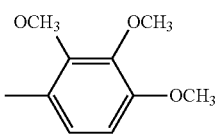 | 92 |
| 153 | 2-(2,3,4-trimethoxyphenyl)-1H-benzimidazole-4-(N-2'-benzimidazolyl)amide | 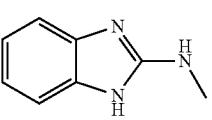 | 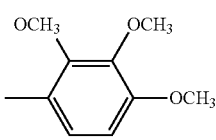 | 93 |
| 154 | 2-(2,3,4-trimethoxyphenyl)-1H-benzimidazole-4-(N-o-aminophenyl)amide | 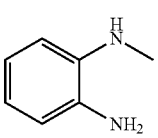 | 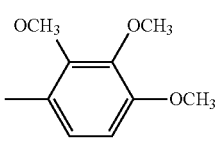 | 90 |
| 155 | 2-(2,3,4-trimethoxyphenyl)-1H-benzimidazole-4-(N-5-benzimidazolonyl)amide | 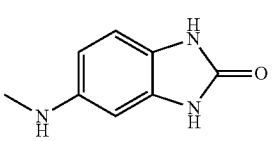 | 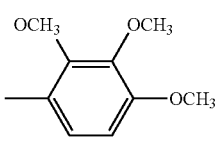 | 92 |
| 156 | 2-(2,3,4-trimethoxyphenyl)-1H-benzimidazole-4-(N-4'-carbonamido-5'-imidazolyl)amide | 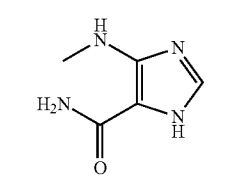 | 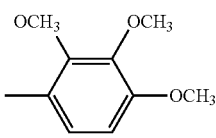 | 87 |
| 157 | 2-(2,3,4-trimethoxyphenyl)-1H-benzimidazole-4-(N-4'-pyrazolyl)amide | 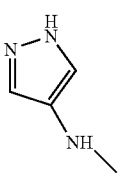 | 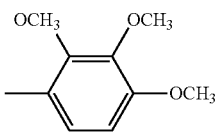 | 93 |
| 158 | 2-(2,3,4-trimethoxyphenyl)-1H-benzimidazole-4-(N-(N'-piperazinyl))amide | 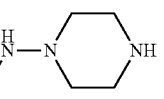 | | 94 |

TABLE 2-continued

| No. Compounds | X | Y | Field % |
|---|---|---|---|
| 159 2-(2,3,4-trimethoxyphenyl)-1H-benzimidazole-4-(N-2-pyrazinyl)amide | 2,3,4-trimethoxyphenyl | N-(pyrazin-2-yl)amino | 90 |
| 160 2-(2,3,4-trimethoxyphenyl)-1H-benzimidazole-4-(N-2-pyrimidinyl)amide | 2,3,4-trimethoxyphenyl | N-(pyrimidin-2-yl)amino | 94 |
| 161 2-(2,3,4-trimethoxyphenyl)-1H-benzimidazole-4-(N-2-pyridyl)amide | 2,3,4-trimethoxyphenyl | N-(pyridin-2-yl)amino | 92 |
| 162 2-(2,3,4-trimethoxyphenyl)-1H-benzimidazole-4-(N-4-methyl-5-thiazolyl)amide | 2,3,4-trimethoxyphenyl | N-(4-methyl-1,3-thiazol-5-yl)amino | 94 |
| 163 2-(2,3,4-trimethoxyphenyl)-1H-benzimidazole-4-(N-2,4-dihydroxyl-5-pyrimidinyl)amide | 2,3,4-trimethoxyphenyl | N-(2,4-dihydroxypyrimidin-5-yl)amino | 94 |
| 164 2-(2,3,4-trimethoxyphenyl)-1H-benzimidazole-4-(N-4,6-dimethoxy-2-pyrimidinyl)amide | 2,3,4-trimethoxyphenyl | N-(4,6-dimethoxypyrimidin-2-yl)amino | 93 |
| 165 2-(2,3,4-trimethoxyphenyl)-1H-benzimidazole-4-(N-4-chloro-6-amino-2-pyrimidinyl)amide | 2,3,4-trimethoxyphenyl | N-(4-chloro-6-aminopyrimidin-2-yl)amino | 90 |
| 166 2-(2,3,4-trimethoxyphenyl)-1H-benzimidazole-4-(N-4,6-dichloro-5-pyrimidinyl)amide | 2,3,4-trimethoxyphenyl | N-(4,6-dichloropyrimidin-5-yl)amino | 91 |

TABLE 2-continued

| No. Compounds | X | Y | Field % |
|---|---|---|---|
| 167 2-(2,3,4-trimethoxyphenyl)-1H-benzimidazole-4-(N-o-fluorophenyl)amide | 2,3,4-trimethoxyphenyl | N-o-fluorophenyl-NH | 93 |
| 168 2-(2,3,4-trimethoxyphenyl)-1H-benzimidazole-4-(N-2-hydroxyl-4-pyrimidinyl)amide | 2,3,4-trimethoxyphenyl | N-methyl-(2-hydroxy-4-pyrimidinyl)amino | 89 |
| 169 2-(2,3,4-trimethoxyphenyl)-1H-benzimidazole-4-(N-6-purinyl)amide | 2,3,4-trimethoxyphenyl | N-methyl-(6-purinyl)amino | 88 |
| 170 2-(2,3,4-trimethoxyphenyl)-1H-benzimidazole-4-(N-6-hydroxyl-2-purinyl)amide | 2,3,4-trimethoxyphenyl | N-methyl-(6-hydroxy-2-purinyl)amino | 89 |
| 171 (L)-2-(3-hydroxyl-4-methoxyphenyl)-1H-benzimidazole-4-[N-(1-hydroxymethyl-2-p-nitrophenylhydroxyethyl)]amide | 3-hydroxy-4-methoxyphenyl | (1-hydroxymethyl-2-p-nitrophenylhydroxyethyl)amino | 87 |
| 172 (L)-2-(3-hydroxyl-4-methoxyphenyl)-1H-benzimidazole-4-[N-(1-hydroxymethyl-2-p-aminophenylhydroxyethyl)]amide | 3-hydroxy-4-methoxyphenyl | (1-hydroxymethyl-2-p-aminophenylhydroxyethyl)amino | 90 |
| 173 2-(3-hydroxyl-4-methoxyphenyl)-1H-benzimidazole-4-[N-(1-methyl-2-p-chlorophenylhydroxyethyl)]amide | 3-hydroxy-4-methoxyphenyl | (1-methyl-2-p-chlorophenylhydroxyethyl)amino | 90 |
| 174 2-(3-hydroxyl-4-methoxyphenyl)-1H-benzimidazole-4-(N-N'-piperidinyl)amide | 3-hydroxy-4-methoxyphenyl | N-methyl-N'-piperidinylamino | 91 |

TABLE 2-continued

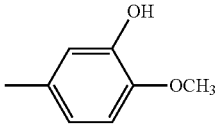

| No. | Compounds | X | Y | Field % |
|---|---|---|---|---|
| 175 | 2-(3-hydroxyl-4-methoxyphenyl)-1H-benzimidazole-4-(N-2-piperazinyl)amide | 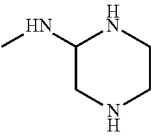 |  | 93 |
| 176 | 2-(3-hydroxyl-4-methoxyphenyl)-1H-benzimidazole-4-(N-2'-benzimidazolyl)amide |  |  | 93 |
| 177 | 2-(3-hydroxyl-4-methoxyphenyl)-1H-benzimidazole-4-(N-o-aminophenyl)amide | 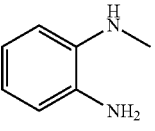 | 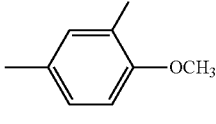 | 94 |
| 178 | 2-(3-hydroxyl-4-methoxyphenyl)-1H-benzimidazole-4-(N-5-benzimidazolonyl)amide | 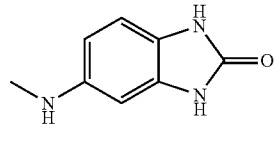 | 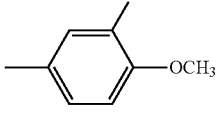 | 90 |
| 179 | 2-(3-hydroxyl-4-methoxyphenyl)-1H-benzimidazole-4-(N-4'-carbonamido-5'-imidazolyl)amide | 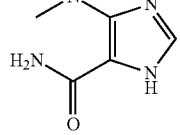 | 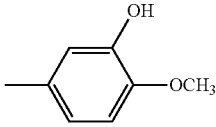 | 86 |
| 180 | 2-(3-hydroxyl-4-methoxyphenyl)-1H-benzimidazole-4-(N-4'-pyrazolyl)amide | 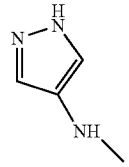 | 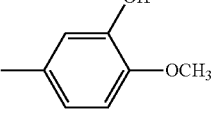 | 92 |
| 181 | 2-(3-hydroxyl-4-methoxyphenyl)-1H-benzimidazole-4-(N-(N'-piperazinyl))amide | 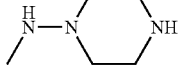 | 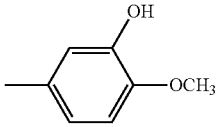 | 91 |
| 182 | 2-(3-hydroxyl-4-methoxyphenyl)-1H-benzimidazole-4-(N-2-pyrazinyl)amide | 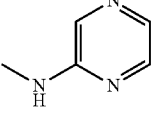 |  | 91 |
| 183 | 2-(3-hydroxyl-4-methoxyphenyl)-1H-benzimidazole-4-(N-2-pyrimidinyl)amide |  | | 93 |

TABLE 2-continued

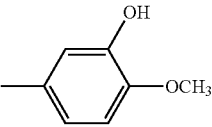

| No. Compounds | X | Y | Field % |
|---|---|---|---|
| 184 2-(3-hydroxyl-4-methoxyphenyl)-1H-benzimidazole-4-(N-2-pyridyl)amide | 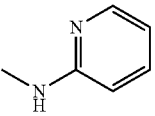 | 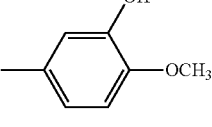 | 92 |
| 185 2-(3-hydroxyl-4-methoxyphenyl)-1H-benzimidazole-4-(N-4-methyl-5-thiazolyl)amide | 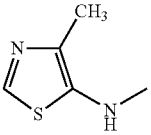 | 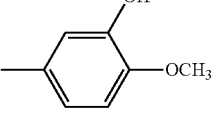 | 93 |
| 186 2-(3-hydroxyl-4-methoxyphenyl)-1H-benzimidazole-4-(N-2,4-dihydroxyl-5-pyrimidinyl)amide | 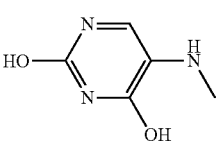 |  | 89 |
| 187 2-(3-hydroxyl-4-methoxyphenyl)-1H-benzimidazole-4-(N-4,6-dimethoxy-2-pyrimidinyl)amide | 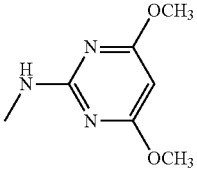 |  | 92 |
| 188 2-(3-hydroxyl-4-methoxyphenyl)-1H-benzimidazole-4-(N-4-chloro-6-amino-2-pyrimidinyl)amide | 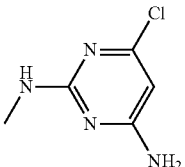 | 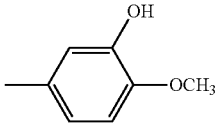 | 92 |
| 189 2-(3-hydroxyl-4-methoxyphenyl)-1H-benzimidazole-4-(N-4,6-dichloro-5-pyrimidinyl)amide | 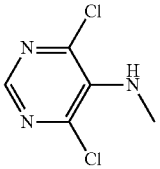 |  | 93 |
| 190 2-(3-hydroxyl-4-methoxyphenyl)-1H-benzimidazole-4-(N-o-fluorophenyl)amide | 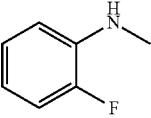 | 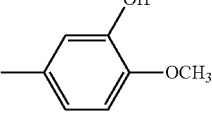 | 94 |
| 191 2-(3-hydroxyl-4-methoxyphenyl)-1H-benzimidazole-4-(N-2-hydroxyl-4-pyrimidinyl)amide | | 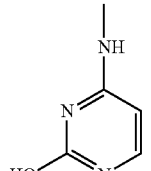 | 90 |

TABLE 2-continued

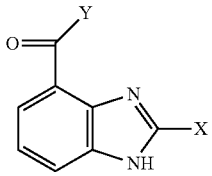

| No. Compounds | X | Y | Field % |
|---|---|---|---|
| 192 2-(3-hydroxyl-4-methoxyphenyl)-1H-benzimidazole-4-(N-6-purinyl)amide | 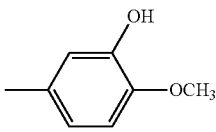 | 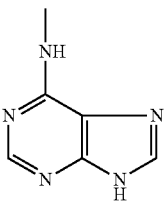 | 94 |
| 193 2-(3-hydroxyl-4-methoxyphenyl)-1H-benzimidazole-4-(N-6-hydroxyl-2-purinyl)amide | 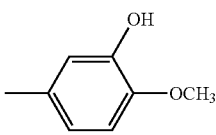 | 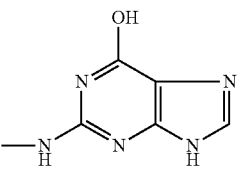 | 89 |
| 194 (L)-2-(2-pyridyl)-1H-benzimidazole-4-[N-(1-hydroxymethyl-2-p-nitrophenylhydroxyethyl])]amide | 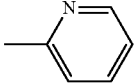 | 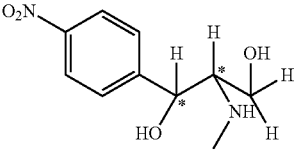 | 94 |
| 195 (L)-2-(2-pyridyl)-1H-benzimidazole-4-[N-(1-hydroxymethyl-2-p-aminophenylhydroxyethyl)]amide | 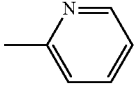 | 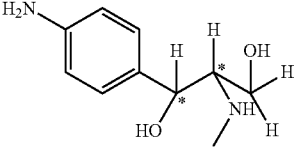 | 90 |
| 196 2-(2-pyridyl)-1H-benzimidazole-4-[N-(1-methyl-2-p-chlorophenylhydroxyethyl)]amide | 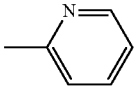 | 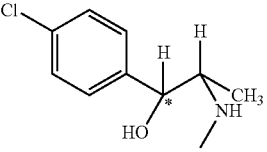 | 93 |
| 197 2-(2-pyridyl)-1H-benzimidazole-4-(N-N'-piperidinyl)amide | 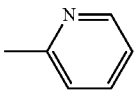 | 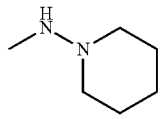 | 90 |
| 198 2-(2-pyridyl)-1H-benzimidazole-4-(N-2-piperazinyl)amide | 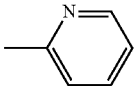 | 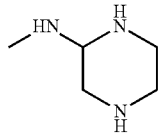 | 91 |
| 199 2-(2-pyridyl)-1H-benzimidazole-4-(N-2'-benzimidazolyl)amide | 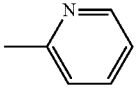 | 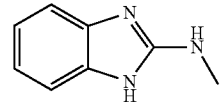 | 93 |

TABLE 2-continued

| No. Compounds | X | Y | Field % |
|---|---|---|---|
| 200 2-(2-pyridyl)-1H-benzimidazole-4-(N-o-aminophenyl)amide | 2-pyridyl | o-aminophenylamino | 89 |
| 201 2-(2-pyridyl)-1H-benzimidazole-4-(N-5-benzimidazolonyl)amide | 2-pyridyl | 5-benzimidazolonylamino | 88 |
| 202 2-(2-pyridyl)-1H-benzimidazole-4-(N-4'-carbonamido-5'-imidazolyl)amide | 2-pyridyl | 4'-carbonamido-5'-imidazolylamino | 86 |
| 203 2-(2-pyridyl)-1H-benzimidazole-4-(N-4'-pyrazolyl)amide | 2-pyridyl | 4'-pyrazolylamino | 87 |
| 204 2-(2-pyridyl)-1H-benzimidazole-4-(N-(N'-piperazinyl))amide | 2-pyridyl | N'-piperazinylamino | 92 |
| 205 2-(2-pyridyl)-1H-benzimidazole-4-(N-2-pyrazinyl)amide | 2-pyridyl | 2-pyrazinylamino | 90 |
| 206 2-(2-pyridyl)-1H-benzimidazole-4-(N-2-pyrimidinyl)amide | 2-pyridyl | 2-pyrimidinylamino | 91 |
| 207 2-(2-pyridyl)-1H-benzimidazole-4-(N-2-pyridyl)amide | 2-pyridyl | 2-pyridylamino | 93 |
| 208 2-(2-pyridyl)-1H-benzimidazole-4-(N-4-methyl-5-thiazolyl)amide | 2-pyridyl | 4-methyl-5-thiazolylamino | 93 |

TABLE 2-continued

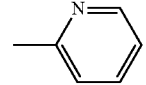

| No. Compounds | X | Y | Field % |
|---|---|---|---|
| 209 2-(2-pyridyl)-1H-benzimidazole-4-(N-2,4-dihydroxyl-5-pyrimidinyl)amide | 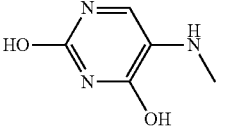 | 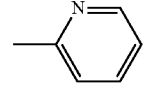 | 88 |
| 210 2-(2-pyridyl)-1H-benzimidazole-4-(N-4,6-dimethoxy-2-pyrimidinyl)amide | 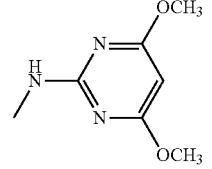 | 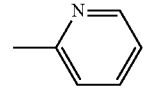 | 90 |
| 211 2-(2-pyridyl)-1H-benzimidazole-4-(N-4-chloro-6-amino-2-pyrimidinyl)amide | 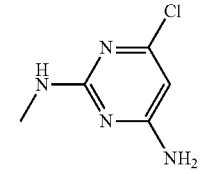 | 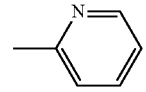 | 93 |
| 212 2-(2-pyridyl)-1H-benzimidazole-4-(N-4,6-dichloro-5-pyrimidinyl)amide | 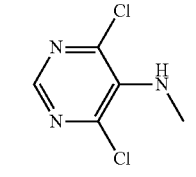 | 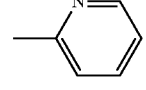 | 92 |
| 213 2-(2-pyridyl)-1H-benzimidazole-4-(N-o-fluorophenyl)amide | 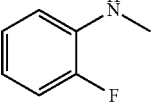 | 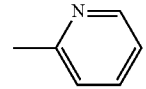 | 91 |
| 214 2-(2-pyridyl)-1H-benzimidazole-4-(N-2-hydroxyl-4-pyrimidinyl)amide | 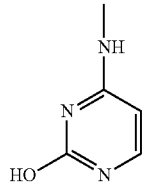 | 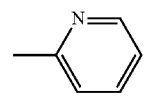 | 91 |
| 215 2-(2-pyridyl)-1H-benzimidazole-4-(N-6-purinyl)amide | 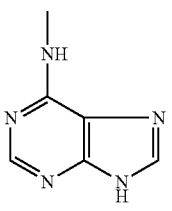 |  | 93 |

TABLE 2-continued

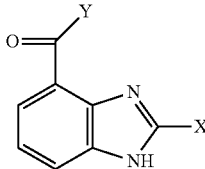

| No. Compounds | X | Y | Field % |
|---|---|---|---|
| 216 2-(2-pyridyl)-1H-benzimidazole-4-(N-6-hydroxyl-2-purinyl)amide | 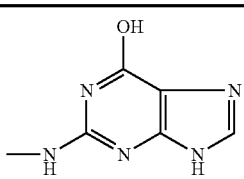 | 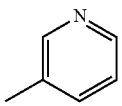 | 88 |
| 217 (L)-2-(3-pyridyl)-1H-benzimidazole-4-[N-(1-hydroxymethyl-2-p-nitrophenylhydroxyethyl)]amide | 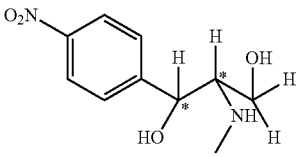 | 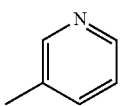 | 93 |
| 218 (L)-2-(3-pyridyl)-1H-benzimidazole-4-[N-(1-hydroxymethyl-2-p-aminophenylhydroxyethyl)]amide | 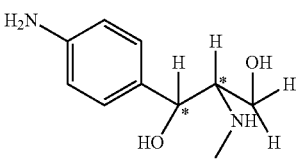 | 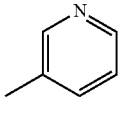 | 94 |
| 219 2-(3-pyridyl)-1H-benzimidazole-4-(N-2-piperazinyl)amide | 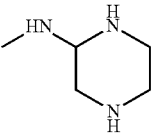 | 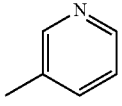 | 92 |
| 220 2-(3-pyridyl)-1H-benzimidazole-4-(N-2-pyrimidinyl)amide | 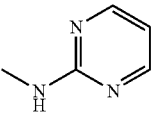 | 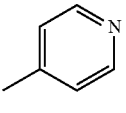 | 92 |
| 221 (L)-2-(4-pyridyl)-1H-benzimidazole-4-[N-(1-hydroxymethyl-2-p-nitrophenylhydroxyethyl)]amide | 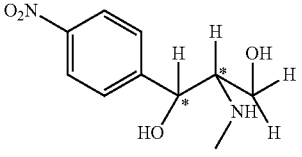 | 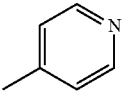 | 93 |
| 222 (L)-2-(4-pyridyl)-1H-benzimidazole-4-[N-(1-hydroxymethyl-2-p-aminophenylhydroxyethyl)]amide | 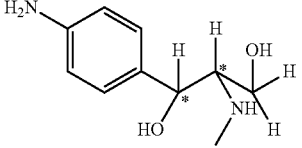 | 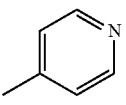 | 94 |
| 223 2-(4-pyridyl)-1H-benzimidazole-4-(N-2-piperazinyl)amide | 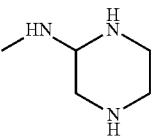 | 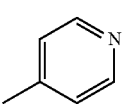 | 90 |
| 224 2-(4-pyridyl)-1H-benzimidazole-4-(N-2-pyrimidinyl)amide | 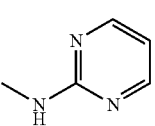 | | 94 |

TABLE 2-continued

| No. Compounds | X | Y | Field % |
|---|---|---|---|
| 225 (L)-2-(3-pyridazinyl)-1H-benzimidazole-4-[N-(1-hydroxymethyl-2-p-nitrophenylhydroxyethyl)]amide | 3-pyridazinyl | 1-hydroxymethyl-2-p-nitrophenylhydroxyethyl group | 92 |
| 226 (L)-2-(3-pyridazinyl)-1H-benzimidazole-4-[N-(1-hydroxymethyl-2-p-aminophenylhydroxyethyl)]amide | 3-pyridazinyl | 1-hydroxymethyl-2-p-aminophenylhydroxyethyl group | 91 |
| 227 2-(3-pyridazinyl)-1H-benzimidazole-4-[N-(1-methyl-2-p-chlorophenylhydroxyethyl)]amide | 3-pyridazinyl | 1-methyl-2-p-chlorophenylhydroxyethyl group | 94 |
| 228 2-(3-pyridazinyl)-1H-benzimidazole-4-(N-N'-piperdinyl)amide | 3-pyridazinyl | N'-piperidinyl | 93 |
| 229 2-(3-pyridazinyl)-1H-benzimidazole-4-(N-2-piperazinyl)amide | 3-pyridazinyl | 2-piperazinyl | 90 |
| 230 2-(3-pyridazinyl)-1H-benzimidazole-4-(N-2'-benzimidazolyl)amide | 3-pyridazinyl | 2'-benzimidazolyl | 91 |
| 231 2-(3-pyridazinyl)-1H-benzimidazole-4-(N-o-aminophenyl)amide | 3-pyridazinyl | o-aminophenyl | 93 |
| 232 2-(3-pyridazinyl)-1H-benzimidazole-4-(N-5-benzimidazolonyl)amide | 3-pyridazinyl | 5-benzimidazolonyl | 93 |
| 233 2-(3-pyridazinyl)-1H-benzimidazole-4-(N-4'-carbonamido-5'-imidazolyl)amide | 3-pyridazinyl | 4'-carbonamido-5'-imidazolyl | 86 |

TABLE 2-continued

| No. Compounds | X | Y | Field % |
|---|---|---|---|
| 234 2-(3-pyridazinyl)-1H-benzimidazole-4-(N-4'-pyrazolyl)amide | 3-pyridazinyl | 4-(NH)-1H-pyrazolyl | 89 |
| 235 2-(3-pyridazinyl)-1H-benzimidazole-4-(N-(N'-piperazinyl))amide | 3-pyridazinyl | N-(N'-piperazinyl) | 87 |
| 236 2-(3-pyridazinyl)-1H-benzimidazole-4-(N-2-pyrazinyl)amide | 3-pyridazinyl | 2-(NH)-pyrazinyl | 92 |
| 237 2-(3-pyridazinyl)-1H-benzimidazole-4-(N-2-pyrimidinyl)amide | 3-pyridazinyl | 2-(NH)-pyrimidinyl | 90 |
| 238 2-(3-pyridazinyl)-1H-benzimidazole-4-(N-2-pyridyl)amide | 3-pyridazinyl | 2-(NH)-pyridyl | 91 |
| 239 2-(3-pyridazinyl)-1H-benzimidazole-4-(N-4-methyl-5-thiazolyl)amide | 3-pyridazinyl | 4-methyl-5-(NH)-thiazolyl | 93 |
| 240 2-(3-pyridazinyl)-1H-benzimidazole-4-(N-2,4-dihydroxyl-5-pyrimidinyl)amide | 3-pyridazinyl | 2,4-dihydroxyl-5-(NH)-pyrimidinyl | 89 |
| 241 2-(3-pyridazinyl)-1H-benzimidazole-4-(N-4,6-dimethoxy-2-pyrimidinyl)amide | 3-pyridazinyl | 4,6-dimethoxy-2-(NH)-pyrimidinyl | 94 |
| 242 2-(3-pyridazinyl)-1H-benzimidazole-4-(N-4-chloro-6-amino-2-pyrimidinyl)amide | 3-pyridazinyl | 4-chloro-6-amino-2-(NH)-pyrimidinyl | 90 |

TABLE 2-continued

| No. Compounds | X | Y | Field % |
|---|---|---|---|
| 243 2-(3-pyridazinyl)-1H-benzimidazole-4-(N-4,6-dichloro-5-pyrimidinyl)amide | 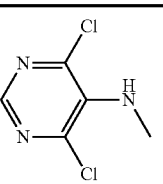 |  | 93 |
| 244 2-(3-pyridazinyl)-1H-benzimidazole-4-(N-o-fluorophenyl)amide | 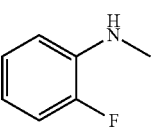 | 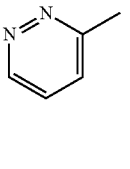 | 92 |
| 245 2-(3-pyridazinyl)-1H-benzimidazole-4-(N-2-hydroxyl-4-pyrimidinyl)amide | 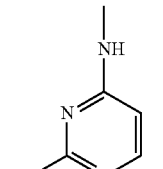 |  | 88 |
| 246 2-(3-pyridazinyl)-1H-benzimidazole-4-(N-6-purinyl)amide | 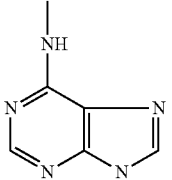 | 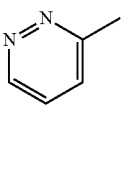 | 91 |
| 247 2-(3-pyridazinyl)-1H-benzimidazole-4-(N-6-hydroxyl-2-purinyl)amide | 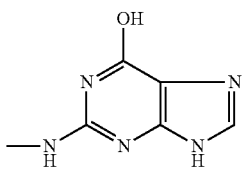 | 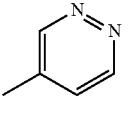 | 87 |
| 248 (L)-2-(4-pyridazinyl)-1H-benzimidazole-4-[N-(1-hydroxymethyl-2-p-nitrophenylhydroxyethyl)]amide | 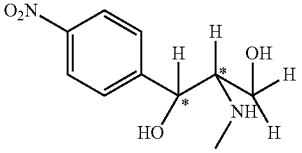 | 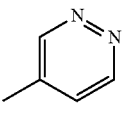 | 92 |
| 249 (L)-2-(4-pyridazinyl)-1H-benzimidazole-4-[N-(1-hydroxymethyl-2-p-aminophenylhydroxyethyl)]amide | 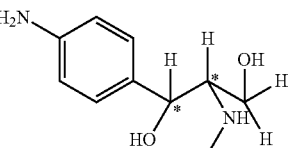 |  | 90 |
| 250 2-(4-pyridazinyl)-1H-benzimidazole-4-(N-2-piperazinyl)amide | 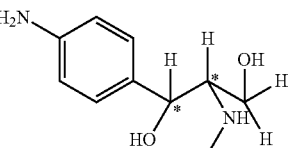 | 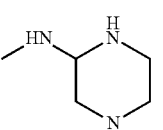 | 94 |

TABLE 2-continued

| No. Compounds | X | Y | Field % |
|---|---|---|---|
| 251 2-(4-pyridazinyl)-1H-benzimidazole-4-(N-2-pyrimidinyl)amide | 4-pyridazinyl | 2-(methylamino)pyrimidinyl | 92 |
| 252 (L)-2-(2-pyrazinyl)-1H-benzimidazole-4-[N-(1-hydroxymethy]-2-p-nitrophenylhydroxyethyl)]amide | 2-pyrazinyl | 1-(4-nitrophenyl)-3-(methylamino)-propane-1,3-diol derivative | 92 |
| 253 (L)-2-(2-pyrazinyl)-1H-benzimidazole-4-[N-(1-hydroxymethyl-2-p-aminophenylhydroxyethyl)]amide | 2-pyrazinyl | 1-(4-aminophenyl)-3-(methylamino)-propane-1,3-diol derivative | 89 |
| 254 2-(2-pyrazinyl)-1H-benzimidazole-4-[N-(1-methyl-2-p-chlorophenylhydroxyethyl)]amide | 2-pyrazinyl | 1-(4-chlorophenyl)-2-(methylamino)-1-hydroxypropyl | 94 |
| 255 2-(2-pyrazinyl)-1H-benzimidazole-4-(N-N'-piperidinyl)amide | 2-pyrazinyl | N'-piperidinyl | 90 |
| 256 2-(2-pyrazinyl)-1H-benzimidazole-4-(N-2-piperazinyl)amide | 2-pyrazinyl | 2-piperazinyl | 94 |
| 257 2-(2-pyrazinyl)-1H-benzimidazole-4-(N-2'-benzimidazolyl)amide | 2-pyrazinyl | 2'-benzimidazolyl | 92 |
| 258 2-(2-pyrazinyl)-1H-benzimidazole-4-(N-o-aminophenyl)amide | 2-pyrazinyl | o-aminophenyl | 90 |
| 259 2-(2-pyrazinyl)-1H-benzimidazole-4-(N-5-benzimidazolonyl)amide | 2-pyrazinyl | 5-benzimidazolonyl | 94 |

TABLE 2-continued

| No. Compounds | X | Y | Field % |
|---|---|---|---|
| 260 2-(2-pyrazinyl)-1H-benzimidazole-4-(N-4'-carbonamido-5'-imidazolyl)amide | 2-methylpyrazinyl | 4-carbonamido-5-imidazolyl-NH- | 87 |
| 261 2-(2-pyrazinyl)-1H-benzimidazole-4-(N-4'-pyrazolyl)amide | 2-methylpyrazinyl | 4-pyrazolyl-NH- | 90 |
| 262 2-(2-pyrazinyl)-1H-benzimidazole-4-(N-(N'-piperazinyl))amide | 2-methylpyrazinyl | N-piperazinyl-NH- | 91 |
| 263 2-(2-pyrazinyl)-1H-benzimidazole-4-(N-2-pyrazinyl)amide | 2-methylpyrazinyl | 2-pyrazinyl-NH- | 93 |
| 264 2-(2-pyrazinyl)-1H-benzimidazole-4-(N-2-pyrimidinyl)amide | 2-methylpyrazinyl | 2-pyrimidinyl-NH- | 93 |
| 265 2-(2-pyrazinyl)-1H-benzimidazole-4-(N-2-pyridyl)amide | 2-methylpyrazinyl | 2-pyridyl-NH- | 88 |
| 266 2-(2-pyrazinyl)-1H-benzimidazole-4-(N-4-methyl-5-thiazolyl)amide | 2-methylpyrazinyl | 4-methyl-5-thiazolyl-NH- | 89 |
| 267 2-(2-pyrazinyl)-1H-benzimidazole-4-(N-2,4-dihydroxyl-5-pyrimidinyl)amide | 2-methylpyrazinyl | 2,4-dihydroxyl-5-pyrimidinyl-NH- | 87 |
| 268 2-(2-pyrazinyl)-1H-benzimidazole-4-(N-4,6-dimethoxy-2-pyrimidinyl)amide | 2-methylpyrazinyl | 4,6-dimethoxy-2-pyrimidinyl-NH- | 92 |

TABLE 2-continued

| No. Compounds | X | Y | Field % |
|---|---|---|---|
| 269 2-(2-pyrazinyl)-1H-benzimidazole-4-(N-4-chloro-6-amino-2-pyrimidinyl)amide | 2-methylpyrazinyl | 4-chloro-6-amino-2-pyrimidinylamino | 90 |
| 270 2-(2-pyrazinyl)-1H-benzimidazole-4-(N-4,6-dichloro-5-pyrimidinyl)amide | 2-methylpyrazinyl | 4,6-dichloro-5-pyrimidinylamino | 91 |
| 271 2-(2-pyrazinyl)-1H-benzimidazole-4-(N-o-fluorophenyl)amide | 2-methylpyrazinyl | o-fluorophenylamino | 93 |
| 272 2-(2-pyrazinyl)-1H-benzimidazole-4-(N-2-hydroxyl-4-pyrimidinyl)amide | 2-methylpyrazinyl | 2-hydroxy-4-pyrimidinylamino | 89 |
| 273 2-(2-pyrazinyl)-1H-benzimidazole-4-(N-6-purinyl)amide | 2-methylpyrazinyl | 6-purinylamino | 94 |
| 274 2-(2-pyrazinyl)-1H-benzimidazole-4-(N-6-hydroxyl-2-purinyl)amide | 2-methylpyrazinyl | 6-hydroxy-2-purinylamino | 89 |
| 275 (L)-2-(2-piperazinyl)-1H-benzimidazole-4-[N-(1-hydroxymethyl-2-p-nitrophenylhydroxyethyl)]amide | 2-piperazinyl | 1-hydroxymethyl-2-p-nitrophenylhydroxyethylamino | 93 |

TABLE 2-continued

| No. | Compounds | X | Y | Field % |
|-----|-----------|---|---|---------|
| 276 | (L)-2-(2-piperazinyl)-1H-benzimidazole-4-[N-(1-hydroxymethyl-2-p-aminophenylhydroxyethyl)]amide | 2-methylpiperazinyl | 1-(4-aminophenyl)-1-hydroxy-2-(methylamino)-3-hydroxypropyl | 90 |
| 277 | 2-(2-piperazinyl)-1H-benzimidazole-4-[N-(1-methyl-2-p-chlorophenylhydroxyethyl)]amide | 2-methylpiperazinyl | 1-(4-chlorophenyl)-1-hydroxy-2-(N-methyl-N-methylamino)ethyl | 91 |
| 278 | 2-(2-piperazinyl)-1H-benzimidazole-4-(N-N'-piperidinyl)amide | 2-methylpiperazinyl | N-piperidinylamino | 91 |
| 279 | 2-(2-piperazinyl)-1H-benzimidazole-4-(N-2-piperazinyl)amide | 2-methylpiperazinyl | 2-piperazinylamino | 93 |
| 280 | 2-(2-piperazinyl)-1H-benzimidazole-4-(N-2,-benzimidazolyl)amide | 2-methylpiperazinyl | 2-benzimidazolylamino | 92 |
| 281 | 2-(2-piperazinyl)-1H-benzimidazole-4-(N-o-aminophenyl)amide | 2-methylpiperazinyl | o-aminophenylamino | 93 |
| 282 | 2-(2-piperazinyl)-1H-benzimidazole-4-(N-5-benzimidazolonyl)amide | 2-methylpiperazinyl | 5-benzimidazolonylamino | 94 |
| 283 | 2-(2-piperazinyl)-1H-benzimidazole-4-(N-4'-carbonamido-5'-imidazolyl)amide | 2-methylpiperazinyl | 4-carbamoyl-5-imidazolylamino | 89 |

TABLE 2-continued

| No. Compounds | X | Y | Field % |
|---|---|---|---|
| 284 2-(2-piperazinyl)-1H-benzimidazole-4-(N-4'-pyrazolyl)amide | 2-piperazinyl | 4-pyrazolylamino | 92 |
| 285 2-(2-piperazinyl)-1H-benzimidazole-4-(N-(N'-piperazinyl))amide | 2-piperazinyl | N'-piperazinylamino | 92 |
| 286 2-(2-piperazinyl)-1H-benzimidazole-4-(N-2-pyrazinyl)amide | 2-piperazinyl | 2-pyrazinylamino | 92 |
| 287 2-(2-piperazinyl)-1H-benzimidazole-4-(N-2-pyrimidinyl)amide | 2-piperazinyl | 2-pyrimidinylamino | 93 |
| 288 2-(2-piperazinyl)-1H-benzimidazole-4-(N-2-pyridyl)amide | 2-piperazinyl | 2-pyridylamino | 92 |
| 289 2-(2-piperazinyl)-1H-benzimidazole-4-(N-4-methyl-5-thiazolyl)amide | 2-piperazinyl | 4-methyl-5-thiazolylamino | 91 |
| 290 2-(2-piperazinyl)-1H-benzimidazole-4-(N-2,4-dihydroxyl-5-pyrimidinyl)amide | 2-piperazinyl | 2,4-dihydroxyl-5-pyrimidinylamino | 87 |
| 291 2-(2-piperazinyl)-1H-benzimidazole-4-(N-4,6-dimethoxy-2-pyrimidinyl)amide | 2-piperazinyl | 4,6-dimethoxy-2-pyrimidinylamino | 90 |

TABLE 2-continued

| No. Compounds | X | Y | Field % |
|---|---|---|---|
| 292 2-(2-piperazinyl)-1H-benzimidazole-4-(N-4-chloro-6-amino-2-pyrimidinyl)amide | 2-methylpiperazinyl | 4-chloro-6-amino-2-pyrimidinyl-NH- | 88 |
| 293 2-(2-piperazinyl)-1H-benzimidazole-4-(N-4,6-dichloro-5-pyrimidinyl)amide | 2-methylpiperazinyl | 4,6-dichloro-5-pyrimidinyl-NH- | 93 |
| 294 2-(2-piperazinyl)-1H-benzimidazole-4-(N-o-fluorophenyl)amide | 2-methylpiperazinyl | o-fluorophenyl-NH- | 94 |
| 295 2-(2-piperazinyl)-1H-benzimidazole-4-(N-2-hydroxyl-4-pyrimidinyl)amide | 2-methylpiperazinyl | 2-hydroxyl-4-pyrimidinyl-NH- | 89 |
| 296 2-(2-piperazinyl)-1H-benzimidazole-4-(N-6-purinyl)amide | 2-methylpiperazinyl | 6-purinyl-NH- | 90 |
| 297 2-(2-piperazinyl)-1H-benzimidazole-4-(N-6-hydroxyl-2-purinyl)amide | 2-methylpiperazinyl | 6-hydroxyl-2-purinyl-NH- | 87 |
| 298 (L)-2-(N,N'-diethyl-2-piperazinyl)-1H-benzimidazole-4-[N-(1-hydroxymethyl-2-p-nitrophenylhydroxyethyl)]amide | N,N'-diethyl-2-methylpiperazinyl | 1-hydroxymethyl-2-p-nitrophenylhydroxyethyl-NH- | 90 |

TABLE 2-continued

| No. Compounds | X | Y | Field % |
|---|---|---|---|
| 299 (L)-2-(N,N'-diethyl-2-piperazinyl)-1H-benzimidazole-4-[N-(1-hydroxymethyl-2-p-aminophenylhydroxyethyl)]amide | 1,4-diethyl-2-methylpiperazinyl | 1-hydroxymethyl-2-(p-aminophenyl)hydroxyethyl-NH- | 91 |
| 300 2-(N,N'-diethyl-2-piperazinyl)-1H-benzimidazole-4-(N-2-piperazinyl)amide | 1,4-diethyl-2-methylpiperazinyl | N-methyl-2-piperazinyl | 90 |
| 301 2-(N,N'-diethyl-2-piperazinyl)-1H-benzimidazole-4-(N-2-pyrimidinyl)amide | 1,4-diethyl-2-methylpiperazinyl | N-methyl-2-pyrimidinyl | 91 |
| 302 (L)-2-(N-piperazinyl)-1H-benzimidazole-4-[N-(1-hydroxymethyl-2-p-nitrophenylhydroxyethyl)]amide | 4-methylpiperazinyl | 1-hydroxymethyl-2-(p-nitrophenyl)hydroxyethyl-NH- | 92 |
| 303 (L)-2-(N-piperazinyl)-1H-benzimidazole-4-[N-(1-hydroxymethyl-2-p-aminophenylhydroxyethyl)]amide | 4-methylpiperazinyl | 1-hydroxymethyl-2-(p-aminophenyl)hydroxyethyl-NH- | 91 |
| 304 2-(N-piperazinyl)-1H-benzimidazole-4-[N-(1-methyl-2-p-chlorophenylhydroxyethyl)]amide | 4-methylpiperazinyl | 1-methyl-2-(p-chlorophenyl)hydroxyethyl-NH- | 92 |
| 305 2-(N-piperazinyl)-1H-benzimidazole-4-(N-N'-piperidinyl)amide | 4-methylpiperazinyl | N-methyl-N'-piperidinyl | 93 |
| 306 2-(N-piperazinyl)-1H-benzimidazole-4-(N-2-piperazinyl)amide | 4-methylpiperazinyl | N-methyl-2-piperazinyl | 91 |
| 307 2-(N-piperazinyl)-1H-benzimidazole-4-(N-2'-benzimidazolyl)amide | 4-methylpiperazinyl | N-methyl-2-benzimidazolyl | 92 |

TABLE 2-continued

| No. | Compounds | X | Y | Field % |
|---|---|---|---|---|
| 308 | 2-(N-piperazinyl)-1H-benzimidazole-4-(N-o-aminophenyl)amide | N-methylpiperazinyl | o-aminophenylamino | 90 |
| 309 | 2-(N-piperazinyl)-1H-benzimidazole-4-(N-5-benzimidazolonyl)amide | N-methylpiperazinyl | 5-benzimidazolonylamino | 91 |
| 310 | 2-(N-piperazinyl)-1H-benzimidazole-4-(N-4'-carbonamido-5'-imidazolyl)amide | N-methylpiperazinyl | 4-carbonamido-5-imidazolylamino | 90 |
| 311 | 2-(N-piperazinyl)-1H-benzimidazole-4-(N-4'-pyrazolyl)amide | N-methylpiperazinyl | 4-pyrazolylamino | 93 |
| 312 | 2-(N-piperazinyl)-1H-benzimidazole-4-(N-(N'-piperazinyl))amide | N-methylpiperazinyl | N-piperazinylamino | 91 |
| 313 | 2-(N-piperazinyl)-1H-benzimidazole-4-(N-2-pyrazinyl)amide | N-methylpiperazinyl | 2-pyrazinylamino | 92 |
| 314 | 2-(N-piperazinyl)-1H-benzimidazole-4-(N-2-pyrimidinyl)amide | N-methylpiperazinyl | 2-pyrimidinylamino | 93 |
| 315 | 2-(N-piperazinyl)-1H-benzimidazole-4-(N-2-pyridyl)amide | N-methylpiperazinyl | 2-pyridylamino | 94 |
| 316 | 2-(N-piperazinyl)-1H-benzimidazole-4-(N-4-methyl-5-thiazolyl)amide | N-methylpiperazinyl | 4-methyl-5-thiazolylamino | 94 |

TABLE 2-continued

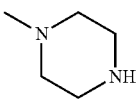

| No. Compounds | X | Y | Field % |
|---|---|---|---|
| 317 2-(N-piperazinyl)-1H-benzimidazole-4-(N-2,4-dihydroxyl-5-pyrimidinyl)amide | 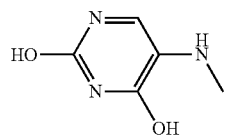 | 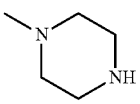 | 88 |
| 318 2-(N-piperazinyl)-1H-benzimidazole-4-(N-4,6-dimethoxy-2-pyrimidinyl)amide | 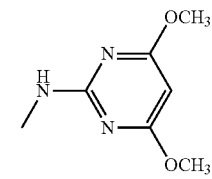 | 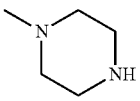 | 90 |
| 319 2-(N-piperazinyl)-1H-benzimidazole-4-(N-4-chloro-6-amino-2-pyrimidinyl)amide | 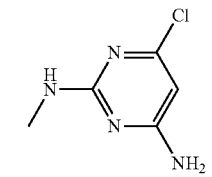 | 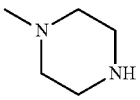 | 91 |
| 320 2-(N-piperazinyl)-1H-benzimidazole-4-(N-4,6-dichloro-5-pyrimidinyl)amide | 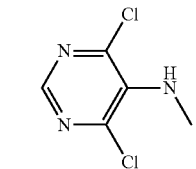 | 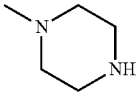 | 93 |
| 321 2-(N-piperazinyl)-1H-benzimidazole-4-(N-o-fluorophenyl)amide | 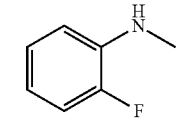 | 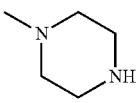 | 93 |
| 322 2-(N-piperazinyl)-1H-benzimidazole-4-(N-2-hydroxyl-4-pyrimidinyl)amide | 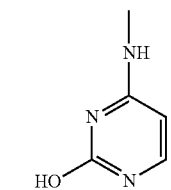 | 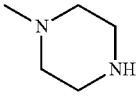 | 88 |
| 323 2-(N-piperazinyl)-1H-benzimidazole-4-(N-6-purinyl)amide | 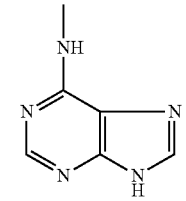 | | 89 |

TABLE 2-continued

| No. Compounds | X | Y | Field % |
|---|---|---|---|
| 324 2-(N-piperazinyl)-1H-benzimidazole-4-(N-6-hydroxyl-2-purinyl)amide | | | 87 |
| 325 (L)-2-(N-ethyl-N'-piperazinyl)-1H-benzimidazole-4-[N-(1-hydroxymethyl-2-p-nitrophenylhydroxyethyl)]amide | | | 92 |
| 326 (L)-2-(N-ethyl-N'-piperazinyl)-1H-benzimidazole-4-[N-(1-hydroxymethyl-2-p-aminophenylhydroxyethyl)]amide | | | 93 |
| 327 2-(N-ethyl-N'-piperazinyl)-1H-benzimidazole-4-(N-2-piperazinyl)amide | | | 92 |
| 328 2-(N-ethyl-N'-piperazinyl)-1H-benzimidazole-4-(N-2-pyrimidinyl)amide | | | 93 |
| 329 (L)-2-(2-pyrrolyl)-1H-benzimidazole-4-[N-(1-hydroxymethyl-2-p-nitrophenylhydroxyethyl)]amide | | | 92 |
| 330 (L)-2-(2-pyrrolyl)-1H-benzimidazole-4-[N-(1-hydroxymethyl-2-p-aminophenylhydroxyethyl)]amide | | | 91 |
| 331 2-(2-pyrrolyl)-1H-benzimidazole-4-[N-(1-methyl-2-p-chlorophenylhydroxyethyl)]amide | | | 92 |

TABLE 2-continued

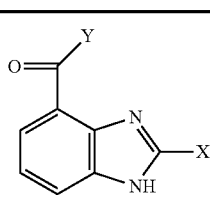

| No. Compounds | X | Y | Field % |
|---|---|---|---|
| 332 2-(2-pyrrolyl)-1H-benzimidazole-4-(N-N'-piperidinyl)amide | 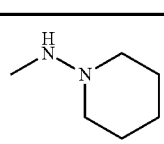 | 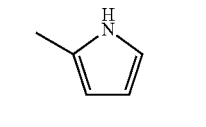 | 93 |
| 333 2-(2-pyrrolyl)-1H-benzimidazole-4-(N-2-piperazinyl)amide | 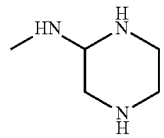 | 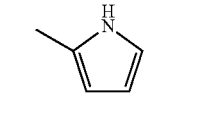 | 90 |
| 334 2-(2-pyrrolyl)-1H-benzimidazole-4-(N-2'-benzimidazolyl)amide | 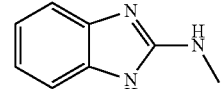 | 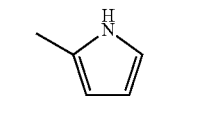 | 93 |
| 335 2-(2-pyrrolyl)-1H-benzimidazole-4-(N-o-aminophenyl)amide | 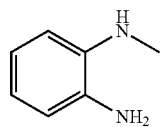 | 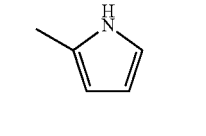 | 90 |
| 336 2-(2-pyrrolyl)-1H-benzimidazole-4-(N-5-benzimidazolonyl)amide | 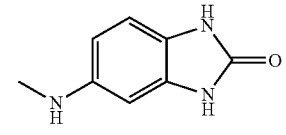 | 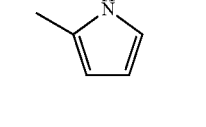 | 91 |
| 337 2-(2-pyrrolyl)-1H-benzimidazole-4-(N-4'-carbonamido-5'-imidazolyl)amide | 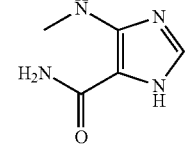 | 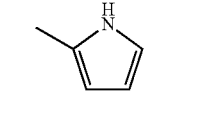 | 85 |
| 338 2-(2-pyrrolyl)-1H-benzimidazole-4-(N-4'-pyrazolyl)amide | 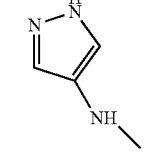 | 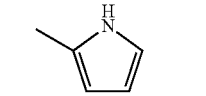 | 90 |
| 339 2-(2-pyrrolyl)-1H-benzimidazole-4-(N-(N'-piperazinyl))amide | 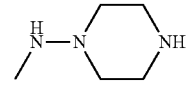 | 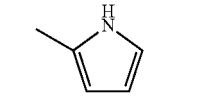 | 92 |
| 340 2-(2-pyrrolyl)-1H-benzimidazole-4-(N-2-pyrazinyl)amide | 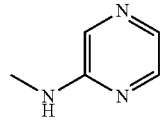 |  | 95 |

TABLE 2-continued

| No. Compounds | X | Y | Field % |
|---|---|---|---|
| 341 2-(2-pyrrolyl)-1H-benzimidazole-4-(N-2-pyrimidinyl)amide | 2-pyrrolyl | 2-pyrimidinylamino | 94 |
| 342 2-(2-pyrrolyl)-1H-benzimidazole-4-(N-2-pyridyl)amide | 2-pyrrolyl | 2-pyridylamino | 94 |
| 343 2-(2-pyrrolyl)-1H-benzimidazole-4-(N-4-methyl-5-thiazolyl)amide | 2-pyrrolyl | 4-methyl-5-thiazolylamino | 95 |
| 344 2-(2-pyrrolyl)-1H-benzimidazole-4-(N-2,4-dihydroxyl-5-pyrimidinyl)amide | 2-pyrrolyl | 2,4-dihydroxyl-5-pyrimidinylamino | 87 |
| 345 2-(2-pyrrolyl)-1H-benzimidazole-4-(N-4,6-dimethoxy-2-pyrimidinyl)amide | 2-pyrrolyl | 4,6-dimethoxy-2-pyrimidinylamino | 94 |
| 346 2-(2-pyrrolyl)-1H-benzimidazole-4-(N-4-chloro-6-amino-2-pyrimidinyl)amide | 2-pyrrolyl | 4-chloro-6-amino-2-pyrimidinylamino | 91 |
| 347 2-(2-pyrrolyl)-1H-benzimidazole-4-(N-4,6-dichloro-5-pyrimidinyl)amide | 2-pyrrolyl | 4,6-dichloro-5-pyrimidinylamino | 93 |
| 348 2-(2-pyrrolyl)-1H-benzimidazole-4-(N-o-fluorophenyl)amide | 2-pyrrolyl | o-fluorophenylamino | 94 |

TABLE 2-continued

| No. Compounds | X | Y | Field % |
|---|---|---|---|
| 349 2-(2-pyrrolyl)-1H-benzimidazole-4-(N-2-hydroxyl-4-pyrimidinyl)amide | 2-pyrrolyl | N-2-hydroxyl-4-pyrimidinyl | 86 |
| 350 2-(2-pyrrolyl)-1H-benzimidazole-4-(N-6-purinyl)amide | 2-pyrrolyl | N-6-purinyl | 92 |
| 351 2-(2-pyrrolyl)-1H-benzimidazole-4-(N-6-hydroxyl-2-purinyl)amide | 2-pyrrolyl | N-6-hydroxyl-2-purinyl | 87 |
| 352 (L)-2-(4-methyl-5-aminothiazolyl)-1H-benzimidazole-4-[N-(1-hydroxymethyl-2-p-nitrophenylhydroxyethyl)]amide | 4-methyl-5-aminothiazolyl | N-(1-hydroxymethyl-2-p-nitrophenylhydroxyethyl) | 93 |
| 353 (L)-2-(4-methyl-5-aminothiazolyl)-1H-benzimidazole-4-[N-(1-hydroxymethyl-2-p-aminophenylhydroxyethyl)]amide | 4-methyl-5-aminothiazolyl | N-(1-hydroxymethyl-2-p-aminophenylhydroxyethyl) | 91 |
| 354 2-(4-methyl-5-aminothiazolyl)-1H-benzimidazole-4-[N-(1-methyl-2-p-chlorophenylhydroxyethyl)]amide | 4-methyl-5-aminothiazolyl | N-(1-methyl-2-p-chlorophenylhydroxyethyl) | 93 |
| 355 2-(4-methyl-5-aminothiazolyl)-1H-benzimidazole-4-(N-N'-piperidinyl)amide | 4-methyl-5-aminothiazolyl | N-N'-piperidinyl | 94 |
| 356 2-(4-methyl-5-aminothiazolyl)-1H-benzimidazole-4-(N-2-piperazinyl)amide | 4-methyl-5-aminothiazolyl | N-2-piperazinyl | 90 |

TABLE 2-continued

| No. Compounds | X | Y | Field % |
|---|---|---|---|
| 357 2-(4-methyl-5-aminothiazolyl)-1H-benzimidazole-4-(N-2'-benzimidazolyl)amide | 4-methyl-5-aminothiazolyl | 2-aminobenzimidazolyl | 94 |
| 358 2-(4-methyl-5-aminothiazolyl)-1H-benzimidazole-4-(N-o-aminophenyl)amide | 4-methyl-5-aminothiazolyl | o-aminophenyl | 93 |
| 359 2-(4-methyl-5-aminothiazolyl)-1H-benzimidazole-4-(N-5-benzimidazolonyl)amide | 4-methyl-5-aminothiazolyl | 5-benzimidazolonyl | 94 |
| 360 2-(4-methyl-5-aminothiazolyl)-1H-benzimidazole-4-(N-4'-carbonamido-5'-imidazolyl)amide | 4-methyl-5-aminothiazolyl | 4-carbonamido-5-imidazolyl | 90 |
| 361 2-(4-methyl-5-aminothiazolyl)-1H-benzimidazole-4-(N-4'-pyrazolyl)amide | 4-methyl-5-aminothiazolyl | 4-pyrazolyl | 94 |
| 362 2-(4-methyl-5-aminothiazolyl)-1H-benzimidazole-4-(N-(N'-piperazinyl))amide | 4-methyl-5-aminothiazolyl | N'-piperazinyl | 92 |
| 363 2-(4-methyl-5-aminothiazolyl)-1H-benzimidazole-4-(N-2-pyrazinyl)amide | 4-methyl-5-aminothiazolyl | 2-pyrazinyl | 94 |
| 364 2-(4-methyl-5-aminothiazolyl)-1H-benzimidazole-4-(N-2-pyrimidinyl)amide | 4-methyl-5-aminothiazolyl | 2-pyrimidinyl | 94 |
| 365 2-(4-methyl-5-aminothiazolyl)-1H-benzimidazole-4-(N-2-pyridyl)amide | 4-methyl-5-aminothiazolyl | 2-pyridyl | 93 |

TABLE 2-continued

| No. Compounds | X | Y | Field % |
|---|---|---|---|
| 366 2-(4-methyl-5-aminothiazolyl)-1H-benzimidazole-4-(N-4-methyl-5-thiazolyl)amide | 4-methyl-5-amino-2-methylthiazolyl | 4-methyl-5-(N-methyl)thiazolyl | 90 |
| 367 2-(4-methyl-5-aminothiazolyl)-1H-benzimidazole-4-(N-2,4-dihydroxyl-5-pyrimidinyl)amide | 4-methyl-5-amino-2-methylthiazolyl | 2,4-dihydroxy-5-pyrimidinyl | 91 |
| 368 2-(4-methyl-5-aminothiazolyl)-1H-benzimidazole-4-(N-4,6-dimethoxy-2-pyrimidinyl)amide | 4-methyl-5-amino-2-methylthiazolyl | 4,6-dimethoxy-2-pyrimidinyl | 93 |
| 369 2-(4-methyl-5-aminothiazolyl)-1H-benzimidazole-4-(N-4-chloro-6-amino-2-pyrimidinyl)amide | 4-methyl-5-amino-2-methylthiazolyl | 4-chloro-6-amino-2-pyrimidinyl | 93 |
| 370 2-(4-methyl-5-aminothiazolyl)-1H-benzimidazole-4-(N-4,6-dichloro-5-pyrimidinyl)amide | 4-methyl-5-amino-2-methylthiazolyl | 4,6-dichloro-5-pyrimidinyl | 88 |
| 371 2-(4-methyl-5-aminothiazolyl)-1H-benzimidazole-4-(N-o-fluorophenyl)amide | 4-methyl-5-amino-2-methylthiazolyl | o-fluorophenyl | 89 |
| 372 2-(4-methyl-5-aminothiazolyl)-1H-benzimidazole-4-(N-2-hydroxyl-4-pyrimidinyl)amide | 4-methyl-5-amino-2-methylthiazolyl | 2-hydroxy-4-pyrimidinyl | 87 |
| 373 2-(4-methyl-5-aminothiazolyl)-1H-benzimidazole-4-(N-6-purinyl)amide | 4-methyl-5-amino-2-methylthiazolyl | 6-purinyl | 92 |

TABLE 2-continued

| No. | Compounds | X | Y | Field % |
|---|---|---|---|---|
| 374 | 2-(4-methyl-5-aminothiazolyl)-1H-benzimidazole-4-(N-6-hydroxyl-2-purinyl)amide | 4-methyl-5-aminothiazolyl | 6-hydroxy-2-purinyl | 90 |
| 375 | (L)-2-(2-quinolinyl)-1H-benzimidazole-4-[N-(1-hydroxymethyl-2-p-nitrophenylhydroxyethyl)]amide | 2-quinolinyl | 1-hydroxymethyl-2-p-nitrophenylhydroxyethyl | 91 |
| 376 | (L)-2-(2-quinolinyl)-1H-benzimidazole-4-[N-(1-hydroxymethyl-2-p-aminophenylhydroxyethyl)]amide | 2-quinolinyl | 1-hydroxymethyl-2-p-aminophenylhydroxyethyl | 93 |
| 377 | 2-(2-quinolinyl)-1H-benzimidazole-4-[N-(1-methyl-2-p-chlorophenylhydroxyethyl)]amide | 2-quinolinyl | 1-methyl-2-p-chlorophenylhydroxyethyl | 93 |
| 378 | 2-(2-quinolinyl)-1H-benzimidazole-4-(N-N'-piperidinyl)amide | 2-quinolinyl | N'-piperidinyl | 94 |
| 379 | 2-(2-quinolinyl)-1H-benzimidazole-4-(N-2-piperazinyl)amide | 2-quinolinyl | 2-piperazinyl | 90 |
| 380 | 2-(2-quinolinyl)-1H-benzimidazole-4-(N-2'-benzimidazolyl)amide | 2-quinolinyl | 2'-benzimidazolyl | 93 |
| 381 | 2-(2-quinolinyl)-1H-benzimidazole-4-(N-o-aminophenyl)amide | 2-quinolinyl | o-aminophenyl | 92 |
| 382 | 2-(2-quinolinyl)-1H-benzimidazole-4-(N-5-benzimidazolonyl)amide | 2-quinolinyl | 5-benzimidazolonyl | 91 |

TABLE 2-continued

| No. Compounds | X | Y | Field % |
|---|---|---|---|
| 383 2-(2-quinolinyl)-1H-benzimidazole-4-(N-4'-carbonamido-5'-imidazolyl)amide | 2-quinolinyl | 4-carbonamido-5-imidazolyl-NH | 91 |
| 384 2-(2-quinolinyl)-1H-benzimidazole-4-(N-4'-pyrazolyl)amide | 2-quinolinyl | 4-pyrazolyl-NH | 93 |
| 385 2-(2-quinolinyl)-1H-benzimidazole-4-(N-(N'-piperazinyl))amide | 2-quinolinyl | N-piperazinyl-NH | 92 |
| 386 2-(2-quinolinyl)-1H-benzimidazole-4-(N-2-pyrazinyl)amide | 2-quinolinyl | 2-pyrazinyl-NH | 93 |
| 387 2-(2-quinolinyl)-1H-benzimidazole-4-(N-2-pyrimidinyl)amide | 2-quinolinyl | 2-pyrimidinyl-NH | 94 |
| 388 2-(2-quinolinyl)-1H-benzimidazole-4-(N-2-pyridyl)amide | 2-quinolinyl | 2-pyridyl-NH | 92 |
| 389 2-(2-quinolinyl)-1H-benzimidazole-4-(N-4-methyl-5-thiazolyl)amide | 2-quinolinyl | 4-methyl-5-thiazolyl-NH | 92 |
| 390 2-(2-quinolinyl)-1H-benzimidazole-4-(N-2,4-dihydroxyl-5-pyrimidinyl)amide | 2-quinolinyl | 2,4-dihydroxyl-5-pyrimidinyl-NH | 87 |
| 391 2-(2-quinolinyl)-1H-benzimidazole-4-(N-4,6-dimethoxy-2-pyrimidinyl)amide | 2-quinolinyl | 4,6-dimethoxy-2-pyrimidinyl-NH | 94 |

TABLE 2-continued

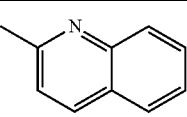

| No. Compounds | X | Y | Field % |
|---|---|---|---|
| 392 2-(2-quinolinyl)-1H-benzimidazole-4-(N-4-chloro-6-amino-2-pyrimidinyl)amide | 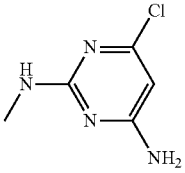 | 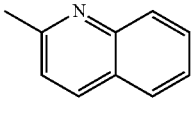 | 93 |
| 393 2-(2-quinolinyl)-1H-benzimidazole-4-(N-4,6-dichloro-5-pyrimidinyl)amide | 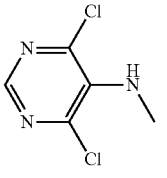 | 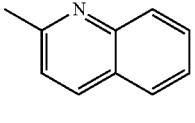 | 93 |
| 394 2-(2-quinolinyl)-1H-benzimidazole-4-(N-o-fluorophenyl)amide | 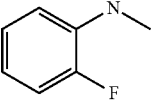 | 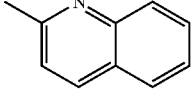 | 93 |
| 395 2-(2-quinolinyl)-1H-benzimidazole-4-(N-2-hydroxyl-4-pyrimidinyl)amide | 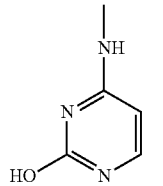 | 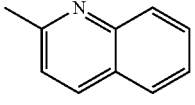 | 88 |
| 396 2-(2-quinolinyl)-1H-benzimidazole-4-(N-6-purinyl)amide | 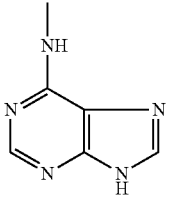 | 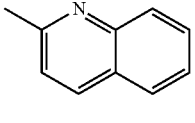 | 90 |
| 397 2-(2-quinolinyl)-1H-benzimidazole-4-(N-6-hydroxyl-2-purinyl)amide | 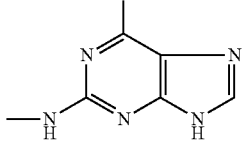 | 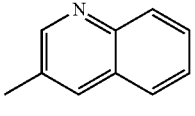 | 85 |
| 398 (L)-2-(3-quinolinyl)-1H-benzimidazole-4-[N-(1-hydroxymethyl-2-p-nitrophenylhydroxyethyl)]amide | 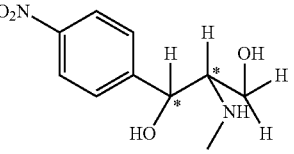 | | 93 |

TABLE 2-continued

| No. Compounds | X | Y | Field % |
|---|---|---|---|
| 399 (L)-2-(3-quinolinyl)-1H-benzimidazole-4-[N-(1-hydroxymethyl-2-p-aminophenylhydroxyethyl)]amide | 3-quinolinyl | 1-hydroxymethyl-2-(4-aminophenyl)-2-hydroxyethyl-N-methyl | 91 |
| 400 2-(3-quinolinyl)-1H-benzimidazole-4-(N-2-piperazinyl)amide | 3-quinolinyl | 2-piperazinyl-N-methyl | 93 |
| 401 2-(3-quinolinyl)-1H-benzimidazole-4-(N-2-pyrimidinyl)amide | 3-quinolinyl | 2-pyrimidinyl-NH | 93 |
| 402 (L)-2-(2-piperidinyl)-1H-benzimidazole-4-[N-(1-hydroxymethyl-2-p-nitrophenylhydroxyethyl)]amide | 2-piperidinyl | 1-hydroxymethyl-2-(4-nitrophenyl)-2-hydroxyethyl-N-methyl | 91 |
| 403 (L)-2-(2-piperidinyl)-1H-benzimidazole-4-[N-(1-hydroxymethyl-2-p-aminophenylhydroxyethyl)]amide | 2-piperidinyl | 1-hydroxymethyl-2-(4-aminophenyl)-2-hydroxyethyl-N-methyl | 89 |
| 404 2-(2-piperidinyl)-1H-benzimidazole-4-[N-(1-methyl-2-p-chlorophenylhydroxyethyl)]amide | 2-piperidinyl | 1-methyl-2-(4-chlorophenyl)-2-hydroxyethyl-N-methyl | 91 |
| 405 2-(2-piperidinyl)-1H-benzimidazole-4-(N-N'-piperidinyl)amide | 2-piperidinyl | N'-piperidinyl-N-methyl | 92 |
| 406 2-(2-piperidinyl)-1H-benzimidazole-4-(N-2-piperazinyl)amide | 2-piperidinyl | 2-piperazinyl-N-methyl | 90 |
| 407 2-(2-piperidinyl)-1H-benzimidazole-4-(N-2'-benzimidazolyl)amide | 2-piperidinyl | 2'-benzimidazolyl-NH | 93 |

TABLE 2-continued

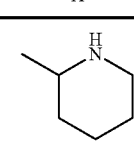

| No. | Compounds | X | Y | Field % |
|---|---|---|---|---|
| 408 | 2-(2-piperidinyl)-1H-benzimidazole-4-(N-o-aminophenyl)amide | 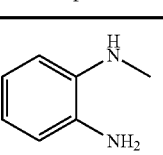 | 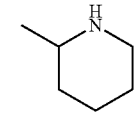 | 93 |
| 409 | 2-(2-piperidinyl)-1H-benzimidazole-4-(N-5-benzimidazolonyl)amide | 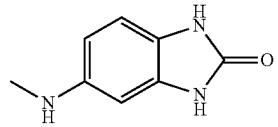 | 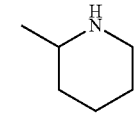 | 93 |
| 410 | 2-(2-piperidinyl)-1H-benzimidazole-4-(N-4'-carbonamido-5'-imidazolyl)amide | 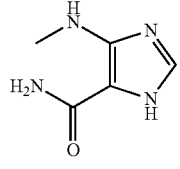 | 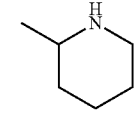 | 85 |
| 411 | 2-(2-piperidinyl)-1H-benzimidazole-4-(N-4'-pyrazolyl)amide | 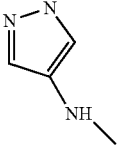 | 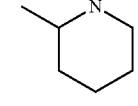 | 89 |
| 412 | 2-(2-piperidinyl)-1H-benzimidazole-4-(N-(N'-piperazinyl))amide | 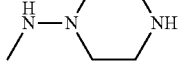 | 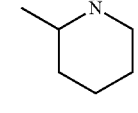 | 87 |
| 413 | 2-(2-piperidinyl)-1H-benzimidazole-4-(N-2-pyrazinyl)amide | 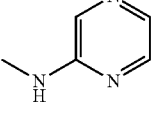 | 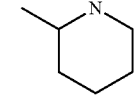 | 93 |
| 414 | 2-(2-piperidinyl)-1H-benzimidazole-4-(N-2-pyrimidinyl)amide | 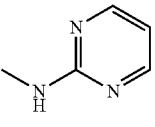 | 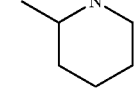 | 92 |
| 415 | 2-(2-piperidinyl)-1H-benzimidazole-4-(N-2-pyridyl)amide | 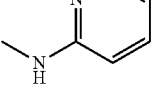 | 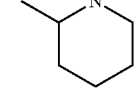 | 91 |
| 416 | 2-(2-piperidinyl)-1H-benzimidazole-4-(N-4-methyl-5-thiazolyl)amide | 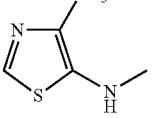 |  | 93 |

TABLE 2-continued

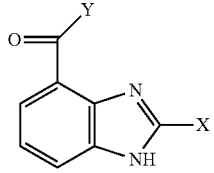

| No. | Compounds | X | Y | Field % |
|---|---|---|---|---|
| 417 | 2-(2-piperidinyl)-1H-benzimidazole-4-(N-2,4-dihydroxyl-5-pyrimidinyl)amide | 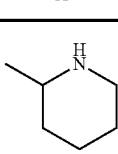 | 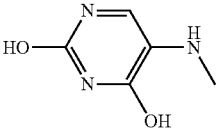 | 88 |
| 418 | 2-(2-piperidinyl)-1H-benzimidazole-4-(N-4,6-dimethoxy-2-pyrimidinyl)amide | 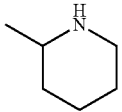 | 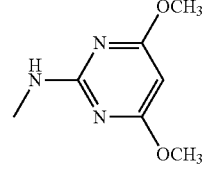 | 93 |
| 419 | 2-(2-piperidinyl)-1H-benzimidazole-4-(N-4-chloro-6-amino-2-pyrimidinyl)amide | 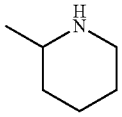 | 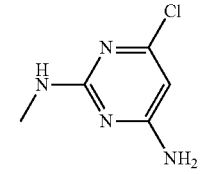 | 89 |
| 420 | 2-(2-piperidinyl)-1H-benzimidazole-4-(N-4,6-dichloro-5-pyrimidinyl)amide | 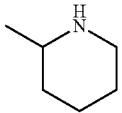 | 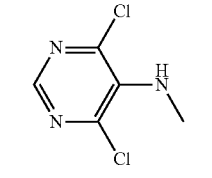 | 93 |
| 421 | 2-(2-piperidinyl)-1H-benzimidazole-4-(N-o-fluorophenyl)amide | 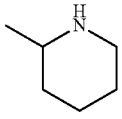 | 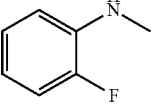 | 92 |
| 422 | 2-(2-piperidinyl)-1H-benzimidazole-4-(N-2-hydroxyl-4-pyrimidinyl)amide | 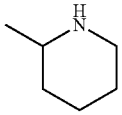 | 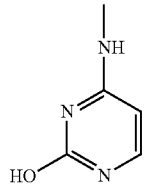 | 86 |
| 423 | 2-(2-piperidinyl)-1H-benzimidazole-4-(N-6-purinyl)amide | 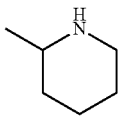 | 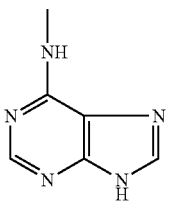 | 91 |

TABLE 2-continued

| No. Compounds | X | Y | Field % |
|---|---|---|---|
| 424 2-(2-piperidinyl)-1H-benzimidazole-4-(N-6-hydroxyl-2-purinyl)amide | 2-methylpiperidinyl | N-6-hydroxy-2-purinyl | 89 |
| 425 (L)-2-(3-piperidinyl)-1H-benzimidazole-4-[N-(1-hydroxymethyl-2-p-nitrophenylhydroxyethyl)]amide | 3-methylpiperidinyl | 1-hydroxymethyl-2-p-nitrophenylhydroxyethyl | 93 |
| 426 (L)-2-(3-piperidinyl)-1H-benzimidazole-4-[N-(1-hydroxymethyl-2-p-aminophenylhydroxyethyl)]amide | 3-methylpiperidinyl | 1-hydroxymethyl-2-p-aminophenylhydroxyethyl | 90 |
| 427 2-(3-piperidinyl)-1H-benzimidazole-4-(N-2-piperazinyl)amide | 3-methylpiperidinyl | N-2-piperazinyl | 90 |
| 428 2-(3-piperidinyl)-1H-benzimidazole-4-(N-2-pyrimidinyl)amide | 3-methylpiperidinyl | N-2-pyrimidinyl | 94 |
| 429 (L)-2-(4-piperidinyl)-1H-benzimidazole-4-[N-(1-hydroxymethyl-2-p-nitrophenylhydroxyethyl)]amide | 4-methylpiperidinyl | 1-hydroxymethyl-2-p-nitrophenylhydroxyethyl | 92 |
| 430 (L)-2-(4-piperidinyl)-1H-benzimidazole-4-[N-(1-hydroxymethyl-2-p-aminophenylhydroxyethyl)]amide | 4-methylpiperidinyl | 1-hydroxymethyl-2-p-aminophenylhydroxyethyl | 90 |
| 431 2-(4-piperidinyl)-1H-benzimidazole-4-(N-2-piperazinyl)amide | 4-methylpiperidinyl | N-2-piperazinyl | 91 |

TABLE 2-continued

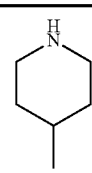

| No. Compounds | X | Y | Field % |
|---|---|---|---|
| 432 2-(4-piperidinyl)-1H-benzimidazole-4-(N-2-pyrimidinyl)amide | 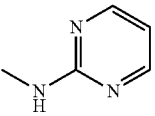 | 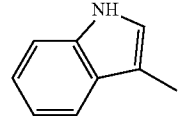 | 93 |
| 433 (L)-2-(3-indolyl)-1H-benzimidazole-4-[N-(1-hydroxymethyl-2-p-nitrophenylhydroxyethyl)]amide | 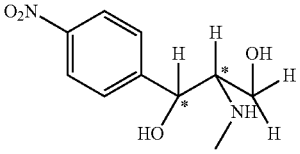 | 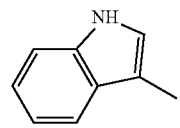 | 93 |
| 434 (L)-2-(3-indolyl)-1H-benzimidazole-4-[N-(1-hydroxymethyl-2-p-aminophenylhydroxyethyl)]amide | 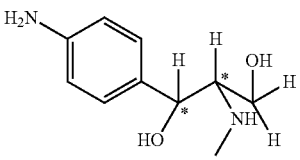 | 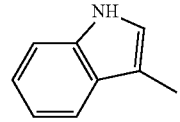 | 88 |
| 435 2-(3-indolyl)-1H-benzimidazole-4-[N-(1-methyl-2-p-chlorophenylhydroxyethyl)]amide | 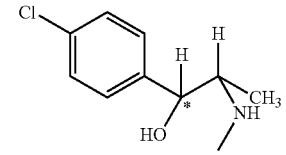 | 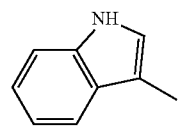 | 90 |
| 436 2-(3-indolyl)-1H-benzimidazole-4-(N-N'-piperidinyl)amide | 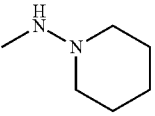 | 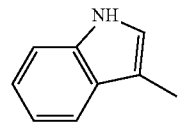 | 94 |
| 437 2-(3-indolyl)-1H-benzimidazole-4-(N-2-piperazinyl)amide | 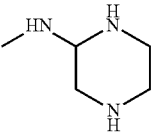 | 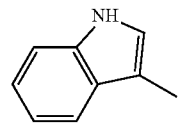 | 92 |
| 438 2-(3-indolyl)-1H-benzimidazole-4-(N-2'-benzimidazolyl)amide | 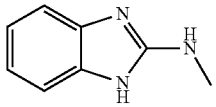 | 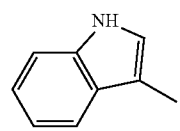 | 90 |
| 439 2-(3-indolyl)-1H-benzimidazole-4-(N-o-aminophenyl)amide | 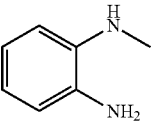 | 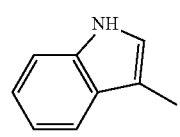 | 91 |
| 440 2-(3-indolyl)-1H-benzimidazole-4-(N-5-benzimidazolonyl)amide | 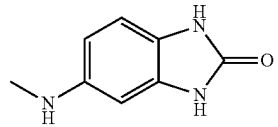 |  | 93 |

TABLE 2-continued

| No. Compounds | X | Y | Field % |
|---|---|---|---|
| 441 2-(3-indolyl)-1H-benzimidazole-4-(N-4'-carbonamido-5'-imidazolyl)amide | 3-indolyl-NH | 4-carbonamido-5-imidazolyl-NH | 93 |
| 442 2-(3-indolyl)-1H-benzimidazole-4-(N-4'-pyrazolyl)amide | 3-indolyl-NH | 4-pyrazolyl-NH | 88 |
| 443 2-(3-indolyl)-1H-benzimidazole-4-(N-(N'-piperazinyl))amide | 3-indolyl-NH | N-piperazinyl-NH | 89 |
| 444 2-(3-indolyl)-1H-benzimidazole-4-(N-2-pyrazinyl)amide | 3-indolyl-NH | 2-pyrazinyl-NH | 94 |
| 445 2-(3-indolyl)-1H-benzimidazole-4-(N-2-pyrimidinyl)amide | 3-indolyl-NH | 2-pyrimidinyl-NH | 92 |
| 446 2-(3-indolyl)-1H-benzimidazole-4-(N-2-pyridyl)amide | 3-indolyl-NH | 2-pyridyl-NH | 93 |
| 447 2-(3-indolyl)-1H-benzimidazole-4-(N-4-methyl-5-thiazolyl)amide | 3-indolyl-NH | 4-methyl-5-thiazolyl-NH | 91 |
| 448 2-(3-indolyl)-1H-benzimidazole-4-(N-2,4-dihydroxyl-5-pyrimidinyl)amide | 3-indolyl-NH | 2,4-dihydroxyl-5-pyrimidinyl-NH | 87 |
| 449 2-(3-indolyl)-1H-benzimidazole-4-(N-4,6-dimethoxy-2-pyrimidinyl)amide | 3-indolyl-NH | 4,6-dimethoxy-2-pyrimidinyl-NH | 93 |

TABLE 2-continued

| No. | Compounds | X | Y | Field % |
|-----|-----------|---|---|---------|
| 450 | 2-(3-indolyl)-1H-benzimidazole-4-(N-4-chloro-6-amino-2-pyrimidinyl)amide | 3-indolyl-NH | 4-chloro-6-amino-2-pyrimidinyl-NH | 88 |
| 451 | 2-(3-indolyl)-1H-benzimidazole-4-(N-4,6-dichloro-5-pyrimidinyl)amide | 3-indolyl-NH | 4,6-dichloro-5-pyrimidinyl-NH | 92 |
| 452 | 2-(3-indolyl)-1H-benzimidazole-4-(N-o-fluorophenyl)amide | 3-indolyl-NH | o-fluorophenyl-NH | 94 |
| 453 | 2-(3-indolyl)-1H-benzimidazole-4-(N-2-hydroxyl-4-pyrimidinyl)amide | 3-indolyl-NH | 2-hydroxyl-4-pyrimidinyl-NH | 86 |
| 454 | 2-(3-indolyl)-1H-benzimidazole-4-(N-6-purinyl)amide | 3-indolyl-NH | 6-purinyl-NH | 90 |
| 455 | 2-(3-indolyl)-1H-benzimidazole-4-(N-6-hydroxyl-2-purinyl)amide | 3-indolyl-NH | 6-hydroxyl-2-purinyl-NH | 86 |
| 456 | (L)-2-(2'-imidazolyl)-1H-benzimidazole-4-[N-(1-hydroxymethyl-2-p-nitrophenylhydroxyethyl)]amide | 2-imidazolyl | 1-hydroxymethyl-2-p-nitrophenylhydroxyethyl-NH | 93 |

TABLE 2-continued

| No. | Compounds | X | Y | Field % |
|-----|-----------|---|---|---------|
| 457 | (L)-2-(2'-imidazolyl)-1H-benzimidazole-4-[N-(1-hydroxymethyl-2-p-aminophenylhydroxyethyl)]amide | 2-imidazolyl | 1-hydroxymethyl-2-(p-aminophenyl)-2-hydroxyethyl-N-methylamino | 93 |
| 458 | 2-(2'-imidazolyl)-1H-benzimidazole-4-[N-(1-methyl-2-p-chlorophenylhydroxyethyl)]amide | 2-imidazolyl | 1-methyl-2-(p-chlorophenyl)-2-hydroxyethyl-N-methylamino | 88 |
| 459 | 2-(2'-imidazolyl)-1H-benzimidazole-4-(N-N'-piperidinyl)amide | 2-imidazolyl | N'-piperidinyl-N-methylamino | 93 |
| 460 | 2-(2'-imidazolyl)-1H-benzimidazole-4-(N-2-piperazinyl)amide | 2-imidazolyl | 2-piperazinyl-N-methyl | 90 |
| 461 | 2-(2'-imidazolyl)-1H-benzimidazole-4-(N-2'-benzimidazolyl)amide | 2-imidazolyl | 2'-benzimidazolyl-N-methyl | 94 |
| 462 | 2-(2'-imidazolyl)-1H-benzimidazole-4-(N-o-aminophenyl)amide | 2-imidazolyl | o-aminophenyl-N-methyl | 86 |
| 463 | 2-(2'-imidazolyl)-1H-benzimidazole-4-(N-5-benzimidazolonyl)amide | 2-imidazolyl | 5-benzimidazolonyl-N-methyl | 90 |
| 464 | 2-(2'-imidazolyl)-1H-benzimidazole-4-(N-4'-carbonamido-5'-imidazolyl)amide | 2-imidazolyl | 4'-carbonamido-5'-imidazolyl-N-methyl | 86 |
| 465 | 2-(2'-imidazolyl)-1H-benzimidazole-4-(N-4'-pyrazolyl)amide | 2-imidazolyl | 4'-pyrazolyl-N-methyl | 93 |

TABLE 2-continued

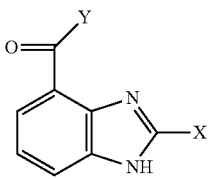

| No. Compounds | X | Y | Field % |
|---|---|---|---|
| 466 2-(2'-imidazolyl)-1H-benzimidazole-4-(N-(N'-piperazinyl))amide | 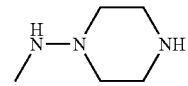 | 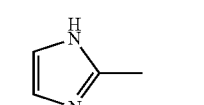 | 93 |
| 467 2-(2'-imidazolyl)-1H-benzimidazole-4-(N-2-pyrazinyl)amide | 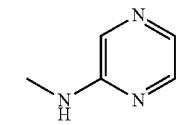 | 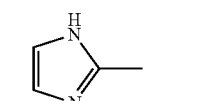 | 94 |
| 468 2-(2'-imidazolyl)-1H-benzimidazole-4-(N-2-pyrimidinyl)amide | 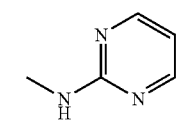 | 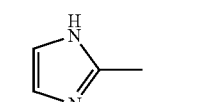 | 93 |
| 469 2-(2'-imidazolyl)-1H-benzimidazole-4-(N-2-pyridyl)amide | 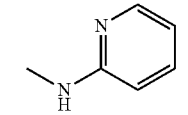 | 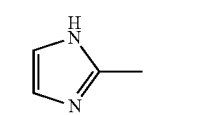 | 90 |
| 470 2-(2'-imidazolyl)-1H-benzimidazole-4-(N-4-methyl-5-thiazolyl)amide | 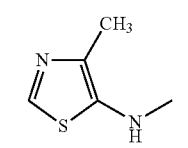 | 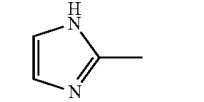 | 94 |
| 471 2-(2'-imidazolyl)-1H-benzimidazole-4-(N-2,4-dihydroxyl-5-pyrimidinyl)amide | 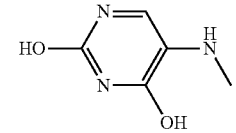 | 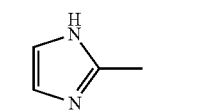 | 86 |
| 472 2-(2'-imidazolyl)-1H-benzimidazole-4-(N-4,6-dimethoxy-2-pyrimidinyl)amide | 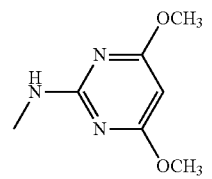 | 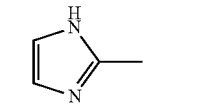 | 94 |
| 473 2-(2'-imidazolyl)-1H-benzimidazole-4-(N-4-chloro-6-amino-2-pyrimidinyl)amide | 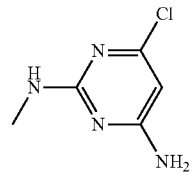 | 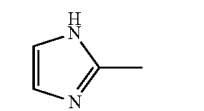 | 86 |
| 474 2-(2'-imidazolyl)-1H-benzimidazole-4-(N-4,6-dichloro-5-pyrimidinyl)amide | 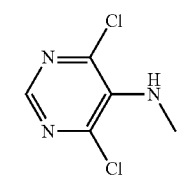 |  | 93 |

TABLE 2-continued

| No. Compounds | X | Y | Field % |
|---|---|---|---|
| 475 2-(2'-imidazolyl)-1H-benzimidazole-4-(N-o-fluorophenyl)amide | 2-imidazolyl | N-methyl-o-fluorophenyl | 93 |
| 476 2-(2'-imidazolyl)-1H-benzimidazole-4-(N-2-hydroxyl-4-pyrimidinyl)amide | 2-imidazolyl | N-methyl-2-hydroxy-4-pyrimidinyl | 88 |
| 477 2-(2'-imidazolyl)-1H-benzimidazole-4-(N-6-purinyl)amide | 2-imidazolyl | N-methyl-6-purinyl | 93 |
| 478 2-(2'-imidazolyl)-1H-benzimidazole-4-(N-6-hydroxyl-2-purinyl)amide | 2-imidazolyl | N-methyl-6-hydroxy-2-purinyl | 87 |
| 479 (L)-2-(3-pyrazolyl)-1H-benzimidazole-4-[N-(1-hydroxymethyl-2-p-nitrophenylhydroxyethyl)]amide | 3-pyrazolyl | 1-hydroxymethyl-2-p-nitrophenylhydroxyethyl-N-methyl | 94 |
| 480 (L)-2-(3-pyrazolyl)-1H-benzimidazole-4-[N-(1-hydroxymethyl-2-p-aminophenylhydroxyethyl)]amide | 3-pyrazolyl | 1-hydroxymethyl-2-p-aminophenylhydroxyethyl-N-methyl | 86 |
| 481 2-(3-pyrazolyl)-1H-benzimidazole-4-[N-(1-methyl-2-p-chlorophenylhydroxyethyl)]amide | 3-pyrazolyl | 1-methyl-2-p-chlorophenylhydroxyethyl-N-methyl | 90 |
| 482 2-(3-pyrazolyl)-1H-benzimidazole-4-(N-N'-piperidinyl)amide | 3-pyrazolyl | N-methyl-N'-piperidinyl | 94 |

TABLE 2-continued

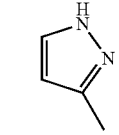

| No. Compounds | X | Y | Field % |
|---|---|---|---|
| 483 2-(3-pyrazolyl)-1H-benzimidazole-4-(N-2-piperazinyl)amide | 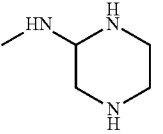 | 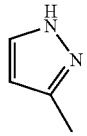 | 93 |
| 484 2-(3-pyrazolyl)-1H-benzimidazole-4-(N-2'-benzimidazolyl)amide | 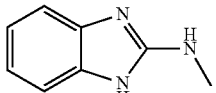 | 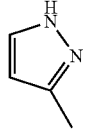 | 93 |
| 485 2-(3-pyrazolyl)-1H-benzimidazole-4-(N-o-aminophenyl)amide | 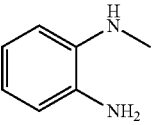 | 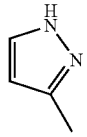 | 88 |
| 486 2-(3-pyrazolyl)-1H-benzimidazole-4-(N-5-benzimidazolonyl)amide | 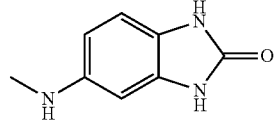 | 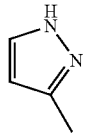 | 93 |
| 487 2-(3-pyrazolyl)-1H-benzimidazole-4-(N-4'-carbonamido-5'-imidazolyl)amide | 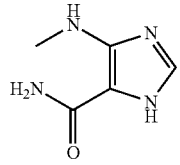 | 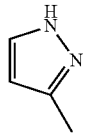 | 87 |
| 488 2-(3-pyrazolyl)-1H-benzimidazole-4-(N-4'-pyrazolyl)amide | 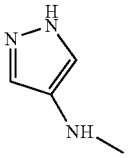 | 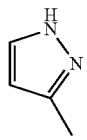 | 94 |
| 489 2-(3-pyrazolyl)-1H-benzimidazole-4-(N-(N'-piperazinyl))amide | 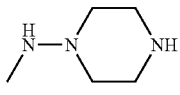 | 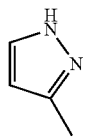 | 86 |
| 490 2-(3-pyrazolyl)-1H-benzimidazole-4-(N-2-pyrazinyl)amide | 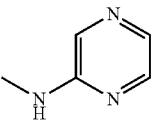 | 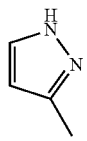 | 90 |
| 491 2-(3-pyrazolyl)-1H-benzimidazole-4-(N-2-pyrimidinyl)amide | | 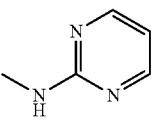 | 86 |

TABLE 2-continued

| No. Compounds | X | Y | Field % |
|---|---|---|---|
| 492 2-(3-pyrazolyl)-1H-benzimidazole-4-(N-2-pyridyl)amide | 3-pyrazolyl | N-(2-pyridyl) | 93 |
| 493 2-(3-pyrazolyl)-1H-benzimidazole-4-(N-4-methyl-5-thiazolyl)amide | 3-pyrazolyl | N-(4-methyl-5-thiazolyl) | 93 |
| 494 2-(3-pyrazolyl)-1H-benzimidazole-4-(N-2,4-dihydroxyl-5-pyrimidinyl)amide | 3-pyrazolyl | N-(2,4-dihydroxyl-5-pyrimidinyl) | 88 |
| 495 2-(3-pyrazolyl)-1H-benzimidazole-4-(N-4,6-dimethoxy-2-pyrimidinyl)amide | 3-pyrazolyl | N-(4,6-dimethoxy-2-pyrimidinyl) | 93 |
| 496 2-(3-pyrazolyl)-1H-benzimidazole-4-(N-4-chloro-6-amino-2-pyrimidinyl)amide | 3-pyrazolyl | N-(4-chloro-6-amino-2-pyrimidinyl) | 88 |
| 497 2-(3-pyrazolyl)-1H-benzimidazole-4-(N-4,6-dichloro-5-pyrimidinyl)amide | 3-pyrazolyl | N-(4,6-dichloro-5-pyrimidinyl) | 94 |
| 498 2-(3-pyrazolyl)-1H-benzimidazole-4-(N-o-fluorophenyl)amide | 3-pyrazolyl | N-(o-fluorophenyl) | 93 |
| 499 2-(3-pyrazolyl)-1H-benzimidazole-4-(N-2-hydroxyl-4-pyrimidinyl)amide | 3-pyrazolyl | N-(2-hydroxyl-4-pyrimidinyl) | 90 |

TABLE 2-continued

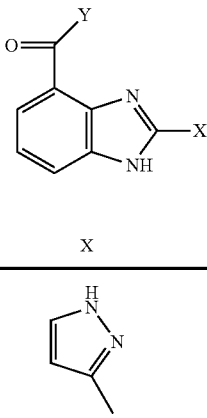

| No. Compounds | X | Y | Field % |
|---|---|---|---|
| 500 2-(3-pyrazolyl)-1H-benzimidazole-4-(N-6-purinyl)amide | 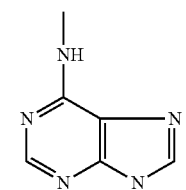 | 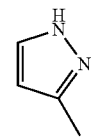 | 86 |
| 501 2-(3-pyrazolyl)-1H-benzimidazole-4-(N-6-hydroxyl-2-purinyl)amide | 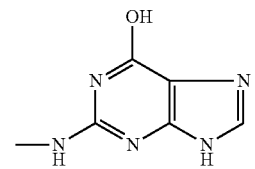 | 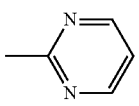 | 89 |
| 502 (L)-2-(2-pyrimidinyl)-1H-benzimidazole-4-[N-(1-hydroxymethyl-2-p-nitrophenylhydroxyethyl)]amide | 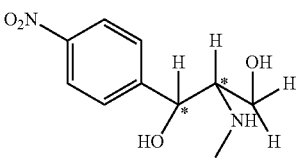 | 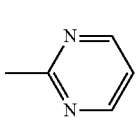 | 93 |
| 503 (L)-2-(2-pyrimidinyl)-1H-benzimidazole-4-[N-(1-hydroxymethyl-2-p-aminophenylhydroxyethyl)]amide | 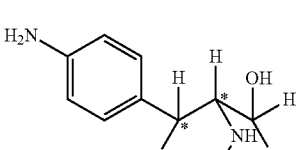 | 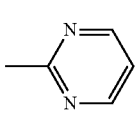 | 88 |
| 504 2-(2-pyrimidinyl)-1H-benzimidazole-4-[N-(1-methyl-2-p-chlorophenylhydroxyethyl)]amide | 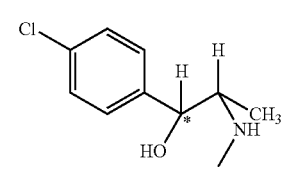 | 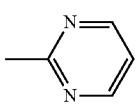 | 93 |
| 505 2-(2-pyrimidinyl)-1H-benzimidazole-4-(N-N'-piperidinyl)amide | 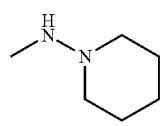 | 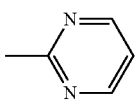 | 90 |
| 506 2-(2-pyrimidinyl)-1H-benzimidazole-4-(N-2-piperazinyl)amide | 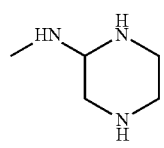 | 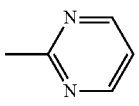 | 94 |
| 507 2-(2-pyrimidinyl)-1H-benzimidazole-4-(N-2'-benzimidazolyl)amide | 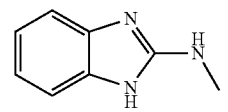 |  | 92 |

TABLE 2-continued

| No. Compounds | X | Y | Field % |
|---|---|---|---|
| 508 2-(2-pyrimidinyl)-1H-benzimidazole-4-(N-o-aminophenyl)amide | 2-pyrimidinyl | o-aminophenylamino | 90 |
| 509 2-(2-pyrimidinyl)-1H-benzimidazole-4-(N-5-benzimidazolonyl)amide | 2-pyrimidinyl | 5-benzimidazolonylamino | 86 |
| 510 2-(2-pyrimidinyl)-1H-benzimidazole-4-(N-4'-carbonamido-5'-imidazolyl)amide | 2-pyrimidinyl | 4'-carbonamido-5'-imidazolylamino | 87 |
| 511 2-(2-pyrimidinyl)-1H-benzimidazole-4-(N-4'-pyrazolyl)amide | 2-pyrimidinyl | 4'-pyrazolylamino | 93 |
| 512 2-(2-pyrimidinyl)-1H-benzimidazole-4-(N-(N'-piperazinyl))amide | 2-pyrimidinyl | N'-piperazinylamino | 88 |
| 513 2-(2-pyrimidinyl)-1H-benzimidazole-4-(N-2-pyrazinyl)amide | 2-pyrimidinyl | 2-pyrazinylamino | 93 |
| 514 2-(2-pyrimidinyl)-1H-benzimidazole-4-(N-2-pyrimidinyl)amide | 2-pyrimidinyl | 2-pyrimidinylamino | 90 |
| 515 2-(2-pyrimidinyl)-1H-benzimidazole-4-(N-2-pyridyl)amide | 2-pyrimidinyl | 2-pyridylamino | 94 |
| 516 2-(2-pyrimidinyl)-1H-benzimidazole-4-(N-4-methyl-5-thiazolyl)amide | 2-pyrimidinyl | 4-methyl-5-thiazolylamino | 93 |

TABLE 2-continued

| No. Compounds | X | Y | Field % |
|---|---|---|---|
| 517 2-(2-pyrimidinyl)-1H-benzimidazole-4-(N-2,4-dihydroxyl-5-pyrimidinyl)amide | 2-pyrimidinyl | 2,4-dihydroxy-5-pyrimidinyl-NH- | 90 |
| 518 2-(2-pyrimidinyl)-1H-benzimidazole-4-(N-4,6-dimethoxy-2-pyrimidinyl)amide | 2-pyrimidinyl | 4,6-dimethoxy-2-pyrimidinyl-NH- | 86 |
| 519 2-(2-pyrimidinyl)-1H-benzimidazole-4-(N-4-chloro-6-amino-2-pyrimidinyl)amide | 2-pyrimidinyl | 4-chloro-6-amino-2-pyrimidinyl-NH- | 93 |
| 520 2-(2-pyrimidinyl)-1H-benzimidazole-4-(N-4,6-dichloro-5-pyrimidinyl)amide | 2-pyrimidinyl | 4,6-dichloro-5-pyrimidinyl-NH- | 93 |
| 521 2-(2-pyrimidinyl)-1H-benzimidazole-4-(N-o-fluorophenyl)amide | 2-pyrimidinyl | o-fluorophenyl-NH- | 93 |
| 522 2-(2-pyrimidinyl)-1H-benzimidazole-4-(N-2-hydroxyl-4-pyrimidinyl)amide | 2-pyrimidinyl | 2-hydroxy-4-pyrimidinyl-NH- | 88 |
| 523 2-(2-pyrimidinyl)-1H-benzimidazole-4-(N-6-purinyl)amide | 2-pyrimidinyl | 6-purinyl-NH- | 90 |

TABLE 2-continued

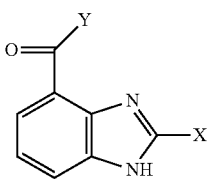

| No. | Compounds | X | Y | Field % |
|---|---|---|---|---|
| 524 | 2-(2-pyrimidinyl)-1H-benzimidazole-4-(N-6-hydroxyl-2-purinyl)amide | 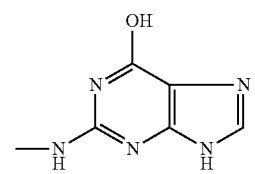 | 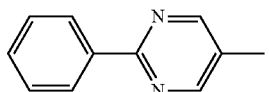 | 86 |
| 525 | (L)-2-(2-phenyl-5-pyrimidinyl)-1H-benzimidazole-4-[N-(1-hydroxymethyl-2-p-nitrophenylhydroxyethyl)]amide | 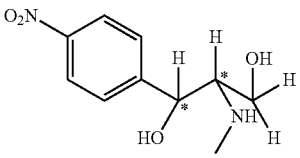 | 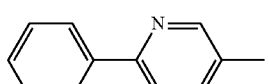 | 90 |
| 526 | (L)-2-(2-phenyl-5-pyrimidinyl)-1H-benzimidazole-4-[N-(1-hydroxymethyl-2-p-aminophenylhydroxyethyl)]amide | 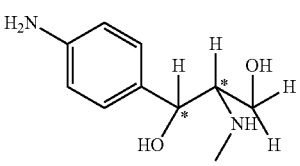 | 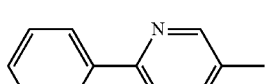 | 90 |
| 527 | 2-(2-phenyl-5-pyrimidinyl)-1H-benzimidazole-4-[N-(1-methyl-2-p-chlorophenylhydroxyethyl)]amide | 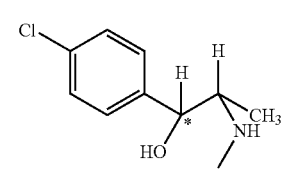 | 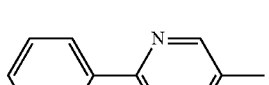 | 86 |
| 528 | 2-(2-phenyl-5-pyrimidinyl)-1H-benzimidazole-4-(N-N'-piperidinyl)amide | 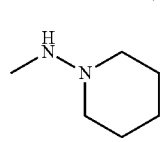 | 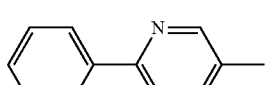 | 93 |
| 529 | 2-(2-phenyl-5-pyrimidinyl)-1H-benzimidazole-4-(N-2-piperazinyl)amide | 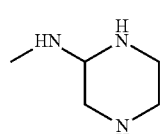 | 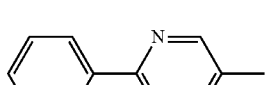 | 93 |
| 530 | 2-(2-phenyl-5-pyrimidinyl)-1H-benzimidazole-4-(N-2'-benzimidazolyl)amide | 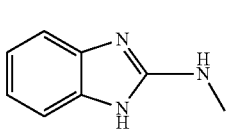 | 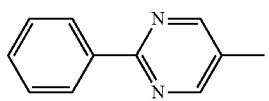 | 88 |
| 531 | 2-(2-phenyl-5-pyrimidinyl)-1H-benzimidazole-4-(N-o-aminophenyl)amide | 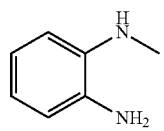 | 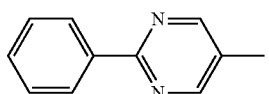 | 93 |
| 532 | 2-(2-phenyl-5-pyrimidinyl)-1H-benzimidazole-4-(N-5-benzimidazolonyl)amide | 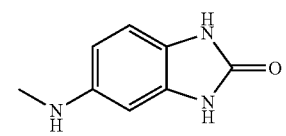 |  | 90 |

TABLE 2-continued

| No. Compounds | X | Y | Field % |
|---|---|---|---|
| 533 2-(2-phenyl-5-pyrimidinyl)-1H-benzimidazole-4-(N-4'-carbonamido-5'-imidazolyl)amide | 2-phenyl-5-pyrimidinyl | 4-carbonamido-5-imidazolyl-NH- | 94 |
| 534 2-(2-phenyl-5-pyrimidinyl)-1H-benzimidazole-4-(N-4'-pyrazolyl)amide | 2-phenyl-5-pyrimidinyl | 4-pyrazolyl-NH- | 90 |
| 535 2-(2-phenyl-5-pyrimidinyl)-1H-benzimidazole-4-(N-(N'-piperazinyl))amide | 2-phenyl-5-pyrimidinyl | N-piperazinyl-NH- | 90 |
| 536 2-(2-phenyl-5-pyrimidinyl)-1H-benzimidazole-4-(N-2-pyrazinyl)amide | 2-phenyl-5-pyrimidinyl | 2-pyrazinyl-NH- | 86 |
| 537 2-(2-phenyl-5-pyrimidinyl)-1H-benzimidazole-4-(N-2-pyrimidinyl)amide | 2-phenyl-5-pyrimidinyl | 2-pyrimidinyl-NH- | 93 |
| 538 2-(2-phenyl-5-pyrimidinyl)-1H-benzimidazole-4-(N-2-pyridyl)amide | 2-phenyl-5-pyrimidinyl | 2-pyridyl-NH- | 93 |
| 539 2-(2-phenyl-5-pyrimidinyl)-1H-benzimidazole-4-(N-4-methyl-5-thiazolyl)amide | 2-phenyl-5-pyrimidinyl | 4-methyl-5-thiazolyl-NH- | 88 |
| 540 2-(2-phenyl-5-pyrimidinyl)-1H-benzimidazole-4-(N-2,4-dihydroxyl-5-pyrimidinyl)amide | 2-phenyl-5-pyrimidinyl | 2,4-dihydroxyl-5-pyrimidinyl-NH- | 93 |
| 541 2-(2-phenyl-5-pyrimidinyl)-1H-benzimidazole-4-(N-4,6-dimethoxy-2-pyrimidinyl)amide | 2-phenyl-5-pyrimidinyl | 4,6-dimethoxy-2-pyrimidinyl-NH- | 90 |

TABLE 2-continued

| No. | Compounds | X | Y | Field % |
|---|---|---|---|---|
| 542 | 2-(2-phenyl-5-pyrimidinyl)-1H-benzimidazole-4-(N-4-chloro-6-amino-2-pyrimidinyl)amide | 2-phenyl-5-pyrimidinyl | N-(4-chloro-6-amino-2-pyrimidinyl) | 94 |
| 543 | 2-(2-phenyl-5-pyrimidinyl)-1H-benzimidazole-4-(N-4,6-dichloro-5-pyrimidinyl)amide | 2-phenyl-5-pyrimidinyl | N-(4,6-dichloro-5-pyrimidinyl) | 94 |
| 544 | 2-(2-phenyl-5-pyrimidinyl)-1H-benzimidazole-4-(N-o-fluorophenyl)amide | 2-phenyl-5-pyrimidinyl | N-(o-fluorophenyl) | 90 |
| 545 | 2-(2-phenyl-5-pyrimidinyl)-1H-benzimidazole-4-(N-2-hydroxyl-4-pyrimidinyl)amide | 2-phenyl-5-pyrimidinyl | N-(2-hydroxyl-4-pyrimidinyl) | 86 |
| 546 | 2-(2-phenyl-5-pyrimidinyl)-1H-benzimidazole-4-(N-6-purinyl)amide | 2-phenyl-5-pyrimidinyl | N-(6-purinyl) | 93 |
| 547 | 2-(2-phenyl-5-pyrimidinyl)-1H-benzimidazole-4-(N-6-hydroxyl-2-purinyl)amide | 2-phenyl-5-pyrimidinyl | N-(6-hydroxyl-2-purinyl) | 93 |
| 548 | (L)-2-(4-amino-6-chloro-5-pyrimidinyl)-1H-benzimidazole-4-[N-(1-hydroxymethyl-2-p-nitrophenylhydroxyethyl)]amide | 4-amino-6-chloro-5-pyrimidinyl | N-(1-hydroxymethyl-2-p-nitrophenylhydroxyethyl) | 88 |

TABLE 2-continued

| No. | Compounds | X | Y | Field % |
|---|---|---|---|---|
| 549 | (L)-2-(4-amino-6-chloro-5-pyrimidinyl)-1H-benzimidazole-4-[N-(1-hydroxymethyl-2-p-aminophenylhydroxyethyl)]amide | 4-amino-6-chloro-5-pyrimidinyl | 1-hydroxymethyl-2-p-aminophenylhydroxyethyl | 93 |
| 550 | 2-(4-amino-6-chloro-5-pyrimidinyl)-1H-benzimidazole-4-[N-(1-methyl-2-p-chlorophenylhydroxyethyl)]amide | 4-amino-6-chloro-5-pyrimidinyl | 1-methyl-2-p-chlorophenylhydroxyethyl | 90 |
| 551 | 2-(4-amino-6-chloro-5-pyrimidinyl)-1H-benzimidazole-4-(N-N'-piperidinyl)amide | 4-amino-6-chloro-5-pyrimidinyl | N'-piperidinyl | 94 |
| 552 | 2-(4-amino-6-chloro-5-pyrimidinyl)-1H-benzimidazole-4-(N-2-piperazinyl)amide | 4-amino-6-chloro-5-pyrimidinyl | 2-piperazinyl | 86 |
| 553 | 2-(4-amino-6-chloro-5-pyrimidinyl)-1H-benzimidazole-4-(N-2'-benzimidazolyl)amide | 4-amino-6-chloro-5-pyrimidinyl | 2'-benzimidazolyl | 90 |
| 554 | 2-(4-amino-6-chloro-5-pyrimidinyl)-1H-benzimidazole-4-(N-o-aminophenyl)amide | 4-amino-6-chloro-5-pyrimidinyl | o-aminophenyl | 86 |
| 555 | 2-(4-amino-6-chloro-5-pyrimidinyl)-1H-benzimidazole-4-(N-5-benzimidazolonyl)amide | 4-amino-6-chloro-5-pyrimidinyl | 5-benzimidazolonyl | 93 |

TABLE 2-continued

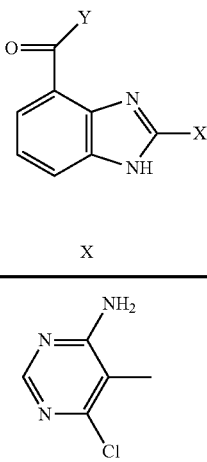

| No. Compounds | X | Y | Field % |
|---|---|---|---|
| 556 2-(4-amino-6-chloro-5-pyrimidinyl)-1H-benzimidazole-4-(N-4'-carbonamido-5'-imidazolyl)amide | 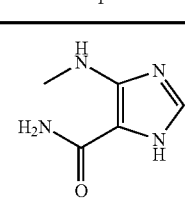 | 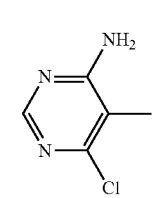 | 86 |
| 557 2-(4-amino-6-chloro-5-pyrimidinyl)-1H-benzimidazole-4-(N-4'-pyrazolyl)amide | 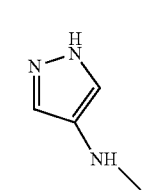 | 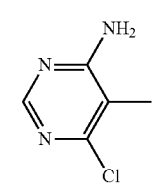 | 88 |
| 558 2-(4-amino-6-chloro-5-pyrimidinyl)-1H-benzimidazole-4-(N-(N'-piperazinyl))amide | 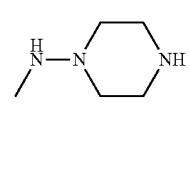 | 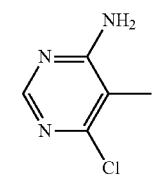 | 93 |
| 559 2-(4-amino-6-chloro-5-pyrimidinyl)-1H-benzimidazole-4-(N-2-pyrazinyl)amide | 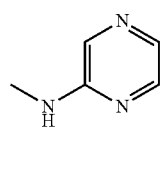 | 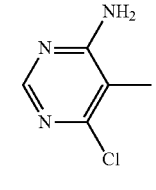 | 90 |
| 560 2-(4-amino-6-chloro-5-pyrimidinyl)-1H-benzimidazole-4-(N-2-pyrimidinyl)amide | 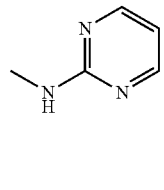 | 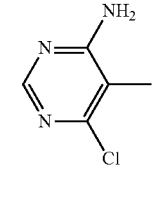 | 90 |
| 561 2-(4-amino-6-chloro-5-pyrimidinyl)-1H-benzimidazole-4-(N-2-pyridyl)amide | 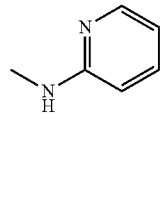 | 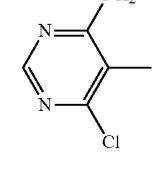 | 86 |
| 562 2-(4-amino-6-chloro-5-pyrimidinyl)-1H-benzimidazole-4-(N-4-methyl-5-thiazolyl)amide | 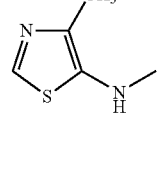 | | 90 |

TABLE 2-continued

| No. | Compounds | X | Y | Field % |
|---|---|---|---|---|
| 563 | 2-(4-amino-6-chloro-5-pyrimidinyl)-1H-benzimidazole-4-(N-2,4-dihydroxyl-5-pyrimidinyl)amide | 4-amino-6-chloro-5-pyrimidinyl | 2,4-dihydroxy-5-pyrimidinyl-NH- | 86 |
| 564 | 2-(4-amino-6-chloro-5-pyrimidinyl)-1H-benzimidazole-4-(N-4,6-dimethoxy-2-pyrimidinyl)amide | 4-amino-6-chloro-5-pyrimidinyl | 4,6-dimethoxy-2-pyrimidinyl-NH- | 90 |
| 565 | 2-(4-amino-6-chloro-5-pyrimidinyl)-1H-benzimidazole-4-(N-4-chloro-6-amino-2-pyrimidinyl)amide | 4-amino-6-chloro-5-pyrimidinyl | 4-chloro-6-amino-2-pyrimidinyl-NH- | 90 |
| 566 | 2-(4-amino-6-chloro-5-pyrimidinyl)-1H-benzimidazole-4-(N-4,6-dichloro-5-pyrimidinyl)amide | 4-amino-6-chloro-5-pyrimidinyl | 4,6-dichloro-5-pyrimidinyl-NH- | 88 |
| 567 | 2-(4-amino-6-chloro-5-pyrimidinyl)-1H-benzimidazole-4-(N-o-fluorophenyl)amide | 4-amino-6-chloro-5-pyrimidinyl | o-fluorophenyl-NH- | 93 |
| 568 | 2-(4-amino-6-chloro-5-pyrimidinyl)-1H-benzimidazole-4-(N-2-hydroxyl-4-pyrimidinyl)amide | 4-amino-6-chloro-5-pyrimidinyl | 2-hydroxy-4-pyrimidinyl-NH- | 90 |
| 569 | 2-(4-amino-6-chloro-5-pyrimidinyl)-1H-benzimidazole-4-(N-6-purinyl)amide | 4-amino-6-chloro-5-pyrimidinyl | 6-purinyl-NH- | 91 |

TABLE 2-continued

| No. Compounds | X | Y | Field % |
|---|---|---|---|
| 570 2-(4-amino-6-chloro-5-pyrimidinyl)-1H-benzimidazole-4-(N-6-hydroxyl-2-purinyl)amide | 4-amino-6-chloro-5-pyrimidinyl | 6-hydroxy-2-purinyl (methylamino) | 93 |
| 571 (L)-2-(2-pyrrolidine-1-yl-5-pyrimidinyl)-1H-benzimidazole-4-[N-(1-hydroxymethyl-2-p-nitrophenylhydroxyethyl)]amide | 2-pyrrolidine-1-yl-5-pyrimidinyl | 1-hydroxymethyl-2-p-nitrophenylhydroxyethyl | 94 |
| 572 (L)-2-(2-pyrrolidine-1-yl-5-pyrimidinyl)-1H-benzimidazole-4-[N-(1-hydroxymethyl-2-p-aminophenylhydroxyethyl)]amide | 2-pyrrolidine-1-yl-5-pyrimidinyl | 1-hydroxymethyl-2-p-aminophenylhydroxyethyl | 90 |
| 573 2-(2-pyrrolidine-1-yl-5-pyrimidinyl)-1H-benzimidazole-4-[N-(1-methyl-2-p-chlorophenylhydroxyethyl)]amide | 2-pyrrolidine-1-yl-5-pyrimidinyl | 1-methyl-2-p-chlorophenylhydroxyethyl | 94 |
| 574 2-(2-pyrrolidine-1-yl-5-pyrimidinyl)-1H-benzimidazole-4-(N-N'-piperidinyl)amide | 2-pyrrolidine-1-yl-5-pyrimidinyl | N'-piperidinyl (methyl) | 92 |
| 575 2-(2-pyrrolidine-1-yl-5-pyrimidinyl)-1H-benzimidazole-4-(N-2-piperazinyl)amide | 2-pyrrolidine-1-yl-5-pyrimidinyl | 2-piperazinyl | 94 |
| 576 2-(2-pyrrolidine-1-yl-5-pyrimidinyl)-1H-benzimidazole-4-(N-2'-benzimidazolyl)amide | 2-pyrrolidine-1-yl-5-pyrimidinyl | 2'-benzimidazolyl | 94 |
| 577 2-(2-pyrrolidine-1-yl-5-pyrimidinyl)-1H-benzimidazole-4-(N-o-aminophenyl)amide | 2-pyrrolidine-1-yl-5-pyrimidinyl | o-aminophenyl | 93 |
| 578 2-(2-pyrrolidine-1-yl-5-pyrimidinyl)-1H-benzimidazole-4-(N-5-benzimidazolonyl)amide | 2-pyrrolidine-1-yl-5-pyrimidinyl | 5-benzimidazolonyl | 90 |

TABLE 2-continued

| No. Compounds | X | Y | Field % |
|---|---|---|---|
| 579 2-(2-pyrrolidine-1-yl-5-pyrimidinyl)-1H-benzimidazole-4-(N-4'-carbonamido-5'-imidazolyl)amide | 2-pyrrolidine-1-yl-5-pyrimidinyl | 4-carbonamido-5-imidazolyl (NH-linked) | 85 |
| 580 2-(2-pyrrolidine-1-yl-5-pyrimidinyl)-1H-benzimidazole-4-(N-4'-pyrazolyl)amide | 2-pyrrolidine-1-yl-5-pyrimidinyl | 4-pyrazolyl (NH-linked) | 93 |
| 581 2-(2-pyrrolidine-1-yl-5-pyrimidinyl)-1H-benzimidazole-4-(N-(N'-piperazinyl))amide | 2-pyrrolidine-1-yl-5-pyrimidinyl | N-piperazinyl (NH-linked) | 93 |
| 582 2-(2-pyrrolidine-1-yl-5-pyrimidinyl)-1H-benzimidazole-4-(N-2-pyrazinyl)amide | 2-pyrrolidine-1-yl-5-pyrimidinyl | 2-pyrazinyl (NH-linked) | 88 |
| 583 2-(2-pyrrolidine-1-yl-5-pyrimidinyl)-1H-benzimidazole-4-(N-2-pyrimidinyl)amide | 2-pyrrolidine-1-yl-5-pyrimidinyl | 2-pyrimidinyl (NH-linked) | 89 |
| 584 2-(2-pyrrolidine-1-yl-5-pyrimidinyl)-1H-benzimidazole-4-(N-2-pyridyl)amide | 2-pyrrolidine-1-yl-5-pyrimidinyl | 2-pyridyl (NH-linked) | 87 |
| 585 2-(2-pyrrolidine-1-yl-5-pyrimidinyl)-1H-benzimidazole-4-(N-4-methyl-5-thiazolyl)amide | 2-pyrrolidine-1-yl-5-pyrimidinyl | 4-methyl-5-thiazolyl (NH-linked) | 92 |
| 586 2-(2-pyrrolidine-1-yl-5-pyrimidinyl)-1H-benzimidazole-4-(N-2,4-dihydroxyl-5-pyrimidinyl)amide | 2-pyrrolidine-1-yl-5-pyrimidinyl | 2,4-dihydroxyl-5-pyrimidinyl (NH-linked) | 90 |
| 587 2-(2-pyrrolidine-1-yl-5-pyrimidinyl)-1H-benzimidazole-4-(N-4,6-dimethoxy-2-pyrimidinyl)amide | 2-pyrrolidine-1-yl-5-pyrimidinyl | 4,6-dimethoxy-2-pyrimidinyl (NH-linked) | 91 |

TABLE 2-continued

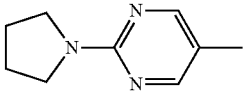

| No. Compounds | X | Y | Field % |
|---|---|---|---|
| 588 2-{ 2-pyrrolidine-1-yl-5-pyrimidinyl)-1H-benzimidazole-4-(N-4-chloro-6-amino-2-pyrimidinyl)amide |  | 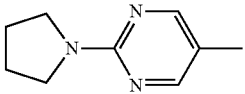 | 93 |
| 589 2-(2-pyrrolidine-1-yl-5-pyrimidinyl)-1H-benzimidazole-4-(N-4,6-dichloro-5-pyrimidinyl)amide |  | 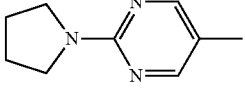 | 93 |
| 590 2-(2-pyrrolidine-1-yl-5-pyrimidinyl)-1H-benzimidazole-4-(N-o-fluorophenyl)amide | 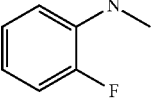 | 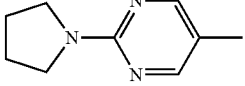 | 94 |
| 591 2-(2-pyrrolidine-1-yl-5-pyrimidinyl)-1H-benzimidazole-4-(N-2-hydroxyl-4-pyrimidinyl)amide | 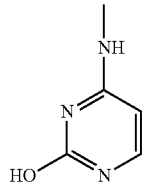 | 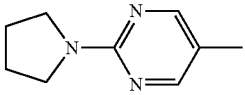 | 90 |
| 592 2-(2-pyrrolidine-1-yl-5-pyrimidinyl)-1H-benzimidazole-4-(N-6-purinyl)amide | 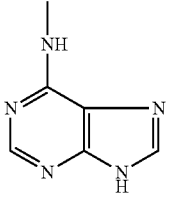 | 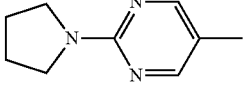 | 93 |
| 593 2-(2-pyrrolidine-1-yl-5-pyrimidinyl)-1H-benzimidazole-4-(N-6-hydroxyl-2-purinyl)amide | 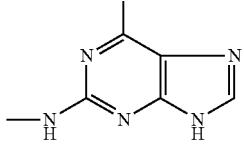 | 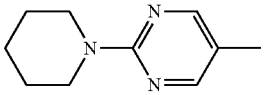 | 92 |
| 594 (L)-2-(2-piperidine-1-yl-5-pyrimidinyl)-1H-benzimidazole-4-[N-(1-hydroxymethyl-2-p-nitrophenylhydroxyethyl)]amide | 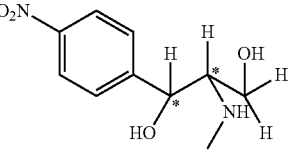 | | 91 |

TABLE 2-continued

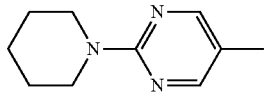

| No. Compounds | X | Y | Field % |
|---|---|---|---|
| 595 (L)-2-(2-piperidine-1-yl-5-pyrimidinyl)-1H-benzimidazole-4-[N-(1-hydroxymethyl-2-p-aminophenylhydroxyethyl)]amide | 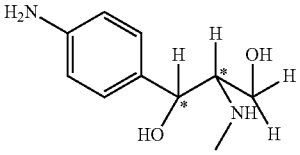 | 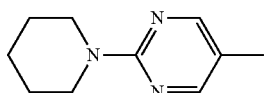 | 91 |
| 596 2-(2-piperidine-1-yl-5-pyrimidinyl)-1H-benzimidazole-4-[N-(1-methyl-2-p-chlorophenylhydroxyethyl)]amide | 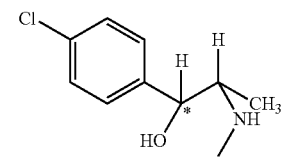 | 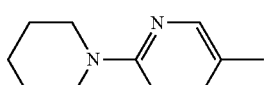 | 93 |
| 597 2-(2-piperidine-1-yl-5-pyrimidinyl)-1H-benzimidazole-4-(N-N'-piperidinyl)amide | 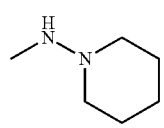 | 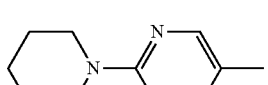 | 92 |
| 598 2-(2-piperidine-1-yl-5-pyrimidinyl)-1H-benzimidazole-4-(N-2-piperazinyl)amide | 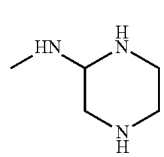 | 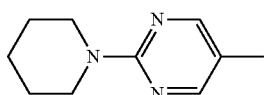 | 93 |
| 599 2-(2-piperidine-1-yl-5-pyrimidinyl)-1H-benzimidazole-4-(N-2'-benzimidazolyl)amide | 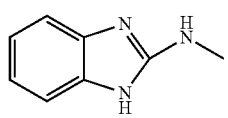 | 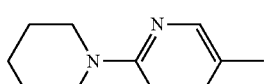 | 94 |
| 600 2-(2-piperidine-1-yl-5-pyrimidinyl)-1H-benzimidazole-4-(N-o-aminophenyl)amide | 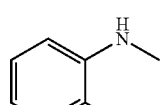 | 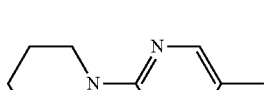 | 92 |
| 601 2-(2-piperidine-1-yl-5-pyrimidinyl)-1H-benzimidazole-4-(N-5-benzimidazolonyl)amide | 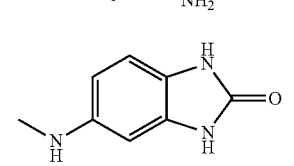 | 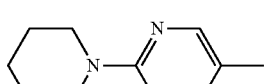 | 92 |
| 602 2-(2-piperidine-1-yl-5-pyrimidinyl)-1H-benzimidazole-4-(N-4'-carbonamido-5'-imidazolyl)amide | 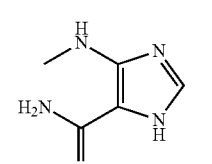 | 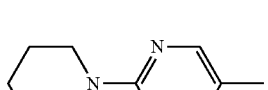 | 85 |
| 603 2-(2-piperidine-1-yl-5-pyrimidinyl)-1H-benzimidazole-4-(N-4'-pyrazolyl)amide | 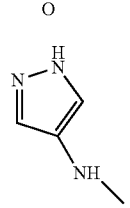 |  | 94 |

TABLE 2-continued

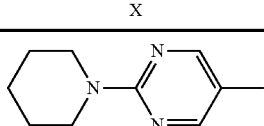

| No. Compounds | X | Y | Field % |
|---|---|---|---|
| 604 2-(2-piperidine-1-yl-5-pyrimidinyl)-1H-benzimidazole-4-(N-(N'-piperazinyl))amide | 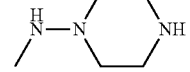 | 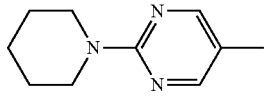 | 90 |
| 605 2-(2-piperidine-1-yl-5-pyrimidinyl)-1H-benzimidazole-4-(N-2-pyrazinyl)amide | 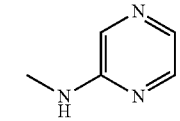 | 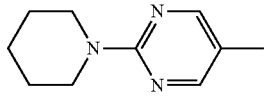 | 94 |
| 606 2-(2-piperidine-1-yl-5-pyrimidinyl)-1H-benzimidazole-4-(N-2-pyrimidinyl)amide | 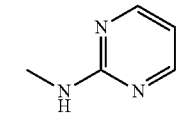 | 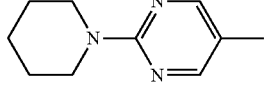 | 92 |
| 607 2-(2-piperidine-1-yl-5-pyrimidinyl)-1H-benzimidazole-4-(N-2-pyridyl)amide | 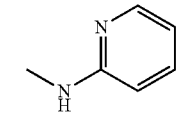 | 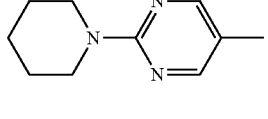 | 94 |
| 608 2-(2-piperidine-1-yl-5-pyrimidinyl)-1H-benzimidazole-4-(N-4-methyl-5-thiazolyl)amide | 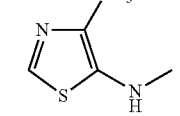 | 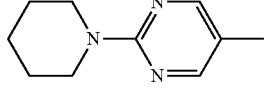 | 94 |
| 609 2-(2-piperidine-1-yl-5-pyrimidinyl)-1H-benzimidazole-4-(N-2,4-dihydroxyl-5-pyrimidinyl)amide | 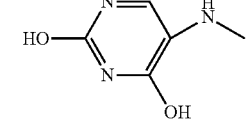 | 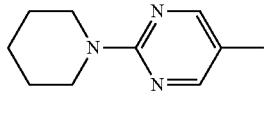 | 93 |
| 610 2-(2-piperidine-1-yl-5-pyrimidinyl)-1H-benzimidazole-4-(N-4,6-dimethoxy-2-pyrimidinyl)amide | 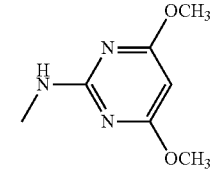 | 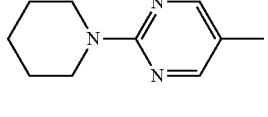 | 90 |
| 611 2-(2-piperidine-1-yl-5-pyrimidinyl)-1H-benzimidazole-4-(N-4-chloro-6-amino-2-pyrimidinyl)amide | 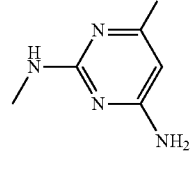 | 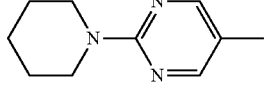 | 91 |
| 612 2-(2-piperidine-1-yl-5-pyrimidinyl)-1H-benzimidazole-4-(N-4,6-dichloro-5-pyrimidinyl)amide | 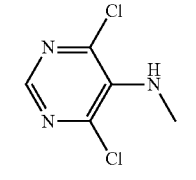 | | 93 |

TABLE 2-continued

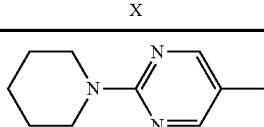

| No. | Compounds | X | Y | Field % |
|---|---|---|---|---|
| 613 | 2-(2-piperidine-1-yl-5-pyrimidinyl)-1H-benzimidazole-4-(N-o-fluorophenyl)amide | 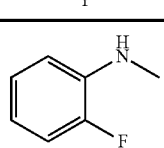 | 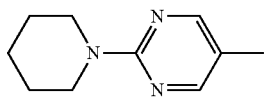 | 93 |
| 614 | 2-(2-piperidine-1-yl-5-pyrimidinyl)-1H-benzimidazole-4-(N-2-hydroxyl-4-pyrimidinyl)amide | 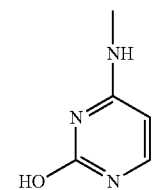 | 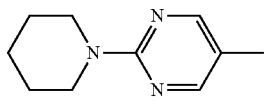 | 88 |
| 615 | 2-(2-piperidine-1-yl-5-pyrimidinyl)-1H-benzimidazole-4-(N-6-purinyl)amide | 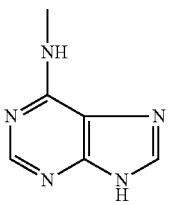 | 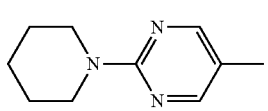 | 89 |
| 616 | 2-(2-piperidine-1-yl-5-pyrimidinyl)-1H-benzimidazole-4-(N-6-hydroxyl-2-purinyl)amide | 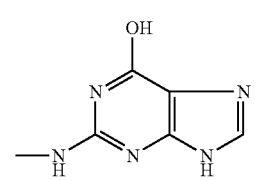 | 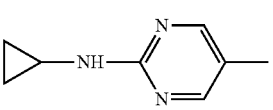 | 87 |
| 617 | (L)-2-(2-cyclopropylamino-5-pyrimidinyl)-1H-benzimidazole-4-[N-(1-hydroxymethyl-2-p-nitrophenylhydroxyethyl)]amide | 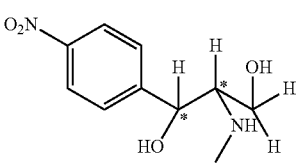 | 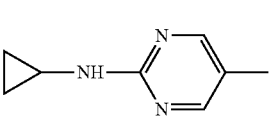 | 92 |
| 618 | (L)-2-(2-cyclopropylamino-5-pyrimidinyl)-1H-benzimidazole-4-[N-(1-hydroxymethyl-2-p-aminophenylhydroxyethyl)]amide | 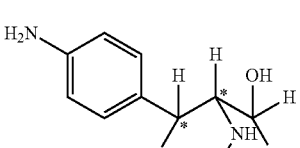 | 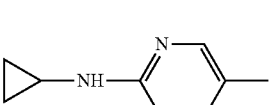 | 90 |
| 619 | 2-(2-cyclopropylamino-5-pyrimidinyl)-1H-benzimidazole-4-[N-(1-methyl-2-p-chlorophenylhydroxyethyl)]amide | 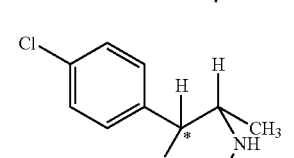 | 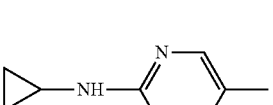 | 91 |
| 620 | 2-(2-cyclopropylamino-5-pyrimidinyl)-1H-benzimidazole-4-(N-N'-piperidinyl)amide | 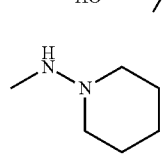 |  | 93 |

TABLE 2-continued

| No. Compounds | X | Y | Field % |
|---|---|---|---|
| 621 2-(2-cyclopropylamino-5-pyrimidinyl)-1H-benzimidazole-4-(N-2-piperazinyl)amide | cyclopropyl-NH-pyrimidin-2-yl | 2-piperazinyl-NH- | 93 |
| 622 2-(2-cyclopropylamino-5-pyrimidinyl)-1H-benzimidazole-4-(N-2'-benzimidazolyl)amide | cyclopropyl-NH-pyrimidin-2-yl | 2-benzimidazolyl-NH- | 94 |
| 623 2-(2-cyclopropylamino-5-pyrimidinyl)-1H-benzimidazole-4-(N-o-aminophenyl)amide | cyclopropyl-NH-pyrimidin-2-yl | o-aminophenyl-NH- | 90 |
| 624 2-(2-cyclopropylamino-5-pyrimidinyl)-1H-benzimidazole-4-(N-5-benzimidazolonyl)amide | cyclopropyl-NH-pyrimidin-2-yl | 5-benzimidazolonyl-NH- | 93 |
| 625 2-(2-cyclopropylamino-5-pyrimidinyl)-1H-benzimidazole-4-(N-4'-carbonamido-5'-imidazolyl)amide | cyclopropyl-NH-pyrimidin-2-yl | 4-carbonamido-5-imidazolyl-NH- | 92 |
| 626 2-(2-cyclopropylamino-5-pyrimidinyl)-1H-benzimidazole-4-(N-4'-pyrazolyl)amide | cyclopropyl-NH-pyrimidin-2-yl | 4-pyrazolyl-NH- | 91 |
| 627 2-(2-cyclopropylamino-5-pyrimidinyl)-1H-benzimidazole-4-(N-(N'-piperazinyl))amide | cyclopropyl-NH-pyrimidin-2-yl | N'-piperazinyl-NH- | 91 |
| 628 2-(2-cyclopropylamino-5-pyrimidinyl)-1H-benzimidazole-4-(N-2-pyrazinyl)amide | cyclopropyl-NH-pyrimidin-2-yl | 2-pyrazinyl-NH- | 93 |
| 629 2-(2-cyclopropylamino-5-pyrimidinyl)-1H-benzimidazole-4-(N-2-pyrimidinyl)amide | cyclopropyl-NH-pyrimidin-2-yl | 2-pyrimidinyl-NH- | 92 |

TABLE 2-continued

| No. | Compounds | X | Y | Field % |
|---|---|---|---|---|
| 630 | 2-(2-cyclopropylamino-5-pyrimidinyl)-1H-benzimidazole-4-(N-2-pyridyl)amide | cyclopropyl-NH-pyrimidin-5-yl | 2-pyridyl-NH- | 93 |
| 631 | 2-(2-cyclopropylamino-5-pyrimidinyl)-1H-benzimidazole-4-(N-4-methyl-5-thiazolyl)amide | cyclopropyl-NH-pyrimidin-5-yl | 4-methyl-thiazol-5-yl-NH- | 94 |
| 632 | 2-(2-cyclopropylamino-5-pyrimidinyl)-1H-benzimidazole-4-(N-2,4-dihydroxyl-5-pyrimidinyl)amide | cyclopropyl-NH-pyrimidin-5-yl | 2,4-dihydroxy-pyrimidin-5-yl-NH- | 92 |
| 633 | 2-(2-cyclopropylamino-5-pyrimidinyl)-1H-benzimidazole-4-(N-4,6-dimethoxy-2-pyrimidinyl)amide | cyclopropyl-NH-pyrimidin-5-yl | 4,6-dimethoxy-pyrimidin-2-yl-NH- | 92 |
| 634 | 2-(2-cyclopropylamino-5-pyrimidinyl)-1H-benzimidazole-4-(N-4-chloro-6-amino-2-pyrimidinyl)amide | cyclopropyl-NH-pyrimidin-5-yl | 4-chloro-6-amino-pyrimidin-2-yl-NH- | 93 |
| 635 | 2-(2-cyclopropylamino-5-pyrimidinyl)-1H-benzimidazole-4-(N-4,6-dichloro-5-pyrimidinyl)amide | cyclopropyl-NH-pyrimidin-5-yl | 4,6-dichloro-pyrimidin-5-yl-NH- | 94 |
| 636 | 2-(2-cyclopropylamino-5-pyrimidinyl)-1H-benzimidazole-4-(N-o-fluorophenyl)amide | cyclopropyl-NH-pyrimidin-5-yl | o-fluorophenyl-NH- | 90 |
| 637 | 2-(2-cyclopropylamino-5-pyrimidinyl)-1H-benzimidazole-4-(N-2-hydroxyl-4-pyrimidinyl)amide | cyclopropyl-NH-pyrimidin-5-yl | 2-hydroxy-pyrimidin-4-yl-NH- | 94 |

TABLE 2-continued

| No. Compounds | X | Y | Field % |
|---|---|---|---|
| 638 2-(2-cyclopropylamino-5-pyrimidinyl)-1H-benzimidazole-4-(N-6-purinyl)amide | | | 92 |
| 639 2-(2-cyclopropylamino-5-pyrimidinyl)-1H-benzimidazole-4-(N-6-hydroxyl-2-purinyl)amide | | | 94 |
| 640 (L)-2-(1,3-dimethyl-5-chloro-4-pyrazolyl)-1H-benzimidazole-4-[N-(1-hydroxymethyl-2-p-nitrophenylhydroxyethyl)] amide | | | 94 |
| 641 (L)-2-(1,3-dimethyl-5-chloro-4-pyrazolyl)-H-benzimidazole-4-[N-(1-hydroxymethyl-2-p-aminophenylhydroxyethyl)]amide | | | 93 |
| 642 2-(1,3-dimethyl-5-chloro-4-pyrazolyl)-1H-benzimidazole-4-[N-(1-methyl-2-p-chlorophenylhydroxyethyl)]amide | | | 90 |
| 643 2-(1,3-dimethyl-5-chloro-4-pyrazolyl)-1H-benzimidazole-4-(N-N'-piperidinyl)amide | | | 91 |
| 644 2-(1,3-dimethyl-5-chloro-4-pyrazolyl)-1H-benzimidazole-4-(N-2-piperazinyl)amide | | | 93 |

TABLE 2-continued

| No. | Compounds | X | Y | Field % |
|---|---|---|---|---|
| 645 | 2-(1,3-dimethyl-5-chloro-4-pyrazolyl)-1H-benzimidazole-4-(N-2'-benzimidazolyl)amide | 5-chloro-1,3-dimethyl-pyrazol-4-yl | 2-benzimidazolylamino | 93 |
| 646 | 2-(1,3-dimethyl-5-chloro-4-pyrazolyl)-1H-benzimidazole-4-(N-o-aminophenyl)amide | 5-chloro-1,3-dimethyl-pyrazol-4-yl | o-aminophenylamino | 88 |
| 647 | 2-(1,3-dimethyl-5-chloro-4-pyrazolyl)-1H-benzimidazole-4-(N-5-benzimidazolonyl)amide | 5-chloro-1,3-dimethyl-pyrazol-4-yl | 5-benzimidazolonylamino | 89 |
| 648 | 2-(1,3-dimethyl-5-chloro-4-pyrazolyl)-1H-benzimidazole-4-(N-4'-carbonamido-5'-imidazolyl)amide | 5-chloro-1,3-dimethyl-pyrazol-4-yl | 4-carbonamido-5-imidazolylamino | 87 |
| 649 | 2-(1,3-dimethyl-5-chloro-4-pyrazolyl)-1H-benzimidazole-4-(N-4'-pyrazolyl)amide | 5-chloro-1,3-dimethyl-pyrazol-4-yl | 4-pyrazolylamino | 92 |
| 650 | 2-(1,3-dimethyl-5-chloro-4-pyrazolyl)-1H-benzimidazole-4-(N-(N'-piperazinyl))amide | 5-chloro-1,3-dimethyl-pyrazol-4-yl | N'-piperazinylamino | 90 |
| 651 | 2-(1,3-dimethyl-5-chloro-4-pyrazolyl)-1H-benzimidazole-4-(N-2-pyrazinyl)amide | 5-chloro-1,3-dimethyl-pyrazol-4-yl | 2-pyrazinylamino | 91 |

TABLE 2-continued

| No. Compounds | X | Y | Field % |
|---|---|---|---|
| 652 2-(1,3-dimethyl-5-chloro-4-pyrazolyl)-1H-benzimidazole-4-(N-2-pyrimidinyl)amide | 5-chloro-1,3-dimethyl-pyrazol-4-yl | 2-pyrimidinylamino | 93 |
| 653 2-(1,3-dimethyl-5-chloro-4-pyrazolyl)-1H-benzimidazole-4-(N-2-pyridyl)amide | 5-chloro-1,3-dimethyl-pyrazol-4-yl | 2-pyridylamino | 93 |
| 654 2-(1,3-dimethyl-5-chloro-4-pyrazolyl)-1H-benzimidazole-4-(N-4-methyl-5-thiazolyl)amide | 5-chloro-1,3-dimethyl-pyrazol-4-yl | 4-methyl-5-thiazolylamino | 94 |
| 655 2-(1,3-dimethyl-5-chloro-4-pyrazolyl)-1H-benzimidazole-4-(N-2,4-dihydroxyl-5-pyrimidinyl)amide | 5-chloro-1,3-dimethyl-pyrazol-4-yl | 2,4-dihydroxy-5-pyrimidinylamino | 90 |
| 656 2-(1,3-dimethyl-5-chloro-4-pyrazolyl)-1H-benzimidazole-4-(N-4,6-dimethoxy-2-pyrimidinyl)amide | 5-chloro-1,3-dimethyl-pyrazol-4-yl | 4,6-dimethoxy-2-pyrimidinylamino | 93 |
| 657 2-(1,3-dimethyl-5-chloro-4-pyrazolyl)-1H-benzimidazole-4-(N-4-chloro-6-amino-2-pyrimidinyl)amide | 5-chloro-1,3-dimethyl-pyrazol-4-yl | 4-chloro-6-amino-2-pyrimidinylamino | 92 |
| 658 2-(1,3-dimethyl-5-chloro-4-pyrazolyl)-1H-benzimidazole-4-(N-4,6-dichloro-5-pyrimidinyl)amide | 5-chloro-1,3-dimethyl-pyrazol-4-yl | 4,6-dichloro-5-pyrimidinylamino | 91 |

TABLE 2-continued

| No. Compounds | X | Y | Field % |
|---|---|---|---|
| 659 2-(1,3-dimethyl-5-chloro-4-pyrazolyl)-1H-benzimidazole-4-(N-o-fluorophenyl)amide | 5-chloro-1,3-dimethyl-1H-pyrazol-4-yl | N-methyl-2-fluoroaniline | 91 |
| 660 2-(1,3-dimethyl-5-chloro-4-pyrazolyl)-1H-benzimidazole-4-(N-2-hydroxyl-4-pyrimidinyl)amide | 5-chloro-1,3-dimethyl-1H-pyrazol-4-yl | N-methyl-2-hydroxypyrimidin-4-amine | 93 |
| 661 2-(1,3-dimethyl-5-chloro-4-pyrazolyl)-1H-benzimidazole-4-(N-6-purinyl)amide | 5-chloro-1,3-dimethyl-1H-pyrazol-4-yl | N-methyl-9H-purin-6-amine | 92 |
| 662 2-(1,3-dimethyl-5-chloro-4-pyrazolyl)-1H-benzimidazole-4-(N-6-hydroxy]-2-purinyl)amide | 5-chloro-1,3-dimethyl-1H-pyrazol-4-yl | 6-hydroxy-N-methyl-9H-purin-2-amine | 93 |
| 663 2-(4-hydroxyphenyl)-1H-benzimidazole-4-(N-o-fluorophenyl)amide | 4-hydroxyphenyl | 2-fluorophenyl | 94 |
| 664 (L)-2-(3-hydroxyphenyl)-1H-benzimidazole-4-[N-(1-hydroxymethyl-2-p-nitrophenylhydroxyethyl)]amide | 3-hydroxyphenyl | (1R,2S)-1-(4-nitrophenyl)-2-(methylamino)propane-1,3-diol | 92 |
| 665 2-(3-hydroxyphenyl)-1H-benzimidazole-4-(N-6-hydroxyl-2-purinyl)amide | 3-hydroxyphenyl | 6-hydroxy-N-methyl-9H-purin-2-amine | 92 |

Figure 3:
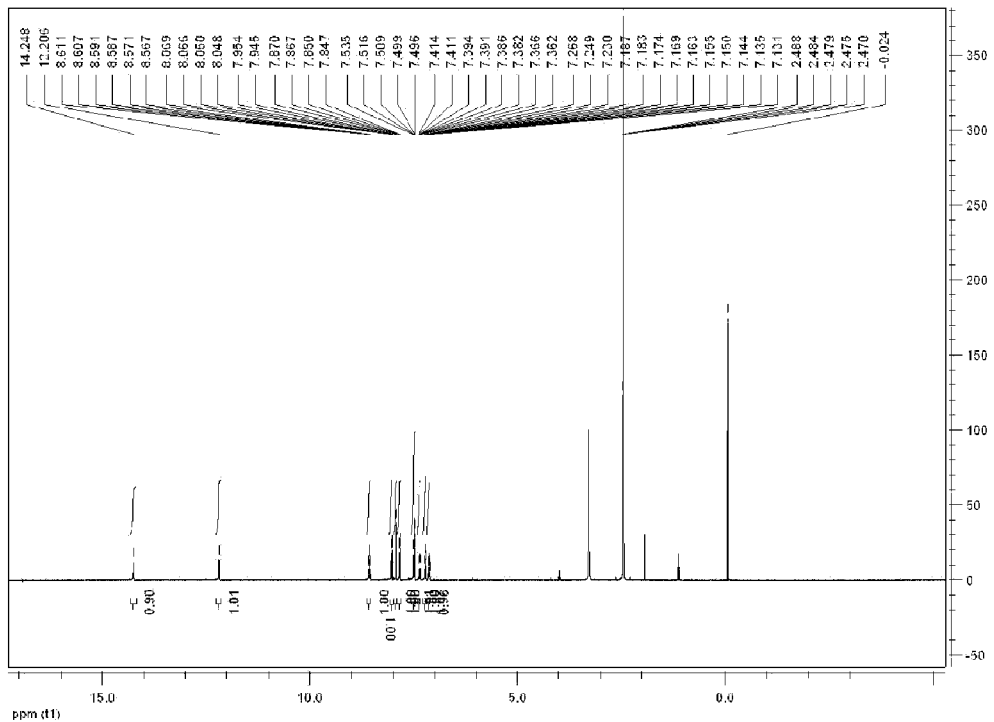
FIG. 3 shows $^1$HNMR spectrogram of 2-(5-nitro-2-thienyl)-1H-benzimidazole-4-(N-o-fluorophenyl)amide in Example 28.

Structure Identification of Product (refer to FIGS. 3-6):

(23) 2-(2-pyridyl)-1H-benzimidazole-4-N-hydroxyethylamide $^1$HNMR (DMSO, 400 MHz) δ: 3.64-3.67(t,1H), 3.73-3.75 (m,2H), 4.39-4.42(t,2H), 7.32-7.36(t,1H), 7.38-7.40(t,1H), 7.73-7.75(d,1H), 7.80-7.81(d,1H), 7.85-7.86(t,1H), 8.38-8.40(d,1H), 8.59-8.61(d,1H);

(24) 2-(2-pyridyl)-1H-benzimidazole-4-N-o-hydroxyphenylcarboxylamide $^1$HNMR (DMSO, 400 MHz) δ: 5.35(s,1H), 7.13(s,1H), 7.15-7.16(d,2H), 7.34-7.36(t,3H), 7.37-7.39(t,1H), 7.83-7.84 (d,1H), 7.85-7.86(t,1H), 7.91-7.92(d,1H), 8.11-8.12(d,1H), 8.38-8.40(d,1H), 8.59-8.61(d,1H);

(25) 2-(2-hydroxyphenyl)-1H-benzimidazole-4-(N-o-fluorophenyl)amide $^1$HNMR (DMSO, 400 MHz) δ: 5.35(s,1H), 6.59-6.61(d, 1H), 6.63-6.64(t,1H), 6.95-6.97(t,1H), 6.99-7.00(d,1H), 7.01-7.02(d,1H), 7.07-7.09(t,1H), 7.24-7.25(t,1H), 7.37-7.39 (t,1H), 7.62-7.63(d,1H), 7.83-7.84(d,1H), 7.91-7.92(d,1H);

(26) (L)-2-(2-hydroxyphenyl)-1H-benzimidazole-4-[N-(1-hydroxyl-2-p-nitrophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 5.35(s,1H), 7.01-7.02(d,1H), 7.07-7.09 (t,1H), 7.24-7.25(d,1H), 7.43-7.45(t,1H), 7.62-7.65(d,2H), 7.66-7.67(d,1H), 7.89-7.90(d,1H), 7.93-7.95(d,1H), 8.17-8.20(d,2H);

(27) 2-(5-nitro-2-thienyl)-1H-benzimidazole-4-(N-6-hydroxyl-2-purinyl)amide $^1$HNMR (DMSO, 400 MHz) δ: 7.43-7.46(t,1H), 7.70-7.72 (d,1H), 7.89-7.91(d,1H), 7.93-7.95(d,1H), 8.30-8.33(d,1H), 8.57-8.60(d,1H), 11.53(s,1H);

(28) 2-(5-nitro-2-thienyl)-1H-benzimidazole-4-(N-o-fluorophenyl)amide (Refer to FIG. 3)

$^1$HNMR(DMSO, 400 MHz)δ:7.13-7.19(m,1H),7.23-7.27 (t,1H),7.36-7.41(t,1H),7.50-7.54(m,2H), 7.85-7.87(d,1H), 7.94-7.95(d,1H), 8.05-8.07(d,1H), 8.57-8.61(t,1H), 12.19-12.20(d,1H), 14.25(s,1H);

(29) 2-(3,4,5-trihydroxyphenyl)-1H-benzimidazole-4-(N-o-fluorophenyl)amide $^1$HNMR (DMSO, 400 MHz) δ: 5.33(s,1H), 5.35(s,1H), 5.38(s,1H), 6.59-6.61(d,1H), 6.63-6.64(t,1H), 6.71(s,2H), 6.95-6.97(t,1H), 6.99-7.01(d,1H), 7.43-7.45(t,1H), 7.90-7.91 (d,1H), 7.93-7.94(d,1H);

(30) 2-(3,4,5-trihydroxyphenyl)-1H-benzimidazole-4-(N-hydroxyethyl)amide $^1$HNMR (DMSO, 400 MHz) δ: 5.33(s,1H), 5.35(s,1H), 5.38(s,1H), 2.84-2.88(m,2H), 3.59-3.62(m,2H), 3.65-3.67(t, 1H), 6.71(s,2H), 7.43-7.45(t,1H), 7.89-7.90 (d,1H), 7.93-7.94(d,1H);

(31) 2-(2-piperidinyl)-1H-benzimidazole-4-(4-N'-ethyl-N-piperazinyl)amide $^1$HNMR (DMSO, 400 MHz) δ: 1.02-1.05(t,3H), 1.43-1.44 (m,1H), 1.45-1.47(m,1H), 1.49-1.52(m,1H), 1.55-1.57(m, 1H), 1.67-1.69(m1H), 1.91-1.94(m,1H), 2.38-2.40(m,2H), 2.50-2.52(t,4H), 2.65-2.67(t,4H), 2.69-2.72(m,1H), 2.79-2.81(m,1H), 4.02-4.04(m,1H), 7.43-7.45(t,1H), 7.90-7.91(d, 1H), 7.93-7.94(d,1H);

(32) 2-(2-pyridyl)-1H-benzimidazole-4-(4-N'-ethyl-N-piperazinyl)amide $^1$HNMR (DMSO, 400 MHz) δ: 1.02-1.05(t,3H), 2.38-2.40 (m,2H), 2.50-2.52(t,4H), 2.65-2.67(t,4H), 7.36-7.38(t,H), 7.43-7.45(t,1H), 7.85-7.86(t,1H), 7.90-7.91(d,1H), 7.93-7.94 (d,1H), 8.38-8.39(d,1H), 8.59-8.61(d,1H);

(33) (L)-2-(2,6-dimethyl-2,6-octadienyl)-1H-benzimidazole-4-[N-(1-hydroxymethyl-2-p-nitrophenylhydroxyethyl)]amide $^1$HNMR (DMSO, 400 MHz) δ: 1.70(s,1H), 1.82(s,1H), 1.85(s,1H), 2.00-2.06(t,4H), 3.17-3.18(m,1H), 3.19-3.20(d, 1H), 3.25-3.28(m,1H), 3.50-3.52(m,1H), 3.65-3.68(t,1H), 3.70-3.72(d,1H), 4.73-4.77(t,1H), 5.13-5.15(t,1H), 5.20-5.23 (t,1H), 7.43-7.45(t,1H), 7.62-7.65(d,2H), 7.89-7.90(d,1H), 7.93-7.95(d,1H), 8.17-8.20(d,2H);

(34) (L)-2-(2,6-dimethyl-2,6-octadienyl)-1H-benzimidazole-4-[N-(1-hydroxymethyl-2-p-aminophenylhydroxyethyl)]amide $^1$HNMR (DMSO, 400 MHz) δ: 1.70(s,1H), 1.82(s,1H), 1.85(s,1H), 2.00-2.06(t,4H), 3.17-3.18(m,1H), 3.19-3.20(d, 1H), 3.25-3.28(m,1H), 3.50-3.52(m,1H), 3.65-3.68(t,1H), 3.70-3.72(d,1H), 4.73-4.77(t,1H), 5.13-5.15(t,1H), 5.20-5.23 (t,1H), 6.27(s,2H), 6.56-6.58(d,2H), 7.11-7.13(d,2H), 7.43-7.45(t,1H), 7.89-7.90(d,1H), 7.93-7.95(d,1H);

(35) 2-(2,6-dimethyl-2,6-octadienyl)-1H-benzimidazole-4-[N-(1-methyl-2-p-chlorophenylhydroxyethyl)]amide $^1$HNMR (DMSO, 400 MHz) δ: 1.12-1.15(d,3H), 1.70(s, 1H), 1.82(s,1H), 1.85(s,1H), 2.00-2.06(t,4H), 3.19-3.20(d, 1H), 3.25-3.28(m,1H), 3.65-3.68(t,1H), 4.73-4.77(t,1H), 5.13-5.15(t,1H), 5.20-5.23(t,1H), 7.29-7.30(d,2H), 7.40-7.41 (d,2H), 7.43-7.45(t,1H), 7.89-7.91(d,1H), 7.93-7.94(d,1H);

(36) 2-(2,6-dimethyl-2,6-octadienyl)-1H-benzimidazole-4-(N-N'-piperidinyl)amide $^1$HNMR (DMSO, 400 MHz) δ: 1.52-1.55(m,4H), 1.59-1.63(m,2H), 1.70(s,1H), 1.82(s,1H), 1.85(s,1H), 2.00-2.06(t, 4H), 3.10-3.15(t,4H), 3.19-3.20(d,1H), 5.13-5.15(t,1H), 5.20-5.23(t,1H), 7.43-7.45(t,1H), 7.89-7.91(d,1H), 7.93-7.94 (d,1H);

(37) 2-(2,6-dimethyl-2,6-octadienyl)-1H-benzimidazole-4-(N-2-piperazinyl)amide $^1$HNMR (DMSO, 400 MHz) δ: 1.70(s,1H), 1.82(s,1H), 1.85(s,1H), 1.91-1.93(m,2H), 2.00-2.06(t,4H), 2.62-2.63(m, 1H), 2.65-2.66(m,1H), 2.69-2.70(m,1H), 2.72-2.74(m,1H), 2.77-2.80(m,1H), 3.02-3.05(m,1H), 3.19-3.20(d,1H), 3.99-

4.01(m,1H), 5.13-5.15(t,1H), 5.20-5.23(t,1H), 7.43-7.45(t,1H), 7.89-7.91(d,1H), 7.93-7.94(d,1H);

(38) 2-(2,6-dimethyl-2,6-octadienyl)-1H-benzimidazole-4-(N-2'-benzimidazolyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.12-7.15(d,2H), 7.22-7.24(t,2H), 7.43-7.45(t,1H), 7.89-7.91(d,1H), 7.93-7.94(d,1H);

(39) 2-(2,6-dimethyl-2,6-octadienyl)-1H-benzimidazole-4-(N-o-aminophenyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H);

(40) 2-(2,6-dimethyl-2,6-octadienyl)-1H-benzimidazole-4-(N-5-benzimidazolonyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 6.35-6.37(d,1H), 6.93(s,1H), 7.43-7.45(t,1H), 7.54-7.56(d,1H), 7.89-7.91(d,1H), 7.93-7.94(d,1H);

(41) 2-(2,6-dimethyl-2,6-octadienyl)-1H-benzimidazole-4-(N-4'-carbonamido-5'-imidazolyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.89-7.91(d,1H), 7.93-7.94(d,1H), 8.37(s,2H), 9.24-9.26(d,1H), 13.00-13.03(d,1H);

(42) 2-(2,6-dimethyl-2,6-octadienyl)-1H-benzimidazole-4-(N-4'-pyrazolyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.89-7.91(d,1H), 7.93-7.94(d,1H), 8.61(s,1H), 8.63-8.65(d,1H), 13.71-13.75(d,1H);

(43) 2-(2,6-dimethyl-2,6-octadienyl)-1H-benzimidazole-4-(N—(N'-piperazinyl))amide ¹HNMR (DMSO, 400 MHz) δ: 1.70(s,1H), 1.82(s,1H), 1.85(s,1H), 1.91-1.95(m,1H), 2.00-2.06(t,4H), 2.65-2.67(t,4H), 2.80-2.83(m,4H), 3.19-3.20(d,1H), 5.13-5.15(t,1H), 5.20-5.23(t,1H), 7.43-7.45(t,1H), 7.90-7.91(d,1H), 7.93-7.94(d,1H);

(44) 2-(2,6-dimethyl-2,6-octadienyl)-1H-benzimidazole-4-(N-2-pyrazinyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.89-7.91(d,1H), 7.93-7.94(d,1H), 8.34-8.35(d,1H), 8.36(s,1H), 8.40-8.42(d,1H);

(45) 2-(2,6-dimethyl-2,6-octadienyl)-1H-benzimidazole-4-(N-2-pyrimidinyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 6.93-6.95(t,1H), 7.43-7.45(t,1H), 7.89-7.91(d,1H), 7.93-7.94(d,1H), 8.45-8.46(d,2H);

(46) 2-(2,6-dimethyl-2,6-octadienyl)-1H-benzimidazole-4-(N-2-pyridyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H);

(47) 2-(2,6-dimethyl-2,6-octadienyl)-1H-benzimidazole-4-(N-4-methyl-5-thiazolyl)amide ¹HNMR (DMSO, 400 MHz) δ: 1.70(s,1H), 1.82(s,1H), 1.85(s,1H), 2.00-2.06(t,4H), 2.45(s,3H), 3.19-3.20(d,1H), 5.13-5.15(t,1H), 5.20-5.23(t,1H), 7.43-7.45(t,1H), 7.89-7.91(d,1H), 7.93-7.94(d,1H), 8.12(s,1H);

(48) 2-(2,6-dimethyl-2,6-octadienyl)-1H-benzimidazole-4-(N-2,4-dihydroxyl-5-pyrimidinyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.82(s,1H), 7.89-7.91(d,1H), 7.93-7.94(d,1H), 8.33(s,1H), 11.53(s,1H);

(49) 2-(2,6-dimethyl-2,6-octadienyl)-1H-benzimidazole-4-(N-4,6-dimethoxy-2-pyrimidinyl)amide ¹HNMR (DMSO, 400 MHz) δ: 1.70(s,1H), 1.82(s,1H), 1.85(s,1H), 2.00-2.06(t,4H), 3.19-3.20(d,1H), 3.82(s,6H), 5.13-5.15(t,1H), 5.20-5.23(t,1H), 5.71(s,1H), 7.43-7.45(t,1H), 7.89-7.91(d,1H), 7.93-7.94(d,1H);

(50) 2-(2,6-dimethyl-2,6-octadienyl)-1H-benzimidazole-4-(N-4-chloro-6-amino-2-pyrimidinyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 5.98(s,1H), 7.43-7.45(t,1H), 7.74(s,2H), 7.89-7.91(d,1H), 7.93-7.94(d,1H);

(51) 2-(2,6-dimethyl-2,6-octadienyl)-1H-benzimidazole-4-(N-4,6-dichloro-5-pyrimidinyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.89-7.91(d,1H), 7.93-7.94(d,1H), 9.34(s,1H);

(52) 2-(2,6-dimethyl-2,6-octadienyl)-1H-benzimidazole-4-(N-o-fluorophenyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H);

(53) 2-(2,6-dimethyl-2,6-octadienyl)-1H-benzimidazole-4-(N-2-hydroxyl-4-pyrimidinyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t, 1H), 5.20-5.23(t,1H), 5.46-5.48(d,1H), 7.10-7.11(d,1H), 7.43-7.45(t,1H), 7.82(s,1H), 7.89-7.91(d,1H), 7.93-7.94(d,1H);

(54) 2-(2,6-dimethyl-2,6-octadienyl)-1H-benzimidazole-4-(N-6-purinyl)amide

¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.86-7.88(d,1H), 7.89-7.91(d,1H), 7.93-7.94(d,1H), 8.16-8.18(d,1H);

(55) 2-(2,6-dimethyl-2,6-octadienyl)-1H-benzimidazole-4-(N-6-hydroxy-2-purinyl)amide ¹HNMR (DMSO, 400 MHz) δ: 1.70(s,1H), 1.82(s,1H), 1.85(s,1H), 2.00-2.06(t,4H), 3.19-3.20(d,1H), 5.13-5.15(t,1H), 5.20-5.23(t,1H), 7.43-7.45(t,1H), 7.89-7.91(d,1H), 7.93-7.94(d,1H), 8.57-8.59(d,1H), 11.53(s,1H);

(56) (L)-2-(2-thienyl)-1H-benzimidzzole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.17-7.19(t,1H), 7.43-7.45(t,1H), 7.62-7.65(d,2H), 7.69-7.71(d,1H), 7.85-7.87(d,1H), 7.89-7.90(d,1H), 7.93-7.95(d,1H), 8.17-8.20(d,2H);

(57) (L)-2-(2-thienyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.17-7.19(t,1H), 7.43-7.45(t,1H), 7.69-7.71(d,1H), 7.85-7.87(d,1H), 7.89-7.90(d,1H), 7.93-7.95(d,1H);

(58) 2-(2-thienyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.17-7.19(t,1H), 7.29-7.30(d,2H), 7.40-7.41(d,2H), 7.43-7.45(t,1H), 7.69-7.71(d,1H), 7.85-7.87(d,1H), 7.89-7.91(d,1H), 7.93-7.94(d,1H);

(59) 2-(2-thienyl)-1H-benzimidazole-4-(N-N'-piperidinyl)amide

¹HNMR (DMSO, 400 MHz) δ: 1.52-1.55(m,4H), 1.59-1.63(m,2H), 3.10-3.15(t,4H), 7.17-7.19(t,1H), 7.43-7.45(t,1H), 7.69-7.71(d,1H), 7.85-7.87(d,1H), 7.89-7.91(d,1H), 7.93-7.94(d,1H);

(60) 2-(2-thienyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.17-7.19(t,1H), 7.43-7.45(t,1H), 7.69-7.71(d,1H), 7.85-7.87(d,1H), 7.89-7.91(d,1H), 7.93-7.94(d,1H);

(61) 2-(2-thienyl)-1H-benzimidazole-4-(N-2'-benzimidazolyl)amide

¹HNMR (DMSO, 400 MHz) δ: 7.12-7.15(d,2H), 7.17-7.19(t,1H), 7.22-7.24(t,2H), 7.43-7.45(t,1H), 7.69-7.71(d,1H), 7.85-7.87(d,1H), 7.89-7.91(d,1H), 7.93-7.94(d,1H);

(62) 2-(2-thienyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.17-7.19(t,1H), 7.43-7.45(t,1H), 7.69-7.71(d,1H), 7.85-7.87(d,1H), 7.89-7.91(d,1H), 7.93-7.94(d,1H);

(63) 2-(2-thienyl)-1H-benzimidazole-4-(N-5-benzimidazolonyl)amide

¹HNMR (DMSO, 400 MHz) δ: 6.35-6.37(d,1H), 6.93(s,1H), 7.17-7.19(t,1H), 7.43-7.45(t,1H), 7.54-7.56(d,1H), 7.69-7.71(d,1H), 7.85-7.87(d,1H), 7.89-7.91(d,1H), 7.93-7.94(d,1H);

(64) 2-(2-thienyl)-1H-benzimidazole-4-(N-4'-carbonamido-5'-imidazolyl)amide

¹HNMR (DMSO, 400 MHz) δ: 7.17-7.19(t,1H), 7.43-7.45(t,1H), 7.69-7.71(d,1H), 7.85-7.87(d,1H), 7.89-7.91(d,1H), 7.93-7.94(d,1H), 8.37(s,2H), 9.24-9.26(d,1H), 13.00-13.03(d,1H);

(65) 2-(2-thienyl)-1H-benzimidazole-4-(N-4'-pyrazolyl)amide

¹HNMR (DMSO, 400 MHz) δ: 7.17-7.19(t,1H), 7.43-7.45(t,1H), 7.69-7.71(d,1H), 7.85-7.87(d,1H), 7.89-7.91(d,1H), 7.93-7.94(d,1H), 8.61(s,1H), 8.63-8.65(d,1H), 13.71-13.75(d,1H);

(66) 2-(2-thienyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.17-7.19(t,1H), 7.43-7.45(t,1H), 7.69-7.71(d,1H), 7.85-7.87(d,1H), 7.90-7.91(d,1H), 7.93-7.94(d,1H);

(67) 2-(2-thienyl)-1H-benzimidazole-4-(N-2-pyrazinyl)amide

¹HNMR (DMSO, 400 MHz) δ: 7.17-7.19(t,1H), 7.43-7.45(t,1H), 7.69-7.71(d,1H), 7.85-7.87(d,1H), 7.89-7.91(d,1H), 7.93-7.94(d,1H), 8.34-8.35(d,1H), 8.36(s,1H), 8.40-8.42(d,1H);

(68) 2-(2-thienyl)-1H-benzimidazole-4-(N-2-pyrimidinyl)amide

¹HNMR (DMSO, 400 MHz) δ: 6.93-6.95(t,1H), 7.17-7.19(t,1H), 7.69-7.71(d,1H), 7.85-7.87(d,1H), 7.43-7.45(t,1H), 7.89-7.91(d,1H), 7.93-7.94(d,1H), 8.45-8.46(d,2H);

(69) 2-(2-thienyl)-1H-benzimidazole-4-(N-2-pyridyl)amide

¹HNMR (DMSO, 400 MHz) δ: 6.62-6.64(t,1H), 6.70-6.72(d,1H), 7.17-7.19(t,1H), 7.43-7.45(t,1H), 7.55-7.57(t,1H), 7.69-7.71(d,1H), 7.85-7.87(d,1H), 7.89-7.91(d,1H), 7.93-7.94(d,1H), 8.07-8.09(d,1H);

(70) 2-(2-thienyl)-1H-benzimidazole-4-(N-4-methyl-5-thiazolyl)amide

¹HNMR (DMSO, 400 MHz) δ: 2.45(s,3H), 7.17-7.19(t,1H), 7.43-7.45(t,1H), 7.69-7.71(d,1H), 7.85-7.87(d,1H), 7.89-7.91(d,1H), 7.93-7.94(d,1H), 8.12(s,1H);

(71) 2-(2-thienyl)-1H-benzimidazole-4-(N-2,4-dihydroxyl-5-pyrimidinyl)amide

¹HNMR (DMSO, 400 MHz) δ: 7.17-7.19(t,1H), 7.43-7.45(t,1H), 7.69-7.71(d,1H), 7.82(s,1H), 7.85-7.87(d,1H), 7.89-7.91(d,1H), 7.93-7.94(d,1H), 8.33(s,1H), 11.53(s,1H);

(72) 2-(2-thienyl)-1H-benzimidazole-4-(N-4,6-dimethoxy-2-pyrimidinyl)amide

¹HNMR (DMSO, 400 MHz) δ: 3.82(s,6H), 5.71(s,1H), 7.17-7.19(t,1H), 7.43-7.45(t,1H), 7.69-7.71(d,1H), 7.85-7.87(d,1H), 7.89-7.91(d,1H), 7.93-7.94(d,1H);

(73) 2-(2-thienyl)-1H-benzimidazole-4-(N-4-chloro-6-amino-2-pyrimidinyl)amide

¹HNMR (DMSO, 400 MHz) δ: 5.98(s,1H), 7.17-7.19(t,1H), 7.43-7.45(t,1H), 7.69-7.71(d,1H), 7.74(s,2H), 7.85-7.87(d,1H), 7.89-7.91(d,1H), 7.93-7.94(d,1H);

(74) 2-(2-thienyl)-1H-benzimidazole-4-(N-4,6-dichloro-5-pyrimidinyl)amide

¹HNMR (DMSO, 400 MHz) δ: 7.17-7.19(t,1H), 7.43-7.45(t,1H), 7.69-7.71(d,1H), 7.85-7.87(d,1H), 7.89-7.91(d,1H), 7.93-7.94(d,1H), 9.34(s,1H);

(75) 2-(2-thienyl)-1H-benzimidazole-4-(N-o-fluorophenyl)amide

¹HNMR (DMSO, 400 MHz) δ: 6.60-6.61(d,1H), 6.63-6.65(t,1H), 6.96-6.98(t,1H), 6.99-7.01(d,1H), 7.17-7.19(t,1H), 7.43-7.45(t,1H), 7.69-7.71(d,1H), 7.85-7.87(d,1H), 7.89-7.91(d,1H), 7.93-7.94(d,1H);

(76) 2-(2-thienyl)-1H-benzimidazole-4-(N-2-hydroxyl-4-pyrimidinyl)amide

¹HNMR (DMSO, 400 MHz) δ: 5.46-5.48(d,1H), 7.10-7.11(d,1H), 7.17-7.19(t,1H), 7.43-7.45(t,1H), 7.69-7.71(d,1H), 7.82(s,1H), 7.85-7.87(d,1H), 7.89-7.91(d,1H), 7.93-7.94(d,1H);

(77) 2-(2-thienyl)-1H-benzimidazole-4-(N-6-purinyl)amide

¹HNMR (DMSO, 400 MHz) δ: 7.17-7.19(t,1H), 7.43-7.45(t,1H), 7.69-7.71(d,1H), 7.85-7.86(d,1H), 7.87-7.88(d,1H), 7.89-7.91(d,1H), 7.93-7.94(d,1H), 8.16-8.18(d,1H);

(78) 2-(2-thienyl)-1H-benzimidazole-4-(N-6-hydroxyl-2-purinyl)amide

¹HNMR (DMSO, 400 MHz) δ: 7.17-7.19(t,1H), 7.43-7.45(t,1H), 7.69-7.71(d,1H), 7.85-7.87(d,1H), 7.89-7.91(d,1H), 7.93-7.94(d,1H), 8.57-8.59(d,1H), 11.53(s,1H);

(79) (L)-2-(4-methoxypyridyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 3.83(s,3H), 4.73-4.77(t,1H), 7.31(s,1H), 7.43-7.45(t,1H), 7.59-7.61(d,1H), 7.62-7.65(d,2H), 7.89-7.90(d,1H), 7.93-7.95(d,1H), 8.17-8.20(d,2H), 8.49-8.51(d,1H);

(80) (L)-2-(4-methoxypyridyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 3.83(s,3H), 4.73-4.77(t,1H), 6.27(s,2H), 6.56-6.58(d,2H), 7.11-7.13(d,2H), 7.31(s,1H), 7.43-7.45(t,1H), 7.59-7.61(d,1H), 7.89-7.90(d,1H), 7.93-7.95(d,1H), 8.49-8.51(d,1H);

(81) 2-(4-methoxypyridyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 3.83(s,3H), 4.73-4.77(t,1H), 7.29-7.30(d,2H), 7.31(s,1H), 7.40-7.41(d,2H), 7.43-7.45(t,1H), 7.59-7.61(d,1H), 7.89-7.91(d,1H), 7.93-7.94(d,1H), 8.49-8.51(d,1H);

(82) 2-(4-methoxypyridyl)-1H-benzimidazole-4-(N-N'-piperidinyl)amide

¹HNMR (DMSO, 400 MHz) δ: 1.52-1.55(m,4H), 1.59-1.63(m,2H), 3.10-3.15(t,4H), 3.83(s,3H), 7.31(s,1H), 7.43-7.45(t,1H), 7.59-7.61(d,1H), 7.89-7.91(d,1H), 7.93-7.94(d,1H), 8.49-8.51(d,1H);

(83) 2-(4-methoxypyridyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.83(s,3H), 3.99-4.01(m,1H), 7.31(s,1H), 7.43-7.45(t,1H), 7.59-7.61(d,1H), 7.89-7.91(d,1H), 7.93-7.94(d,1H), 8.49-8.51(d,1H);

(84) 2-(4-methoxypyridyl)-1H-benzimidazole-4-(N-2'-benzimidazolyl)amide

¹HNMR (DMSO, 400 MHz) δ: 3.83(s,3H), 7.12-7.15(d,2H), 7.22-7.24(t,2H), 7.43-7.45(t,1H), 7.59-7.61(d,1H), 7.89-7.91(d,1H), 7.93-7.94(d,1H), 8.49-8.51(d,1H);

(85) 2-(4-methoxypyridyl)-1H-benzimidazole-4-(N-o-aminophenyl)amide

¹HNMR (DMSO, 400 MHz) δ: 3.83(s,3H), 6.27(s,2H), 6.38-6.40(d,1H), 6.56-6.58(t,1H), 6.75-6.76(d,1H), 7.02-

7.04(t,1H), 7.31(s,1H), 7.43-7.45(t,1H), 7.59-7.61(d,1H), 7.89-7.91(d,1H), 7.93-7.94(d,1H), 8.49-8.51(d,1H);

(86) 2-(4-methoxypyridyl)-1H-benzimidazole-4-(N-5-benzimidazolonyl)amide

¹HNMR (DMSO, 400 MHz) δ: 3.83(s,3H), 6.35-6.37(d, 1H), 6.93(s,1H), 7.31(s,1H), 7.43-7.45(t,1H), 7.54-7.56(d, 1H), 7.59-7.61(d,1H), 7.89-7.91(d,1H), 7.93-7.94(d,1H), 8.49-8.51(d,1H);

(87) 2-(4-methoxypyridyl)-1H-benzimidazole-4-(N-4'-carbonamido-5'-imidazolyl)amide ¹HNMR (DMSO, 400 MHz) δ: 3.83(s,3H), 7.31(s,1H), 7.43-7.45(t,1H), 7.59-7.61(d,1H), 7.89-7.91(d,1H), 7.93-7.94(d,1H), 8.37(s,2H), 8.49-8.51(d,1H), 9.24-9.26(d,1H), 13.00-13.03(d,1H);

(88) 2-(4-methoxypyridyl)-1H-benzimidazole-4-(N-4'-pyrazolyl)amide

¹HNMR (DMSO, 400 MHz) δ: 3.83(s,3H), 7.31(s,1H), 7.43-7.45(t,1H), 7.59-7.61(d,1H), 7.89-7.91(d,1H), 7.93-7.94(d,1H), 8.49-8.51(d,1H), 8.61(s,1H), 8.63-8.65(d,1H), 13.71-13.75(d,1H);

(89) 2-(4-methoxypyridyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 3.83(s,3H), 7.31(s,1H), 7.43-7.45(t,1H), 7.59-7.61(d,1H), 7.90-7.91(d,1H), 7.93-7.94(d,1H), 8.49-8.51(d,1H);

(90) 2-(4-methoxypyridyl)-1H-benzimidazole-4-(N-2-pyrazinyl)amide

¹HNMR (DMSO, 400 MHz) δ: 3.83(s,3H), 7.31(s,1H), 7.43-7.45(t,1H), 7.59-7.61(d,1H), 7.89-7.91(d,1H), 7.93-7.94(d,1H), 8.34-8.35(d,1H), 8.36(s,1H), 8.40-8.42(d,1H), 8.49-8.51(d,1H);

(91) 2-(4-methoxypyridyl)-1H-benzimidazole-4-(N-2-pyrimidinyl)amide

¹HNMR (DMSO, 400 MHz) δ: 3.83(s,3H), 6.93-6.95(t, 1H), 7.31(s,1H), 7.43-7.45(t,1H), 7.59-7.61(d,1H), 7.89-7.91 (d,1H), 7.93-7.94(d,1H), 8.45-8.46(d,2H), 8.49-8.51(d,1H);

(92) 2-(4-methoxypyridyl)-1H-benzimidazole-4-(N-2-pyridyl)amide

¹HNMR (DMSO, 400 MHz) δ: 3.83(s,3H), 6.62-6.64(t, 1H), 6.70-6.72(d,1H), 7.31(s,1H), 7.43-7.45(t,1H), 7.55-7.57 (t,1H), 7.59-7.61(d,1H), 7.89-7.91(d,1H), 7.93-7.94(d,1H), 8.07-8.09(d,1H), 8.49-8.51(d,1H);

(93) 2-(4-methoxypyridyl)-1H-benzimidazole-4-(N-4-methyl-5-thiazolyl)amide

¹HNMR (DMSO, 400 MHz) δ: 2.45(s,3H), 3.83(s,3H), 7.31(s,1H), 7.43-7.45(t,1H), 7.59-7.61(d,1H), 7.89-7.91(d, 1H), 7.93-7.94(d,1H), 8.12(s,1H), 8.49-8.51(d,1H);

(94) 2-(4-methoxypyridyl)-1H-benzimidazole-4-(N-2,4-dihydroxyl-5-pyrimidinyl)amide ¹HNMR (DMSO, 400 MHz) δ: 3.83(s,3H), 7.31(s,1H), 7.43-7.45(t,1H), 7.59-7.61(d,1H), 7.82(s,1H), 7.89-7.91(d, 1H), 7.93-7.94(d,1H), 8.33(s,1H), 8.49-8.51(d,1H), 11.53(s, 1H);

(95) 2-(4-methoxypyridyl)-1H-benzimidazole-4-(N-4,6-dimethoxy-2-pyrimidinyl)amide ¹HNMR (DMSO, 400 MHz) δ: 3.82(s,6H), 3.85(s,3H), 5.71(s,1H), 7.31(s,1H), 7.43-7.45(t,1H), 7.59-7.61(d,1H), 7.89-7.91(d,1H), 7.93-7.94(d,1H), 8.49-8.51(d,1H);

(96) 2-(4-methoxypyridyl)-1H-benzimidazole-4-(N-4-chloro-6-amino-2-pyrimidinyl)amide ¹HNMR (DMSO, 400 MHz) δ: 3.83(s,3H), 5.98(s,1H), 7.31(s,1H), 7.43-7.45(t,1H), 7.74(s,2H), 7.89-7.91(d,1H), 7.93-7.94(d,1H), 8.49-8.51(d,1H);

(97) 2-(4-methoxypyridyl)-1H-benzimidazole-4-(N-4,6-dichloro-5-pyrimidinyl)amide ¹HNMR (DMSO, 400 MHz) δ: 3.83(s,3H), 7.31(s,1H), 7.43-7.45(t,1H), 7.59-7.61(d,1H), 7.89-7.91(d,1H), 7.93-7.94(d,1H), 8.49-8.51(d,1H), 9.34(s,1H);

(98) 2-(4-methoxypyridyl)-1H-benzimidazole-4-(N-o-fluorophenyl)amide

¹HNMR (DMSO, 400 MHz) δ: 3.83(s,3H), 6.60-6.61(d, 1H), 6.63-6.65(t,1H), 6.96-6.98(t,1H), 6.99-7.01(d,1H), 7.31 (s,1H), 7.43-7.45(t,1H), 7.59-7.61(d,1H), 7.89-7.91(d,1H), 7.93-7.94(d,1H), 8.49-8.51(d,1H);

(99) 2-(4-methoxypyridyl)-1H-benzimidazole-4-(N-2-hydroxyl-4-pyrimidinyl)amide

¹HNMR (DMSO, 400 MHz) δ: 3.83(s,3H), 5.46-5.48(d, 1H), 7.10-7.11(d,1H), 7.31(s,1H), 7.43-7.45(t,1H), 7.59-7.61 (d,1H), 7.82(s,1H), 7.89-7.91(d,1H), 7.93-7.94(d,1H), 8.49-8.51(d,1H);

(100) 2-(4-methoxypyridyl)-1H-benzimidazole-4-(N-6-purinyl)amide

¹HNMR (DMSO, 400 MHz) δ: 3.83(s,3H), 7.31(s,1H), 7.43-7.45(t,1H), 7.59-7.61(d,1H), 7.86-7.88(d,1H), 7.89-7.91(d,1H), 7.93-7.94(d,1H), 8.16-8.18(d,1H), 8.49-8.51(d, 1H);

(101) 2-(4-methoxypyridyl)-1H-benzimidazole-4-(N-6-hydroxyl-2-purinyl)amide

¹HNMR (DMSO, 400 MHz) δ: 3.83(s,3H), 7.31(s,1H), 7.43-7.45(t,1H), 7.59-7.61(d,1H), 7.89-7.91(d,1H), 7.93-7.94(d,1H), 8.49-8.51(d,1H), 8.57-8.59(d,1H), 11.53(s,1H);

(102) (L)-2-(6-methoxypyridyl)-1H-benzimidazole-4-[N-(1-hydroxymethyl-2-p-nitrophenylhydroxy-ethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 3.80(s,1H), 4.73-4.77(t,1H), 6.50-6.52(d,1H), 7.38-7.40

(d,1H), 7.43-7.45(t,1H), 7.62-7.65(d,2H), 7.72-7.74(t,1H), 7.89-7.90(d,1H), 7.93-7.95(d,1H), 8.17-8.20(d,2H);

(103) (L)-2-(6-methoxypyridyl)-1H-benzimidazole-4-[N-(1-hydroxymethyl-2-p-aminophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 3.80(s,1H), 4.73-4.77(t,1H), 6.27(s,2H), 6.50-6.52(d, 1H), 6.56-6.58(d,2H), 7.11-7.13(d,2H), 7.38-7.40(d,1H), 7.43-7.45(t,1H), 7.72-7.74(t,1H), 7.89-7.90(d,1H), 7.93-7.95 (d,1H);

(104) 2-(6-methoxypyridyl)-1H-benzimidazole-4-[N-(1-methyl-2-p-chlorophenylhydroxyethyl)]amide $^1$HNMR (DMSO, 400 MHz) δ: 1.12-1.15(d,3H), 3.25-3.28 (m,1H), 3.65-3.68(t,1H), 3.80(s,1H), 4.73-4.77(t,1H), 6.50-6.52(d,1H), 7.29-7.30(d,2H), 7.38-7.39(d,1H), 7.40-7.41(d, 2H), 7.43-7.45(t,1H), 7.89-7.91(d,1H), 7.72-7.74(t,1H), 7.93-7.94(d,1H);

(105) 2-(6-methoxypyridyl)-1H-benzimidazole-4-(N-N'-piperidinyl)amide $^1$HNMR (DMSO, 400 MHz) δ: 1.52-1.55(m,4H), 1.59-1.63(m,2H), 3.10-3.15(t,4H), 3.80(s,1H), 6.50-6.52(d,1H), 7.38-7.40(d,1H), 7.43-7.45(t,1H), 7.72-7.74(t,1H), 7.89-7.91 (d,1H), 7.93-7.94(d,1H);

(106) 2-(6-methoxypyridyl)-1H-benzimidazole-4-(N-2-piperazinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74 (m,1H), 2.77-2.80(m,1H), 3.02-3.05(m,1H), 3.80(s,1H), 3.99-4.01(m,1H), 6.50-6.52(d,1H), 7.38-7.40(d,1H), 7.43-7.45(t,1H), 7.72-7.74(t,1H), 7.89-7.91(d,1H), 7.93-7.94(d, 1H);

(107) 2-(6-methoxypyridyl)-1H-benzimidazole-4-(N-2'-benzimidazolyl)amide $^1$HNMR (DMSO, 400 MHz) δ: 3.80(s,1H), 6.50-6.52(d, 1H), 7.12-7.15(d,2H), 7.22-7.24(t,2H), 7.38-7.40(d,1H), 7.43-7.45(t,1H), 7.72-7.74(t,1H), 7.89-7.91(d,1H), 7.93-7.94 (d,1H);

(108) 2-(6-methoxypyridyl)-1H-benzimidazole-4-(N-o-aminophenyl)amide $^1$HNMR (DMSO, 400 MHz) δ: 3.80(s,1H), 6.27(s,2H), 6.38-6.40(d,1H), 6.50-6.52(d,1H), 6.56-6.58(t,1H), 6.75-6.76(d,1H), 7.02-7.04(t,1H), 7.38-7.40(d,1H), 7.43-7.45(t, 1H), 7.72-7.74(t,1H), 7.89-7.91(d,1H), 7.93-7.94(d,1H);

(109) 2-(6-methoxypyridyl)-1H-benzimidazole-4-(N-5-benzimidazolonyl)amide $^1$HNMR (DMSO, 400 MHz) δ: 3.80(s,1H), 6.35-6.37(d, 1H), 6.50-6.52(d,1H), 6.93(s,1H), 7.38-7.40(d,1H), 7.43-7.45(t,1H), 7.54-7.56(d,1H), 7.72-7.74(t,1H), 7.89-7.91(d, 1H), 7.93-7.94(d,1H);

(110) 2-(6-methoxypyridyl)-1H-benzimidazole-4-(N-4'-carbonamido-5'-imidazolyl)amide $^1$HNMR (DMSO, 400 MHz) δ: 3.80(s,1H), 6.50-6.52(d, 1H), 7.38-7.40(d,1H), 7.43-7.45(t,1H), 7.72-7.74(t,1H), 7.89-7.91(d,1H), 7.93-7.94(d,1H), 8.37(s,2H), 9.24-9.26(d, 1H), 13.00-13.03(d,1H);

(111) 2-(6-methoxypyridyl)-1H-benzimidazole-4-(N-4'-pyrazolyl)amide $^1$HNMR (DMSO, 400 MHz) δ: 3.80(s,1H), 6.50-6.52(d, 1H), 7.38-7.40(d,1H), 7.43-7.45(t,1H), 7.72-7.74(t,1H), 7.89-7.91(d,1H), 7.93-7.94(d,1H), 8.61(s,1H), 8.63-8.65(d, 1H), 13.71-13.75(d,1H);

(112) 2-(6-methoxypyridyl)-1H-benzimidazole-4-(N—(N'-piperazinyl))amide $^1$HNMR (DMSO, 400 MHz) δ: 1.91-1.95(m,1H), 2.65-2.67(t,4H), 2.80-2.83(m,4H), 3.80(s,1H), 6.50-6.52(d,1H), 7.38-7.40(d,1H), 7.43-7.45(t,1H), 7.90-7.91(d,1H), 7.72-7.74(t,1H), 7.93-7.94(d,1H);

(113) 2-(6-methoxypyridyl)-1H-benzimidazole-4-(N-2-pyrazinyl)amide $^1$HNMR (DMSO, 400 MHz) δ: 3.80(s,1H), 6.50-6.52(d, 1H), 7.38-7.40(d,1H), 7.43-7.45(t,1H), 7.72-7.74(t,1H), 7.89-7.91(d,1H), 7.93-7.94(d,1H), 8.34-8.35(d,1H), 8.36(s, 1H), 8.40-8.42(d,1H);

(114) 2-(6-methoxypyridyl)-1H-benzimidazole-4-(N-2-pyrimidinyl)amide $^1$HNMR (DMSO, 400 MHz) δ: 3.80(s,1H), 6.50-6.52(d, 1H), 6.93-6.95(t,1H), 7.38-7.40(d,1H), 7.43-7.45(t,1H), 7.72-7.74(t,1H), 7.89-7.91(d,1H), 7.93-7.94(d,1H), 8.45-8.46(d,2H);

(115) 2-(6-methoxypyridyl)-1H-benzimidazole-4-(N-2-pyridyl)amide $^1$HNMR (DMSO, 400 MHz) δ: 3.80(s,1H), 6.50-6.52(d, 1H), 6.62-6.64(t,1H), 6.70-6.72(d,1H), 7.38-7.40(d,1H), 7.43-7.45(t,1H), 7.55-7.57(t,1H), 7.72-7.74(t,1H), 7.89-7.91 (d,1H), 7.93-7.94(d,1H), 8.07-8.09(d,1H);

(116) 2-(6-methoxypyridyl)-1H-benzimidazole-4-(N-4-methyl-5-thiazolyl)amide $^1$HNMR (DMSO, 400 MHz) δ: 2.45(s,3H), 3.80(s,1H), 6.50-6.52(d,1H), 7.38-7.40(d,1H), 7.43-7.45(t,1H), 7.72-7.74(t,1H), 7.89-7.91(d,1H), 7.93-7.94(d,1H), 8.12(s,1H);

(117) 2-(6-methoxypyridyl)-1H-benzimidazole-4-(N-2,4-dihydroxyl-5-pyrimidinyl)amide $^1$HNMR (DMSO, 400 MHz) δ: 3.80(s,1H), 6.50-6.52(d, 1H), 7.38-7.40(d,1H), 7.43-7.45(t,1H), 7.72-7.74(t,1H), 7.82 (s,1H), 7.89-7.91(d,1H), 7.93-7.94(d,1H), 8.33(s,1H), 11.53 (s,1H);

(118) 2-(6-methoxypyridyl)-1H-benzimidazole-4-(N-4,6-dimethoxy-2-pyrimidinyl)amide ¹HNMR (DMSO, 400 MHz) δ: 3.80(s,1H), 3.82(s,6H), 5.71(s,1H), 6.50-6.52(d,1H), 7.38-7.40(d,1H), 7.43-7.45(t,1H), 7.72-7.74(t,1H), 7.89-7.91(d,1H), 7.93-7.94(d,1H);

(119) 2-(6-methoxypyridyl)-1H-benzimidazole-4-(N-4-chloro-6-amino-2-pyrimidinyl)amide ¹HNMR (DMSO, 400 MHz) δ: 3.80(s,1H), 5.98(s,1H), 6.50-6.52(d,1H), 7.38-7.40(d,1H), 7.43-7.45(t,1H), 7.74(s,2H), 7.89-7.91(d,1H), 7.72-7.74(t,1H), 7.93-7.94(d,1H);

(120) 2-(6-methoxypyridyl)-1H-benzimidazole-4-(N-4,6-dichloro-5-pyrimidinyl)amide ¹HNMR (DMSO, 400 MHz) δ: 3.80(s,1H), 6.50-6.52(d,1H), 7.38-7.40(d,1H), 7.43-7.45(t,1H), 7.72-7.74(t,1H), 7.89-7.91(d,1H), 7.93-7.94(d,1H), 9.34(s,1H);

(121) 2-(6-methoxypyridyl)-1H-benzimidazole-4-(N-o-fluorophenyl)amide

¹HNMR (DMSO, 400 MHz) δ: 3.80(s,1H), 6.50-6.52(d,1H), 6.60-6.61(d,1H), 6.63-6.65(t,1H), 6.96-6.98(t,1H), 6.99-7.01(d,1H), 7.38-7.40(d,1H), 7.43-7.45(t,1H), 7.72-7.74(t,1H), 7.89-7.91(d,1H), 7.93-7.94(d,1H);

(122) 2-(6-methoxypyridyl)-1H-benzimidazole-4-(N-2-hydroxyl-4-pyrimidinyl)amide

¹HNMR (DMSO, 400 MHz) δ: 3.80(s,1H), 5.46-5.48(d,1H), 6.50-6.52(d,1H), 7.10-7.11(d,1H), 7.38-7.40(d,1H), 7.43-7.45(t,1H), 7.72-7.74(t,1H), 7.82(s,1H), 7.89-7.91(d,1H), 7.93-7.94(d,1H);

(123) 2-(6-methoxypyridyl)-1H-benzimidazole-4-(N-6-purinyl)amide

¹HNMR (DMSO, 400 MHz) δ: 3.80(s,1H), 6.50-6.52(d,1H), 7.38-7.40(d,1H), 7.43-7.45(t,1H), 7.72-7.74(t,1H), 7.86-7.88(d,1H), 7.89-7.91(d,1H), 7.93-7.94(d,1H), 8.16-8.18(d,1H);

(124) 2-(6-methoxypyridyl)-1H-benzimidazole-4-(N-6-hydroxyl-2-purinyl)amide

¹HNMR (DMSO, 400 MHz) δ: 3.80(s,1H), 6.50-6.52(d,1H), 7.38-7.40(d,1H), 7.43-7.45(t,1H), 7.72-7.74(t,1H), 7.89-7.91(d,1H), 7.93-7.94(d,1H), 8.57-8.59(d,1H), 11.53(s,1H);

(125) (L)-2-(4-dimethylaminopyridyl)-1H-benzimidazole-4-[N-(1-hydroxymethyl-2-p-nitrophenylhydroxyethyl)]amide ¹HNMR (DMSO, 400 MHz) δ: 2.68(s,6H), 3.17-3.18(m,1H), 3.25-3.28(m,1H), 3.50-3.52(m,1H), 3.65-3.68(t,1H), 3.70-3.72(d,1H), 4.73-4.77(t,1H), 6.65-6.67(d,1H), 6.86(s,1H), 7.43-7.45(t,1H), 7.62-7.65(d,2H), 7.89-7.90(d,1H), 7.93-7.95(d,1H), 8.17-8.20(d,2H), 8.32-8.35(d,1H);

(126) (L)-2-(4-dimethylaminopyridyl)-1H-benzimidazole-4-[N-(1-hydroxymethyl-2-p-aminophenylhydroxyethyl)]amide ¹HNMR (DMSO, 400 MHz) δ: 2.68(s,6H), 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 6.65-6.67(d,1H), 6.86(s,1H), 7.11-7.13(d,2H), 7.43-7.45(t,1H), 7.89-7.90(d,1H), 7.93-7.95(d,1H), 8.32-8.35(d,1H);

(127) 2-(4-dimethylaminopyridyl)-1H-benzimidazole-4-[N-(1-methyl-2-p-chlorophenylhydroxyethyl)]amide ¹HNMR (DMSO, 400 MHz) δ: 1.12-1.15(d,3H), 2.68(s,6H), 3.25-3.28(m,1H), 3.65-3.68(t,1H), 4.73-4.77(t,1H), 6.65-6.67(d,1H), 6.86(s,1H), 7.29-7.30(d,2H), 7.40-7.41(d,2H), 7.43-7.45(t,1H), 7.89-7.91(d,1H), 7.93-7.94(d,1H), 8.32-8.35(d,1H);

(128) 2-(4-dimethylaminopyridyl)-1H-benzimidazole-4-(N-N'-piperidinyl)amide

¹HNMR (DMSO, 400 MHz) δ: 1.52-1.55(m,4H), 1.59-1.63(m,2H), 2.68(s,6H), 3.10-3.15(t,4H), 6.65-6.67(d,1H), 6.86(s,1H), 7.43-7.45(t,1H), 7.89-7.91(d,1H), 7.93-7.94(d,1H), 8.32-8.35(d,1H);

(129) 2-(4-dimethylaminopyridyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.68(s,6H), 2.69-2.70(m,1H), 2.72-2.74(m,1H), 2.77-2.80(m,1H), 3.02-3.05(m,1H), 3.99-4.01(m,1H), 6.65-6.67(d,1H), 6.86(s,1H), 7.43-7.45(t,1H), 7.89-7.91(d,1H), 7.93-7.94(d,1H), 8.32-8.35(d,1H);

(130) 2-(4-dimethylaminopyridyl)-1H-benzimidazole-4-(N-2'-benzimidazolyl)amide

¹HNMR (DMSO, 400 MHz) δ: 2.68(s,6H), 6.65-6.67(d,1H), 6.86(s,1H), 7.12-7.15(d,2H), 7.22-7.24(t,2H), 7.43-7.45(t,1H), 7.89-7.91(d,1H), 7.93-7.94(d,1H), 8.32-8.35(d,1H);

(131) 2-(4-dimethylaminopyridyl)-1H-benzimidazole-4-(N-o-aminophenyl)amide

¹HNMR (DMSO, 400 MHz) δ: 2.68(s,6H), 6.27(s,2H), 6.38-6.40(d,1H), 6.56-6.58(t,1H), 6.65-6.67(d,1H), 6.75-6.76(d,1H), 6.86(s,1H), 7.02-7.04(t,1H), 7.43-7.45(t,1H), 7.89-7.91(d,1H), 7.93-7.94(d,1H), 8.32-8.35(d,1H);

(132) 2-(4-dimethylaminopyridyl)-1H-benzimidazole-4-(N-5-benzimidazolonyl)amide

¹HNMR (DMSO, 400 MHz) δ: 2.68(s,6H), 6.35-6.37(d,1H), 6.65-6.67(d,1H), 6.86(s,1H), 6.93(s,1H), 7.43-7.45(t,1H), 7.54-7.56(d,1H), 7.89-7.91(d,1H), 7.93-7.94(d,1H), 8.32-8.35(d,1H);

(133) 2-(4-dimethylaminopyridyl)-1H-benzimidazole-4-(N-4'-carbonamido-5'-imidazolyl)amide ¹HNMR (DMSO, 400 MHz) δ: 2.68(s,6H), 6.65-6.67(d,1H), 6.86(s,1H), 7.43-7.45(t,1H), 7.89-7.91(d,1H), 7.93-7.94(d,1H), 8.32-8.35(d,1H), 8.37(s,2H), 9.24-9.26(d,1H), 13.00-13.03(d,1H);

(134) 2-(4-dimethylaminopyridyl)-1H-benzimidazole-4-(N-4'-pyrazolyl)amide

¹HNMR (DMSO, 400 MHz) δ: 2.68(s,6H), 6.65-6.67(d,1H), 6.86(s,1H), 7.43-7.45(t,1H), 7.89-7.91(d,1H), 7.93-7.94(d,1H), 8.32-8.35(d,1H), 8.61(s,1H), 8.63-8.65(d,1H), 13.71-13.75(d,1H);

(135) 2-(4-dimethylaminopyridyl)-1H-benzimidazole-4-(N—(N'-piperazinyl))amide

¹HNMR (DMSO, 400 MHz) δ: 1.91-1.95(m,1H), 2.65-2.67(t,4H), 2.68(s,6H), 2.80-2.83(m,4H), 6.65-6.67(d,1H), 6.86(s,1H), 7.43-7.45(t,1H), 7.90-7.91(d,1H), 7.93-7.94(d,1H);

(136) 2-(4-dimethylaminopyridyl)-1H-benzimidazole-4-(N-2-pyrazinyl)amide

¹HNMR (DMSO, 400 MHz) δ: 2.68(s,6H), 6.65-6.67(d,1H), 6.86(s,1H), 7.43-7.45(t,1H), 7.89-7.91(d,1H), 7.93-7.94(d,1H), 8.32-8.35(d,1H), 8.34-8.35(d,1H), 8.36(s,1H), 8.40-8.42(d,1H);

(137) 2-(4-dimethylaminopyridyl)-1H-benzimidazole-4-(N-2-pyrimidinyl)amide

¹HNMR (DMSO, 400 MHz) δ: 2.68(s,6H), 6.65-6.67(d,1H), 6.86(s,1H), 6.93-6.95(t,1H), 7.43-7.45(t,1H), 7.89-7.91(d,1H), 7.93-7.94(d,1H), 8.32-8.35(d,1H), 8.45-8.46(d,2H);

(138) 2-(4-dimethylaminopyridyl)-1H-benzimidazole-4-(N-2-pyridyl)amide

¹HNMR (DMSO, 400 MHz) δ: 2.68(s,6H), 6.62-6.64(t,1H), 6.65-6.67(d,1H), 6.70-6.72(d,1H), 6.86(s,1H), 7.43-7.45(t,1H), 7.55-7.57(t,1H), 7.89-7.91(d,1H), 7.93-7.94(d,1H), 8.07-8.09(d,1H), 8.32-8.35(d,1H);

(139) 2-(4-dimethylaminopyridyl)-1H-benzimidazole-4-(N-4-methyl-5-thiazolyl)amide ¹HNMR (DMSO, 400 MHz) δ: 2.45(s,3H), 2.68(s,6H), 6.65-6.67(d,1H), 6.86(s,1H), 7.43-7.45(t,1H), 7.89-7.91(d,1H), 7.93-7.94(d,1H), 8.12(s,1H), 8.32-8.35(d,1H);

(140) 2-(4-dimethylaminopyridyl)-1H-benzimidazole-4-(N-2,4-dihydroxyl-5-pyrimidinyl)amide ¹HNMR (DMSO, 400 MHz) δ: 2.68(s,6H), 6.65-6.67(d,1H), 6.86(s,1H), 7.43-7.45(t,1H), 7.82(s,1H), 7.89-7.91(d,1H), 7.93-7.94(d,1H), 8.30(s,1H), 8.32-8.35(d,1H), 11.53(s,1H);

(141) 2-(4-dimethylaminopyridyl)-1H-benzimidazole-4-(N-4,6-dimethoxy-2-pyrimidinyl)amide ¹HNMR (DMSO, 400 MHz) δ: 2.68(s,6H), 3.82(s,6H), 5.71(s,1H), 6.65-6.67(d,1H), 6.86(s,1H), 7.43-7.45(t,1H), 7.89-7.91(d,1H), 7.93-7.94(d,1H), 8.32-8.35(d,1H);

(142) 2-(4-dimethylaminopyridyl)-1H-benzimidazole-4-(N-4-chloro-6-amino-2-pyrimidinyl)amide ¹HNMR (DMSO, 400 MHz) δ: 2.68(s,6H), 5.98(s,1H), 6.65-6.67(d,1H), 6.86(s,1H), 7.43-7.45(t,1H), 7.74(s,2H), 7.89-7.91(d,1H), 7.93-7.94(d,1H), 8.32-8.35(d,1H);

(143) 2-(4-dimethylaminopyridyl)-1H-benzimidazole-4-(N-4,6-dichloro-5-pyrimidinyl)amide ¹HNMR (DMSO, 400 MHz) δ: 2.68(s,6H), 6.65-6.67(d,1H), 6.86(s,1H), 7.43-7.45(t,1H), 7.89-7.91(d,1H), 7.93-7.94(d,1H), 8.32-8.35(d,1H), 9.34(s,1H);

(144) 2-(4-dimethylaminopyridyl)-1H-benzimidazole-4-(N-o-fluorophenyl)amide

¹HNMR (DMSO, 400 MHz) δ: 2.68(s,6H), 6.60-6.61(d,1H), 6.63-6.64(t,1H), 6.66-6.67(d,1H), 6.86(s,1H), 6.96-6.98(t,1H), 6.99-7.01(d,1H), 7.43-7.45(t,1H), 7.89-7.91(d,1H), 7.93-7.94(d,1H), 8.32-8.35(d,1H);

(145) 2-(4-dimethylaminopyridyl)-1H-benzimidazole-4-(N-2-hydroxyl-4-pyrimidinyl)amide ¹HNMR (DMSO, 400 MHz) δ: 2.68(s,6H), 5.46-5.48(d,1H), 6.65-6.67(d,1H), 6.86(s,1H), 7.10-7.11(d,1H), 7.43-7.45(t,1H), 7.82(s,1H), 7.89-7.91(d,1H), 7.93-7.94(d,1H), 8.32-8.35(d,1H);

(146) 2-(4-dimethylaminopyridyl)-1H-benzimidazole-4-(N-6-purinyl)amide

¹HNMR (DMSO, 400 MHz) δ: 2.68(s,6H), 6.65-6.67(d,1H), 6.86(s,1H), 7.43-7.45(t,1H), 7.86-7.88(d,1H), 7.89-7.91(d,1H), 7.93-7.94(d,1H), 8.16-8.18(d,1H), 8.32-8.35(d,1H);

(147) 2-(4-dimethylaminopyridyl)-1H-benzimidazole-4-(N-6-hydroxyl-2-purinyl)amide ¹HNMR (DMSO, 400 MHz) δ: 2.68(s,6H), 6.65-6.67(d,1H), 6.86(s,1H), 7.43-7.45(t,1H), 7.89-7.91(d,1H), 7.93-7.94(d,1H), 8.32-8.35(d,1H), 8.57-8.59(d,1H), 11.53(s,1H);

(148) (L)-2-(2,3,4-trimethoxyphenyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 3.83(s,9H), 4.73-4.77(t,1H), 6.50-6.52(d,1H), 7.13-7.14(d,1H), 7.43-7.45(t,1H), 7.62-7.65(d,2H), 7.89-7.90(d,1H), 7.93-7.95(d,1H), 8.17-8.20(d,2H);

(149) (L)-2-(2,3,4-trimethoxyphenyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 3.83(s,9H), 4.73-4.77(t,1H), 6.27(s,2H), 6.50-6.52(d,1H), 6.56-6.58(d,2H), 7.11-7.12(d,2H), 7.13-7.14(d,1H), 7.43-7.45(t,1H), 7.89-7.90(d,1H), 7.93-7.95(d,1H);

(150) 2-(2,3,4-trimethoxyphenyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 3.83(s,9H), 4.73-4.77(t,1H), 6.50-6.52(d,1H), 7.13-7.14(d,1H), 7.29-7.30(d,2H), 7.40-7.41(d,2H), 7.43-7.45(t,1H), 7.89-7.91(d,1H), 7.93-7.94(d,1H);

(151) 2-(2,3,4-trimethoxyphenyl)-1H-benzimidazole-4-(N-N'-piperidinyl)amide

¹HNMR (DMSO, 400 MHz) δ: 1.52-1.55(m,4H), 1.59-1.63(m,2H), 3.10-3.15(t,4H), 3.83(s,9H), 6.50-6.52(d,1H), 7.13-7.14(d,1H), 7.43-7.45(t,1H), 7.89-7.91(d,1H), 7.93-7.94(d,1H);

(152) 2-(2,3,4-trimethoxyphenyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.83(s,9H), 3.99-4.01(m,1H), 6.50-6.52(d,1H), 7.13-7.14(d,1H), 7.43-7.45(t,1H), 7.89-7.91(d,1H), 7.93-7.94(d,1H);

(153) 2-(2,3,4-trimethoxyphenyl)-1H-benzimidazole-4-(N-2'-benzimidazolyl)amide

¹HNMR (DMSO, 400 MHz) δ: 3.83(s,9H), 6.50-6.52(d, 1H), 7.10-7.11(d,1H), 7.12-7.15(d,2H), 7.22-7.24(t,2H), 7.43-7.45(t,1H), 7.89-7.91(d,1H), 7.93-7.94(d,1H);

(154) 2-(2,3,4-trimethoxyphenyl)-1H-benzimidazole-4-(N-o-aminophenyl)amide

¹HNMR (DMSO, 400 MHz) δ: 3.83(s,9H), 6.27(s,2H), 6.38-6.40(d,1H), 6.50-6.52(d,1H), 6.56-6.58(t,1H), 6.75-6.76(d,1H), 7.02-7.04(t,1H), 7.13-7.14(d,1H), 7.43-7.45(t,1H), 7.89-7.91(d,1H), 7.93-7.94(d,1H);

(155) 2-(2,3,4-trimethoxyphenyl)-1H-benzimidazole-4-(N-5-benzimidazolonyl)amide

¹HNMR (DMSO, 400 MHz) δ: 3.83(s,9H), 6.35-6.37(d, 1H), 6.50-6.52(d,1H), 6.93(s,1H), 7.13-7.14(d,1H), 7.43-7.45(t,1H), 7.54-7.56(d,1H), 7.89-7.91(d,1H), 7.93-7.94(d, 1H);

(156) 2-(2,3,4-trimethoxyphenyl)-1H-benzimidazole-4-(N-4'-carbonamido-5'-imidazolyl)amide ¹HNMR (DMSO, 400 MHz) δ: 3.83(s,9H), 6.50-6.52(d, 1H), 7.13-7.14(d,1H), 7.43-7.45(t,1H), 7.89-7.91(d,1H), 7.93-7.94(d,1H), 8.37(s,2H), 9.24-9.26(d,1H), 13.00-13.03(d,1H);

(157) 2-(2,3,4-trimethoxyphenyl)-1H-benzimidazole-4-(N-4'-pyrazolyl)amide

¹HNMR (DMSO, 400 MHz) δ: 3.83(s,9H), 6.50-6.52(d, 1H), 7.13-7.14(d,1H), 7.43-7.45(t,1H), 7.89-7.91(d,1H), 7.93-7.94(d,1H), 8.61(s,1H), 8.63-8.65(d,1H), 13.71-13.75(d,1H);

(158) 2-(2,3,4-trimethoxyphenyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 3.83(s,9H), 6.50-6.52(d,1H), 7.13-7.14(d,1H), 7.43-7.45(t,1H), 7.90-7.91(d,1H), 7.93-7.94(d,1H);

(159) 2-(2,3,4-trimethoxyphenyl)-1H-benzimidazole-4-(N-2-pyrazinyl)amide

¹HNMR (DMSO, 400 MHz) δ: 3.83(s,9H), 6.50-6.52(d, 1H), 7.13-7.14(d,1H), 7.43-7.45(t,1H), 7.89-7.91(d,1H), 7.93-7.94(d,1H), 8.34-8.35(d,1H), 8.36(s,1H), 8.40-8.42(d, 1H);

(160) 2-(2,3,4-trimethoxyphenyl)-1H-benzimidazole-4-(N-2-pyrimidinyl)amide

¹HNMR (DMSO, 400 MHz) δ: 3.83(s,9H), 6.50-6.52(d, 1H), 6.93-6.95(t,1H), 7.13-7.14(d,1H), 7.43-7.45(t,1H), 7.89-7.91(d,1H), 7.93-7.94(d,1H), 8.45-8.46(d,2H);

(161) 2-(2,3,4-trimethoxyphenyl)-1H-benzimidazole-4-(N-2-pyridyl)amide

¹HNMR (DMSO, 400 MHz) δ: 3.83(s,9H), 6.50-6.52(d, 1H), 6.62-6.64(t,1H), 6.70-6.72(d,1H), 7.13-7.14(d,1H), 7.43-7.45(t,1H), 7.55-7.57(t,1H), 7.89-7.91(d,1H), 7.93-7.94(d,1H), 8.07-8.09(d,1H);

(162) 2-(2,3,4-trimethoxyphenyl)-1H-benzimidazole-4-(N-4-methyl-5-thiazolyl)amide ¹HNMR (DMSO, 400 MHz) δ: 2.45(s,3H), 3.83(s,9H), 6.50-6.52(d,1H), 7.13-7.14(d,1H), 7.43-7.45(t,1H), 7.89-7.91(d,1H), 7.93-7.94(d,1H), 8.12(s,1H);

(163) 2-(2,3,4-trimethoxyphenyl)-1H-benzimidazole-4-(N-2,4-dihydroxyl-5-pyrimidinyl)amide ¹HNMR (DMSO, 400 MHz) δ: 3.83(s,9H), 6.50-6.52(d, 1H), 7.13-7.14(d,1H), 7.43-7.45(t,1H), 7.82(s,1H), 7.89-7.91(d,1H), 7.93-7.94(d,1H), 8.33(s,1H), 11.53(s,1H);

(164) 2-(2,3,4-trimethoxyphenyl)-1H-benzimidazole-4-(N-4,6-dimethoxy-2-pyrimidinyl)amide ¹HNMR (DMSO, 400 MHz) δ: 3.82(s,6H), 3.83(s,9H), 5.71(s,1H), 3.83(s,9H), 6.50-6.52(d,1H), 7.13-7.14(d,1H), 7.43-7.45(t,1H), 7.89-7.91(d,1H), 7.93-7.94(d,1H);

(165) 2-(2,3,4-trimethoxyphenyl)-1H-benzimidazole-4-(N-4-chloro-6-amino-2-pyrimidinyl)amide ¹HNMR (DMSO, 400 MHz) δ: 3.83(s,9H), 5.98(s,1H), 6.50-6.52(d,1H), 7.13-7.14(d,1H), 7.43-7.45(t,1H), 7.74(s, 2H), 7.89-7.91(d,1H), 7.93-7.94(d,1H);

(166) 2-(2,3,4-trimethoxyphenyl)-1H-benzimidazole-4-(N-4,6-dichloro-5-pyrimidinyl)amide ¹HNMR (DMSO, 400 MHz) δ: 3.83(s,9H), 6.50-6.52(d, 1H), 7.13-7.14(d,1H), 7.43-7.45(t,1H), 7.89-7.91(d,1H), 7.93-7.94(d,1H), 9.34(s,1H);

(167) 2-(2,3,4-trimethoxyphenyl)-1H-benzimidazole-4-(N-o-fluorophenyl)amide

¹HNMR (DMSO, 400 MHz) δ: 3.83(s,9H), 6.50-6.52(d, 1H), 6.60-6.61(d,1H), 6.63-6.65(t,1H), 6.96-6.98(t,1H), 6.99-7.01(d,1H), 7.13-7.14(d,1H), 7.43-7.45(t,1H), 7.89-7.91(d,1H), 7.93-7.94(d,1H);

(168) 2-(2,3,4-trimethoxyphenyl)-1H-benzimidazole-4-(N-2-hydroxyl-4-pyrimidinyl)amide ¹HNMR (DMSO, 400 MHz) δ: 3.83(s,9H), 5.46-5.48(d, 1H), 6.50-6.52(d,1H), 7.10-7.11(d,1H), 7.13-7.14(d,1H), 7.43-7.45(t,1H), 7.82(s,1H), 7.89-7.91(d,1H), 7.93-7.94(d, 1H);

(169) 2-(2,3,4-trimethoxyphenyl)-1H-benzimidazole-4-(N-6-purinyl)amide

¹HNMR (DMSO, 400 MHz) δ: 3.83(s,9H), 6.50-6.52(d, 1H), 7.13-7.14(d,1H), 7.43-7.45(t,1H), 7.86-7.88(d,1H), 7.89-7.91(d,1H), 7.93-7.94(d,1H), 8.16-8.18(d,1H);

(170) 2-(2,3,4-trimethoxyphenyl)-1H-benzimidazole-4-(N-6-hydroxyl-2-purinyl)amide ¹HNMR (DMSO, 400 MHz) δ: 3.83(s,9H), 6.50-6.52(d, 1H), 7.13-7.14(d,1H), 7.43-7.45(t,1H), 7.89-7.91(d,1H), 7.93-7.94(d,1H), 8.57-8.59(d,1H), 11.53(s,1H);

(171) (L)-2-(3-hydroxyl-4-methoxyphenyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 3.83(s,3H), 4.73-4.77(t,1H), 5.35(s,1H), 6.88-6.90(d, 1H), 7.21(s,1H), 7.43-7.45(t,1H), 7.53-7.55(d,1H), 7.62-7.65 (d,2H), 7.89-7.90(d,1H), 7.93-7.95(d,1H), 8.17-8.20(d,2H);

(172) (L)-2-(3-hydroxyl-4-methoxyphenyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 3.83(s,3H), 4.73-4.77(t,1H), 5.35(s,1H), 6.27(s,2H), 6.56-6.58(d,2H), 6.88-6.90(d,1H), 7.11-7.13(d,2H), 7.21(s, 1H), 7.43-7.45(t,1H), 7.53-7.55(d,1H), 7.89-7.90(d,1H), 7.93-7.95(d,1H);

(173) 2-(3-hydroxyl-4-methoxyphenyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28 (m,1H), 3.65-3.68(t,1H), 3.83(s,3H), 4.73-4.77(t,1H), 5.35 (s,1H), 6.88-6.90(d,1H), 7.21(s,1H), 7.29-7.30(d,2H), 7.40-7.41(d,2H), 7.43-7.45(t,1H), 7.53-7.55(d,1H), 7.89-7.91(d, 1H), 7.93-7.94(d,1H);

(174) 2-(3-hydroxyl-4-methoxyphenyl)-1H-benzimidazole-4-(N-N'-piperidinyl)amide

¹HNMR (DMSO, 400 MHz) δ: 1.52-1.55(m,4H), 1.59-1.63(m,2H), 3.10-3.15(t,4H), 3.83(s,3H), 5.35(s,1H), 6.88-6.90(d,1H), 7.21(s,1H), 7.43-7.45(t,1H), 7.53-7.55(d,1H), 7.89-7.91(d,1H), 7.93-7.94(d,1H);

(175) 2-(3-hydroxyl-4-methoxyphenyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74 (m,1H), 2.77-2.80(m,1H), 3.02-3.05(m,1H), 3.83(s,3H), 3.99-4.01(m,1H), 5.35(s,1H), 6.88-6.90(d,1H), 7.21(s,1H), 7.43-7.45(t,1H), 7.53-7.55(d,1H), 7.89-7.91(d,1H), 7.93-7.94(d,1H);

(176) 2-(3-hydroxyl-4-methoxyphenyl)-1H-benzimidazole-4-(N-2'-benzimidazolyl)amide ¹HNMR (DMSO, 400 MHz) δ: 3.83(s,3H), 5.35(s,1H), 6.88-6.90(d,1H), 7.12-7.15(d,2H), 7.21(s,1H), 7.22-7.24(t, 2H), 7.43-7.45(t,1H), 7.53-7.55(d,1H), 7.89-7.91(d,1H), 7.93-7.94(d,1H);

(177) 2-(3-hydroxyl-4-methoxyphenyl)-1H-benzimidazole-4-(N-o-aminophenyl)amide

¹HNMR (DMSO, 400 MHz) δ: 3.83(s,3H), 5.35(s,1H), 6.27(s,2H), 6.38-6.40(d,1H), 6.56-6.58(t,1H), 6.75-6.76(d, 1H), 6.88-6.90(d,1H), 7.02-7.04(t,1H), 7.21(s,1H), 7.53-7.55 (d,1H), 7.43-7.45(t,1H), 7.89-7.91(d,1H), 7.93-7.94(d,1H);

(178) 2-(3-hydroxyl-4-methoxyphenyl)-1H-benzimidazole-4-(N-5-benzimidazolonyl)amide ¹HNMR (DMSO, 400 MHz) δ: 3.83(s,3H), 5.35(s,1H), 6.35-6.37(d,1H), 6.88-6.90(d,1H), 6.93(s,1H), 7.21(s,1H), 7.43-7.45(t,1H), 7.49-7.52(d,1H), 7.54-7.56(d,1H), 7.89-7.91(d,1H), 7.93-7.94(d,1H);

(179) 2-(3-hydroxyl-4-methoxyphenyl)-1H-benzimidazole-4-(N-4'-carbonamido-5'-imidazolyl)amide ¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.89-7.91(d,1H), 7.93-7.94(d,1H), 8.37(s,2H), 9.24-9.26(d,1H), 13.00-13.03(d,1H);

(180) 2-(3-hydroxyl-4-methoxyphenyl)-1H-benzimidazole-4-(N-4'-pyrazolyl)amide

¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.89-7.91(d,1H), 7.93-7.94(d,1H), 8.61(s,1H), 8.63-8.65(d,1H), 13.71-13.75(d,1H);

(181) 2-(3-hydroxyl-4-methoxyphenyl)-1H-benzimidazole-4-(N—(N'-piperazinyl))amide ¹HNMR (DMSO, 400 MHz) δ: 1.91-1.95(m,1H), 2.65-2.67(t,4H), 2.80-2.83(m,4H), 3.83(s,3H), 5.35(s,1H), 6.88-6.90(d,1H), 7.21(s,1H), 7.43-7.45(t,1H), 7.53-7.55(d,1H), 7.90-7.91(d,1H), 7.93-7.94(d,1H);

(182) 2-(3-hydroxyl-4-methoxyphenyl)-1H-benzimidazole-4-(N-2-pyrazinyl)amide

¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.89-7.91(d,1H), 7.93-7.94(d,1H), 8.34-8.35(d,1H), 8.36(s,1H), 8.40-8.42(d,1H);

(183) 2-(3-hydroxyl-4-methoxyphenyl)-1H-benzimidazole-4-(N-2-pyrimidinyl)amide

¹HNMR (DMSO, 400 MHz) δ: 3.83(s,3H), 5.35(s,1H), 6.88-6.90(d,1H), 6.93-6.95(t,1H), 7.21(s,1H), 7.43-7.45(t, 1H), 7.53-7.55(d,1H), 7.89-7.91(d,1H), 7.93-7.94(d,1H), 8.45-8.46(d,2H);

(184) 2-(3-hydroxyl-4-methoxyphenyl)-1H-benzimidazole-4-(N-2-pyridyl)amide

¹HNMR (DMSO, 400 MHz) δ: 3.83(s,3H), 5.35(s,1H), 6.62-6.64(t,1H), 6.70-6.72(d,1H), 6.88-6.90(d,1H), 7.21(s, 1H), 7.43-7.45(t,1H), 7.51-7.52(d,1H), 7.55-7.57(t,1H), 7.89-7.91(d,1H), 7.93-7.94(d,1H), 8.07-8.09(d,1H);

(185) 2-(3-hydroxyl-4-methoxyphenyl)-1H-benzimidazole-4-(N-4-methyl-5-thiazolyl)amide ¹HNMR (DMSO, 400 MHz) δ: 2.45(s,3H), 3.83(s,3H), 5.35(s,1H), 6.88-6.90(d,1H), 7.21(s,1H), 7.43-7.45(t,1H), 7.53-7.55(d,1H), 7.89-7.91(d,1H), 7.93-7.94(d,1H), 8.12(s, 1H);

(186) 2-(3-hydroxyl-4-methoxyphenyl)-1H-benzimidazole-4-(N-2,4-dihydroxyl-5-pyrimidinyl)amide ¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.82(s,1H), 7.89-7.91(d,1H), 7.93-7.94(d,1H), 8.33(s, 1H), 11.53(s,1H);

(187) 2-(3-hydroxyl-4-methoxyphenyl)-1H-benzimidazole-4-(N-4,6-dimethoxy-2-pyrimidinyl)amide ¹HNMR (DMSO, 400 MHz) δ: 3.79(s,6H), 3.83(s,3H), 5.35(s,1H), 5.71(s,1H), 6.88-6.90(d,1H), 7.21(s,1H), 7.43-7.45(t,1H), 7.53-7.55(d,1H), 7.89-7.91(d,1H), 7.93-7.94(d, 1H);

(188) 2-(3-hydroxyl-4-methoxyphenyl)-1H-benzimidazole-4-(N-4-chloro-6-amino-2-pyrimidinyl)amide ¹HNMR (DMSO, 400 MHz) δ: 3.83(s,3H), 5.35(s,1H), 5.98(s,1H), 6.88-6.90(d,1H), 7.21(s,1H), 7.43-7.45(t,1H), 7.53-7.55(d,1H), 7.74(s,2H), 7.89-7.91(d,1H), 7.93-7.94(d, 1H);

(189) 2-(3-hydroxyl-4-methoxyphenyl)-1H-benzimidazole-4-(N-4,6-dichloro-5-pyrimidinyl)amide ¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.89-7.91(d,1H), 7.93-7.94(d,1H), 9.34(s,1H);

(190) 2-(3-hydroxyl-4-methoxyphenyl)-1H-benzimidazole-4-(N-o-fluorophenyl)amide

¹HNMR (DMSO, 400 MHz) δ: 3.83(s,3H), 5.35(s,1H), 6.60-6.61(d,1H), 6.63-6.65(t,1H), 6.88-6.90(d,1H), 6.96-6.98(t,1H), 6.99-7.01(d,1H), 7.21(s,1H), 7.43-7.45(t,1H), 7.53-7.55(d,1H), 7.89-7.91(d,1H), 7.93-7.94(d,1H);

(191) 2-(3-hydroxyl-4-methoxyphenyl)-1H-benzimidazole-4-(N-2-hydroxyl-4-pyrimidinyl)amide ¹HNMR (DMSO, 400 MHz) δ: 3.83(s,3H), 5.35(s,1H), 5.46-5.48(d,1H), 6.88-6.90(d,1H), 7.10-7.11(d,1H), 7.21(s, 1H), 7.43-7.45(t,1H), 7.53-7.55(d,1H), 7.82(s,1H), 7.89-7.91 (d,1H), 7.93-7.94(d,1H);

(192) 2-(3-hydroxyl-4-methoxyphenyl)-1H-benzimidazole-4-(N-6-purinyl)amide

Figure 4:
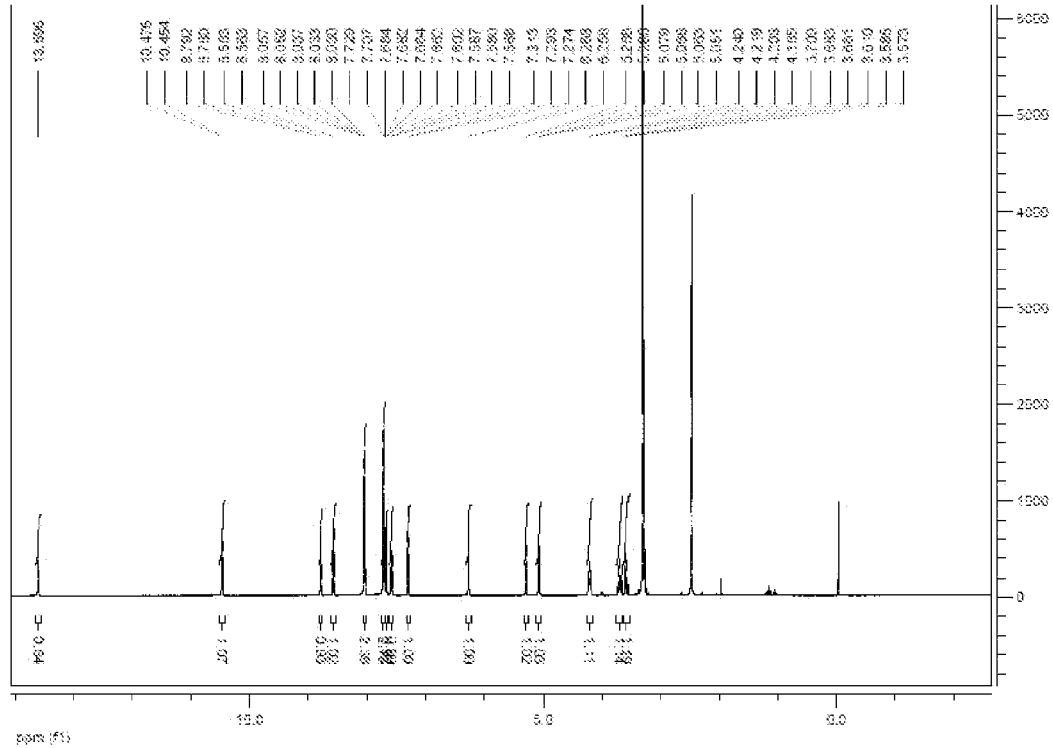
FIG. 4 shows $^1$HNMR spectrogram of (L)-2-(2-pyridyl)-1H-benzimidazole-4-(N-(1-hydroxymethyl-2-p-nitrophenylhydroxyethyl)amide in Example 194.

¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.86-7.88(d,1H), 7.89-7.91(d,1H), 7.93-7.94(d,1H), 8.16-8.18(d,1H);

(193) 2-(3-hydroxyl-4-methoxyphenyl)-1H-benzimidazole-4-(N-6-hydroxyl-2-purinyl)amide ¹HNMR (DMSO, 400 MHz) δ: 3.83(s,3H), 5.35(s,1H), 6.88-6.90(d,1H), 7.21(s,1H), 7.43-7.45(t,1H), 7.53-7.55(d, 1H), 7.89-7.91(d,1H), 7.93-7.94(d,1H), 8.57-8.59(d,1H), 11.53(s,1H);

(194) (L)-2-(2-pyridyl)-1H-benzimidazole-4-[N-(1-hydroxymethyl-2-p-nitrophenylhydroxyethyl)]amide (Refer to FIG. 4)

¹HMNR(DMSO, 400 MHz)δ:3.57-3.61(m,1H),3.66-3.70 (m,1H),4.20-4.22(m,1H),5.08-5.11(q,1H),5.28-5.29(d,1H), 6.29-6.30(d,1H), 7.28-7.32(t,1H), 7.57-7.61(m,1H), 7.67-7.73(m,4H), 8.02-8.06(m,3H), 8.57-8.59(m,1H), 8.78-8.80 (m,1H), 10.47-10.49(d,1H), 13.62(s,1H);

(195) (L)-2-(2-pyridyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 6.27(s,2H), 6.56-6.58(d,2H), 7.11-7.13 (d,2H), 7.36-7.38(t,1H), 7.43-7.45(t,1H), 7.85-7.86(t,1H), 7.89-7.90(d,1H), 7.93-7.95(d,1H), 8.38-8.41(d,1H), 8.59-8.60(d,1H);

(196) 2-(2-pyridyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28 (m,1H), 3.65-3.68(t,1H), 4.73-4.77(t,1H), 7.29-7.30(d,2H), 7.36-7.38(t,1H), 7.40-7.41(d,2H), 7.43-7.45(t,1H), 7.85-7.86 (t,1H), 7.89-7.91(d,1H), 7.93-7.94(d,1H), 8.38-8.41(d,1H), 8.59-8.60(d,1H);

(197) 2-(2-pyridyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.36-7.38(t,1H), 7.43-7.45(t, 1H), 7.85-7.86(t,1H), 7.89-7.91(d,1H), 7.93-7.94(d,1H), 8.38-8.41(d,1H), 8.59-8.60(d,1H);

(198) 2-(2-pyridyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74 (m,1H), 2.77-2.80(m,1H), 3.02-3.05(m,1H), 3.99-4.01(m, 1H), 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d, 1H);

(199) 2-(2-pyridyl)-1H-benzimidazole-4-(N-2'-benzimidazolyl)amide $^1$HNMR (DMSO, 400 MHz) δ: 7.12-7.15(d,2H), 7.22-7.24(t,2H), 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H);

(200) 2-(2-pyridyl)-1H-benzimidazole-4-(N-o-aminophenyl)amide $^1$HNMR (DMSO, 400 MHz) δ: 6.27(s,2H), 6.38-6.40(d,1H), 6.56-6.58(t,1H), 6.75-6.76(d,1H), 7.02-7.04(t,1H), 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H);

(201) 2-(2-pyridyl)-1H-benzimidazole-4-(N-5-benzimidazolonyl)amide $^1$HNMR (DMSO, 400 MHz) δ: 6.35-6.37(d,1H), 6.93(s,1H), 7.36-7.38(t,1H), 7.43-7.45(t,1H), 7.54-7.56(d,1H), 7.85-7.86(t,1H), 7.89-7.91(d,1H), 7.93-7.94(d,1H), 8.38-8.41(d,1H), 8.59-8.60(d,1H);

(202) 2-(2-pyridyl)-1H-benzimidazole-4-(N-4'-carbonamido-5'-imidazolyl)amide $^1$HNMR (DMSO, 400 MHz) δ: 7.36-7.38(t,1H), 7.43-7.45(t,1H), 7.85-7.86(t,1H), 7.89-7.91(d,1H), 7.93-7.94(d,1H), 8.37(s,2H), 8.38-8.41(d,1H), 8.59-8.60(d,1H), 9.24-9.26(d,1H), 13.00-13.03(d,1H);

(203) 2-(2-pyridyl)-1H-benzimidazole-4-(N-4'-pyrazolyl)amide $^1$HNMR (DMSO, 400 MHz) δ: 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H), 8.61(s,1H), 8.63-8.65(d,1H), 13.71-13.75(d,1H);

(204) 2-(2-pyridyl)-1H-benzimidazole-4-(N—(N'-piperazinyl))amide $^1$HNMR (DMSO, 400 MHz) δ: 1.91-1.95(m,1H), 2.65-2.67(t,4H), 2.80-2.83(m,4H), 7.36-7.38(t,1H), 7.43-7.45(t,1H), 7.85-7.86(t,1H), 7.90-7.91(d,1H), 7.93-7.94(d,1H), 8.38-8.41(d,1H), 8.59-8.60(d,1H);

(205) 2(2-pyridyl)-1H-benzimidazole-4-(N-2-pyrazinyl)amide $^1$HNMR (DMSO, 400 MHz) δ: 7.36-7.38(t,1H), 7.43-7.45(t,1H), 7.85-7.86(t,1H), 7.89-7.91(d,1H), 7.93-7.94(d,1H), 8.34-8.35(d,1H), 8.36(s,1H), 8.38-8.41(d,1H), 8.43-8.45(d,1H), 8.59-8.60(d,1H);

(206) 2-(2-pyridyl)-1H-benzimidazole-4-(N-2-pyrimidinyl)amide $^1$HNMR (DMSO, 400 MHz) δ: 6.93-6.95(t,1H), 7.36-7.38(t,1H), 7.43-7.45(t,1H), 7.85-7.86(t,1H), 7.89-7.91(d,1H), 7.93-7.94(d,1H), 8.38-8.41(d,1H), 8.45-8.46(d,2H), 8.59-8.60(d,1H);

(207) 2-(2-pyridyl)-1H-benzimidazole-4-(N-2-pyridyl)amide $^1$HNMR (DMSO, 400 MHz) δ: 6.62-6.64(t,1H), 6.70-6.72(d,1H), 7.36-7.38(t,1H), 7.43-7.45(t,1H), 7.55-7.57(t,1H), 7.85-7.86(t,1H), 7.89-7.91(d,1H), 7.93-7.94(d,1H), 8.07-8.09(d,1H), 8.38-8.41(d,1H), 8.59-8.60(d,1H);

(208) 2-(2-pyridyl)-1H-benzimidazole-4-(N-4-methyl-5-thiazolyl)amide $^1$HNMR (DMSO, 400 MHz) δ: 2.45(s,3H), 7.36-7.38(t,1H), 7.43-7.45(t,1H), 7.85-7.86(t,1H), 7.89-7.91(d,1H), 7.93-7.94(d,1H), 8.12(s,1H), 8.38-8.41(d,1H), 8.59-8.60(d,1H);

(209) 2-(2-pyridyl)-1H-benzimidazole-4-(N-2,4-dihydroxyl-5-pyrimidinyl)amide $^1$HNMR (DMSO, 400 MHz) δ: 7.36-7.38(t,1H), 7.43-7.45(t,1H), 7.82(s,1H), 7.85-7.86(t,1H), 7.89-7.91(d,1H), 7.93-7.94(d,1H), 8.33(s,1H), 8.38-8.41(d,1H), 8.59-8.60(d,1H), 11.53(s,1H);

(210) 2-(2-pyridyl)-1H-benzimidazole-4-(N-4,6-dimethoxy-2-pyrimidinyl)amide $^1$HNMR (DMSO, 400 MHz) δ: 3.82(s,6H), 5.71(s,1H), 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H);

(211) 2-(2-pyridyl)-1H-benzimidazole-4-(N-4-chloro-6-amino-2-pyrimidinyl)amide $^1$HNMR (DMSO, 400 MHz) δ: 5.98(s,1H), 7.36-7.38(t,1H), 7.43-7.45(t,1H), 7.74(s,2H), 7.85-7.86(t,1H), 7.89-7.91(d,1H), 7.93-7.94(d,1H), 8.38-8.41(d,1H), 8.59-8.60(d,1H);

(212) 2-(2-pyridyl)-1H-benzimidazole-4-(N-4,6-dichloro-5-pyrimidinyl)amide $^1$HNMR (DMSO, 400 MHz) δ: 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H), 9.34(s,1H);

(213) 2-(2-pyridyl)-1H-benzimidazole-4-(N-o-fluorophenyl)amide $^1$HNMR (DMSO, 400 MHz) δ: 6.60-6.61(d,1H), 6.63-6.65(t,1H), 6.96-6.98(t,1H), 6.99-7.01(d,1H), 7.36-7.38(t,1H), 7.43-7.45(t,1H), 7.85-7.86(t,1H), 7.89-7.91(d,1H), 7.93-7.94(d,1H), 8.38-8.41(d,1H), 8.59-8.60(d,1H);

(214) 2-(2-pyridyl)-1H-benzimidazole-4-(N-2-hydroxyl-4-pyrimidinyl)amide $^1$HNMR (DMSO, 400 MHz) δ: 5.46-5.48(d,1H), 7.10-7.11(d,1H), 7.36-7.38(t,1H), 7.43-7.45(t,1H), 7.82(s,1H), 7.85-7.86(t,1H), 7.89-7.91(d,1H), 7.93-7.94(d,1H), 8.38-8.41(d,1H), 8.59-8.60(d,1H);

(215) 2-(2-pyridyl)-1H-benzimidazole-4-(N-6-purinyl)amide $^1$HNMR (DMSO, 400 MHz) δ: 7.36-7.38(t,1H), 7.43-7.45(t,1H), 7.85-7.86(t,1H), 7.87-7.88(d,1H), 7.89-7.91(d,1H), 7.93-7.94(d,1H), 8.16-8.18(d,1H), 8.38-8.41(d,1H), 8.59-8.60(d,1H);

(216) 2-(2-pyridyl)-1H-benzimidazole-4(N-6-hydroxyl-2-purinyl)amide

¹HNMR (DMSO, 400 MHz) δ: 7.36-7.38(t,1H), 7.43-7.45(t,1H), 7.85-7.86(t,1H), 7.89-7.91(d,1H), 7.93-7.94(d,1H), 8.38-8.41(d,1H), 8.57-8.59(d,1H), 8.59-8.60(d,1H), 11.53(s,1H);

(217) (L)-2-(3-pyridyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.57-7.60(t,1H), 7.62-7.65(d,2H), 7.89-7.90(d,1H), 7.93-7.95(d,1H), 8.17-8.20(d,2H), 8.42-8.44(d,1H), 8.70-8.72(d,1H), 9.24(s,1H);

(218) (L)-2-(3-pyridyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.57-7.60(t,1H), 7.89-7.90(d,1H), 7.93-7.95(d,1H), 8.42-8.44(d,1H), 8.70-8.72(d,1H), 9.24(s,1H);

(219) 2-(3-pyridyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.57-7.60(t,1H), 7.89-7.91(d,1H), 7.93-7.94(d,1H), 8.42-8.44(d,1H), 8.70-8.72(d,1H), 9.24(s,1H);

(220) 2-(3-pyridyl)-1H-benzimidazole-4(N-2-pyrimidinyl)amide

¹HNMR (DMSO, 400 MHz) δ: 6.93-6.95(t,1H), 7.43-7.45(t,1H), 7.57-7.60(t,1H), 7.89-7.91(d,1H), 7.93-7.94(d,1H), 8.41-8.43(d,1H), 8.45-8.46(d,2H), 8.70-8.72(d,1H), 9.24(s,1H);

(221) (L)-2-(4-pyridyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(222) (L)-2-(4-pyridyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H), 8.25-8.28(d,2H), 8.75-8.77(d,2H);

(223) 2-(4-pyridyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.89-7.91(d,1H), 7.93-7.94(d,1H), 8.25-8.28(d,2H), 8.75-8.77(d,2H);

(224) 2-(4-pyridyl)-1H-benzimidazole-4-(N-2-pyrimidinyl)amide

¹HNMR (DMSO, 400 MHz) δ: 6.93-6.95(t,1H), 7.43-7.45(t,1H), 7.89-7.91(d,1H), 7.93-7.94(d,1H), 8.25-8.28(d,2H), 8.45-8.46(d,2H), 8.75-8.77(d,2H);

(225) (L)-2-(3-pyridazinyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.61-7.63(t,1H), 7.64-7.67(d,2H), 7.89-7.90(d,1H), 7.93-7.95(d,1H), 8.09-8.11(d,1H), 8.17-8.20(d,2H), 9.34-9.37(d,1H);

(226) (L)-2-(3-pyridazinyl)-1H-benzimidazole-4-N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.61-7.63(t,1H), 7.89-7.90(d,1H), 7.93-7.95(d,1H), 8.09-8.11(d,1H), 9.34-9.37(d,1H);

(227) 2-(3-pyridazinyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.29-7.30(d,2H), 7.40-7.41(d,2H), 7.43-7.45(t,1H), 7.61-7.63(t,1H), 7.89-7.91(d,1H), 7.93-7.94(d,1H), 8.09-8.11(d,1H), 9.34-9.37(d,1H);

(228) 2-(3-pyridazinyl)-1H-benzimidazole-4-(N—N'-piperdinyl)amide

¹HNMR (DMSO, 400 MHz) δ: 1.52-1.55(m,4H), 1.59-1.63(m,2H), 3.10-3.15(t,4H), 7.43-7.45(t,1H), 7.61-7.63(t,1H), 7.89-7.91(d,1H), 7.93-7.94(d,1H), 8.09-8.11(d,1H), 9.34-9.37(d,1H);

(229) 2-(3-pyridazinyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.61-7.63(t,1H), 7.89-7.91(d,1H), 7.93-7.94(d,1H), 8.09-8.11(d,1H), 9.34-9.37(d,1H);

(230) 2-(3-pyridazinyl)-1H-benzimidazole-4-(N-2'-benzimidazolyl)amide

¹HNMR (DMSO, 400 MHz) δ: 7.12-7.15(d,2H), 7.22-7.24(t,2H), 7.43-7.45(t,1H), 7.61-7.63(t,1H), 7.89-7.91(d,1H), 7.93-7.94(d,1H), 8.09-8.11(d,1H), 9.34-9.37(d,1H);

(231) 2-(3-pyridazinyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.43-7.45(t,1H), 7.61-7.63(t,1H), 7.89-7.91(d,1H), 7.93-7.94 (d,1H), 8.09-8.11(d,1H), 9.34-9.37(d,1H);

(232) 2-(3-pyridazinyl)-1H-benzimidazole-4-(N-5-benzimidazolonyl)amide

¹HNMR (DMSO, 400 MHz) δ: 6.35-6.37(d,1H), 6.93(s, 1H), 7.43-7.45(t,1H), 7.54-7.56(d,1H), 7.61-7.63(t,1H), 7.89-7.91(d,1H), 7.93-7.94(d,1H), 8.09-8.11(d,1H), 9.34-9.37(d,1H);

(233) 2-(3-pyridazinyl)-1H-benzimidazole-4-(N-4'-carbonamido)-5'-imidazolyl)amide ¹HNMR (DMSO, 400 MHz) δ: 7.43-7.45(t,1H), 7.61-7.63 (t,1H), 7.89-7.91(d,1H), 7.93-7.94(d,1H), 8.09-8.11(d,1H), 8.37(s,2H), 9.24-9.26(d,1H), 9.34-9.37(d,1H), 13.00-13.03 (d,1H);

(234) 2-(3-pyridazinyl)-1H-benzimidazole-4-(N-4'-pyrazolyl)amide

¹HNMR (DMSO, 400 MHz) δ: 7.43-7.45(t,1H), 7.61-7.63 (t,1H), 7.89-7.91(d,1H), 7.93-7.94(d,1H), 8.09-8.11(d,1H), 8.61(s,1H), 8.63-8.65(d,1H), 9.34-9.37(d,1H), 13.71-13.75 (d,1H);

(235) 2-(3-pyridazinyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.43-7.45(t,1H), 7.61-7.63(t, 1H), 7.90-7.91(d,1H), 7.93-7.94(d,1H), 8.09-8.11(d,1H), 9.34-9.37(d,1H);

(236) 2-(3-pyridazinyl)-1H-benzimidazole-4-(N-2-pyrazinyl)amide

¹HNMR (DMSO, 400 MHz) δ: 7.43-7.45(t,1H), 7.61-7.63 (t,1H), 7.89-7.91(d,1H), 7.93-7.94(d,1H), 8.09-8.11(d,1H), 8.34-8.35(d,1H), 8.36(s,1H), 8.40-8.42(d,1H), 9.34-9.37(d, 1H);

(237) 2-(3-pyridazinyl)-1H-benzimidazole-4-(N-2-pyrimidinyl)amide

¹HNMR (DMSO, 400 MHz) δ: 6.93-6.95(t,1H), 7.43-7.45 (t,1H), 7.61-7.63(t,1H), 7.89-7.91(d,1H), 7.93-7.94(d,1H), 8.09-8.11(d,1H), 8.45-8.46(d,2H), 9.34-9.37(d,1H);

(238) 2-(3-pyridazinyl)-1H-benzimidazole-4-(N-2-pyridyl)amide

¹HNMR (DMSO, 400 MHz) δ: 6.62-6.64(t,1H), 6.70-6.72 (d,1H), 7.43-7.45(t,1H), 7.55-7.57(t,1H), 7.61-7.63(t,1H), 7.89-7.91(d,1H), 7.93-7.94(d,1H), 8.07-8.09(d,1H), 8.11-8.13(d,1H), 8.59-8.60(d,1H);

(239) 2-(3-pyridazinyl)-1H-benzimidazole-4-(N-4-methyl-5-thiazolyl)amide

¹HNMR (DMSO, 400 MHz) δ: 2.45(s,3H), 7.43-7.45(t, 1H), 7.61-7.63(t,1H), 7.89-7.91(d,1H), 7.93-7.94(d,1H), 8.09-8.11(d,1H), 8.12(s,1H), 9.34-9.37(d,1H);

(240) 2-(3-pyridazinyl)-1H-benzimidazole-4-(N-2,4-dihydroxyl-5-pyrimidinyl)amide ¹HNMR (DMSO, 400 MHz) δ: 7.43-7.45(t,1H), 7.61-7.63 (t,1H), 7.89-7.91(d,1H), 7.82(s,1H), 7.93-7.94(d,1H), 8.09-8.11(d,1H), 8.33(s,1H), 9.34-9.37(d,1H), 11.53(s,1H);

(241) 2-(3-pyridazinyl)-1H-benzimidazole-4-(N-4-,6-dimethoxy-2-pyrimidinyl)amide ¹HNMR (DMSO, 400 MHz) δ: 3.82(s,6H), 5.71(s,1H), 7.43-7.45(t,1H), 7.61-7.63(t,1H), 7.89-7.91(d,1H), 7.93-7.94 (d,1H), 8.09-8.11(d,1H), 9.34-9.37(d,1H);

(242) 2-(3-pyridazinyl)-1H-benzimidazole-4(N-4-chloro-6-amino-2-pyrimidinyl)amide ¹HNMR (DMSO, 400 MHz) δ: 5.98(s,1H), 7.43-7.45(t, 1H), 7.61-7.63(t,1H), 7.74(s,2H), 7.89-7.91(d,1H), 7.93-7.94 (d,1H), 8.09-8.11(d,1H), 9.34-9.37(d,1H);

(243) 2-(3-pyridazinyl)-1H-benzimidazole-4-(N-4,6-dichloro-5-pyrimidinyl)amide

¹HNMR (DMSO, 400 MHz) δ: 7.43-7.45(t,1H), 7.61-7.63 (t,1H), 7.89-7.91(d,1H), 7.93-7.94(d,1H), 8.09-8.11(d,1H), 9.32(s,1H), 9.34-9.37(d,1H);

(244) 2-(3-pyridazinyl)-1H-benzimidazole-4-(N-o-fluorophenyl)amide

¹HNMR (DMSO, 400 MHz) δ: 6.60-6.61(d,1H), 6.63-6.65 (t,1H), 6.96-6.98(t,1H), 6.99-7.01(d,1H), 7.43-7.45(t,1H), 7.61-7.63(t,1H), 7.89-7.91(d,1H), 7.93-7.94(d,1H), 8.09-8.11(d,1H), 9.34-9.37(d,1H);

(245) 2-(3-pyridazinyl)-1H-benzimidazole-4-(N-2-hydroxyl-4-pyrimidinyl)amide

¹HNMR (DMSO, 400 MHz) δ: 5.46-5.48(d,1H), 7.10-7.11 (d,1H), 7.43-7.45(t,1H), 7.61-7.63(t,1H), 7.82(s,1H), 7.89-7.91(d,1H), 7.93-7.94(d,1H), 8.09-8.11(d,1H), 9.34-9.37(d, 1H);

(246) 2-(3-pyridazinyl)-1H-benzimidazole-4-(N-6-purinyl)amide

¹HNMR (DMSO, 400 MHz) δ: 7.43-7.45(t,1H), 7.61-7.63 (t,1H), 7.86-7.88(d,1H), 7.89-7.91(d,1H), 7.93-7.94(d,1H), 8.09-8.11(d,1H), 8.16-8.18(d,1H), 9.34-9.37(d,1H);

(247) 2-(3-pyridazinyl)-1H-benzimidazole-4-(N-6-hydroxyl-2-purinyl)amide

¹HNMR (DMSO, 400 MHz) δ: 7.43-7.45(t,1H), 7.61-7.63 (t,1H), 7.89-7.91(d,1H), 7.93-7.94(d,1H), 8.09-8.11(d,1H), 8.57-8.59(d,1H), 9.34-9.37(d,1H), 11.53(s,1H);

(248) (L)-2-(4-pyridazinyl)-1H-benzimidazole-4-[N-(1-hydroxymethyl-2-p-nitrophenylhydroxyethyl)] amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 7.43-7.45(t,1H), 7.62-7.65(d,2H), 7.77-7.80(d,1H), 7.89-7.90(d,1H), 7.93-7.95(d,1H), 8.17-8.20(d,2H), 9.30-9.32(d,1H), 9.46(s,1H);

(249) (L)-2-(4-pyridazinyl)-1H-benzimidazole-4-[N-(1-hydroxymethyl-2-p-aminophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.77-7.80(d,1H), 7.89-7.90(d,1H), 7.93-7.95(d,1H), 9.30-9.32(d,1H), 9.46(s,1H);

(250) 2-(4-pyridazinyl)-1H-benzimidazole-4-(N-2-piperazinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.77-7.80(d,1H), 7.89-7.91(d,1H), 7.93-7.94(d,1H), 9.30-9.32(d,1H), 9.46(s,1H);

(251) 2-(4-pyridazinyl)-1H-benzimidazole-4-(N-2-pyrimidinyl)amide $^1$HNMR (DMSO, 400 MHz) δ: 6.93-6.95(t,1H), 7.43-7.45(t,1H), 7.77-7.80(d,1H), 7.89-7.91(d,1H), 7.93-7.94(d,1H), 8.45-8.46(d,2H), 9.30-9.32(d,1H), 9.46(s,1H);

(252) (L)-2-(2-pyrazinyl)-1H-benzimidazole-4-[N-(1-hydroxymethyl-2-p-nitrophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H), 8.76-8.79(d,2H), 9.34(s,1H);

(253) (L)-2-(2-pyrazinyl)-1H-benzimidazole-4-[N-(1-hydroxymethyl-2-p-aminophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H), 8.76-8.79(d,2H), 9.34(s,1H);

(254) 2-(2-pyrazinyl)-1H-benzimidazole-4-[N-(1-methyl-2-p-chlorophenylhydroxyethyl)]amide $^1$HNMR (DMSO, 400 MHz) δ: 1.12-1.15(d,3H), 3.25-3.28(m,1H), 3.65-3.68(t,1H), 7.93-7.94(d,2H), 8.76-8.79(d,2H), 9.34(s,1H);

(255) 2-(2-pyrazinyl)-1H-benzimidazole-4-(N—N'-piperidinyl)amide $^1$HNMR (DMSO, 400 MHz) δ: 1.52-1.55(m,4H), 1.59-1.63(m,2H), 3.10-3.15(t,4H), 7.43-7.45(t,1H), 7.89-7.91(d,1H), 7.93-7.94(d,1H), 9.34(s,1H);

(256) 2-(2-pyrazinyl)-1H-benzimidazole-4-(N-2-piperazinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m, 1H), 3.02-3.05(m, 1H), 3.99-4.01(m, 1H), 7.43-7.45(t,1H), 7.89-7.91(d,1H), 7.93-7.94(d,1H), 8.76-8.79(d,2H), 9.34(s,1H);

(257) 2-(2-pyrazinyl)-1H-benzimidazole-4-(N-2'-benzimidazolyl)amide $^1$HNMR (DMSO, 400 MHz) δ: 7.12-7.15(d,2H), 7.22-7.24(t,2H), 7.43-7.45(t,1H), 7.89-7.91(d,1H), 7.93-7.94(d,1H), 8.76-8.79(d,2H), 9.34(s,1H);

(258) 2-(2-pyrazinyl)-1H-benzimidazole-4-(N-o-aminophenyl)amide $^1$HNMR (DMSO, 400 MHz) δ: 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H), 8.76-8.79(d,2H), 9.34(s,1H);

(259) 2-(2-pyrazinyl)-b 1-l H-benzimidazole-4-(N-5-benzimidazolonyl)amide $^1$HNMR (DMSO, 400 MHz) δ: 6.35-6.37(d,1H), 6.93(s,1H), 7.43-7.45(t,1H), 7.54-7.56(d,1H), 7.89-7.931(d,1H), 7.93-7.94(d,1H), 8.76-8.79(d,2H), 9.34(s,1H);

(260) 2-(2-pyrazinyl)-1H-benzimidazole-4(N-4'-carbonamido-5'-imidazolyl)amide $^1$HNMR (DMSO, 400 MHz) δ: 7.43-7.45(t,1H), 7.89-7.91(d,1H), 7.93-7.94(d,1H), 8.37(s,2H), 8.76-8.79(d,2H), 9.24-9.26(d,1H), 9.34(s,1H), 13.00-13.03(d,1H);

(261) 2-(2-pyrazinyl)-1H-benzimidazole-4-(N-4'-pyrazolyl)amide $^1$HNMR (DMSO, 400 MHz) δ: 7.43-7.45(t,1H), 7.89-7.91(d,1H), 7.93-7.94(d,1H), 8.61(s,1H), 8.63-8.65(d,1H), 8.76-8.79(d,2H), 9.34(s,1H), 13.71-13.75(d,1H);

(262) 2-(2-pyrazinyl)-1H-benzimidazole-4-(N—(N'-piperazinyl))amide $^1$HNMR (DMSO, 400 MHz) δ: 1.91-1.95(m,1H), 2.65-2.67(t,4H), 2.80-2.83(m,4H), 7.43-7.45(t,1H), 7.90-7.91(d,1H), 7.93-7.94(d,1H), 8.76-8.79(d,2H), 9.34(s,1H);

(263) 2-(2-pyrazinyl)-1H-benzimidazole-4-(N-2-pyrazinyl)amide $^1$HNMR (DMSO, 400 MHz) δ: 7.43-7.45(t,1H), 7.89-7.91(d,1H), 7.93-7.94(d,1H), 8.34-8.35(d,1H), 8.36(s,1H), 8.40-8.42(d,1H), 8.76-8.79(d,2H), 9.34(s,1H);

(264) 2-(2-pyrazinyl)-1H-benzimidazole-4-(N-2-pyrimidinyl)amide $^1$HNMR (DMSO, 400 MHz) δ: 6.93-6.95(t,1H), 7.43-7.45(t,1H), 7.89-7.91(d,1H), 7.93-7.94(d,1H), 8.45-8.46(d,2H), 8.76-8.79(d,2H), 9.34(s,1H);

(265) 2-(2-pyrazinyl)-1H-benzimidazole-4-(N-2-pyridyl)amide $^1$HNMR (DMSO, 400 MHz) δ: 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H), 8.76-8.79(d,2H), 9.34(s,1H);

(266) 2-(2-pyrazinyl)-1H-benzimidazole-4-(N-4-methyl-5-thiazolyl)amide

¹HNMR (DMSO, 400 MHz) δ: 2.45(s,3H), 7.43-7.45(t, 1H), 7.89-7.91(d,1H), 7.93-7.94(d,1H), 8.12(s,1H), 8.76-8.79(d,2H), 9.34(s,1H);

(267) 2-(2-pyrazinyl)-1H-benzimidazole-4-(N-2,4-dihydroxyl-5-pyrimidinyl)amide

¹HNMR (DMSO, 400 MHz) δ: 7.43-7.45(t,1H), 7.89-7.91(d,1H), 7.82(s,1H), 7.93-7.94(d,1H), 8.33(s,1H), 8.76-8.79(d,2H), 9.34(s,1H), 11.53(s,1H);

(268) 2-(2-pyrazinyl)1H-benzimidazole-4(N-4,6-dimethoxy-2-pyrimidinyl)amide

¹HNMR (DMSO, 400 MHz) δ: 3.82(s,6H), 5.71(s,1H), 7.43-7.45(t,1H), 7.89-7.91(d,1H), 7.93-7.94(d,1H), 8.76-8.79(d,2H), 9.34(s,1H);

(269) 2-(2-pyrazinyl)1H-benzimidazole-4(N-4-chloro-6-amino-2-pyrimidinyl)amide

¹HNMR (DMSO, 400 MHz) δ: 5.98(s,1H), 7.43-7.45(t, 1H), 7.74(s,2H), 7.89-7.91(d,1H), 7.93-7.94(d,1H), 8.76-8.79(d,2H), 9.34(s,1H);

(270) 2-(2-pyrazinyl)-1H-benzimidazole-4-(N-4,6-dichloro-5-pyrimidinyl)amide

¹HNMR (DMSO, 400 MHz) δ: 7.43-7.45(t,1H), 7.89-7.91(d,1H), 7.93-7.94(d,1H), 8.76-8.79(d,2H), 9.34(s,1H), 9.37(s,1H);

(271) 2-(2-pyrazinyl)1H-benzimidazole-4-(N-o-fluorophenyl)amide

¹HNMR (DMSO, 400 MHz) δ: 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H), 8.76-8.79(d,2H), 9.34(s,1H);

(272) 2-(2-pyrazinyl)-1H-benzimidazole-4-(N-2-hydroxyl-4-pyrimidinyl)amide

¹HNMR (DMSO, 400 MHz) δ: 5.46-5.48(d,1H), 7.10-7.11(d,1H), 7.43-7.45(t,1H), 7.82(s,1H), 7.89-7.91(d,1H), 7.93-7.94(d,1H), 8.76-8.79(d,2H), 9.34(s,1H);

(273) 2-(2-pyrazinyl)-1H-benzimidazole-4-(N-6-purinyl)amide

¹HNMR (DMSO, 400 MHz) δ: 7.43-7.45(t,1H), 7.86-7.88(d,1H), 7.89-7.91(d,1H), 7.93-7.94(d,1H), 8.16-8.18(d,1H), 8.76-8.79(d,2H), 9.34(s,1H);

(274) 2-(2-pyrazinyl)-1H-benzimidazole-4-(N-6-hydroxyl-2-purinyl)amide

¹HNMR (DMSO, 400 MHz) δ: 7.43-7.45(t,1H), 7.89-7.91(d,1H), 7.93-7.94(d,1H), 8.57-8.59(d,1H), 8.76-8.79(d,2H), 9.34(s,1H), 11.53(s,1H);

(275) (L)-2-(2-piperazinyl)-1H-benzimidazole-4-[N-(1-hydroxymethyl-2-p-nitrophenylhydroxyethyl)]amide ¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 3.17-3.18(m,1H), 3.25-3.28(m,1H), 3.50-3.52(m,1H), 3.65-3.68(t,1H), 3.70-3.72(d,1H), 4.14-4.17(m,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(276) (L)-2-(2-piperazinyl)-1H-benzimidazole-4-[N-(1-hydroxymethyl-2-p-aminophenylhydroxyethyl)]amide ¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 3.17-3.18(m,1H), 3.25-3.28(m,1H), 3.50-3.52(m,1H), 3.65-3.68(t,1H), 3.70-3.72(d,1H), 4.14-4.17(m,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(277) 2-(2-piperazinyl)-1H-benzimidazole-4-[N-(1-methyl-2-p-chlorophenylhydroxyethyl)]amide ¹HNMR (DMSO, 400 MHz) δ: 1.12-1.15(d,3H), 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 3.25-3.28(m,1H), 3.65-3.68(t,1H), 4.14-4.17(m,1H), 4.73-4.77(t,1H), 7.29-7.30(d,2H), 7.40-7.41(d,2H), 7.43-7.45(t,1H), 7.89-7.91(d,1H), 7.93-7.94(d,1H);

(278) 2-(2-piperazinyl)-1H-benzimidazole-4-(N—N'-piperidinyl)amide

¹HNMR (DMSO, 400 MHz) δ: 1.52-1.55(m,4H), 1.59-1.63(m,2H), 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 3.13-3.15(m,1H), 4.14-4.17(m,1H), 7.43-7.45(t,1H), 7.89-7.91(d,1H), 7.93-7.94(d,1H);

(279) 2-(2-piperazinyl)-1H-benzimidazole-4-(N-2-piperazinyl)amide

¹HNMR (DMSO, 400 MHz) δ: 1.91-1.93(m,4H), 2.62-2.63(m,2H), 2.65-2.66(m,2H), 2.69-2.70(m,2H), 2.72-2.74(m,2H), 2.77-2.80(m,1H), 2.84-2.86(m,1H), 3.02-3.05(m,1H), 3.09-3.11(m,1H), 3.99-4.01(m,1H), 4.14-4.17(m,1H), 7.43-7.45(t,1H), 7.89-7.91(d,1H), 7.93-7.94(d,1H);

(280) 2-(2-piperazinyl)-1H-benzimidazole-4-(N-2'-benzimidazolyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.12-7.15(d,2H), 7.22-7.24(t,2H), 7.43-7.45(t,1H), 7.89-7.91(d,1H), 7.93-7.94(d,1H);

(281) 2-(2-piperazinyl)-1H-benzimidazole-4-(N-o-aminophenyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H);

(282) 2-(2-piperazinyl)-1H-benzimidazole-4-(N-5-benzimidazolonyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74

(m,1H), 2.84-2.86(m,1H), 3.09-3.11(m,1H), 4.14-4.17(m,1H), 6.35-6.37(d,1H), 6.93(s,1H), 7.43-7.45(t,1H), 7.54-7.56(d,1H), 7.89-7.91(d,1H), 7.93-7.94(d,1H);

(283) 2-(2-piperazinyl)-1H-benzimidazole-4-(N-4'-carbonamido-5'-imidazolyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 8.37(s,2H), 9.24-9.26(d,1H), 13.00-13.03(d,1H);

(284) 2(2-piperazinyl)-1H-benzimidazole-4-(N-4'-pyrazolyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 8.61(s,1H), 8.63-8.65(d,1H), 13.71-13.75(d,1H);

(285) 2-(2-piperazinyl)-1H-benzimidazole-4-(N—(N'-piperazinyl))amide $^1$HNMR (DMSO, 400 MHz) δ: 1.91-1.93(m,2H), 1.94-1.95(m,1H), 2.62-2.63(m,1H), 2.65-2.67(t,5H), 2.69-2.70(m,1H), 2.72-2.74(m,1H), 2.80-2.83(m,4H), 2.84-2.86(m,1H), 3.09-3.11(m,1H), 4.14-4.17(m,1H), 7.43-7.45(t,1H), 7.90-7.91(d,1H), 7.93-7.94(d,1H);

(286) 2-(2-piperazinyl)-1H-benzimidazole-4-(N-2-pyrazinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 8.34-8.35(d,1H), 8.36(s,1H), 8.40-8.42(d,1H);

(287) 2-(2-piperazinyl)-1H-benzimidazole-4-(N-2-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 6.93-6.95(t,1H), 7.43-7.45(t,1H), 7.89-7.91(d,1H), 7.93-7.94(d,1H), 8.45-8.46(d,2H);

(288) 2-(2-piperazinyl)-1H-benzimidazole-4-(N-2-pyridyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H);

(289) 2-(2-piperazinyl)-1H-benzimidazole-4-(N-4-methyl-5-thiazolyl)amide $^1$HNMR (DMSO, 400 MHz) δ: 1.91-1.93(m,2H), 2.45(s,3H), 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 8.12(s,1H);

(290) 2-(2-piperazinyl)-1H-benzimidazole-4-(N-2,4-dihydroxyl-5-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.82(s,1H), 7.93-7.94(d,1H), 8.33(s,1H), 11.53(s,1H);

(291) 2-(2-piperazinyl)-1H-benzimidazole-4-(N-4,6-dimethoxy-2-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 3.82(s,6H), 5.71(s,1H), 4.14-4.17(m,1H), 7.43-7.45(t,1H), 7.89-7.91(d,1H), 7.93-7.94(d,1H);

(292) 2-(2-piperazinyl)-1H-benzimidazole-4-(N-4-chloro-6-amino-2-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 5.98(s,1H), 7.43-7.45(t,1H), 7.74(s,2H), 7.89-7.91(d,1H), 7.93-7.94(d,1H);

(293) 2-(2-piperazinyl)-1H-benzimidazole-4-(N-4,6-dichloro-5-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 9.34(s,1H);

(294) 2-(2-piperazinyl)-1H-benzimidazole-4-(N-o-fluorophenyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H);

(295) 2-(2-piperazinyl)-1H-benzimidazole-4-(N-2-hydroxyl-4-pyrimidinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 5.46-5.48(d,1H), 7.10-7.11(d,1H), 7.43-7.45(t,1H), 7.82(s,1H), 7.89-7.91(d,1H), 7.93-7.94(d,1H);

(296) 2-(2-piperazinyl)-1H-benzimidazole-4-(N-6-purinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.86-7.88(d,1H), 7.89-7.91(d,1H), 7.93-7.94(d,1H), 8.16-8.18(d,1H);

(297) 2-(2-piperazinyl)-1H-benzimidazole-4-(N-6-hydroxyl-2-purinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.84-2.86(m,1H), 3.09-3.11(m,1H), 4.14-4.17(m,1H), 7.43-7.45(t,1H), 7.89-7.91(d,1H), 7.93-7.94(d,1H), 8.57-8.59(d,1H), 11.53(s,1H);

(298) (L)-2-(N,N'-diethyl-2-piperazinyl)-1H-benzimidazole-4-[N-(1-hydroxymethyl-2-p-nitrophenyl-hydroxyethyl)]amide $^1$HNMR (DMSO, 400 MHz) δ: 1.02-1.06(t,6H), 2.40-2.43(m,4H), 2.61-2.63(d,1H), 2.65-2.67(t,1H), 2.69-2.71(t,1H), 2.72-2.74(t,1H), 2.76-2.78(t,1H), 2.88-2.90(d,1H), 3.17-3.18(m,1H), 3.25-3.28(m,1H), 3.50-3.52(m,1H), 3.65-3.68(t,1H), 3.70-3.72(d,1H), 4.14-4.16(t,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(299) (L)-2-(N,N'-diethyl-2-piperazinyl)-1H-benzimidazole-4-[N-(1-hydroxymethyl-2-p-aminophenyl-hydroxyethyl)]amide $^1$HNMR (DMSO, 400 MHz) δ: 1.02-1.06(t,6H), 2.40-2.43(m,4H), 2.61-2.63(d,1H), 2.65-2.67(t,1H), 2.69-2.71(t,1H), 2.72-2.74(t,1H), 2.76-2.78(t,1H), 2.88-2.90(d,1H), 3.17-3.18(m,1H), 3.25-3.28(m,1H), 3.50-3.52(m,1H), 3.65-3.68(t,1H), 3.70-3.72(d,1H), 4.14-4.16(t,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(300) 2-(N,N'-diethyl-2-piperazinyl)-1H-benzimidazole-4-(N-2-piperazinyl)amide $^1$HNMR (DMSO, 400 MHz) δ: 1.02-1.06(t,6H), 1.91-1.93(m,2H), 2.40-2.43(m,4H), 2.59-2.60(d,1H), 2.62-2.63(m,1H), 2.64-2.65(t,1H), 2.66-2.67(m,1H), 2.68-2.70(t,2H), 2.72-2.73(m,1H), 2.74-2.75(t,1H), 2.76-2.78(t,1H), 2.77-2.80(m,1H), 2.88-2.90(d,1H), 3.02-3.05(m,1H), 3.99-4.01(m,1H), 4.14-4.16(t,1H), 7.43-7.45(t,1H), 7.89-7.91(d,1H), 7.93-7.94(d,1H);

(301) 2-(N,N'-diethyl-2-piperazinyl)-1H-benzimidazole-4-(N-2-pyrimidinyl)amide $^1$HNMR (DMSO, 400 MHz) δ: 1.02-1.06(t,6H), 2.40-2.43(m,4H), 2.61-2.63(d,1H), 2.65-2.67(t,1H), 2.69-2.71(t,1H), 2.72-2.74(t,1H), 2.76-2.78(t,1H), 2.88-2.90(d,1H), 4.14-4.16(t,1H), 6.93-6.95(t,1H), 7.43-7.45(t,1H), 7.89-7.91(d,1H), 7.93-7.94(d,1H), 8.45-8.46(d,2H);

(302) (L)-2-(N-piperazinyl)-1H-benzimidazole-4-[N-(1-hydroxymethyl-2-p-nitrophenylhydroxyethyl)]amide $^1$HNMR (DMSO, 400 MHz) δ: 1.91-1.92(m,1H), 2.78-2.82(m,4H), 3.15-3.16(m,1H), 3.18-3.22(t,4H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(303) (L)-2-(N-piperazinyl)-1H-benzimidazole-4-[N-(1-hydroxymethyl-2-p-aminophenylhydroxyethyl)]amide $^1$HNMR (DMSO, 400 MHz) δ: 1.91-1.92(m,1H), 2.78-2.82(m,4H), 3.15-3.16(m,1H), 3.18-3.22(t,4H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(304) 2-(N-piperazinyl)-1H-benzimidazole-4-[N-(1-methyl-2-p-chlorophenylhydroxyethyl)]amide $^1$HNMR (DMSO, 400 MHz) δ: 1.12-1.15(d,3H), 1.91-1.92(m,1H), 2.78-2.82(m,4H), 3.17-3.22(t,4H), 3.25-3.28(m,1H), 3.65-3.68(t,1H), 4.73-4.77(t,1H), 7.29-7.30(d,2H), 7.40-7.41(d,2H), 7.43-7.45(t,1H), 7.89-7.91(d,1H), 7.93-7.94(d,1H);

(305) 2-(N-piperazinyl)-1H-benzimidazole-4-(N—N'-piperidinyl)amide $^1$HNMR (DMSO, 400 MHz) δ: 1.52-1.55(m,4H), 1.59-1.63(m,2H), 1.91-1.92(m,1H), 2.78-2.82(m,4H), 3.10-3.15(t,4H), 3.17-3.22(t,4H), 7.43-7.45(t,1H), 7.89-7.91(d,1H), 7.93-7.94(d,1H);

(306) 2-(N-piperazinyl)-1H-benzimidazole-4-(N-2-piperazinyl)amide $^1$HNMR (DMSO, 400 MHz) δ: 1.91-1.93(m,3H), 2.62-2.63(m,1H), 2.65-2.66(m,1H), 2.69-2.70(m,1H), 2.72-2.74(m,1H), 2.78-2.82(m,5H), 3.02-3.05(m,1H), 3.17-3.22(t,4H), 3.99-4.01(m,1H), 7.43-7.45(t,1H), 7.89-7.91(d,1H), 7.93-7.94(d,1H);

(307) 2-(N-piperazinyl)-1H-benzimidazole-4-(N-2'-benzimidazolyl)amide $^1$HNMR (DMSO, 400 MHz) δ: 1.91-1.92(m,1H), 2.78-2.82(m,4H), 3.17-3.22(t,4H), 7.12-7.15(d,2H), 7.22-7.24(t,2H), 7.43-7.45(t,1H), 7.89-7.91(d,1H), 7.93-7.94(d,1H);

(308) 2-(N-piperazinyl)-1H-benzimidazole-4-(N-o-aminophenyl)amide $^1$HNMR (DMSO, 400 MHz) δ: 1.91-1.92(m,1H), 2.78-2.82(m,4H), 3.17-3.22(t,4H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H);

(309) 2-(N-piperazinyl)-1H-benzimidazole-4-(N-5-benzimidazolonyl)amide $^1$HNMR (DMSO, 400 MHz) δ: 1.91-1.92(m,1H), 2.78-2.82(m,4H), 3.17-3.22(t,4H), 6.35-6.37(d,1H), 6.93(s,1H), 7.43-7.45(t,1H), 7.54-7.56(d,1H), 7.89-7.91(d,1H), 7.93-7.94(d,1H);

(310) 2-(N-piperazinyl)-1H-benzimidazole-4-(N-4'-carbonamido-5'-imidazolyl)amide $^1$HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.93-7.94(d,1H), 8.37(s,2H), 9.24-9.26(d,1H), 13.00-13.03(d,1H);

(311) 2-(N-piperazinyl)-1H-benzimidazole-4-(N-4'-pyrazolyl)amide $^1$HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.93-7.94(d,1H), 8.61(s,1H), 8.63-8.65(d,1H), 13.71-13.75(d,1H);

(312) 2-(N-piperazinyl)-1H-benzimidazole-4-(N—(N'-piperazinyl))amide

¹HNMR (DMSO, 400 MHz) δ: 1.91-1.95(m,2H), 2.65-2.67(t,4H), 2.78-2.80(m,4H), 2.81-2.83(m,4H), 3.17-3.22(t,4H), 7.43-7.45(t,1H), 7.90-7.91(d,1H), 7.93-7.94(d,1H);

(313) 2-(N-piperazinyl)-1H-benzimidazole-4-(N-2-pyrazinyl)amide

¹HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.93-7.94(d,1H), 8.34-8.35(d,1H), 8.36(s,1H), 8.40-8.42(d,1H);

(314) 2-(N-piperazinyl)-1H-benzimidazole-4-(N-2-pyrimidinyl)amide

¹HNMR (DMSO, 400 MHz) δ: 1.91-1.92(m,1H), 2.78-2.82(m,4H), 3.17-3.22(t,4H), 6.93-6.95(t,1H), 7.43-7.45(t,1H), 7.89-7.91(d,1H), 7.93-7.94(d,1H), 8.45-8.46(d,2H);

(315) 2-(N-piperazinyl)-1H-benzimidazole-4-(N-2-pyridyl)amide

¹HNMR (DMSO, 400 MHz) δ: 1.91-1.92(m,1H), 2.78-2.82(m,4H), 3.17-3.22(t,4H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H);

(316) 2-(N-piperazinyl)-1H-benzimidazole-4-(N-4-methyl-5-thiazolyl)amide

¹HNMR (DMSO, 400 MHz) δ: 1.91-1.92(m,1H), 2.45(s,3H), 2.78-2.82(m,4H), 3.17-3.22(t,4H), 7.43-7.45(t,1H), 7.89-7.91(d,1H), 7.93-7.94(d,1H), 8.12(s,1H);

(317) 2-(N-piperazinyl)-1H-benzimidazole-4-(N-2,4-dihydroxyl-5-pyrimidinyl)amide ¹HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.82(s,1H), 7.93-7.94(d,1H), 8.33(s,1H), 11.53(s,1H);

(318) 2-(N-piperazinyl)-1H-benzimidazole-4-(N-4,6-dimethoxy-2-pyrimidinyl)amide

¹HNMR (DMSO, 400 MHz) δ: 1.91-1.92(m,1H), 2.78-2.82(m,4H), 3.17-3.22(t,4H), 3.82(s,6H), 5.71(s,1H), 7.43-7.45(t,1H), 7.89-7.91(d,1H), 7.93-7.94(d,1H);

(319) 2-(N-piperazinyl)-1H-benzimidazole-4-(N-4-chloro-6-amino-2-pyrimidinyl)amide ¹HNMR (DMSO, 400 MHz) δ: 1.91-1.92(m,1H), 2.78-2.82(m,4H), 3.17-3.22(t,4H), 5.98(s,1H), 7.43-7.45(t,1H), 7.74(s,2H), 7.89-7.91(d,1H), 7.93-7.94(d,1H);

(320) 2-(N-piperazinyl)-1H-benzimidazole-4-(N-4,6-dichloro-5-pyrimidinyl)amide

¹HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.93-7.94(d,1H), 9.34(s,1H);

(321) 2-(N-piperazinyl)-1H-benzimidazole-4-(N-o-fluorophenyl)amide

¹HNMR (DMSO, 400 MHz) δ: 1.91-1.92(m,1H), 2.78-2.82(m,4H), 3.17-3.22(t,4H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H);

(322) 2-(N-piperazinyl)-1H-benzimidazole-4-(N-2-hydroxyl-4-pyrimidinyl)amide

¹HNMR (DMSO, 400 MHz) δ: 1.91-1.92(m,1H), 2.78-2.82(m,4H), 3.17-3.22(t,4H), 5.46-5.48(d,1H), 7.10-7.11(d,1H), 7.43-7.45(t,1H), 7.82(s,1H), 7.89-7.91(d,1H), 7.93-7.94(d,1H);

(323) 2-(N-piperazinyl)-1H-benzimidazole-4-(N-6-purinyl)amide

¹HNMR (DMSO, 400 MHz) δ: 1.91-1.92(m,1H), 2.78-2.82(m,4H), 3.17-3.22(t,4H), 7.43-7.45(t,1H), 7.86-7.88(d,1H), 7.89-7.91(d,1H), 7.93-7.94(d,1H), 8.16-8.18(d,1H);

(324) 2-(N-piperazinyl)-1H-benzimidazole-4-(N-6-hydroxyl-2-purinyl)amide

¹HNMR (DMSO, 400 MHz) δ: 1.91-1.92(m,1H), 2.78-2.82(m,4H), 3.17-3.22(t,4H), 7.43-7.45(t,1H), 7.89-7.91(d,1H), 7.93-7.94(d,1H), 8.57-8.59(d,1H), 11.53(s,1H);

(325) (L)-2-(N-ethyl-N'-piperazinyl)-1H-benzimidazole-4-[N-(1-hydroxymethyl-2-p-nitrophenylhydroxyethyl)]amide ¹HNMR (DMSO, 400 MHz) δ: 1.02-1.05(t,3H), 2.38-2.41(m,2H), 3.15-3.17(t,4H), 3.19-3.21(m,1H), 3.25-3.28(m,1H), 3.44-3.46(t,4H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(326) (L)-2-(N-ethyl-N'-piperazinyl)-1H-benzimidazole-4-[N-(1-hydroxymethyl-2-p-aminophenylhydroxyethyl)]amide ¹HNMR (DMSO, 400 MHz) δ: 1.02-1.05(t,3H), 2.38-2.41(m,2H), 3.15-3.17(t,4H), 3.19-3.21(m,1H), 3.25-3.28(m,1H), 3.44-3.46(t,4H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(327) 2-(N-ethyl-N'-piperazinyl)-1H-benzimidazole-4-(N-2-piperazinyl)amide

¹HNMR (DMSO, 400 MHz) δ: 1.02-1.05(t,3H), 1.91-1.93(m,2H), 2.38-2.41(m,2H), 2.62-2.36(m,1H), 2.65-2.66(m,1H), 2.69-2.70(m,1H), 2.72-2.74(m,1H), 2.77-2.80(m,1H), 3.02-3.05(m,1H), 3.15-3.17(t,4H), 3.44-3.46(t,4H), 3.99-4.01(m,1H), 7.43-7.45(t,1H), 7.89-7.91(d,1H), 7.93-7.94(d,1H);

(328) 2-(N-ethyl-N'-piperazinyl)-1H-benzimidazole-4-(N-2-pyrimidinyl)amide

¹HNMR (DMSO, 400 MHz) δ: 1.02-1.05(t,3H), 2.38-2.41(m,2H), 3.15-3.17(t,4H), 3.44-3.46(t,4H), 6.93-6.95(t,1H), 7.43-7.45(t,1H), 7.89-7.91(d,1H), 7.93-7.94(d,1H), 8.45-8.46(d,2H);

(329) (L)-2-(2-pyrrolyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 6.15-6.18(t,1H), 6.40-6.42(d,1H), 6.95-6.97(d,1H), 7.43-7.45(t,1H), 7.62-7.65(d,2H), 7.89-7.90(d,1H), 7.93-7.95(d,1H), 8.17-8.20(d,2H);

(330) (L)-2-(2-pyrrolyl)-1H-benzimidazole-4-[N-(1-hydroxymethyl-2-p-aminophenylhydroxyethyl)]amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 6.15-6.18(t,1H), 6.40-6.42(d,1H), 6.27(s,2H), 6.56-6.58(d,2H), 6.95-6.97(d,1H), 7.11-7.13(d,2H), 7.43-7.45(t,1H), 7.89-7.90(d,1H), 7.93-7.95(d,1H);

(331) 2-(2-pyrrolyl)-1H-benzimidazole-4-[N-(1-methyl-2-p-chlorophenylhydroxyethyl)]amide $^1$HNMR (DMSO, 400 MHz) δ: 1.12-1.15(d,3H), 3.25-3.28(m,1H), 3.65-3.68(t,1H), 4.73-4.77(t,1H), 6.15-6.18(t,1H), 6.40-6.42(d,1H), 6.95-6.97(d,1H), 7.29-7.30(d,2H), 7.40-7.41(d,2H), 7.43-7.45(t,1H), 7.89-7.91(d,1H), 7.93-7.94(d,1H);

(332) 2-(2-pyrrolyl)-1H-benzimidazole-4-(N—N'-piperidinyl)amide $^1$HNMR (DMSO, 400 MHz) δ: 1.52-1.55(m,4H), 1.59-1.63(m,2H), 3.10-3.15(t,4H), 6.15-6.18(t,1H), 6.40-6.42(d, 1H), 6.95-6.97(d,1H), 7.43-7.45(t,1H), 7.89-7.91(d,1H), 7.93-7.94(d,1H);

(333) 2-(2-pyrrolyl)-1H-benzimidazole-4-(N-2-piperazinyl)amide $^1$HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m, 1H), 6.15-6.18(t,1H), 6.40-6.42(d,1H), 6.95-6.97(d,1H), 7.43-7.45(t,1H), 7.89-7.91(d,1H), 7.93-7.94(d,1H);

(334) 2-(2-pyrrolyl)-1H-benzimidazole-4-(N-2'-benzimidazolyl)amide $^1$HNMR (DMSO, 400 MHz) δ: 6.15-6.18(t,1H), 6.40-6.42(d,1H), 6.95-6.97(d,1H), 7.12-7.15(d,2H), 7.22-7.24(t,2H), 7.43-7.45(t,1H), 7.89-7.91(d,1H), 7.93-7.94(d,1H);

(335) 2-(2-pyrrolyl)-1H-benzimidazole-4-(N-o-aminophenyl)amide $^1$HNMR (DMSO, 400 MHz) δ: 6.15-6.18(t,1H), 6.27(s, 2H), 6.38-6.39(d,1H), 6.40-6.42(d,1H), 6.56-6.58(t,1H), 6.75-6.76(d,1H), 6.95-6.97(d,1H), 7.02-7.04(t,1H), 7.43-7.45(t,1H), 7.89-7.91(d,1H), 7.93-7.94(d,1H);

(336) 2-(2-pyrrolyl)-1H-benzimidazole-4-(N-5-benzimidazolonyl)amide $^1$HNMR (DMSO, 400 MHz) δ: 6.15-6.18(t,1H), 6.35-6.37(d,1H), 6.40-6.42(d,1H), 6.93(s,1H), 6.95-6.97(d,1H), 7.43-7.45(t,1H), 7.54-7.56(d,1H), 7.89-7.91(d,1H), 7.93-7.94(d, 1H);

(337) 2-(2-pyrrolyl)-1H-benzimidazole-4-(N-4'-carbonamido-5'-imidazolyl)amide $^1$HNMR (DMSO, 400 MHz) δ: 6.15-6.18(t,1H), 6.40-6.42(d,1H), 6.95-6.97(d,1H), 7.43-7.45(t,1H), 7.89-7.91(d,1H), 7.93-7.94(d,1H), 8.37(s,2H), 9.24-9.26(d,1H), 13.00-13.03(d,1H);

(338) 2-(2-pyrrolyl)-1H-benzimidazole-4-(N-4'-pyrazolyl)amide $^1$HNMR (DMSO, 400 MHz) δ: 6.15-6.18(t,1H), 6.40-6.42(d,1H), 6.95-6.97(d,1H), 7.43-7.45(t,1H), 7.89-7.91(d,1H), 7.93-7.94(d,1H), 8.61(s,1H), 8.63-8.65(d,1H), 13.71-13.75(d,1H);

(339) 2-(2-pyrrolyl)-1H-benzimidazole-4-(N—(N'-piperazinyl))amide $^1$HNMR (DMSO, 400 MHz) δ: 1.91-1.95(m,1H), 2.65-2.67(t,4H), 2.80-2.83(m,4H), 6.15-6.18(t,1H), 6.40-6.42(d, 1H), 6.95-6.97(d,1H), 7.43-7.45(t,1H), 7.90-7.91(d,1H), 7.93-7.94(d,1H);

(340) 2-(2-pyrrolyl)-1H-benzimidazole-4-(N-2-pyrazinyl)amide $^1$HNMR (DMSO, 400 MHz) δ: 6.15-6.18(t,1H), 6.40-6.42(d,1H), 6.95-6.97(d,1H), 7.43-7.45(t,1H), 7.89-7.91(d,1H), 7.93-7.94(d,1H), 8.34-8.35(d,1H), 8.36(s,1H), 8.40-8.42(d, 1H);

(341) 2-(2-pyrrolyl)-1H-benzimidazole-4-(N-2-pyrimidinyl)amide $^1$HNMR(DMSO, 400 MHz)δ:6.15-6.18(t,1H),6.40-6.42(d,1H),6.93-6.95(t,1H), 6.98-7.01(d,1H), 7.43-7.45(t,1H), 7.89-7.91(d,1H), 7.93-7.94(d,1H), 8.45-8.46(d,2H);

(342) 2-(2-pyrrolyl)-1H-benzimidazole-4-(N-2-pyridyl)amide $^1$HNMR (DMSO, 400 MHz) δ: 6.15-6.18(t,1H), 6.40-6.42(d,1H), 6.62-6.64(t,1H), 6.70-6.72(d,1H), 6.95-6.97(d,1H), 7.43-7.45(t,1H), 7.55-7.57(t,1H), 7.89-7.91(d,1H), 7.93-7.94(d,1H), 8.07-8.09(d,1H);

(343) 2-(2-pyrrolyl)-1H-benzimidazole-4-(N-4-methyl-5-thiazolyl)amide $^1$HNMR (DMSO, 400 MHz) δ: 2.45(s,3H), 6.15-6.18(t, 1H), 6.40-6.42(d,1H), 6.95-6.97(d,1H), 7.43-7.45(t,1H), 7.89-7.91(d,1H), 7.93-7.94(d,1H), 8.12(s,1H);

(344) 2-(2-pyrrolyl)-1H-benzimidazole-4-(N-2,4-dihydroxyl-5-pyrimidinyl)amide $^1$HNMR(DMSO, 400 MHz)δ:6.15-6.18(t,1H),6.40-6.42(d,1H),6.95-6.97(d,1H),7.43-7.45(t,1H), 7.89-7.91(d,1H), 7.82(s,1H), 7.93-7.94(d,1H), 8.33(s,1H), 11.53(s,1H);

(345) 2-(2-pyrrolyl)-1H-benzimidazole-4-(N-4,6-dimethoxy-2-pyrimidinyl)amide $^1$HNMR(DMSO, 400 MHz)δ:3.82(s,6H), 5.71(s,1H), 6.15-6.18(t,1H), 6.40-6.42(d,1H), 6.95-6.97(d,1H), 7.43-7.45(t,1H), 7.89-7.91(d,1H), 7.93-7.94(d,1H);

(346) 2-(2-pyrrolyl)-1H-benzimidazole-4-(N-4-chloro-6-amino-2-pyrimidinyl)amide ¹HNMR (DMSO, 400 MHz) δ: 5.98(s,1H), 6.15-6.18(t,1H), 6.40-6.42(d,1H), 6.95-6.97(d,1H), 7.43-7.45(t,1H), 7.74(s,2H), 7.89-7.91(d,1H), 7.93-7.94(d,1H);

(347) 2-(2-pyrrolyl)-1H-benzimidazole-4-(N-4,6-dichloro-5-pyrimidinyl)amide

¹HNMR (DMSO, 400 MHz) δ: 6.15-6.18(t,1H), 6.40-6.42(d,1H), 6.95-6.97(d,1H), 7.43-7.45(t,1H), 7.89-7.91(d,1H), 7.93-7.94(d,1H), 9.34(s,1H);

(348) 2-(2-pyrrolyl)-1H-benzimidazole-4-(N-o-fluorophenyl)amide

¹HNMR (DMSO, 400 MHz) δ: 6.15-6.18(t,1H), 6.40-6.42(d,1H), 6.60-6.61(d,1H), 6.63-6.65(t,1H), 6.90-6.93(d,1H), 6.96-6.98(t,1H), 6.99-7.01(d,1H), 7.43-7.45(t,1H), 7.89-7.91(d,1H), 7.93-7.94(d,1H);

(349) 2-(2-pyrrolyl)-1H-benzimidazole-4-(N-2-hydroxyl-4-pyrimidinyl)amide

¹HNMR(DMSO, 400 MHz)δ:5.46-5.48(d,1H),6.15-6.18(t,1H),6.40-6.42(d,1H),6.95-6.97(d,1H),7.10-7.11(d,1H),7.43-7.45(t,1H),7.82(s,1H),7.89-7.91(d,1H),7.93-7.94(d,1H);

(350) 2-(2-pyrrolyl)-1H-benzimidazole-4-(N-6-purinyl)amide

¹HNMR (DMSO, 400 MHz) δ: 6.15-6.18(t,1H), 6.40-6.42(d,1H), 6.95-6.97(d,1H), 7.43-7.45(t,1H),7.86-7.88(d,1H), 7.89-7.91(d,1H), 7.93-7.94(d,1H), 8.16-8.18(d,1H);

(351) 2-(2-pyrrolyl)-1H-benzimidazole-4-(N-6-hydroxyl-2-purinyl)amide

¹HNMR (DMSO, 400 MHz) δ: 6.15-6.18(t,1H), 6.40-6.42(d,1H), 6.95-6.97(d,1H), 7.43-7.45(t,1H), 7.89-7.91(d,1H), 7.93-7.94(d,1H), 8.57-8.59(d,1H), 11.53(s,1H);

(352) (L)-2-(4-methyl-5-aminothiazolyl)-1H-benzimidazole-4-[N-(1-hydroxymethyl-2-p-nitrophenylhydroxyethyl)]amide ¹HNMR (DMSO, 400 MHz) δ: 2.45(s,3H), 3.17-3.18(m,1H), 3.25-3.28(m,1H), 3.50-3.52(m,1H), 3.65-3.68(t,1H), 3.70-3.72(d,1H), 4.73-4.77(t,1H), 6.99(s,2H),7.43-7.45(t,1H), 7.62-7.65(d,2H), 7.89-7.90(d,1H), 7.93-7.95(d,1H), 8.17-8.20(d,2H);

(353) (L)-2-(4-methyl-5-aminothiazolyl)-1H-benzimidazole-4-[N-(1-hydroxymethyl-2-p-aminophenylhydroxyethyl)]amide ¹HNMR(DMSO, 400 MHz)δ: 2.45(s,3H), 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 6.99(s,2H), 7.11-7.13(d,2H), 7.43-7.45(t,1H), 7.89-7.90(d,1H), 7.93-7.95(d,1H);

(354) 2-(4-methyl-5-aminothiazolyl)-1H-benzimidazole-4-[N-(1-methyl-2-p-chlorophenylhydroxyethyl)]amide ¹HNMR (DMSO, 400 MHz) δ: 1.12-1.15(d,3H), 2.45(s,3H), 3.25-3.28(m,1H), 3.65-3.68(m,1H), 4.73-4.77(t,1H), 6.99(s,2H), 7.29-7.30(d,2H), 7.40-7.41(d,2H), 7.43-7.45(t,1H), 7.89-7.91(d,1H), 7.93-7.94(d,1H);

(355) 2-(4-methyl-5-aminothiazolyl)-1H-benzimidazole-4-(N—N'-piperidinyl)amide ¹HNMR (DMSO, 400 MHz) δ: 1.52-1.55(m,4H), 1.59-1.63(m,2H), 2.45(s,3H), 3.10-3.15(t,4H), 6.99(s,2H), 7.43-7.45(t,1H), 7.89-7.91(d,1H), 7.93-7.94(d,1H);

(356) 2-(4-methyl-5-aminothiazolyl)-1H-benzimidazole-4-(N-2-piperazinyl)amide ¹HNMR (DMSO, 400 MHz) δ: 1.91-1.93(m,2H), 2.45(s,3H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 6.99(s,2H), 7.43-7.45(t,1H), 7.89-7.91(d,1H), 7.93-7.94(d,1H);

(357) 2-(4-methyl-5-aminothiazolyl)-1H-benzimidazole-4-(N-2'-benzimidazolyl)amide ¹HNMR (DMSO, 400 MHz) δ: 2.45(s,3H), 6.99(s,2H), 7.12-7.15(d,2H), 7.22-7.24(t,2H), 7.43-7.45(t,1H), 7.89-7.91(d,1H), 7.93-7.94(d,1H);

(358) 2-(4-methyl-5-aminothiazolyl)-1H-benzimidazole-4-(N-o-aminophenyl)amide ¹HNMR (DMSO, 400 MHz) δ: 2.45(s,3H), 6.27(s,2H), 6.38-6.40(d,1H), 6.56-6.58(t,1H), 6.75-6.76(d,1H), 6.99(s,2H), 7.02-7.04(t,1H), 7.43-7.45(t,1H), 7.89-7.91(d,1H), 7.93-7.94(d,1H);

(359) 2-(4-methyl-5-aminothiazolyl)-1H-benzimidazole-4-(N-5-benzimidazolonyl)amide ¹HNMR (DMSO, 400 MHz) δ: 2.45(s,3H), 6.35-6.37(d,1H), 6.93(s,1H), 6.99(s,2H), 7.43-7.45(t,1H), 7.54-7.56(d,1H), 7.89-7.91(d,1H), 7.93-7.94(d,1H);

(360) 2-(4-methyl-5-aminothiazolyl)-1H-benzimidazole-4-(N-4'-carbonamido-5'-imidazolyl)amide ¹HNMR (DMSO, 400 MHz) δ: 2.45(s,3H), 6.99(s,2H), 7.43-7.45(t,1H), 7.89-7.91(d,1H), 7.93-7.94(d,1H), 8.37(s,2H), 9.24-9.26(d,1H), 13.00-13.03(d,1H);

(361) 2-(4-methyl-5-aminothiazolyl)-1H-benzimidazole-4-(N-4'-pyrazolyl)amide ¹HNMR (DMSO, 400 MHz) δ: 2.45(s,3H), 6.99(s,2H), 7.43-7.45(t,1H), 7.89-7.91(d,1H), 7.93-7.94(d,1H), 8.61(s,1H), 8.63-8.65(d,1H), 13.71-13.75(d,1H);

(362) 2-(4-methyl-5-aminothiazolyl)-1H-benzimidazole-4-(N—(N'-piperazinyl))amide ¹HNMR (DMSO, 400 MHz) δ: 1.91-1.95(m,1H), 2.45(s,3H), 2.65-2.67(t,4H), 2.80-2.83(m,4H), 6.99(s,2H), 7.43-7.45(t,1H), 7.90-7.91(d,1H), 7.93-7.94(d,1H);

(363) 2-(4-methyl-5-aminothiazolyl)-1H-benzimidazole-4-(N-2-pyrazinyl)amide

¹HNMR (DMSO, 400 MHz) δ: 2.45(s,3H), 6.99(s,2H), 7.43-7.45(t,1H), 7.89-7.91(d,1H), 7.93-7.94(d,1H), 8.34-8.35(d,1H), 8.36(s,1H), 8.40-8.42(d,1H);

(364) 2-(4-methyl-5-aminothiazolyl)-1H-benzimidazole-4-(N-2-pyrimidinyl)amide

¹HNMR (DMSO, 400 MHz) δ: 2.45(s,3H), 6.93-6.95(t, 1H), 6.99(s,2H), 7.43-7.45(t,1H), 7.89-7.91(d,1H), 7.93-7.94(d,1H), 8.45-8.46(d,2H);

(365) 2-(4-methyl-5-aminothiazolyl)-1H-benzimidazole-4-(N-2-pyridyl)amide

¹HNMR (DMSO, 400 MHz) δ: 2.45(s,3H), 6.62-6.64(t, 1H), 6.70-6.72(d,1H), 6.99(s,2H), 7.43-7.45(t,1H), 7.55-7.57(t,1H), 7.89-7.91(d,1H), 7.93-7.94(d,1H), 8.07-8.09(d,1H);

(366) 2-(4-methyl-5-aminothiazolyl)-1H-benzimidazole-4-(N-4-methyl-5-thiazolyl)amide ¹HNMR (DMSO, 400 MHz) δ: 2.45(s,6H), 6.99(s,2H), 7.43-7.45(t,1H), 7.89-7.91(d,1H), 7.93-7.94(d,1H), 8.12(s,1H);

(367) 2-(4-methyl-5-aminothiazolyl-1H-benzimidazole-4-(N-2,4-dihydroxyl-5-pyrimidinyl)amide ¹HNMR (DMSO, 400 MHz) δ: 2.45(s,3H), 6.99(s,2H), 7.43-7.45(t,1H), 7.89-7.91(d,1H), 7.82(s,1H), 7.93-7.94(d,1H), 8.33(s,1H), 11.53(s,1H);

(368) 2-(4-methyl-5-aminothiazolyl)-1H-benzimidazole-4-(N-4,6-dimethoxy-2-pyrimidinyl)amide ¹HNMR (DMSO, 400 MHz) δ: 2.45(s,3H), 3.82(s,6H), 5.71(s,1H), 6.99(s,2H), 7.43-7.45(t,1H), 7.89-7.91(d,1H), 7.93-7.94(d,1H);

(369) 2-(4-methyl-5-aminothiazolyl)-1H-benzimidazole-4-(N-4-chloro-6-amino-2-pyrimidinyl)amide ¹HNMR (DMSO, 400 MHz) δ: 2.45(s,3H), 5.98(s,1H), 6.99(s,2H), 7.43-7.45(t,1H), 7.74(s,2H), 7.89-7.91(d,1H), 7.93-7.94(d,1H);

(370) 2-(4-methyl-5-aminothiazolyl)-1H-benzimidazole-4-(N-4,6-dichloro-5-pyrimidinyl)amide ¹HNMR (DMSO, 400 MHz) δ: 2.45(s,3H), 6.99(s,2H), 7.43-7.45(t,1H), 7.89-7.91(d,1H), 7.93-7.94(d,1H), 9.34(s,1H);

(371) 2-(4-methyl-5-aminothiazolyl)-1H-benzimidazole-4-(N-o-fluorophenyl)amide

¹HNMR (DMSO, 400 MHz) δ: 2.45(s,3H), 6.60-6.61(d, 1H), 6.63-6.65(t,1H), 6.96-6.97(t,1H), 6.99(s,2H), 7.02-7.05(d,1H), 7.43-7.45(t,1H), 7.89-7.91(d,1H), 7.93-7.94(d,1H);

(372) 2-(4-methyl-5-aminothiazolyl)-1H-benzimidazole-4-(N-2-hydroxyl-4-pyrimidinyl)amide ¹HNMR (DMSO, 400 MHz) δ: 2.45(s,3H), 5.46-5.48(d, 1H), 6.99(s,2H), 7.10-7.11(d,1H), 7.43-7.45(t,1H), 7.82(s, 1H), 7.89-7.91(d,1H), 7.93-7.94(d,1H);

(373) 2-(4-methyl-5-aminothiazolyl)-1H-benzimidazole-4-(N-6-purinyl)amide

¹HNMR (DMSO, 400 MHz) δ: 2.45(s,3H), 6.99(s,2H), 7.43-7.45(t,1H), 7.86-7.88(d,1H), 7.89-7.91(d,1H), 7.93-7.94(d,1H), 8.16-8.18(d,1H);

(374) 2-(4-methyl-5-aminothiazolyl)-1H-benzimidazole-4-(N-6-hydroxyl-2-purinyl)amide ¹HNMR (DMSO, 400 MHz) δ: 2.45(s,3H), 6.99(s,2H), 7.43-7.45(t,1H), 7.89-7.91(d,1H), 7.93-7.94(d,1H), 8.57-8.59(d,1H), 11.53(s,1H);

(375) (L)-2-(2-quinolinyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 7.39-7.40(d,1H), 7.43-7.45(t,1H), 7.60-7.62(t,1H), 7.64-7.65(d,2H), 7.76-7.77 (t,1H), 7.89-7.90(d,1H), 7.93-7.95(d,1H), 7.98-8.00(d,1H), 8.06-8.07(d, 1H), 8.17-8.20(d,2H), 8.44-8.46(d,1H);

(376) (L)-2-(2-quinolinyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 6.27(s,2H), 6.56-6.58(d,2H), 7.11-7.13 (d,2H), 7.39-7.40(d,1H), 7.43-7.45(t,1H), 7.60-7.62(t,1H), 7.78-7.79 (t,1H), 7.89-7.90(d,1H), 7.93-7.95(d,1H), 7.98-8.00(d,1H), 8.06-8.07(d,1H), 8.40-8.41(d,1H), 8.44-8.46(d, 1H);

(377) 2-(2-quinolinyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28 (m,1H), 3.65-3.68(t,1H), 4.73-4.77(t,1H), 7.29-7.30(d,2H), 7.35-7.37(d,1H), 7.40-7.41(d,2H), 7.43-7.45(t,1H), 7.60-7.62(t,1H), 7.78-7.79 (t,1H), 7.89-7.91(d,1H), 7.93-7.94(d, 1H), 7.98-8.00(d,1H), 8.06-8.07(d,1H), 8.44-8.46(d,1H);

(378) 2-(2-quinolinyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.39-7.40(d,1H), 7.43-7.45(t, 1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H);

(379) 2-(2-quinolinyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74

(m,1H), 2.77-2.80(m,1H), 3.02-3.05(m,1H), 3.99-4.01(m, 1H), 7.39-7.40(d,1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H);

(380) 2-(2-quinolinyl)-1H-benzimidazole-4-(N-2'-benzimidazolyl)amide $^1$HNMR (DMSO, 400 MHz) δ: 7.12-7.15(d,2H), 7.22-7.24 (t,2H), 7.39-7.40(d,1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H);

(381) 2-(2-quinolinyl)-1H-benzimidazole-4-(N-o-aminophenyl)amide $^1$HNMR (DMSO, 400 MHz) δ: 6.27(s,2H), 6.38-6.40(d, 1H), 6.56-6.58(t,1H), 6.75-6.76(d,1H), 7.02-7.04(t,1H), 7.39-7.40(d,1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H);

(382) 2-(2-quinolinyl)-1H-benzimidazole-4-(N-5-benzimidazolonyl)amide $^1$HNMR (DMSO, 400 MHz) δ: 6.35-6.37(d,1H), 6.93(s, 1H), 7.39-7.40(d,1H), 7.43-7.45(t,1H), 7.54-7.56(d,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d, 1H);

(383) 2-(2-quinolinyl)-1H-benzimidazole-4-(N-4'-carbonamido-5'-imidazolyl)amide $^1$HNMR (DMSO, 400 MHz) δ: 7.39-7.40(d,1H), 7.43-7.45 (t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.37(s, 2H), 8.44-8.46(d,1H), 9.24-9.26(d,1H), 13.00-13.03(d,1H);

(384) 2-(2-quinolinyl)-1H-benzimidazole-4-(N-4'-pyrazolyl)amide $^1$HNMR (DMSO, 400 MHz) δ: 7.39-7.40(d,1H), 7.43-7.45 (t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H), 8.61(s,1H), 8.63-8.65(d,1H), 13.71-13.75(d, 1H);

(385) 2-(2-quinolinyl)-1H-benzimidazole-4-(N—(N'-piperazinyl))amide $^1$HNMR (DMSO, 400 MHz) δ: 1.91-1.95(m,1H), 2.65-2.67(t,4H), 2.80-2.83(m,4H), 7.39-7.40(d,1H), 7.43-7.45(t, 1H), 7.60-7.62(t,1H), 7.78-7.79 (t,1H), 7.90-7.91(d,1H), 7.93-7.94(d,1H), 7.98-8.00(d,1H), 8.06-8.07(d,1H), 8.44-8.46(d,1H);

(386) 2-(2-quinolinyl)-1H-benzimidazole-4-(N-2-pyrazinyl)amide $^1$HNMR (DMSO, 400 MHz) δ: 7.39-7.40(d,1H), 7.43-7.45 (t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.34-8.35(d,1H), 8.36(s,1H), 8.40-8.42(d,1H), 8.44-8.46(d,1H);

(387) 2-(2-quinolinyl)-1H-benzimidazole-4-(N-2-pyrimidinyl)amide $^1$HNMR (DMSO, 400 MHz) δ: 6.93-6.95(t,1H), 7.39-7.40 (d,1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.40-8.43(d,1H), 8.45-8.46(d,2H);

(388) 2-(2-quinolinyl)-1H-benzimidazole-4-(N-2-pyridyl)amide $^1$HNMR (DMSO, 400 MHz) δ: 6.62-6.64(t,1H), 6.70-6.72 (d,1H), 7.39-7.40(d,1H), 7.43-7.45(t,1H), 7.55-7.57(t,1H), 7.60-7.62(t,1H), 7.78-7.79 (t,1H), 7.89-7.91(d,1H), 7.93-7.94(d,1H), 7.98-8.00(d,1H), 8.04-8.05(d,1H), 8.07-8.09(d, 1H), 8.44-8.46(d,1H);

(389) 2-(2-quinolinyl)-1H-benzimidazole-4-(N-4-methyl-5-thiazolyl)amide $^1$HNMR (DMSO, 400 MHz) δ: 2.45(s,3H), 7.39-7.40(d, 1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.12(s,1H), 8.44-8.46(d,1H);

(390) 2-(2-quinolinyl)-1H-benzimidazole-4-(N-2,4-dihydroxyl-5-pyrimidinyl)amide $^1$HNMR (DMSO, 400 MHz) δ: 7.39-7.40(d,1H), 7.43-7.45 (t,1H), 7.60-7.62(t,1H), 7.78-7.79 (t,1H), 7.89-7.91(d,1H), 7.82(s,1H), 7.93-7.94(d,1H), 7.98-8.00(d,1H), 8.06-8.07(d, 1H), 8.33(s,1H), 8.44-8.46(d,1H), 11.53(s,1H);

(391) 2-(2-quinolinyl)-1H-benzimidazole-4-(N-4,6-dimethoxy-2-pyrimidinyl)amide $^1$HNMR (DMSO, 400 MHz) δ: 3.82(s,6H), 5.71(s,1H), 7.39-7.40(d,1H), 7.43-7.45(t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H);

(392) 2-(2-quinolinyl)-1H-benzimidazole-4-(N-4-chloro-6-amino-2-pyrimidinyl)amide $^1$HNMR (DMSO, 400 MHz) δ: 5.98(s,1H), 7.39-7.40(d, 1H), 7.43-7.45(t,1H), 7.60-7.62(t,1H), 7.74(s,2H), 7.78-7.79 (t,1H), 7.89-7.91(d,1H), 7.93-7.94(d,1H), 7.98-8.00(d,1H), 8.06-8.07(d,1H), 8.44-8.46(d,1H);

(393) 2-(2-quinolinyl)-1H-benzimidazole-4-(N-4,6-dichloro-5-pyrimidinyl)amide $^1$HNMR (DMSO, 400 MHz) δ: 7.39-7.40(d,1H), 7.43-7.45 (t,1H), 7.60-7.62(t,1H), 7.78-7.79 (t,1H), 7.89-7.91(d,1H), 7.93-7.94(d,1H), 7.98-8.00(d,1H), 8.06-8.07(d,1H), 8.44-8.46(d,1H), 9.34(s,1H);

(394) 2-(2-quinolinyl)-1H-benzimidazole-4-(N-o-fluorophenyl)amide $^1$HNMR (DMSO, 400 MHz) δ: 6.60-6.61(d,1H), 6.63-6.65 (t,1H), 6.96-6.98(t,1H), 6.99-7.01(d,1H), 7.39-7.40(d,1H), 7.43-7.45(t,1H), 7.60-7.62(t,1H), 7.78-7.79 (t,1H), 7.89-7.91 (d,1H), 7.93-7.94(d,1H), 7.98-8.00(d,1H), 8.06-8.07(d,1H), 8.44-8.46(d,1H);

(395) 2-(2-quinolinyl)-1H-benzimidazole-4-(N-2-hydroxyl-4-pyrimidinyl)amide $^1$HNMR (DMSO, 400 MHz) δ: 5.46-5.48(d,1H), 7.10-7.11 (d,1H), 7.39-7.40(d,1H), 7.43-7.45(t,1H), 7.60-7.62(t,1H), 7.78-7.79 (t,1H), 7.82(s,1H), 7.89-7.91(d,1H), 7.93-7.94(d, 1H), 7.98-8.00(d,1H), 8.06-8.07(d,1H), 8.44-8.46(d,1H);

(396) 2-(2-quinolinyl)-1H-benzimidazole-4-(N-6-purinyl)amide $^1$HNMR (DMSO, 400 MHz) δ: 7.39-7.40(d,1H), 7.43-7.45(t,1H), 7.60-7.62(t,1H), 7.78-7.79 (t,1H), 7.86-7.88(d,1H), 7.89-7.91(d,1H), 7.93-7.94(d,1H), 7.98-8.00(d,1H), 8.06-8.07(d,1H), 8.16-8.18(d,1H), 8.44-8.46(d,1H);

(397) 2-(2-quinolinyl)-1H-benzimidazole-4-(N-6-hydroxyl-2-purinyl)amide $^1$HNMR (DMSO, 400 MHz) δ: 7.39-7.40(d,1H), 7.43-7.45(t,1H), 7.60-7.62(t,1H), 7.78-7.79 (t,1H), 7.89-7.91(d,1H), 7.93-7.94(d,1H), 8.57-8.59(d,1H), 7.98-8.00(d,1H), 8.06-8.07(d,1H), 8.44-8.46(d,1H), 11.53(s,1H);

(398) (L)-2-(3-quinolinyl)-1H-benzimidazole-4-[N-(1-hydroxymethyl-2-p-nitrophenylhydroxyethyl)] amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.59-7.60(t,1H), 7.62-7.65(d,2H), 7.77-7.79(t,1H), 7.89-7.90(d,1H), 7.93-7.95(d,1H), 7.98-8.00(d,1H), 8.06-8.08(d,1H), 8.17-8.20(d,2H), 8.22(s,1H), 8.57(s,1H);

(399) (L)-2-(3-quinolinyl)-1H-benzimidazole-4-[N-(1-hydroxymethyl-2-p-aminophenylhydroxyethyl)] amide $^1$HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.60-7.62(t,1H), 7.77-7.79(t,1H), 7.89-7.90(d,1H), 7.93-7.95(d,1H), 7.98-8.00(d,1H), 8.06-8.08(d,1H), 8.22(s,1H), 8.57(s,1H);

(400) 2-(3-quinolinyl)-1H-benzimidazole-4-(N-2-piperazinyl)amide $^1$HNMR (DMSO, 400 MHz) δ: 1.91-1.93(m,2H), 2.62-2.36(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.60-7.62(t,1H), 7.89-7.91(d,1H), 7.93-7.94(d,1H), 7.98-8.00(d,1H), 8.06-8.08(d,1H), 8.22(s,1H), 8.57(s,1H);

(401) 2-(3-quinolinyl)-1H-benzimidazole-4-(N-2-pyrimidinyl)amide $^1$HNMR (DMSO, 400 MHz) δ: 6.93-6.95(t,1H), 7.43-7.45(t,1H), 7.60-7.62(t,1H), 7.77-7.79(t,1H), 7.89-7.91(d,1H), 7.93-7.94(d,1H), 7.98-8.00(d,1H), 8.06-8.08(d,1H), 8.22(s,1H), 8.45-8.46(d,2H), 8.57(s,1H);

(402) (L)-2-(2-piperidinyl)-1H-benzimidazole-4-[N-(1-hydroxymethyl-2-p-nitrophenylhydroxyethyl)] amide $^1$HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 3.17-3.18(m,1H), 3.25-3.28(m,1H), 3.50-3.52(m,1H), 3.65-3.68(t,1H), 3.70-3.72(d,1H), 4.02-4.05(m,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(403) (L)-2-(2-piperidinyl)-1H-benzimidazole-4-[N-(1-hydroxymethyl-2-p-aminophenylhydroxyethyl)] amide $^1$HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 3.17-3.18(m,1H), 3.25-3.28(m,1H), 3.50-3.52(m,1H), 3.65-3.68(t,1H), 3.70-3.72(d,1H), 4.02-4.05(m,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(404) 2-(2-piperidinyl)-1H-benzimidazole-4-[N-(1-methyl-2-p-chlorophenylhydroxyethyl)]amide $^1$HNMR (DMSO, 400 MHz) δ: 1.12-1.15(d,3H), 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 3.25-3.28(m,1H), 3.65-3.68(t,1H), 4.02-4.05(m,1H), 4.73-4.77(t,1H), 7.29-7.30(d,2H), 7.40-7.41(d,2H), 7.43-7.45(t,1H), 7.89-7.91(d,1H), 7.93-7.94(d,1H);

(405) 2-(2-piperidinyl)-1H-benzimidazole-4-(N—N'-piperidinyl)amide $^1$HNMR (DMSO, 400 MHz) δ: 1.43-1.45(m,1H), 1.47-1.48(m,1H), 1.50-1.51(m,1H), 1.53-1.55(m,4H), 1.55-1.57(m,1H), 1.59-1.63(m,2H), 1.67-1.69(m,1H), 1.92-1.95(m,1H), 2.69-2.72(m,1H), 2.79-2.81(m,1H), 3.10-3.15(t,4H), 4.02-4.05(m,1H), 7.43-7.45(t,1H), 7.89-7.91(d,1H), 7.93-7.94(d,1H);

(406) 2-(2-piperidinyl)-1H-benzimidazole-4-(N-2-piperazinyl)amide $^1$HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.87-1.88(m,1H), 1.91-1.93(m,2H), 2.62-2.63(m,1H), 2.65-2.66(m,1H), 2.69-2.70(m,1H), 2.72-2.73(m,1H), 2.75-2.76(m,1H), 2.77-2.80(m,1H), 2.82-2.85(m,1H), 3.02-3.05(m,1H), 3.99-4.01(m,1H), 4.03-4.05(m,1H), 7.43-7.45(t,1H), 7.89-7.91(d,1H), 7.93-7.94(d,1H);

(407) 2-(2-piperidinyl)-1H-benzimidazole-4-(N-2'-benzimidazolyl)amide $^1$HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.12-7.15(d,2H), 7.22-7.24(t,2H), 7.43-7.45(t,1H), 7.89-7.91(d,1H), 7.93-7.94(d,1H);

(408) 2-(2-piperidinyl)-1H-benzimidazole-4-(N-o-aminophenyl)amide $^1$HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H);

(409) 2-(2-piperidinyl)-1H-benzimidazole-4-(N-5-benzimidazolonyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 6.35-6.37(d,1H), 6.93(s,1H), 7.43-7.45(t,1H), 7.54-7.56(d,1H), 7.89-7.91(d,1H), 7.93-7.94(d,1H);

(410) 2-(2-piperidinyl)-1H-benzimidazole-4-(N-4'-carbonamido-5'-imidazolyl)amide ¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.93-7.94(d,1H), 8.37(s,2H), 9.24-9.26(d,1H), 13.00-13.03(d,1H);

(411) 2-(2-piperidinyl)-1H-benzimidazole-4-(N-4'-pyrazolyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.93-7.94(d,1H), 8.61(s,1H), 8.63-8.65(d,1H), 13.71-13.75(d,1H);

(412) 2-(2-piperidinyl)-1H-benzimidazole-4-(N—(N'-piperazinyl))amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.84-1.89(m,1H), 1.91-1.95(m,1H), 2.65-2.67(t,4H), 2.69-2.72(m,1H), 2.79-2.81(m,1H), 2.84-2.85(m,4H), 4.02-4.05(m,1H), 7.43-7.45(t,1H), 7.90-7.91(d,1H), 7.93-7.94(d,1H);

(413) 2-(2-piperidinyl)-1H-benzimidazole-4-(N-2-pyrazinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.93-7.94(d,1H), 8.34-8.35(d,1H), 8.36(s,1H), 8.40-8.42(d,1H);

(414) 2-(2-piperidinyl)-1H-benzimidazole-4-(N-2-pyrimidinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 6.93-6.95(t,1H), 7.43-7.45(t,1H), 7.89-7.91(d,1H), 7.93-7.94(d,1H), 8.45-8.46(d,2H);

(415) 2-(2-piperidinyl)-1H-benzimidazole-4-(N-2-pyridyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H);

(416) 2-(2-piperidinyl)-1H-benzimidazole-4-(N-4-methyl-5-thiazolyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.45(s,3H), 2.69-2.72(m,1H), 2.79-2.81(m,1H), 4.02-4.05(m,1H), 7.43-7.45(t,1H), 7.89-7.91(d,1H), 7.93-7.94(d,1H), 8.12(s,1H);

(417) 2-(2-piperidinyl)-1H-benzimidazole-4-(N-2,4-dihydroxyl-5-pyrimidinyl)amide ¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.82(s,1H), 7.93-7.94(d,1H), 8.33(s,1H), 11.53(s,1H);

(418) 2-(2-piperidinyl)-1H-benzimidazole-4-(N-4,6-dimethoxy-2-pyrimidinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 3.82(s,6H), 4.02-4.05(m,1H), 5.71(s,1H), 7.43-7.45(t,1H), 7.89-7.91(d,1H), 7.93-7.94(d,1H);

(419) 2-(2-piperidinyl)-1H-benzimidazole-4-(N-4-chloro-6-amino-2-pyrimidinyl)amide ¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 5.98(s,1H), 7.43-7.45(t,1H), 7.74(s,2H), 7.89-7.91(d,1H), 7.93-7.94(d,1H);

(420) 2-(2-piperidinyl)-1H-benzimidazole-4-(N-4,6-dichloro-5-pyrimidinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.93-7.94(d,1H), 9.34(s,1H);

(421) 2-(2-piperidinyl)-1H-benzimidazole-4-(N-o-fluorophenyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H);

(422) 2-(2-piperidinyl)-1H-benzimidazole-4-(N-2-hydroxyl-4-pyrimidinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,

(423) 2-(2-piperidinyl)-1H-benzimidazole-4-(N-6-purinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.86-7.88(d,1H), 7.89-7.91(d,1H), 7.93-7.94(d,1H), 8.16-8.18(d,1H);

(424) 2-(2-piperidinyl)-1H-benzimidazole-4-(N-6-hydroxyl-2-purinyl)amide

¹HNMR (DMSO, 400 MHz) δ: 1.43-1.45(m,1H), 1.47-1.48(m,1H), 1.50-1.52(m,1H), 1.55-1.57(m,1H), 1.67-1.69(m,1H), 1.92-1.95(m,1H), 2.69-2.72(m,1H), 2.79-2.81(m,1H), 4.02-4.05(m,1H), 7.43-7.45(t,1H), 7.89-7.91(d,1H), 7.93-7.94(d,1H), 8.57-8.59(d,1H), 11.53(s,1H);

(425) (L)-2-(3-piperidinyl)-1H-benzimidazole-4-[N-(1-hydroxymethyl-2-p-nitrophenylhydroxyethyl)]amide ¹HNMR (DMSO, 400 MHz) δ: 1.43-1.45(m,1H), 1.53-1.55(m,1H), 1.67-1.69(m,1H), 1.92-1.95(m,1H), 2.71-2.73(m,1H), 2.74-7.76(m,1H), 2.78-2.80(m,1H), 2.90-2.92(t,1H), 3.12-3.15(t,1H), 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(426) (L)-2-(3-piperidinyl)-1H-benzimidazole-4-[N-(1-hydroxymethyl-2-p-aminophenylhydroxyethyl)]amide ¹HNMR (DMSO, 400 MHz) δ: 1.43-1.45(m,1H), 1.53-1.55(m,1H), 1.67-1.69(m,1H), 1.92-1.95(m,1H), 2.71-2.73(m,1H), 2.74-7.76(m,1H), 2.78-2.80(m,1H), 2.90-2.92(t,1H), 3.12-3.15(t,1H), 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(427) 2-(3-piperidinyl)-1H-benzimidazole-4-(N-2-piperazinyl)amide

¹HNMR (DMSO, 400 MHz) δ: 1.43-1.45(m,1H), 1.53-1.55(m,1H), 1.67-1.69(m,1H), 1.89-1.90(m,2H), 1.92-1.95(m,1H), 2.62-2.36(m,1H), 2.65-2.66(m,1H), 2.69-2.70(m,1H), 2.69-2.70(m,1H), 2.71-2.72(m,1H), 2.74-7.76(m,1H), 2.77-2.80(m,1H), 2.82-2.84(m,1H), 2.90-2.92(t,1H), 3.02-3.05(m,1H), 3.15-3.17(t,1H), 3.99-4.01(m,1H), 7.43-7.45(t,1H), 7.89-7.91(d,1H), 7.93-7.94(d,1H);

(428) 2-(3-piperidinyl)-1H-benzimidazole-4-(N-2-pyrimidinyl)amide

¹HNMR (DMSO, 400 MHz) δ: 1.43-1.45(m,1H), 1.53-1.55(m,1H), 1.67-1.69(m,1H), 1.92-1.95(m,1H), 2.71-2.73(m,1H), 2.74-7.76(m,1H), 2.78-2.80(m,1H), 2.90-2.92(t,1H), 3.15-3.17(t,1H), 6.93-6.95(t,1H), 7.43-7.45(t,1H), 7.89-7.91(d,1H), 7.93-7.94(d,1H), 8.45-8.46(d,2H);

(429) (L)-2-(4-piperidinyl)-1H-benzimidazole-4-[N-(1-hydroxymethyl-2-p-nitrophenylhydroxyethyl)]amide ¹HNMR (DMSO, 400 MHz) δ: 1.67-1.69(m,2H), 1.92-1.95(m,2H), 2.69-2.71(m,2H), 2.78-2.80(m,1H), 2.82-2.83(m,2H), 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H);

(430) (L)-2-(4-piperidinyl)-1H-benzimidazole-4-[N-(1-hydroxymethyl-2-p-aminophenylhydroxyethyl)]amide ¹HNMR (DMSO, 400 MHz) δ: 1.67-1.69(m,2H), 1.92-1.95(m,2H), 2.69-2.71(m,2H), 2.78-2.80(m,1H), 2.82-2.83(m,2H), 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H);

(431) 2-(4-piperidinyl)-1H-benzimidazole-4-(N-2-piperazinyl)amide

¹HNMR (DMSO, 400 MHz) δ: 1.67-1.69(m,2H), 1.89-1.90(m,2H), 1.92-1.95(m,2H), 2.62-2.36(m,1H), 2.65-2.66(m,1H), 2.67-2.68(m,1H), 2.69-2.71(m,2H), 2.72-2.74(m,1H), 2.75-2.76(m,1H), 2.78-2.80(m,1H), 2.82-2.83(m,2H), 3.02-3.05(m,1H), 3.99-4.01(m,1H), 7.43-7.45(t,1H), 7.89-7.91(d,1H), 7.93-7.94(d,1H);

(432) 2-(4-piperidinyl)-1H-benzimidazole-4-(N-2-pyrimidinyl)amide

¹HNMR (DMSO, 400 MHz) δ: 1.67-1.69(m,2H), 1.92-1.95(m,2H), 2.69-2.71(m,2H), 2.78-2.80(m,1H), 2.82-2.83(m,2H), 6.93-6.95(t,1H), 7.43-7.45(t,1H), 7.89-7.91(d,1H), 7.93-7.94(d,1H), 8.45-8.46(d,2H);

(433) (L)-2-(3-indolyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.01-7.04(t,1H), 7.31-7.33(t,1H), 7.43-7.45(t,1H), 7.54-7.56(d,1H), 7.62-7.65(d,2H), 7.89-7.90(d,1H), 7.93-7.95(d,1H), 8.14-8.16(d,1H), 8.17-8.20(d,2H), 8.60-8.62(d,1H);

(434) (L)-2-(3-indolyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.01-7.04(t,1H), 7.11-7.13(d,2H), 7.31-7.33(t,1H), 7.43-7.45(t,1H), 7.54-7.56(d,1H), 7.89-7.90(d,1H), 7.93-7.95(d,1H), 8.14-8.16(d,1H), 8.60-8.62(d,1H);

(435) 2-(3-indolyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.01-7.04(t,1H), 7.29-7.30(d,2H), 7.31-7.33(t,1H), 7.40-7.41(d,2H), 7.43-

7.45(t,1H), 7.54-7.56(d,1H), 7.89-7.91(d,1H), 7.93-7.94(d,1H), 8.14-8.16(d,1H), 8.60-8.62(d,1H);

(436) 2-(3-indolyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(437) 2-(3-indolyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(438) 2-(3-indolyl)-1H-benzimidazole-4-(N-2'-benzimidazolyl)amide

¹HNMR (DMSO, 400 MHz) δ: 7.01-7.04(t,1H), 7.12-7.15(d,2H), 7.22-7.24(t,2H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(439) 2-(3-indolyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.06-7.08(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(440) 2-(3-indolyl)-1H-benzimidazole-4-(N-5-benzimidazolonyl)amide

¹HNMR (DMSO, 400 MHz) δ: 6.35-6.37(d,1H), 6.93(s,1H), 7.01-7.04(t,1H), 7.31-7.33(t,1H), 7.43-7.45(t,1H), 7.50-7.52(d,1H), 7.54-7.56(d,1H), 7.89-7.91(d,1H), 7.93-7.94(d,1H), 8.14-8.16(d,1H), 8.60-8.62(d,1H);

(441) 2-(3-indolyl)-1H-benzimidazole-4-(N-4'-carbonamido-5'-imidazolyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H), 8.37(s,2H), 9.24-9.26(d,1H), 13.00-13.03(d,1H);

(442) 2-(3-indolyl)-1H-benzimidazole-4-(N-4'-pyrazolyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.57-8.59(d,1H), 8.61(s,1H), 8.63-8.65(d,1H), 13.71-13.75(d,1H);

(443) 2-(3-indolyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.01-7.04(t,1H), 7.31-7.33(t,1H), 7.43-7.45(t,1H), 7.54-7.56(d,1H), 7.90-7.91(d,1H), 7.93-7.94(d,1H), 8.14-8.16(d,1H), 8.60-8.62(d,1H);

(444) 2-(3-indolyl)-1H-benzimidazole-4-(N-2-pyrazinyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.34-8.35(d,1H), 8.36(s,1H), 8.40-8.42(d,1H), 8.60-8.62(d,1H);

(445) 2-(3-indolyl)-1H-benzimidazole-4-(N-2-pyrimidinyl)amide

¹HNMR (DMSO, 400 MHz) δ: 6.93-6.95(t,1H), 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.45-8.46(d,2H), 8.60-8.62(d,1H);

(446) 2-(3-indolyl)-1H-benzimidazole-4-(N-2-pyridyl)amide

¹HNMR (DMSO, 400 MHz) δ: 6.62-6.64(t,1H), 6.70-6.72(d,1H), 7.01-7.04(t,1H), 7.31-7.33(t,1H), 7.43-7.45(t,1H), 7.54-7.56(d,1H), 7.57-7.58(t,1H), 7.89-7.91(d,1H), 7.93-7.94(d,1H), 8.07-8.09(d,1H), 8.14-8.16(d,1H), 8.60-8.62(d,1H);

(447) 2-(3-indolyl)-1H-benzimidazole-4-(N-4-methyl-5-thiazolyl)amide

¹HNMR (DMSO, 400 MHz) δ: 2.45(s,3H), 7.01-7.04(t,1H), 7.31-7.33(t,1H), 7.43-7.45(t,1H), 7.54-7.56(d,1H), 7.89-7.91(d,1H), 7.93-7.94(d,1H), 8.12(s,1H), 8.14-8.16(d,1H), 8.60-8.62(d,1H);

(448) 2-(3-indolyl)-1H-benzimidazole-4-(N-2,4-dihydroxyl-5-pyrimidinyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.82(s,1H), 7.93-7.94(d,1H), 8.14-8.16(d,1H), 8.33(s,1H), 8.60-8.62(d,1H), 11.53(s,1H);

(449) 2-(3-indolyl)-1H-benzimidazole-4-(N-4,6-dimethoxy-2-pyrimidinyl)amide

¹HNMR (DMSO, 400 MHz) δ: 3.82(s,6H), 5.71(s,1H), 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(450) 2-(3-indolyl)-1H-benzimidazole-4-(N-4-chloro-6-amino-2-pyrimidinyl)amide

¹HNMR (DMSO, 400 MHz) δ: 5.98(s,1H), 7.01-7.04(t,1H), 7.31-7.33(t,1H), 7.43-7.45(t,1H), 7.54-7.56(d,1H), 7.74(s,2H), 7.89-7.91(d,1H), 7.93-7.94(d,1H), 8.14-8.16(d,1H), 8.60-8.62(d,1H);

(451) 2-(3-indolyl)-1H-benzimidazole-4-(N-4,6-dichloro-5-pyrimidinyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H), 9.34(s,1H);

(452) 2-(3-indolyl)-1H-benzimidazole-4-(N-o-fluorophenyl)amide

¹HNMR (DMSO, 400 MHz) δ: 6.60-6.61(d,1H), 6.63-6.65(t,1H), 6.96-6.98(t,1H), 6.99-7.01(d,1H), 7.02-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.60-8.62(d,1H);

(453) 2-(3-indolyl)-1H-benzimidazole-4-(N-2-hydroxyl-4-pyrimidinyl)amide

¹HNMR (DMSO, 400 MHz) δ: 5.46-5.48(d,1H), 7.01-7.04(t,1H), 7.10-7.11(d,1H), 7.31-7.33(t,1H), 7.43-7.45(t,1H), 7.54-7.56(d,1H), 7.82(s,1H), 7.89-7.91(d,1H), 7.93-7.94(d,1H), 8.14-8.16(d,1H), 8.60-8.62(d,1H);

(454) 2-(3-indolyl)-1H-benzimidazole-4-(N-6-purinyl)amide

¹HNMR (DMSO, 400 MHz) δ: 7.01-7.04(t,1H), 7.31-7.33(t,1H), 7.43-7.45(t,1H), 7.54-7.56(d,1H), 7.86-7.88(d,1H), 7.89-7.91(d,1H), 7.93-7.94(d,1H), 8.13-8.15(d,1H), 8.17-8.19(d,1H), 8.60-8.62(d,1H);

(455) 2-(3-indolyl)-1H-benzimidazole-4-(N-6-hydroxyl-2-purinyl)amide

¹HNMR (DMSO, 400 MHz) δ: 7.01-7.04(t,1H), 7.31-7.33(t,1H), 7.43-7.45(t,1H), 7.54-7.56(d,1H), 7.89-7.91(d,1H), 7.93-7.94(d,1H), 8.14-8.16(d,1H), 8.57-8.59(d,1H), 8.60-8.62(d,1H), 11.53(s,1H);

(456) (L)-2-(2'-imidazolyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.00-7.01(d,1H), 7.02-7.04(t,1H), 7.43-7.45(t,1H), 7.62-7.65(d,2H), 7.89-7.90(d,1H), 7.93-7.95(d,1H), 8.17-8.20(d,2H), 13.00-13.03(d,1H);

(457) (L)-2-(2'-imidazolyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.00-7.01(d,1H), 7.02-7.04(t,1H), 7.11-7.13(d,2H), 7.43-7.45(t,1H), 7.89-7.90(d,1H), 7.93-7.95(d,1H), 13.00-13.03(d,1H);

(458) 2-(2'-imidazolyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.00-7.01(d,1H), 7.02-7.04(t,1H), 7.29-7.30(d,2H), 7.40-7.41(d,2H), 7.43-7.45(t,1H), 7.89-7.91(d,1H), 7.93-7.94(d,1H), 13.00-13.03(d,1H);

(459) 2-(2'-imidazolyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.00-7.01(d,1H), 7.02-7.04(t,1H), 7.43-7.45(t,1H), 7.89-7.91(d,1H), 7.93-7.94(d,1H), 13.00-13.03(d,1H);

(460) 2-(2-imidazolyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.00-7.01(d,1H), 7.02-7.04(t,1H), 7.43-7.45(t,1H), 7.89-7.91(d,1H), 7.93-7.94(d,1H), 13.00-13.03(d,1H);

(461) 2-(2-imidazolyl)-1H-benzimidazole-4-(N-2'-benzimidazolyl)amide

¹HNMR (DMSO, 400 MHz) δ: 7.00-7.01(d,1H), 7.02-7.04(t,1H), 7.12-7.15(d,2H), 7.22-7.24(t,2H), 7.43-7.45(t,1H), 7.89-7.91(d,1H), 7.93-7.94(d,1H), 13.00-13.03(d,1H);

(462) 2-(2-imidazolyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.00-7.01(d,1H), 7.02-7.04(t,1H), 7.05-7.08(t,1H), 7.43-7.45(t,1H), 7.89-7.91(d,1H), 7.93-7.94(d,1H), 13.00-13.03(d,1H);

(463) 2-(2-imidazolyl)-1H-benzimidazole-4-(N-5-benzimidazolonyl)amide

¹HNMR (DMSO, 400 MHz) δ: 6.35-6.37(d,1H), 6.93(s,1H), 7.00-7.01(d,1H), 7.02-7.04(t,1H), 7.43-7.45(t,1H), 7.54-7.56(d,1H), 7.89-7.91(d,1H), 7.93-7.94(d,1H), 13.00-13.03(d,1H);

(464) 2-(2-imidazolyl)-1H-benzimidazole-4-(N-4'-carbonamido-5-imidazolyl)amide

¹HNMR (DMSO, 400 MHz) δ: 7.00-7.01(d,1H), 7.02-7.04(t,1H), 7.43-7.45(t,1H), 7.89-7.91(d,1H), 7.93-7.94(d,1H), 8.37(s,2H), 9.24-9.26(d,1H), 13.00-13.03(d,1H), 13.05-13.07(d,1H);

(465) 2-(2-imidazolyl)-1H-benzimidazole-4-(N-4'-pyrazolyl)amide

¹HNMR (DMSO, 400 MHz) δ: 7.00-7.01(d,1H), 7.02-7.04(t,1H), 7.43-7.45(t,1H), 7.89-7.91(d,1H), 7.93-7.94(d,1H), 8.61(s,1H), 8.63-8.65(d,1H), 13.00-13.03(d,1H), 13.71-13.75(d,1H);

(466) 2-(2-imidazolyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.00-7.01(d,1H), 7.02-7.04(t,1H), 7.43-7.45(t,1H), 7.90-7.91(d,1H), 7.93-7.94(d,1H), 13.00-13.03(d,1H);

(467) 2-(2-imidazolyl)-1H-benzimidazole-4-(N-2-pyrazinyl)amide

¹HNMR (DMSO, 400 MHz) δ: 7.00-7.01(d,1H), 7.02-7.04(t,1H), 7.43-7.45(t,1H), 7.89-7.91(d,1H), 7.93-7.94(d,1H), 8.34-8.35(d,1H), 8.36(s,1H), 8.40-8.42(d,1H), 13.00-13.03(d,1H);

(468) 2-(2-imidazolyl)-1H-benzimidazole-4-(N-2-pyrimidinyl)amide

¹HNMR (DMSO, 400 MHz) δ: 6.93-6.95(t,1H), 7.00-7.01(d,1H), 7.02-7.04(t,1H), 7.43-7.45(t,1H), 7.89-7.91(d,1H), 7.93-7.94(d,1H), 8.45-8.46(d,2H), 13.00-13.03(d,1H);

(469) 2-(2-imidazolyl)-1H-benzimidazole-4-(N-2-pyridyl)amide

¹HNMR (DMSO, 400 MHz) δ: 6.62-6.64(t,1H), 6.70-6.72(d,1H), 7.00-7.01(d,1H), 7.02-7.04(t,1H), 7.43-7.45(t,1H), 7.55-7.57(t,1H), 7.89-7.91(d,1H), 7.93-7.94(d,1H), 8.07-8.09(d,1H), 13.00-13.03(d,1H);

(470) 2-(2-imidazolyl)-1H-benzimidazole-4-(N-4-methyl-5-thiazolyl)amide

¹HNMR (DMSO, 400 MHz) δ: 2.45(s,3H), 7.00-7.01(d,1H), 7.02-7.04(t,1H), 7.43-7.45(t,1H), 7.89-7.91(d,1H), 7.93-7.94(d,1H), 8.12(s,1H), 13.00-13.03(d,1H);

(471) 2-(2-imidazolyl)-1H-benzimidazole-4-(N-2,4-dihydroxyl-5-pyrimidinyl)amide

¹HNMR (DMSO, 400 MHz) δ: 7.00-7.01(d,1H), 7.02-7.04(t,1H), 7.43-7.45(t,1H), 7.89-7.91(d,1H), 7.82(s,1H), 7.93-7.94(d,1H), 8.33(s,1H), 11.53(s,1H), 13.00-13.03(d,1H);

(472) 2-(2-imidazolyl)-1H-benzimidazole-4-(N-4,6-dimethoxy-2-pyrimidinyl)amide

¹HNMR (DMSO, 400 MHz) δ: 3.82(s,6H), 5.71(s,1H), 7.00-7.01(d,1H), 7.02-7.04(t,1H), 7.43-7.45(t,1H), 7.89-7.91(d,1H), 7.93-7.94(d,1H), 13.00-13.03(d,1H);

(473) 2-(2-imidazolyl)-1H-benzimidazole-4-(N-4-chloro-6-amino-2-pyrimidinyl)amide ¹HNMR (DMSO, 400 MHz) δ: 5.98(s,1H), 7.00-7.01(d,1H), 7.02-7.04(t,1H), 7.43-7.45(t,1H), 7.74(s,2H), 7.89-7.91(d,1H), 7.93-7.94(d,1H), 13.00-13.03(d,1H);

(474) 2-(2-imidazolyl)-1H-benzimidazole-4-(N-4,6-dichloro-5-pyrimidinyl)amide

¹HNMR (DMSO, 400 MHz) δ: 7.00-7.01(d,1H), 7.02-7.04(t,1H), 7.43-7.45(t,1H), 7.89-7.91(d,1H), 7.93-7.94(d,1H), 9.34(s,1H), 13.00-13.03(d,1H);

(475) 2-(2-imidazolyl)-1H-benzimidazole-4-(N-o-fluorophenyl)amide

¹HNMR (DMSO, 400 MHz) δ: 6.60-6.61(d,1H), 6.63-6.65(t,1H), 6.95-6.96(t,1H), 6.97-6.99(d,1H), 7.00-7.01(d,1H), 7.02-7.04(t,1H), 7.43-7.45(t,1H), 7.89-7.91(d,1H), 7.93-7.94(d,1H), 13.00-13.03(d,1H);

(476) 2-(2-imidazolyl)-1H-benzimidazole-4-(N-2-hydroxyl-4-pyrimidinyl)amide

¹HNMR (DMSO, 400 MHz) δ: 5.46-5.48(d,1H), 7.00-7.01(d,1H), 7.02-7.04(t,1H), 7.10-7.11(d,1H), 7.43-7.45(t,1H), 7.82(s,1H), 7.89-7.91(d,1H), 7.93-7.94(d,1H), 13.00-13.03(d,1H);

(477) 2-(2-imidazolyl)-1H-benzimidazole-4-(N-6-purinyl)amide

¹HNMR (DMSO, 400 MHz) δ: 7.00-7.01(d,1H), 7.02-7.04(t,1H), 7.43-7.45(t,1H), 7.86-7.88(d,1H), 7.89-7.91(d,1H), 7.93-7.94(d,1H), 8.16-8.18(d,1H), 13.00-13.03(d,1H);

(478) 2-(2-imidazolyl)-1H-benzimidazole-4-(N-6-hydroxyl-2-purinyl)amide

¹HNMR (DMSO, 400 MHz) δ: 7.00-7.01(d,1H), 7.02-7.04(t,1H), 7.43-7.45(t,1H), 7.89-7.91(d,1H), 7.93-7.94(d,1H), 8.57-8.59(d,1H), 11.53(s,1H), 13.00-13.03(d,1H);

(479) (L)-2-(3-pyrazolyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.48-6.50(d,1H), 7.43-7.45(t,1H), 7.62-7.65(d,2H), 7.85-7.87(t,1H), 7.89-7.90(d,1H), 7.93-7.95(d,1H), 8.17-8.20(d,2H), 12.62-12.64(d,1H);

(480) (L)-2-(3-pyrazolyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.48-6.50(d,1H), 6.56-6.58(d,2H), 7.11-7.13(d,2H), 7.43-7.45(t,1H), 7.85-7.87(t,1H), 7.89-7.90(d,1H), 7.93-7.95(d,1H), 12.62-12.64(d,1H);

(481) 2-(3-pyrazolyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 6.48-6.50(d,1H), 7.29-7.30(d,2H), 7.40-7.41(d,2H), 7.43-7.45(t,1H), 7.85-7.87(t,1H), 7.89-7.91(d,1H), 7.93-7.94(d,1H), 12.62-12.64(d,1H);

(482) 2-(3-pyrazolyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 6.48-6.50(d,1H), 7.43-7.45(t,1H), 7.85-7.87(t,1H), 7.89-7.91(d,1H), 7.93-7.94(d,1H), 12.62-12.64(d,1H);

(483) 2-(3-pyrazolyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 6.48-6.50(d,1H), 7.43-7.45(t,1H), 7.85-7.87(t,1H), 7.89-7.91(d,1H), 7.93-7.94(d,1H), 12.62-12.64(d,1H);

(484) 2-(3-pyrazolyl)-1H-benzimidazole-4-(N-2'-benzimidazolyl)amide

¹HNMR (DMSO, 400 MHz) δ: 6.48-6.50(d,1H), 7.12-7.15(d,2H), 7.22-7.24(t,2H), 7.43-7.45(t,1H), 7.85-7.87(t,1H), 7.89-7.91(d,1H), 7.93-7.94(d,1H), 12.62-12.64(d,1H);

(485) 2-(3-pyrazolyl)-1H-benzimidazole-4-(N-o-aminophenyl)amide

¹HNMR (DMSO, 400 MHz) δ: 6.27(s,2H), 6.38-6.40(d,1H), 6.48-6.50(d,1H), 6.56-6.58(t,1H), 6.75-6.76(d,1H), 7.02-7.04(t,1H), 7.43-7.45(t,1H), 7.85-7.87(t,1H), 7.89-7.91(d,1H), 7.93-7.94(d,1H), 12.62-12.64(d,1H);

(486) 2-(3-pyrazolyl)-1H-benzimidazole-4-(N-5-benzimidazolonyl)amide

¹HNMR (DMSO, 400 MHz) δ: 6.35-6.37(d,1H), 6.48-6.50(d,1H), 6.93(s,1H), 7.43-7.45(t,1H), 7.54-7.56(d,1H), 7.85-7.87(t,1H), 7.89-7.91(d,1H), 7.93-7.94(d,1H), 12.62-12.64(d,1H);

(487) 2-(3-pyrazolyl)-1H-benzimidazole-4-(N-4'-carbonamido-5-imidazolyl)amide

¹HNMR (DMSO, 400 MHz) δ: 6.48-6.50(d,1H), 7.43-7.45(t,1H), 7.85-7.87(t,1H), 7.89-7.91(d,1H), 7.93-7.94(d,1H), 8.37(s,2H), 9.24-9.26(d,1H), 12.62-12.64(d,1H), 13.00-13.03(d,1H);

(488) 2-(3-pyrazolyl)-1H-benzimidazole-4-(N-4'-pyrazolyl)amide

¹HNMR (DMSO, 400 MHz) δ: 6.48-6.50(d,1H), 7.43-7.45(t,1H), 7.85-7.87(t,1H), 7.89-7.91(d,1H), 7.93-7.94(d,1H), 8.61(s,1H), 8.63-8.65(d,1H), 12.62-12.64(d,1H), 13.71-13.75(d,1H);

(489) 2-(3-pyrazolyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 6.48-6.50(d,1H), 7.43-7.45(t,1H), 7.85-7.87(t,1H), 7.90-7.91(d,1H), 7.93-7.94(d,1H), 12.62-12.64(d,1H);

(490) 2-(3-pyrazolyl)-1H-benzimidazole-4-(N-2-pyrazinyl)amide

¹HNMR (DMSO, 400 MHz) δ: 6.48-6.50(d,1H), 7.43-7.45(t,1H), 7.85-7.87(t,1H), 7.89-7.91(d,1H), 7.93-7.94(d,1H), 8.34-8.35(d,1H), 8.36(s,1H), 8.40-8.42(d,1H), 12.62-12.64(d,1H);

(491) 2-(3-pyrazolyl)-1H-benzimidazole-4-(N-2-pyrimidinyl)amide

¹HNMR (DMSO, 400 MHz) δ: 6.48-6.50(d,1H), 6.93-6.95(t,1H), 7.43-7.45(t,1H), 7.85-7.87(t,1H), 7.89-7.91(d,1H), 7.93-7.94(d,1H), 8.45-8.46(d,2H), 12.62-12.64(d,1H);

(492) 2-(3-pyrazolyl)-1H-benzimidazole-4-(N-2-pyridyl)amide

¹HNMR (DMSO, 400 MHz) δ: 6.48-6.50(d,1H), 6.62-6.64(t,1H), 6.70-6.72(d,1H), 7.43-7.45(t,1H), 7.55-7.57(t,1H), 7.85-7.87(t,1H), 7.89-7.91(d,1H), 7.93-7.94(d,1H), 8.07-8.09(d,1H), 12.62-12.64(d,1H);

(493) 2-(3-pyrazolyl)-1H-benzimidazole-4-(N-4-methyl-5-thiazolyl)amide

¹HNMR (DMSO, 400 MHz) δ: 2.45(s,3H), 6.48-6.50(d,1H), 7.43-7.45(t,1H), 7.85-7.87(t,1H), 7.89-7.91(d,1H), 7.93-7.94(d,1H), 8.12(s,1H), 12.62-12.64(d,1H);

(494) 2-(3-pyrazolyl)-1H-benzimidazole-4-(N-2,4-dihydroxyl-5-pyrimidinyl)amide

¹HNMR (DMSO, 400 MHz) δ: 6.48-6.50(d,1H), 7.43-7.45(t,1H), 7.89-7.91(d,1H), 7.82(s,1H), 7.85-7.87(t,1H), 7.93-7.94(d,1H), 8.33(s,1H), 11.53(s,1H), 12.62-12.64(d,1H);

(495) 2-(3-pyrazolyl)-1H-benzimidazole-4-(N-4,6-dimethoxy-2-pyrimidinyl)amide

¹HNMR (DMSO, 400 MHz) δ: 3.82(s,6H), 5.71(s,1H), 6.48-6.50(d,1H), 7.43-7.45(t,1H), 7.85-7.87(t,1H), 7.89-7.91(d,1H), 7.93-7.94(d,1H), 12.62-12.64(d,1H);

(496) 2-(3-pyrazolyl)-1H-benzimidazole-4-(N-4-chloro-6-amino-2-pyrimidinyl)amide ¹HNMR (DMSO, 400 MHz) δ: 5.98(s,1H), 6.48-6.50(d,1H), 7.43-7.45(t,1H), 7.74(s,2H), 7.85-7.87(t,1H), 7.89-7.91(d,1H), 7.93-7.94(d,1H), 12.62-12.64(d,1H);

(497) 2-(3-pyrazolyl)-1H-benzimidazole-4-(N-4,6-dichloro-5-pyrimidinyl)amide

¹HNMR (DMSO, 400 MHz) δ: 6.48-6.50(d,1H), 7.43-7.45(t,1H), 7.85-7.87(t,1H), 7.89-7.91(d,1H), 7.93-7.94(d,1H), 9.34(s,1H), 12.62-12.64(d,1H);

(498) 2-(3-pyrazolyl)-1H-benzimidazole-4-(N-o-fluorophenyl)amide

¹HNMR (DMSO, 400 MHz) δ: 6.48-6.50(d,1H), 6.60-6.61(d,1H), 6.63-6.65(t,1H), 6.96-6.98(t,1H), 6.99-7.01(d,1H), 7.43-7.45(t,1H), 7.85-7.87(t,1H), 7.89-7.91(d,1H), 7.93-7.94(d,1H), 12.62-12.64(d,1H);

(499) 2-(3-pyrazolyl)-1H-benzimidazole-4-(N-2-hydroxyl-4-pyrimidinyl)amide

¹HNMR (DMSO, 400 MHz) δ: 5.46-5.48(d,1H), 6.48-6.50(d,1H), 7.10-7.11(d,1H), 7.43-7.45(t,1H), 7.82(s,1H), 7.85-7.87(t,1H), 7.89-7.91(d,1H), 7.93-7.94(d,1H), 12.62-12.64(d,1H);

(500) 2-(3-pyrazolyl)-1H-benzimidazole-4-(N-6-purinyl)amide

¹HNMR (DMSO, 400 MHz) δ: 6.48-6.50(d,1H), 7.43-7.45(t,1H), 7.86-7.88(d,1H), 7.85-7.87(t,1H), 7.89-7.91(d,1H), 7.93-7.94(d,1H), 8.16-8.18(d,1H), 12.62-12.64(d,1H);

(501) 2-(3-pyrazolyl)-1H-benzimidazole-4-(N-6-hydroxyl-2-purinyl)amide

¹HNMR (DMSO, 400 MHz) δ: 6.48-6.50(d,1H), 7.43-7.45(t,1H), 7.85-7.87(t,1H), 7.89-7.91(d,1H), 7.93-7.94(d,1H), 8.57-8.59(d,1H), 11.53(s,1H), 12.62-12.64(d,1H);

(502) (L)-2-(2-pyrimidinyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d, 1H), 4.73-4.77(t,1H), 7.43-7.45(t,1H), 7.62-7.65(d,2H), 7.67-7.70(t,1H), 7.89-7.90(d,1H), 7.93-7.95(d,1H), 8.17-8.20(d,2H), 9.08-9.11(d,2H);

(503) (L)-2-(2-pyrimidinyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.67-7.70(t,1H), 7.11-7.13(d,2H), 7.43-7.45(t,1H), 7.89-7.90(d,1H), 7.93-7.95(d,1H), 9.08-9.11(d,2H);

(504) 2-(2-pyrimidinyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.29-7.30(d,2H), 7.40-7.41(d,2H), 7.43-7.45(t,1H), 7.67-7.70(t,1H), 7.89-7.91(d,1H), 7.93-7.94(d,1H), 9.08-9.11(d,2H);

(505) 2-(2-pyrimidinyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.43-7.45(t,1H), 7.67-7.70(t,1H), 7.89-7.91(d,1H), 7.93-7.94(d,1H), 9.08-9.11(d,2H);

(506) 2-(2-pyrimidinyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.67-7.70(t,1H), 7.89-7.91(d,1H), 7.93-7.94(d,1H), 9.08-9.11(d,2H);

(507) 2-(2-pyrimidinyl)-1H-benzimidazole-4-(N-2'-benzimidazolyl)amide

¹HNMR (DMSO, 400 MHz) δ: 7.12-7.15(d,2H), 7.22-7.24(t,2H), 7.43-7.45(t,1H), 7.67-7.70(t,1H), 7.89-7.91(d,1H), 7.93-7.94(d,1H), 9.08-9.11(d,2H);

(508) 2-(2-pyrimidinyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.43-7.45(t,1H), 7.67-7.70(t,1H), 7.89-7.91(d,1H), 7.93-7.94(d,1H), 9.08-9.11(d,2H);

(509) 2-(2-pyrimidinyl)-1H-benzimidazole-4-(N-5-benzimidazolonyl)amide

¹HNMR (DMSO, 400 MHz) δ: 6.35-6.37(d,1H), 6.93(s,1H), 7.43-7.45(t,1H), 7.54-7.56(d,1H), 7.67-7.70(t,1H), 7.89-7.91(d,1H), 7.93-7.94(d,1H), 9.08-9.11(d,2H);

(510) 2-(2-pyrimidinyl)-1H-benzimidazole-4-(N-4'-carbonamido-5'-imidazolyl)amide ¹HNMR (DMSO, 400 MHz) δ: 7.43-7.45(t,1H), 7.67-7.70(t,1H), 7.89-7.91(d,1H), 7.93-7.94(d,1H), 8.37(s,2H), 9.08-9.11(d,2H), 9.24-9.26(d,1H), 13.00-13.03(d,1H);

(511) 2-(2-pyrimidinyl)-1H-benzimidazole-4-(N-4'-pyrazolyl)amide

¹HNMR (DMSO, 400 MHz) δ: 7.43-7.45(t,1H), 7.67-7.70(t,1H), 7.89-7.91(d,1H), 7.93-7.94(d,1H), 8.61(s,1H), 8.63-8.65(d,1H), 9.08-9.11(d,2H), 13.71-13.75(d,1H);

(512) 2-(2-pyrimidinyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.43-7.45(t,1H), 7.67-7.70(t,1H), 7.90-7.91(d,1H), 7.93-7.94(d,1H), 9.08-9.11(d,2H);

(513) 2-(2-pyrimidinyl)-1H-benzimidazole-4-(N-2-pyrazinyl)amide

¹HNMR (DMSO, 400 MHz) δ: 7.43-7.45(t,1H), 7.67-7.70(t,1H), 7.89-7.91(d,1H), 7.93-7.94(d,1H), 8.34-8.35(d,1H), 8.36(s,1H), 8.40-8.42(d,1H), 9.08-9.11(d,2H);

(514) 2-(2-pyrimidinyl)-1H-benzimidazole-4-(N-2-pyrimidinyl)amide

¹HNMR (DMSO, 400 MHz) δ: 6.93-6.95(t,1H), 7.43-7.45(t,1H), 7.67-7.70(t,1H), 7.89-7.91(d,1H), 7.93-7.94(d,1H), 8.45-8.46(d,2H), 9.08-9.11(d,2H);

(515) 2-(2-pyrimidinyl)-1H-benzimidazole-4-(N-2-pyridyl)amide

¹HNMR (DMSO, 400 MHz) δ: 6.62-6.64(t,1H), 6.70-6.72(d,1H), 7.43-7.45(t,1H), 7.55-7.57(t,1H), 7.67-7.70(t,1H), 7.89-7.91(d,1H), 7.93-7.94(d,1H), 8.07-8.09(d,1H), 9.08-9.11(d,2H);

(516) 2-(2-pyrimidinyl)-1H-benzimidazole-4-(N-4-methyl-5-thiazolyl)amide

¹HNMR (DMSO, 400 MHz) δ: 2.45(s,3H), 7.43-7.45(t,1H), 7.67-7.70(t,1H), 7.89-7.91(d,1H), 7.93-7.94(d,1H), 8.12(s,1H), 9.08-9.11(d,2H);

(517) 2-(2-pyrimidinyl)-1H-benzimidazole-4-(N-2,4-dihydroxyl-5-pyrimidinyl)amide ¹HNMR (DMSO, 400 MHz) δ: 7.43-7.45(t,1H), 7.67-7.70(t,1H), 7.89-7.91(d,1H), 7.82(s,1H), 7.93-7.94(d,1H), 8.33(s,1H), 9.08-9.11(d,2H), 11.53(s,1H);

(518) 2-(2-pyrimidinyl)-1H-benzimidazole-4-(N-4,6-dimethoxy-2-pyrimidinyl)amide

¹HNMR (DMSO, 400 MHz) δ: 3.82(s,6H), 5.71(s,1H), 7.67-7.70(t,1H), 7.43-7.45(t,1H), 7.89-7.91(d,1H), 7.93-7.94(d,1H), 9.08-9.11(d,2H);

(519) 2-(2-pyrimidinyl)-1H-benzimidazole-4-(N-4-chloro-6-amino-2-pyrimidinyl)amide ¹HNMR (DMSO, 400 MHz) δ: 5.98(s,1H), 7.43-7.45(t,1H), 7.67-7.70(t,1H), 7.74(s,2H), 7.89-7.91(d,1H), 7.93-7.94(d,1H), 9.08-9.11(d,2H);

(520) 2-(2-pyrimidinyl)-1H-benzimidazole-4-(N-4,6-dichloro-5-pyrimidinyl)amide

¹HNMR (DMSO, 400 MHz) δ: 7.43-7.45(t,1H), 7.67-7.70(t,1H), 7.89-7.91(d,1H), 7.93-7.94(d,1H), 9.08-9.11(d,2H), 9.34(s,1H);

(521) 2-(2-pyrimidinyl)-1H-benzimidazole-4-(N-o-fluorophenyl)amide

¹HNMR (DMSO, 400 MHz) δ: 6.60-6.61(d,1H), 6.63-6.65(t,1H), 6.96-6.98(t,1H), 6.99-7.01(d,1H), 7.43-7.45(t,1H), 7.67-7.70(t,1H), 7.89-7.91(d,1H), 7.93-7.94(d,1H), 9.08-9.11(d,2H);

(522) 2-(2-pyrimidinyl)-1H-benzimidazole-4-(N-2-hydroxyl-4-pyrimidinyl)amide

¹HNMR (DMSO, 400 MHz) δ: 5.46-5.48(d,1H), 7.10-7.11(d,1H), 7.43-7.45(t,1H), 7.67-7.70(t,1H), 7.82(s,1H), 7.89-7.91(d,1H), 7.93-7.94(d,1H), 9.08-9.11(d,2H);

(523) 2-(2-pyrimidinyl)-1H-benzimidazole-4-(N-6-purinyl)amide

¹HNMR (DMSO, 400 MHz) δ: 7.43-7.45(t,1H), 7.67-7.70(t,1H), 7.86-7.88(d,1H), 7.89-7.91(d,1H), 7.93-7.94(d,1H), 8.16-8.18(d,1H), 9.08-9.11(d,2H);

(524) 2-(2-pyrimidinyl)-1H-benzimidazole-4-(N-6-hydroxyl-2-purinyl)amide

¹HNMR (DMSO, 400 MHz) δ: 7.43-7.45(t,1H), 7.67-7.70(t,1H), 7.89-7.91(d,1H), 7.93-7.94(d,1H), 8.57-8.59(d,1H), 9.08-9.11(d,2H), 11.53(s,1H);

(525) (L)-2-(2-phenyl-5-pyrimidinyl)-1H-benzimidazole-4-[N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.38-7.41(t,1H), 7.43-7.45(t,1H), 7.51-7.53(t,2H), 7.62-7.65(d,2H), 7.89-7.90(d,1H), 7.93-7.95(d,1H), 8.17-8.20(d,2H), 8.28-8.31(d,2H), 9.26(s,2H);

(526) (L)-2-(2-phenyl-5-pyrimidinyl)-1H-benzimidazole-4-[N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.38-7.41(t,1H), 7.43-7.45(t,1H), 7.51-7.53(t,2H), 7.89-7.90(d,1H), 7.93-7.95(d,1H), 8.28-8.31(d,2H), 9.26(s,2H);

(527) 2-(2-phenyl-5-pyrimidinyl)-1H-benzimidazole-4-[N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.29-7.30(d,2H), 7.38-7.39(t,1H), 7.40-7.41(d,2H), 7.43-7.45(t,1H), 7.51-7.53(t,2H), 7.89-7.91(d,1H), 7.93-7.94(d,1H), 8.28-8.31(d,2H), 9.26(s,2H);

(528) 2-(2-phenyl-5-pyrimidinyl)-1H-benzimidazole-4-(N—N'-piperidinyl)amide

¹HNMR (DMSO, 400 MHz) δ: 1.52-1.55(m,4H), 1.59-1.63(m,2H), 3.10-3.15(t,4H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(529) 2-(2-phenyl-5-pyrimidinyl)-1H-benzimidazole-4-(N-2-piperazinyl)amide

¹HNMR (DMSO, 400 MHz) δ: 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(530) 2-(2-phenyl-5-pyrimidinyl)-1H-benzimidazole-4-(N-2'-benzimidazolyl)amide

¹HNMR (DMSO, 400 MHz) δ: 7.12-7.15(d,2H), 7.22-7.24(t,2H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(531) 2-(2-phenyl-5-pyrimidinyl)-1H-benzimidazole-4-(N-o-aminophenyl)amide

¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(532) 2-(2-phenyl-5-pyrimidinyl)-1H-benzimidazole-4-(N-5-benzimidazolonyl)amide

¹HNMR (DMSO, 400 MHz) δ: 6.35-6.37(d,1H), 6.93(s,1H), 7.38-7.41(t,1H), 7.43-7.45(t,1H), 7.51-7.53(t,2H), 7.54-7.56(d,1H), 7.89-7.91(d,1H), 7.93-7.94(d,1H), 8.28-8.31(d,2H), 9.26(s,2H);

(533) 2-(2-phenyl-5-pyrimidinyl)-1H-benzimidazole-4-(N-4'-carbonamido-5'-imidazolyl)amide ¹HNMR (DMSO, 400 MHz) δ: 7.38-7.41(t,1H), 7.43-7.45(t,1H), 7.51-7.53(t,2H), 7.89-7.91(d,1H), 7.93-7.94(d,1H), 8.28-8.31(d,2H), 8.37(s,2H), 9.24-9.26(d,1H), 9.29(s,2H) 13.00-13.03(d,1H);

(534) 2-(2-phenyl-5-pyrimidinyl)-1H-benzimidazole-4-(N-4'-pyrazolyl)amide

¹HNMR (DMSO, 400 MHz) δ: 7.38-7.41(t,1H), 7.43-7.45(t,1H), 7.51-7.53(t,2H), 7.89-7.91(d,1H), 7.93-7.94(d,1H), 8.28-8.31(d,2H), 8.61(s,1H), 8.63-8.65(d,1H), 9.26(s,2H), 13.71-13.75(d,1H);

(535) 2-(2-phenyl-5-pyrimidinyl)-1H-benzimidazole-4-(N—(N'-piperazinyl))amide

¹HNMR (DMSO, 400 MHz) δ: 1.91-1.95(m,1H), 2.65-2.67(t,4H), 2.80-2.83(m,4H), 7.38-7.41(t,1H), 7.43-7.45(t,1H), 7.51-7.53(t,2H), 7.90-7.91(d,1H), 7.93-7.94(d,1H), 8.28-8.31(d,2H), 9.26(s,2H);

(536) 2-(2-phenyl-5-pyrimidinyl)-1H-benzimidazole-4-(N-2-pyrazinyl)amide

¹HNMR (DMSO, 400 MHz) δ: 7.38-7.41(t,1H), 7.43-7.45(t,1H), 7.51-7.53(t,2H), 7.89-7.91(d,1H), 7.93-7.94(d,1H), 8.28-8.31(d,2H), 8.34-8.35(d,1H), 8.36(s,1H), 8.40-8.42(d,1H), 9.26(s,2H);

(537) 2-(2-phenyl-5-pyrimidinyl)-1H-benzimidazole-4-(N-2-pyrimidinyl)amide

¹HNMR (DMSO, 400 MHz) δ: 6.93-6.95(t,1H), 7.38-7.41(t,1H), 7.43-7.45(t,1H), 7.51-7.53(t,2H), 7.89-7.91(d,1H), 7.93-7.94(d,1H), 8.28-8.31(d,2H), 8.45-8.46(d,2H), 9.26(s,2H);

(538) 2-(2-phenyl-5-pyrimidinyl)-1H-benzimidazole-4-(N-2-pyridyl)amide

¹HNMR (DMSO, 400 MHz) δ: 6.62-6.64(t,1H), 6.70-6.72(d,1H), 7.38-7.41(t,1H), 7.43-7.45(t,1H), 7.51-7.53(t,2H), 7.55-7.57(t,1H), 7.89-7.91(d,1H), 7.93-7.94(d,1H), 8.07-8.09(d,1H), 8.28-8.31(d,2H), 9.26(s,2H);

(539) 2-(2-phenyl-5-pyrimidinyl)-1H-benzimidazole-4-(N-4-methyl-5-thiazolyl)amide ¹HNMR (DMSO, 400 MHz) δ: 2.45(s,3H), 7.38-7.41(t,1H), 7.43-7.45(t,1H), 7.51-7.53(t,2H), 7.89-7.91(d,1H), 7.93-7.94(d,1H), 8.12(s,1H), 8.28-8.31(d,2H), 9.26(s,2H);

(540) 2-(2-phenyl-5-pyrimidinyl)-1H-benzimidazole-4-(N-2,4-dihydroxyl-5-pyrimidinyl)amide ¹HNMR (DMSO, 400 MHz) δ: 7.38-7.41(t,1H), 7.43-7.45(t,1H), 7.51-7.53(t,2H), 7.89-7.91(d,1H), 7.82(s,1H), 7.93-7.94(d,1H), 8.28-8.31(d,2H), 8.33(s,1H), 9.26(s,2H), 11.53(s,1H);

(541) 2-(2-phenyl-5-pyrimidinyl)-1H-benzimidazole-4-(N-4,6-dimethoxy-2-pyrimidinyl)amide ¹HNMR (DMSO, 400 MHz) δ: 3.82(s,6H), 5.71(s,1H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(542) 2-(2-phenyl-5-pyrimidinyl)-1H-benzimidazole-4-(N-4-chloro-6-amino-2-pyrimidinyl)amide ¹HNMR (DMSO, 400 MHz) δ: 5.98(s,1H), 7.38-7.41(t,1H), 7.43-7.45(t,1H), 7.51-7.53(t,2H), 7.74(s,2H), 7.89-7.91(d,1H), 7.93-7.94(d,1H), 8.28-8.31(d,2H), 9.26(s,2H);

(543) 2-(2-phenyl-5-pyrimidinyl)-1H-benzimidazole-4-(N-4,6-dichloro-5-pyrimidinyl)amide ¹HNMR (DMSO, 400 MHz) δ: 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H), 9.34(s,1H);

(544) 2-(2-phenyl-5-pyrimidinyl)-1H-benzimidazole-4-(N-o-fluorophenyl)amide

¹HNMR (DMSO, 400 MHz) δ: 6.60-6.61(d,1H), 6.63-6.65(t,1H), 6.96-6.98(t,1H), 6.99-7.01(d,1H), 7.38-7.41(t,1H), 7.43-7.45(t,1H), 7.51-7.53(t,2H), 7.89-7.91(d,1H), 7.93-7.94(d,1H), 8.28-8.31(d,2H), 9.26(s,2H);

(545) 2-(2-phenyl-5-pyrimidinyl)-1H-benzimidazole-4-(N-2-hydroxyl-4-pyrimidinyl)amide ¹HNMR (DMSO, 400 MHz) δ: 5.46-5.48(d,1H), 7.10-7.11(d,1H), 7.38-7.41(t,1H), 7.43-7.45(t,1H), 7.51-7.53(t,2H), 7.82(s,1H), 7.89-7.91(d,1H), 7.93-7.94(d,1H), 8.28-8.31(d,2H), 9.26(s,2H);

(546) 2-(2-phenyl-5-pyrimidinyl)-1H-benzimidazole-4-(N-6-purinyl)amide

¹HNMR (DMSO, 400 MHz) δ: 7.38-7.41(t,1H), 7.43-7.45(t,1H), 7.51-7.53(t,2H), 7.86-7.88(d,1H), 7.89-7.91(d,1H), 7.93-7.94(d,1H), 8.16-8.18(d,1H), 8.28-8.31(d,2H), 9.26(s,2H);

(547) 2-(2-phenyl-5-pyrimidinyl)-1H-benzimidazole-4-(N-6-hydroxyl-2-purinyl)amide ¹HNMR (DMSO, 400 MHz) δ: 7.38-7.41(t,1H), 7.43-7.45(t,1H), 7.51-7.53(t,2H), 7.89-7.91(d,1H), 7.93-7.94(d,1H), 8.28-8.31(d,2H), 8.57-8.59(d,1H), 9.26(s,2H), 11.53(s,1H);

(548) (L)-2-(4-amino-6-chloro-5-pyrimidinyl)-1H-benzimidazole-4-N-(1-hydroxymethyl-2-p-nitrophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.74(s,2H), 7.89-7.90(d,1H), 7.93-7.95(d,1H), 8.17-8.20(d,2H), 8.59(s,1H);

(549) (L)-2-(4-amino-6-chloro-5-pyrimidinyl)-1H-benzimidazole-4-N-(1-hydroxymethyl-2-p-aminophenylhydroxyethyl)]amide ¹HNMR (DMSO, 400 MHz) δ: 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.74(s,2H), 7.89-7.90(d,1H), 7.93-7.95(d,1H), 8.59(s,1H);

(550) 2-(4-amino-6-chloro-5-pyrimidinyl)-1H-benzimidazole-4-N-(1-methyl-2-p-chlorophenylhydroxyethyl)]amide ¹HNMR (DMSO, 400 MHz) δ: 1.12-1.15(d,3H), 3.25-3.28(m,1H), 3.65-3.68(t,1H), 4.73-4.77(t,1H), 7.29-7.30(d,2H), 7.40-7.41(d,2H), 7.43-7.45(t,1H), 7.74(s,2H), 7.89-7.91(d,1H), 7.93-7.94(d,1H), 8.59(s,1H);

(551) 2-(4-amino-6-chloro-5-pyrimidinyl)-1H-benzimidazole-4-(N—N'-piperidinyl)amide ¹HNMR (DMSO, 400 MHz) δ: 1.52-1.55(m,4H), 1.59-1.63(m,2H), 3.10-3.15(t,4H), 7.43-7.45(t,1H), 7.74(s,2H), 7.89-7.91(d,1H), 7.93-7.94(d,1H), 8.59(s,1H);

(552) 2-(4-amino-6-chloro-5-pyrimidinyl)-1H-benzimidazole-4-(N-2-piperazinyl)amide ¹HNMR (DMSO, 400 MHz) δ: 1.91-1.93(m,2H), 2.62-2.63(m,1H), 2.65-2.66(m,1H), 2.69-2.70(m,1H), 2.72-2.74

(m,1H), 2.77-2.80(m,1H), 3.02-3.05(m,1H), 3.99-4.01(m,1H), 7.43-7.45(t,1H), 7.74(s,2H), 7.89-7.91(d,1H), 7.93-7.94(d,1H), 8.59(s,1H);

(553) 2-(4-amino-6-chloro-5-pyrimidinyl)-1H-benzimidazole-4-(N-2'-benzimidazolyl)amide ¹HNMR (DMSO, 400 MHz) δ: 7.12-7.15(d,2H), 7.22-7.24(t,2H), 7.43-7.45(t,1H), 7.74(s,2H), 7.89-7.91(d,1H), 7.93-7.94(d,1H), 8.59(s,1H);

(554) 2-(4-amino-6-chloro-5-pyrimidinyl)-1H-benzimidazole-4-(N-o-aminophenyl)amide ¹HNMR (DMSO, 400 MHz) δ: 6.27(s,2H), 6.38-6.40(d,1H), 6.56-6.58(t,1H), 6.75-6.76(d,1H), 7.02-7.04(t,1H), 7.43-7.45(t,1H), 7.74(s,2H), 7.89-7.91(d,1H), 7.93-7.94(d,1H), 8.59(s,1H);

(555) 2-(4-amino-6-chloro-5-pyrimidinyl)-1H-benzimidazole-4-(N-5-benzimidazolonyl)amide ¹HNMR (DMSO, 400 MHz) δ: 6.35-6.37(d,1H), 6.93(s,1H), 7.43-7.45(t,1H), 7.54-7.56(d,1H), 7.74(s,2H), 7.89-7.91(d,1H), 7.93-7.94(d,1H), 8.59(s,1H);

(556) 2-(4-amino-6-chloro-5-pyrimidinyl)-1H-benzimidazole-4-(N-4'-carbonamido-5'-imidazolyl)amide ¹HNMR (DMSO, 400 MHz) δ: 7.43-7.45(t,1H), 7.74(s,2H), 7.89-7.91(d,1H), 7.93-7.94(d,1H), 8.37(s,2H), 8.59(s,1H), 9.24-9.26(d,1H), 13.00-13.03(d,1H);

(557) 2-(4-amino-6-chloro-5-pyrimidinyl)-1H-benzimidazole-4-(N-4'-pyrazolyl)amide ¹HNMR (DMSO, 400 MHz) δ: 7.43-7.45(t,1H), 7.74(s,2H), 7.89-7.91(d,1H), 7.93-7.94(d,1H), 8.59(s,1H), 8.61(s,1H), 8.63-8.65(d,1H), 13.71-13.75(d,1H);

(558) 2-(4-amino-6-chloro-5-pyrimidinyl)-1H-benzimidazole-4-(N—(N'-piperazinyl))amide ¹HNMR (DMSO, 400 MHz) δ: 1.91-1.95(m,1H), 2.65-2.67(t,4H), 2.80-2.83(m,4H), 7.43-7.45(t,1H), 7.74(s,2H), 7.90-7.91(d,1H), 7.93-7.94(d,1H), 8.59(s,1H);

(559) 2-(4-amino-6-chloro-5-pyrimidinyl)-1H-benzimidazole-4-(N-2-pyrazinyl)amide ¹HNMR (DMSO, 400 MHz) δ: 7.43-7.45(t,1H), 7.74(s,2H), 7.89-7.91(d,1H), 7.93-7.94(d,1H), 8.34-8.35(d,1H), 8.36(s,1H), 8.40-8.42(d,1H), 8.59(s,1H);

(560) 2-(4-amino-6-chloro-5-pyrimidinyl)-1H-benzimidazole-4-(N-2-pyrimidinyl)amide ¹HNMR (DMSO, 400 MHz) δ: 6.93-6.95(t,1H), 7.43-7.45(t,1H), 7.74(s,2H), 7.89-7.91(d,1H), 7.93-7.94(d,1H), 8.45-8.46(d,2H), 8.59(s,1H);

(561) 2-(4-amino-6-chloro-5-pyrimidinyl)-1H-benzimidazole-4-(N-2-pyridyl)amide

¹HNMR (DMSO, 400 MHz) δ: 6.62-6.64(t,1H), 6.70-6.72(d,1H), 7.43-7.45(t,1H), 7.55-7.57(t,1H), 7.74(s,2H), 7.89-7.91(d,1H), 7.93-7.94(d,1H), 8.07-8.09(d,1H), 8.59(s,1H);

(562) 2-(4-amino-6-chloro-5-pyrimidinyl)-1H-benzimidazole-4-(N-4-methyl-5-thiazolyl)amide ¹HNMR (DMSO, 400 MHz) δ: 2.45(s,3H), 7.43-7.45(t,1H), 7.74(s,2H), 7.89-7.91(d,1H), 7.93-7.94(d,1H), 8.12(s,1H), 8.59(s,1H);

(563) 2-(4-amino-6-chloro-5-pyrimidinyl)-1H-benzimidazole-4-(N-2,4-dihydroxyl-5-pyrimidinyl)amide ¹HNMR (DMSO, 400 MHz) δ: 7.43-7.45(t,1H), 7.74(s,2H), 7.89-7.91(d,1H), 7.82(s,1H), 7.93-7.94(d,1H), 8.33(s,1H), 8.59(s,1H), 11.53(s,1H);

(564) 2-(4-amino-6-chloro-5-pyrimidinyl)-1H-benzimidazole-4-(N-4,6-dimethoxy-2-pyrimidinyl)amide ¹HNMR (DMSO, 400 MHz) δ: 3.82(s,6H), 5.71(s,1H), 7.43-7.45(t,1H), 7.74(s,2H), 7.89-7.91(d,1H), 7.93-7.94(d,1H), 8.59(s,1H);

(565) 2-(4-amino-6-chloro-5-pyrimidinyl)-1H-benzimidazole-4-(N-4-chloro-6-amino-2-pyrimidinyl)amide ¹HNMR (DMSO, 400 MHz) δ: 5.98(s,1H), 7.43-7.45(t,1H), 7.74(s,4H), 7.89-7.91(d,1H), 7.93-7.94(d,1H), 8.59(s,1H);

(566) 2-(4-amino-6-chloro-5-pyrimidinyl)-1H-benzimidazole-4-(N-4,6-dichloro-5-pyrimidinyl)amide ¹HNMR (DMSO, 400 MHz) δ: 7.43-7.45(t,1H), 7.74(s,2H), 7.89-7.91(d,1H), 7.93-7.94(d,1H), 8.59(s,1H), 9.34(s,1H);

(567) 2-(4-amino-6-chloro-5-pyrimidinyl)-1H-benzimidazole-4-(N-o-fluorophenyl)amide ¹HNMR (DMSO, 400 MHz) δ: 6.60-6.61(d,1H), 6.63-6.65(t,1H), 6.96-6.98(t,1H), 6.99-7.01(d,1H), 7.43-7.45(t,1H), 7.74(s,2H), 7.89-7.91(d,1H), 7.93-7.94(d,1H), 8.59(s,1H);

(568) 2-(4-amino-6-chloro-5-pyrimidinyl)-1H-benzimidazole-4-(N-2-hydroxyl-4-pyrimidinyl)amide ¹HNMR (DMSO, 400 MHz) δ: 5.46-5.48(d,1H), 7.10-7.11(d,1H), 7.43-7.45(t,1H), 7.74(s,2H), 7.82(s,1H), 7.89-7.91(d,1H), 7.93-7.94(d,1H), 8.59(s,1H);

(569) 2-(4-amino-6-chloro-5-pyrimidinyl)-1H-benzimidazole-4-(N-6-purinyl)amide

¹HNMR (DMSO, 400 MHz) δ: 7.43-7.45(t,1H), 7.74(s,2H), 7.86-7.88(d,1H), 7.89-7.91(d,1H), 7.93-7.94(d,1H), 8.16-8.18(d,1H), 8.59(s,1H);

(570) 2-(4-amino-6-chloro-5-pyrimidinyl)-1H-benzimidazole-4-(N-6-hydroxyl-2-purinyl)amide ¹HNMR (DMSO, 400 MHz) δ: 7.43-7.45(t,1H), 7.74(s,2H), 7.89-7.91(d,1H), 7.93-7.94(d,1H), 8.57-8.59(d,1H), 8.62(s,1H), 11.53(s,1H);

(571) (L)-2-(2-pyrrolidine-1-yl-5-pyrimidinyl)-1H-benzimidazole-4-[N-(1-hydroxymethyl-2-p-nitrophenylhydroxyethyl)]amide ¹HNMR (DMSO, 400 MHz) δ: 1.92-1.95(m,4H), 3.17-3.18(m,1H), 3.25-3.28(m,1H), 3.44-3.48(t,4H), 3.50-3.52

(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H), 9.02(s,2H);

(572) (L)-2-(2-pyrrolidine-1-yl-5-pyrimidinyl)-1H-benzimidazole-4-[N-(1-hydroxymethyl-2-p-aminophenylhydroxyethyl)]amide ¹HNMR (DMSO, 400 MHz) δ: 1.92-1.95(m,4H), 3.17-3.18(m,1H), 3.25-3.28(m,1H), 3.44-3.48(t,4H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H), 9.02(s,2H);

(573) 2-(2-pyrrolidine-1-yl-5-pyrimidinyl)-1H-benzimidazole-4-[N-(1-methyl-2-p-chlorophenylhydroxyethyl)]amide ¹HNMR (DMSO, 400 MHz) δ: 1.12-1.15(d,3H), 1.92-1.95(m,4H), 3.25-3.28(m,1H), 3.44-3.48(t,4H), 3.65-3.68(t,1H), 4.73-4.77(t,1H), 7.29-7.30(d,2H), 7.40-7.41(d,2H), 7.43-7.45(t,1H), 7.89-7.91(d,1H), 7.93-7.94(d,1H), 9.02(s,2H);

(574) 2-(2-pyrrolidine-1-yl-5-pyrimidinyl)-1H-benzimidazole-4-(N—N'-piperidinyl)amide ¹HNMR (DMSO, 400 MHz) δ: 1.52-1.55(m,4H), 1.59-1.63(m,2H), 1.92-1.95(m,4H), 3.10-3.15(t,4H), 3.44-3.48(t,4H), 7.43-7.45(t,1H), 7.89-7.91(d,1H), 7.93-7.94(d,1H), 9.02(s,2H);

(575) 2-(2-pyrrolidine-1-yl-5-pyrimidinyl)-1H-benzimidazole-4-(N-2-piperazinyl)amide ¹HNMR (DMSO, 400 MHz) δ: 1.87-1.89(m,2H), 1.92-1.95(m,4H), 2.62-2.63(m,1H), 2.65-2.66(m,1H), 2.69-2.70(m,1H), 2.72-2.74(m,1H), 2.77-2.80(m,1H), 3.02-3.05(m,1H), 3.44-3.48(t,4H), 3.99-4.01(m,1H), 7.43-7.45(t,1H), 7.89-7.91(d,1H), 7.93-7.94(d,1H), 9.02(s,2H);

(576) 2-(2-pyrrolidine-1-yl-5-pyrimidinyl)-1H-benzimidazole-4-(N-2'-benzimidazolyl)amide ¹HNMR (DMSO, 400 MHz) δ: 1.92-1.95(m,4H), 3.44-3.48(t,4H), 7.12-7.15(d,2H), 7.22-7.24(t,2H), 7.43-7.45(t,1H), 7.89-7.91(d,1H), 7.93-7.94(d,1H), 9.02(s,2H);

(577) 2-(2-pyrrolidine-1-yl-5-pyrimidinyl)-1H-benzimidazole-4-(N-o-aminophenyl)amide ¹HNMR (DMSO, 400 MHz) δ: 1.92-1.95(m,4H), 3.44-3.48(t,4H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H), 9.02(s,2H);

(578) 2-(2-pyrrolidine-1-yl-5-pyrimidinyl)-1H-benzimidazole-4-(N-5-benzimidazolonyl)amide ¹HNMR (DMSO, 400 MHz) δ: 1.92-1.95(m,4H), 3.44-3.48(t,4H), 6.35-6.37(d,1H), 6.93(s,1H), 7.43-7.45(t,1H), 7.54-7.56(d,1H), 7.89-7.91(d,1H), 7.93-7.94(d,1H), 9.02(s,2H);

(579) 2-(2-pyrrolidine-1-yl-5-pyrimidinyl)-1H-benzimidazole-4-(N-4'-carbonamido-5'-imidazolyl)amide ¹HNMR (DMSO, 400 MHz) δ: 1.92-1.95(m,4H), 3.44-3.48(t,4H), 7.43-7.45(t,1H), 7.89-7.91(d,1H), 7.93-7.94(d,1H), 8.37(s,2H), 9.02(s,2H), 9.24-9.26(d,1H), 13.00-13.03(d,1H);

(580) 2-(2-pyrrolidine-1-yl-5-pyrimidinyl)-1H-benzimidazole-4-(N-4'-pyrazolyl)amide ¹HNMR (DMSO, 400 MHz) δ: 1.92-1.95(m,4H), 3.44-3.48(t,4H), 7.43-7.45(t,1H), 7.89-7.91(d,1H), 7.93-7.94(d,1H), 8.61(s,1H), 8.63-8.65(d,1H), 9.02(s,2H), 13.71-13.75(d,1H);

(581) 2-(2-pyrrolidine-1-yl-5-pyrimidinyl)-1H-benzimidazole-4-(N—(N'-piperazinyl))amide ¹HNMR (DMSO, 400 MHz) δ: 1.87-1.89(m,1H), 1.92-1.95(m,4H), 2.65-2.67(t,4H), 2.80-2.83(m,4H), 3.44-3.48(t,4H), 7.43-7.45(t,1H), 7.90-7.91(d,1H), 7.93-7.94(d,1H), 9.02(s,2H);

(582) 2-(2-pyrrolidine-1-yl-5-pyrimidinyl)-1H-benzimidazole-4-(N-2-pyrazinyl)amide ¹HNMR (DMSO, 400 MHz) δ: 1.92-1.95(m,4H), 3.44-3.48(t,4H), 7.43-7.45(t,1H), 7.89-7.91(d,1H), 7.93-7.94(d,1H), 8.34-8.35(d,1H), 8.36(s,1H), 8.40-8.42(d,1H), 9.02(s,2H);

(583) 2-(2-pyrrolidine-1-yl-5-pyrimidinyl)-1H-benzimidazole-4-(N-2-pyrimidinyl)amide ¹HNMR (DMSO, 400 MHz) δ: 1.92-1.95(m,4H), 3.44-3.48(t,4H), 6.93-6.95(t,1H), 7.43-7.45(t,1H), 7.89-7.91(d,1H), 7.93-7.94(d,1H), 8.45-8.46(d,2H), 9.02(s,2H);

(584) 2-(2-pyrrolidine-1-yl-5-pyrimidinyl)-1H-benzimidazole-4-(N-2-pyridyl)amide ¹HNMR (DMSO, 400 MHz) δ: 1.92-1.95(m,4H), 3.44-3.48(t,4H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H), 9.02(s,2H);

(585) 2-(2-pyrrolidine-1-yl-5-pyrimidinyl)-1H-benzimidazole-4-(N-4-methyl-5-thiazolyl)amide ¹HNMR (DMSO, 400 MHz) δ: 1.92-1.95(m,4H), 2.45(s,3H), 3.44-3.48(t,4H), 7.43-7.45(t,1H), 7.89-7.91(d,1H), 7.93-7.94(d,1H), 8.12(s,1H), 9.02(s,2H);

(586) 2-(2-pyrrolidine-1-yl-5-pyrimidinyl)-1H-benzimidazole-4-(N-2,4-dihydroxyl-5-pyrimidinyl)amide ¹HNMR (DMSO, 400 MHz) δ: 1.92-1.95(m,4H), 3.44-3.48(t,4H), 7.43-7.45(t,1H), 7.89-7.91(d,1H), 7.82(s,1H), 7.93-7.94(d,1H), 8.33(s,1H), 9.02(s,2H), 11.53(s,1H);

(587) 2-(2-pyrrolidine-1-yl-5-pyrimidinyl)-1H-benzimidazole-4-(N-4,6-dimethoxy-2-pyrimidinyl)amide ¹HNMR (DMSO, 400 MHz) δ: 1.92-1.95(m,4H), 3.44-3.48(t,4H), 3.82(s,6H), 5.71(s,1H), 7.43-7.45(t,1H), 7.89-7.91(d,1H), 7.93-7.94(d,1H), 9.02(s,2H);

(588) 2-(2-pyrrolidine-1-yl-5-pyrimidinyl)-1H-benzimidazole-4-(N-4-chloro-6-amino-2-pyrimidinyl)amide ¹HNMR (DMSO, 400 MHz) δ: 1.92-1.95(m,4H), 3.44-3.48(t,4H), 5.98(s,1H), 7.43-7.45(t,1H), 7.74(s,2H), 7.89-7.91(d,1H), 7.93-7.94(d,1H), 9.02(s,2H);

(589) 2-(2-pyrrolidine-1-yl-5-pyrimidinyl)-1H-benzimidazole-4-(N-4,6-dichloro-5-pyrimidinyl)amide ¹HNMR (DMSO, 400 MHz) δ: 1.92-1.95(m,4H), 3.44-3.48(t,4H), 7.43-7.45(t,1H), 7.89-7.91(d,1H), 7.93-7.94(d,1H), 9.02(s,2H), 9.34(s,1H);

(590) 2-(2-pyrrolidine-1-yl-5-pyrimidinyl)-1H-benzimidazole-4-(N-o-fluorophenyl)amide ¹HNMR (DMSO, 400 MHz) δ: 1.92-1.95(m,4H), 3.44-3.48(t,4H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H), 9.02(s,2H);

(591) 2-(2-pyrrolidine-1-yl-5-pyrimidinyl)-1H-benzimidazole-4-(N-2-hydroxyl-4-pyrimidinyl)amide ¹HNMR (DMSO, 400 MHz) δ: 1.92-1.95(m,4H), 3.44-3.48(t,4H), 5.46-5.48(d,1H), 7.10-7.11(d,1H), 7.43-7.45(t,1H), 7.82(s,1H), 7.89-7.91(d,1H), 7.93-7.94(d,1H), 9.02(s,2H);

(592) 2-(2-pyrrolidine-1-yl-5-pyrimidinyl)-1H-benzimidazole-4-(N-6-purinyl)amide ¹HNMR (DMSO, 400 MHz) δ: 1.92-1.95(m,4H), 3.44-3.48(t,4H), 7.43-7.45(t,1H), 7.86-7.88(d,1H), 7.89-7.91(d,1H), 7.93-7.94(d,1H), 8.16-8.18(d,1H), 9.02(s,2H);

(593) 2-(2-pyrrolidine-1-yl-5-pyrimidinyl)-1H-benzimidazole-4-(N-6-hydroxyl-2-purinyl)amide ¹HNMR (DMSO, 400 MHz) δ: 1.92-1.95(m,4H), 3.44-3.48(t,4H), 7.43-7.45(t,1H), 7.89-7.91(d,1H), 7.93-7.94(d,1H), 8.57-8.59(d,1H), 9.02(s,2H), 11.53(s,1H);

(594) (L)-2-(2-piperidine-1-yl-5-pyrimidinyl)-1H-benzimidazole-4-[N-(1-hydroxymethyl-2-p-nitrophenylhydroxyethyl)]amide ¹HNMR (DMSO, 400 MHz) δ: 1.53-1.56(m,4H), 1.59-1.62(m,2H), 3.17-3.18(m,1H), 3.25-3.28(m,1H), 3.50-3.52(m,1H), 3.65-3.68(t,1H), 3.70-3.72(d,1H), 3.73-3.77(t,4H), 4.73-4.77(t,1H), 7.43-7.45(t,1H), 7.62-7.65(d,2H), 7.89-7.90(d,1H), 7.93-7.95(d,1H), 8.17-8.20(d,2H), 9.02(s,2H);

(595) (L)-2-(2-piperidine-1-yl-5-pyrimidinyl)-1H-benzimidazole-4-[N-(1-hydroxymethyl-2-p-aminophenylhydroxyethyl)]amide ¹HNMR (DMSO, 400 MHz) δ: 1.53-1.56(m,4H), 1.59-1.62(m,2H), 3.17-3.18(m,1H), 3.25-3.28(m,1H), 3.50-3.52(m,1H), 3.65-3.68(t,1H), 3.70-3.72(d,1H), 3.71-3.75(t,4H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H), 9.02(s,2H);

(596) 2-(2-piperidine-1-yl-5-pyrimidinyl)-1H-benzimidazole-4-[N-(1-methyl-2-p-chlorophenylhydroxyethyl)]amide ¹HNMR (DMSO, 400 MHz) δ: 1.12-1.15(d,3H), 1.53-1.56(m,4H), 1.59-1.62(m,2H), 3.25-3.28(m,1H), 3.65-3.68(t,1H), 3.71-3.75(t,4H), 4.73-4.77(t,1H), 7.29-7.30(d,2H), 7.40-7.41(d,2H), 7.43-7.45(t,1H), 7.89-7.91(d,1H), 7.93-7.94(d,1H), 9.02(s,2H);

(597) 2-(2-piperidine-1-yl-5-pyrimidinyl)-1H-benzimidazole-4-(N—N'-piperidinyl)amide ¹HNMR (DMSO, 400 MHz) δ: 1.52-1.55(m,8H), 1.59-1.63(m,2H), 3.10-3.15(t,4H), 3.71-3.75(t,4H), 7.43-7.45(t,1H), 7.89-7.91(d,1H), 7.93-7.94(d,1H), 9.02(s,2H);

(598) 2-(2-piperidine-1-yl-5-pyrimidinyl)-1H-benzimidazole-4-(N-2-piperazinyl)amide ¹HNMR (DMSO, 400 MHz) δ: 1.53-1.56(m,4H), 1.59-1.62(m,2H), 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.71-3.75(t,4H), 3.99-4.01(m,1H), 7.43-7.45(t,1H), 7.89-7.91(d,1H), 7.93-7.94(d,1H), 9.02(s,2H);

(599) 2-(2-piperidine-1-yl-5-pyrimidinyl)-1H-benzimidazole-4-(N-2'-benzimidazolyl)amide ¹HNMR (DMSO, 400 MHz) δ: 1.53-1.56(m,4H), 1.59-1.62(m,2H), 3.71-3.75(t,4H), 7.12-7.15(d,2H), 7.22-7.24(t,2H), 7.43-7.45(t,1H), 7.89-7.91(d,1H), 7.93-7.94(d,1H), 9.02(s,2H);

(600) 2-(2-piperidine-1-yl-5-pyrimidinyl)-1H-benzimidazole-4-(N-o-aminophenyl)amide ¹HNMR (DMSO, 400 MHz) δ: 1.53-1.56(m,4H), 1.59-1.62(m,2H), 3.71-3.75(t,4H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H), 9.02(s,2H);

(601) 2-(2-piperidine-1-yl-5-pyrimidinyl)-1H-benzimidazole-4-(N-5-benzimidazolonyl)amide ¹HNMR (DMSO, 400 MHz) δ: 1.53-1.56(m,4H), 1.59-1.62(m,2H), 3.71-3.75(t,4H), 6.35-6.37(d,1H), 6.93(s,1H), 7.43-7.45(t,1H), 7.54-7.56(d,1H), 7.89-7.91(d,1H), 7.93-7.94(d,1H), 9.02(s,2H);

(602) 2-(2-piperidine-1-yl-5-pyrimidinyl)-1H-benzimidazole-4-(N-4'-carbonamido-5'-imidazolyl)amide ¹HNMR (DMSO, 400 MHz) δ: 1.53-1.56(m,4H), 1.59-1.62(m,2H), 3.71-3.75(t,4H), 7.43-7.45(t,1H), 7.89-7.91(d,1H), 7.93-7.94(d,1H), 8.37(s,2H), 9.02(s,2H), 9.24-9.26(d,1H), 13.00-13.03(d,1H);

(603) 2-(2-piperidine-1-yl-5-pyrimidinyl)-1H-benzimidazole-4-(N-4'-pyrazolyl)amide ¹HNMR (DMSO, 400 MHz) δ: 1.53-1.56(m,4H), 1.59-1.62(m,2H), 3.71-3.75(t,4H), 7.43-7.45(t,1H), 7.89-7.91(d,1H), 7.93-7.94(d,1H), 8.61(s,1H), 8.63-8.65(d,1H), 9.02(s,2H), 13.71-13.75(d,1H);

(604) 2-(2-piperidine-1-yl-5-pyrimidinyl)-1H-benzimidazole-4-(N—(N'-piperazinyl)amide ¹HNMR (DMSO, 400 MHz) δ: 1.53-1.56(m,4H), 1.59-1.62(m,2H), 1.91-1.95(m,1H), 2.65-2.67(t,4H), 2.80-2.83(m,4H), 3.71-3.75(t,4H), 7.43-7.45(t,1H), 7.90-7.91(d,1H), 7.93-7.94(d,1H), 9.02(s,2H);

(605) 2-(2-piperidine-1-yl-5-pyrimidinyl)-1H-benzimidazole-4-(N-2-pyrazinyl)amide ¹HNMR (DMSO, 400 MHz) δ: 1.53-1.56(m,4H), 1.59-1.62(m,2H), 3.71-3.75(t,4H), 7.43-7.45(t,1H), 7.89-7.91(d,1H), 7.93-7.94(d,1H), 8.34-8.35(d,1H), 8.36(s,1H), 8.40-8.42(d,1H), 9.02(s,2H);

(606) 2-(2-piperidine-1-yl-5-pyrimidinyl)-1H-benzimidazole-4-(N-2-pyrimidinyl)amide ¹HNMR (DMSO, 400 MHz) δ: 1.53-1.56(m,4H), 1.59-1.62(m,2H), 3.71-3.75(t,4H), 6.93-6.95(t,1H), 7.43-7.45(t,1H), 7.89-7.91(d,1H), 7.93-7.94(d,1H), 8.45-8.46(d,2H), 9.02(s,2H);

(607) 2-(2-piperidine-1-yl-5-pyrimidinyl)-1H-benzimidazole-4-(N-2-pyridyl)amide

¹HNMR (DMSO, 400 MHz) δ: 1.53-1.56(m,4H), 1.59-1.62(m,2H), 3.71-3.75(t,4H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H), 9.02(s,2H);

(608) 2-(2-piperidine-1-yl-5-pyrimidinyl)-1H-benzimidazole-4-(N-4-methyl-5-thiazolyl)amide ¹HNMR (DMSO, 400 MHz) δ: 1.53-1.56(m,4H), 1.59-1.62(m,2H), 2.45(s,3H), 3.71-3.75(t,4H), 7.43-7.45(t,1H), 7.89-7.91(d,1H), 7.93-7.94(d,1H), 8.12(s,1H), 9.02(s,2H);

(609) 2-(2-piperidine-1-yl-5-pyrimidinyl)-1H-benzimidazole-4-(N-2,4-dihydroxyl-5-pyrimidinyl)amide ¹HNMR (DMSO, 400 MHz) δ: 1.53-1.56(m,4H), 1.59-1.62(m,2H), 3.71-3.75(t,4H), 7.43-7.45(t,1H), 7.89-7.91(d,1H), 7.82(s,1H), 7.93-7.94(d,1H), 8.33(s,1H), 9.02(s,2H), 11.53(s,1H);

(610) 2-(2-piperidine-1-yl-5-pyrimidinyl)-1H-benzimidazole-4-(N-4,6-dimethoxy-2-pyrimidinyl)amide ¹HNMR (DMSO, 400 MHz) δ: 1.53-1.56(m,4H), 1.59-1.62(m,2H), 3.71-3.75(t,4H), 3.82(s,6H), 5.71(s,1H), 7.43-7.45(t,1H), 7.89-7.91 (d,1H), 7.93-7.94(d,1H), 9.02(s,2H);

(611) 2-(2-piperidine-1-yl-5-pyrimidinyl)-1H-benzimidazole-4-(N-4-chloro-6-amino-2-pyrimidinyl)amide ¹HNMR (DMSO, 400 MHz) δ: 1.53-1.56(m,4H), 1.59-1.62(m,2H), 3.71-3.75(t,4H), 5.98(s,1H), 7.43-7.45(t,1H), 7.74(s,2H), 7.89-7.91(d,1H), 7.93-7.94(d,1H), 9.02(s,2H);

(612) 2-(2-piperidine-1-yl-5-pyrimidinyl)-1H-benzimidazole-4-(N-4,6-dichloro-5-pyrimidinyl)amide ¹HNMR (DMSO, 400 MHz) δ: 1.53-1.56(m,4H), 1.59-1.62(m,2H), 3.71-3.75(t,4H), 7.43-7.45 (t,1H), 7.89-7.91(d,1H), 7.93-7.94(d,1H), 9.02(s,2H), 9.34(s,1H);

(613) 2-(2-piperidine-1-yl-5-pyrimidinyl)-1H-benzimidazole-4-(N-o-fluorophenyl)amide ¹HNMR (DMSO, 400 MHz) δ: 1.53-1.56(m,4H), 1.59-1.62(m,2H), 3.71-3.75(t,4H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H), 9.02(s,2H);

(614) 2-(2-piperidine-1-yl-5-pyrimidinyl)-1H-benzimidazole-4-(N-2-hydroxyl-4-pyrimidinyl)amide ¹HNMR (DMSO, 400 MHz) δ: 1.53-1.56(m,4H), 1.59-1.62(m,2H), 3.71-3.75(t,4H), 5.46-5.48(d,1H), 7.10-7.11(d,1H), 7.43-7.45(t,1H), 7.82(s,1H), 7.89-7.91(d,1H), 7.93-7.94(d,1H), 9.02(s,2H);

(615) 2-(2-piperidine-1-yl-5-pyrimidinyl)-1H-benzimidazole-4-(N-6-purinyl)amide

Figures 5, 6:
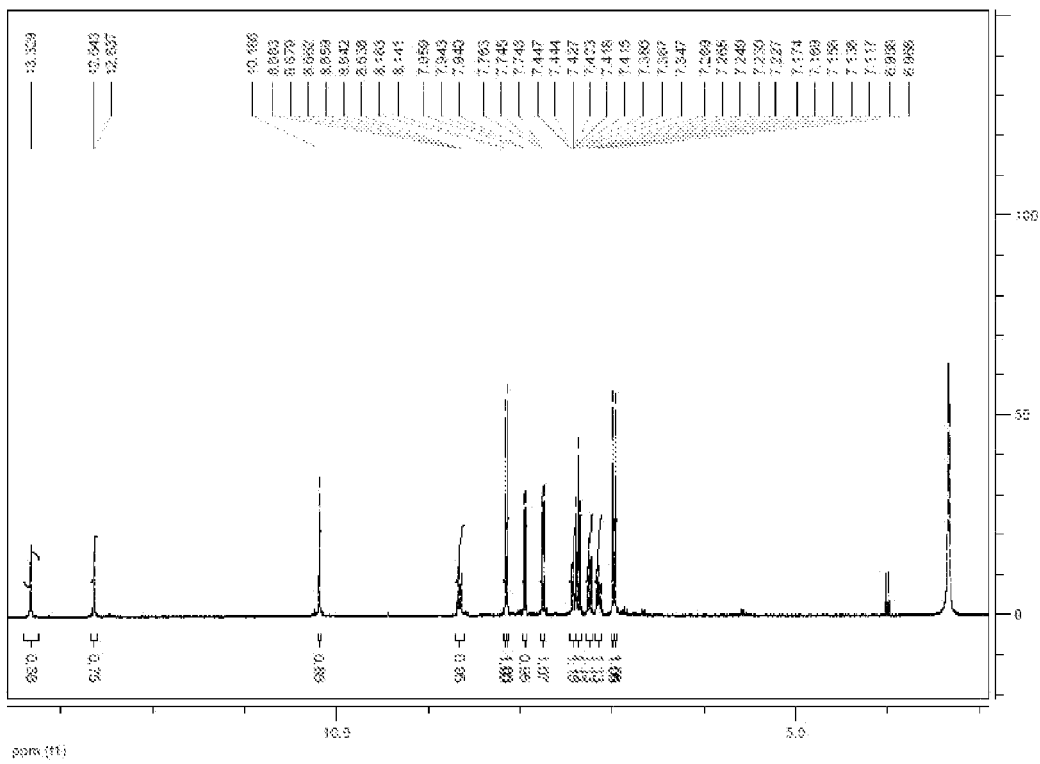
FIG. 5 shows $^1$HNMR spectrogram of 2-(4-hydroxyphenyl)-1H-benzimidazole-4-(N-o-fluorophenyl)amide in Example 663.
FIG. 6 shows $^1$HNMR spectrogram of (L)-2-(3-hydroxyphenyl)-1H-benzimidazole-4-(N-(1-hydroxymethyl-2-p-nitrophenylhydroxyethyl)amide in Example 664.

¹HNMR (DMSO, 400 MHz) δ: 1.53-1.56(m,4H), 1.59-1.62(m,2H), 3.71-3.75(t,4H), 7.43-7.45(t,1H), 7.86-7.88(d,1H), 7.89-7.91(d,1H), 7.93-7.94(d,1H), 8.16-8.18(d,1H), 9.02(s,2H);

(616) 2-(2-piperidine-1-yl-5-pyrimidinyl)-1H-benzimidazole-4-(N-6-hydroxyl-2-purinyl)amide ¹HNMR (DMSO, 400 MHz) δ: 1.53-1.56(m,4H), 1.59-1.62(m,2H), 3.71-3.75(t,4H), 7.43-7.45(t,1H), 7.89-7.91(d,1H), 7.93-7.94(d,1H), 8.57-8.59(d,1H), 9.02(s,2H), 11.53(s,1H);

(617) (L)-2-(2-cyclopropylamino-5-pyrimidinyl)-1H-benzimidazole-4-[N-(1-hydroxymethyl-2-p-nitrophenylhydroxyethyl)]amide ¹HNMR (DMSO, 400 MHz) δ: 0.55-0.58(m,2H), 0.78-0.82(m,2H), 1.35-1.37(m,1H), 3.17-3.18(m,1H), 3.25-3.28(m,1H), 3.50-3.52(m,1H), 3.65-3.68(t,1H), 3.70-3.72(d,1H), 4.73-4.77(t,1H), 7.43-7.45(t,1H), 7.62-7.65(d,2H), 7.89-7.90(d,1H), 7.93-7.95(d,1H), 8.17-8.20(d,2H), 9.02(s,2H);

(618) (L)-2-(2-cyclopropylamino-5-pyrimidinyl)-1H-benzimidazole-4-N-(1-hydroxymethyl-2-p-aminophenylhydroxyethyl)]amide ¹HNMR (DMSO, 400 MHz) δ: 0.55-0.58(m,2H), 0.78-0.82(m,2H), 1.35-1.37(m,1H), 3.17-3.18(m,1H), 3.25-3.28(m,1H), 3.50-3.52(m,1H), 3.65-3.68(t,1H), 3.70-3.72(d,1H), 4.73-4.77(t,1H), 6.27(s,2H), 6.56-6.58(d,2H), 7.11-7.13(d,2H), 7.43-7.45(t,1H), 7.89-7.90(d,1H), 7.93-7.95(d,1H), 9.02(s,2H);

(619) 2-(2-cyclopropylamino-5-pyrimidinyl)-1H-benzimidazole-4-N-(1-methyl-2-p-chlorophenylhydroxyethyl)]amide ¹HNMR (DMSO, 400 MHz) δ: 0.55-0.58(m,2H), 0.78-0.82(m,2H), 1.12-1.15(d,3H), 1.35-1.37(m,1H), 3.25-3.28(m,1H), 3.65-3.68(t,1H), 4.73-4.77(t,1H), 7.29-7.30(d,2H), 7.40-7.41(d,2H), 7.43-7.45(t,1H), 7.89-7.91(d,1H), 7.93-7.94(d,1H), 9.02(s,2H);

(620) 2-(2-cyclopropylamino-5-pyrimidinyl)-1H-benzimidazole-4-(N—N'-piperodinyl)amide $^1$HNMR (DMSO, 400 MHz) δ: 0.55-0.58(m,2H), 0.78-0.82(m,2H), 1.35-1.37(m,1H), 1.52-1.55(m,4H),1.59-1.63(m,2H), 3.10-3.15(t,4H), 7.43-7.45(t,1H), 7.89-7.91(d,1H), 7.93-7.94(d,1H), 9.02(s,2H);

(621) 2-(2-cyclopropylamino-5-pyrimidinyl)-1H-benzimidazole-4-(N-2-piperazinyl)amide $^1$HNMR (DMSO, 400 MHz) δ: 0.55-0.58(m,2H), 0.78-0.82(m,2H), 1.35-1.37(m,1H), 1.91-1.93(m,2H), 2.62-2.63(m,1H), 2.65-2.66(m,1H), 2.69-2.70(m,1H), 2.72-2.74(m,1H), 2.77-2.80(m,1H), 3.02-3.05(m,1H), 3.99-4.01(m,1H), 7.43-7.45(t,1H), 7.89-7.91(d,1H), 7.93-7.94(d,1H), 9.02(s,2H);

(622) 2-(2-cyclopropylamino-5-pyrimidinyl)-1H-benzimidazole-4-(N-2'-benzimidazolyl)amide $^1$HNMR (DMSO, 400 MHz) δ: 0.55-0.58(m,2H), 0.78-0.82(m,2H), 1.35-1.37(m,1H), 7.12-7.15(d,2H), 7.22-7.24(t,2H), 7.43-7.45(t,1H), 7.89-7.91(d,1H), 7.93-7.94(d,1H), 9.02(s,2H);

(623) 2-(2-cyclopropylamino-5-pyrimidinyl)-1H-benzimidazole-4-(N-o-aminophenyl)amide $^1$HNMR (DMSO, 400 MHz) δ: 0.55-0.58(m,2H), 0.78-0.82(m,2H), 1.35-1.37(m,1H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H), 9.02(s,2H);

(624) 2-(2-cyclopropylamino-5-pyrimidinyl)-1H-benzimidazole-4-(N-5-benzimidazolonyl)amide $^1$HNMR (DMSO, 400 MHz) δ: 0.55-0.58(m,2H), 0.78-0.82(m,2H), 1.35-1.37(m,1H), 6.35-6.37(d,1H), 6.93(s,1H), 7.43-7.45(t,1H), 7.54-7.56(d,1H), 7.89-7.91(d,1H), 7.93-7.94(d,1H), 9.02(s,2H);

(625) 2-(2-cyclopropylamino-5-pyrimidinyl)-1H-benzimidazole-4-(N-4'-carbonamido-5'-imidazolyl)amide $^1$HNMR (DMSO, 400 MHz) δ: 0.55-0.58(m,2H), 0.78-0.82(m,2H), 1.35-1.37(m,1H), 7.43-7.45(t,1H), 7.89-7.91(d,1H), 7.93-7.94(d,1H), 8.37(s,2H), 9.02(s,2H), 9.24-9.26(d,1H), 13.00-13.03(d,1H);

(626) 2-(2-cyclopropylamino-5-pyrimidinyl)-1H-benzimidazole-4-(N-4'-pyrazolyl)amide $^1$HNMR (DMSO, 400 MHz) δ: 0.55-0.58(m,2H), 0.78-0.82(m,2H), 1.35-1.37(m,1H), 7.43-7.45(t,1H), 7.89-7.91(d,1H), 7.93-7.94(d,1H), 8.61(s,1H), 8.63-8.65(d,1H), 9.02(s,2H), 13.71-13.75(d,1H);

(627) 2-(2-cyclopropylamino-5-pyrimidinyl)1H-benzimidazole-4-(N—N'-piperazinyl))amide $^1$HNMR (DMSO, 400 MHz) δ: 0.55-0.58(m,2H), 0.78-0.82(m,2H), 1.35-1.37(m,1H), 1.91-1.95(m,1H),2.65-2.67(t,4H), 2.80-2.83(m,4H), 7.43-7.45(t,1H), 7.90-7.91(d,1H), 7.93-7.94(d,1H), 9.02(s,2H);

(628) 2-(2-cyclopropylamino-5-pyrimidinyl)-1H-benzimidazole-4-(N-2-pyrazinyl)amide $^1$HNMR (DMSO, 400 MHz) δ: 0.55-0.58(m,2H), 0.78-0.82(m,2H), 1.35-1.37(m,1H), 7.43-7.45(t,1H), 7.89-7.91(d,1H), 7.93-7.94(d,1H), 8.34-8.35(d,1H), 8.36(s,1H), 8.40-8.42(d,1H), 9.02(s,2H);

(629) 2-(2-cyclopropylamino-5-pyrimidinyl)-1H-benzimidazole-4-(N-2-pyrimidinyl)amide $^1$HNMR (DMSO, 400 MHz) δ: 0.55-0.58(m,2H), 0.78-0.82(m,2H), 1.35-1.37(m,1H), 6.93-6.95(t,1H), 7.43-7.45(t,1H), 7.89-7.91(d,1H), 7.93-7.94(d,1H), 8.45-8.46(d,2H), 9.02(s,2H);

(630) 2-(2-cyclopropylamino-5-pyrimidinyl)-1H-benzimidazole-4-(N-2-pyridyl)amide $^1$HNMR (DMSO, 400 MHz) δ: 0.55-0.58(m,2H), 0.78-0.82(m,2H), 1.35-1.37(m,1H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H), 9.02(s,2H);

(631) 2-(2-cyclopropylamino-5-pyrimidinyl)-1H-benzimidazole-4-(N-4-methyl-5-thiazolyl)amide $^1$HNMR (DMSO, 400 MHz) δ: 0.55-0.58(m,2H), 0.78-0.82(m,2H), 1.35-1.37(m,1H), 2.45(s,3H), 7.43-7.45(t,1H), 7.89-7.91(d,1H), 7.93-7.94(d,1H), 8.12(s,1H), 9.02(s,2H);

(632) 2-(2-cyclopropylamino-5-pyrimidinyl)-1H-benzimidazole-4-(N-2,4-dihydroxyl-5-pyrimidinyl)amide $^1$HNMR (DMSO, 400 MHz) δ: 0.55-0.58(m,2H), 0.78-0.82(m,2H), 1.35-1.37(m,1H), 7.43-7.45(t,1H),7.89-7.91(d,1H), 7.82(s,1H), 7.93-7.94(d,1H), 8.33(s,1H), 9.02(s,2H), 11.53(s,1H);

(633) 2-(2-cyclopropylamino-5-pyrimidinyl)-1H-benzimidazole-4-(N-4,6-dimethoxy-2-pyrimidinyl)amide $^1$HNMR (DMSO, 400 MHz) δ: 0.55-0.58(m,2H), 0.78-0.82(m,2H), 1.35-1.37(m,1H), 3.82(s,6H),5.71(s,1H), 7.43-7.45(t,1H), 7.89-7.91(d,1H), 7.93-7.94(d,1H), 9.02(s,2H);

(634) 2-(2-cyclopropylamino-5-pyrimidinyl)-1H-benzimidazole-4-(N-4-chloro-6-amino-2-pyrimidinyl)amide $^1$HNMR (DMSO, 400 MHz) δ: 0.55-0.58(m,2H), 0.78-0.82(m,2H), 1.35-1.37(m,1H), 5.98(s,1H), 7.43-7.45(t,1H), 7.74(s,2H), 7.89-7.91(d,1H), 7.93-7.94(d,1H), 9.02(s,2H);

(635) 2-(2-cyclopropylamino-5-pyrimidinyl)-1H-benzimidazole-4-(N-4,6-dichloro-5-pyrimidinyl)amide $^1$HNMR (DMSO, 400 MHz) δ: 0.55-0.58(m,2H), 0.78-0.82(m,2H), 1.35-1.37(m,1H), 7.43-7.45(t,1H), 7.89-7.91(d,1H), 7.93-7.94(d,1H), 9.02(s,2H), 9.34(s,1H);

(636) 2-(2-cyclopropylamino-5-pyrimidinyl)-1H-benzimidazole-4-(N-o-fluorophenyl)amide $^1$HNMR (DMSO, 400 MHz) δ: 0.55-0.58(m,2H), 0.78-0.82(m,2H), 1.35-1.37(m,1H), 6.60-6.61(d,1H), 6.63-6.65(t, 1H), 6.96-6.98(t,1H), 6.99-7.01(d,1H), 7.43-7.45(t,1H), 7.89-7.91(d,1H), 7.93-7.94(d,1H), 9.02(s,2H);

(637) 2-(2-cyclopropylamino-5-pyrimidinyl)-1H-benzimidazole-4-(N-2-hydroxyl-4-pyrimidinyl) amide ¹HNMR (DMSO, 400 MHz) δ: 0.55-0.58(m,2H), 0.78-0.82(m,2H), 1.35-1.37(m,1H), 5.46-5.48(d,1H), 7.10-7.11(d, 1H), 7.43-7.45(t,1H), 7.82(s,1H), 7.89-7.91(d,1H), 7.93-7.94 (d,1H), 9.02(s,2H);

(638) 2-(2-cyclopropylamino-5-pyrimidinyl)-1H-benzimidazole-4-(N-6-purinyl)amide ¹HNMR (DMSO, 400 MHz) δ: 0.55-0.58(m,2H), 0.78-0.82(m,2H), 1.35-1.37(m,1H), 7.43-7.45(t,1H), 7.86-7.88(d, 1H), 7.89-7.91(d,1H), 7.93-7.94(d,1H), 8.16-8.18(d,1H), 9.02(s,2H);

(639) 2-(2-cyclopropylamino-5-pyrimidinyl)-1H-benzimidazole-4-(N-6-hydroxyl-2-purinyl)amide ¹HNMR (DMSO, 400 MHz) δ: 0.55-0.58(m,2H), 0.78-0.82(m,2H), 1.35-1.37(m,1H), 7.43-7.45(t,1H), 7.89-7.91(d, 1H), 7.93-7.94(d,1H), 8.57-8.59(d,1H), 9.02(s,2H), 11.53(s, 1H);

(640) (L)-2-(1,3-dimethyl-5-chloro-4-pyrazolyl)-1H-benzimidazole-4-[N-(1-hydroxymethyl-2-p-nitrophenylhydroxyethyl)]amide ¹HNMR (DMSO, 400 MHz) δ: 2.06(s,3H), 3.17-3.18(m, 1H), 3.25-3.28(m,1H), 3.50-3.52(m,1H), 3.65-3.68(t,1H), 3.70-3.72(d,1H), 3.95(s,3H), 4.73-4.77(t,1H), 7.43-7.45(t, 1H), 7.62-7.65(d,2H), 7.89-7.90(d,1H), 7.93-7.95(d,1H), 8.17-8.20(d,2H);

(641) (L)-2-(1,3-dimethyl-5-chloro-4-pyrazolyl)-1H-benzimidazole-4-[N-(1-hydroxymethyl-2-p-aminophenylhydroxyethyl)]amide ¹HNMR(DMSO,400 MHz)δ:2.06(s,3H),3.17-3.18(m, 1H),3.25-3.28(m,1H),3.50-3.52 (m,1H),3.65-3.68(t,1H), 3.70-3.72(d,1H),3.95(s,3H),4.73-4.77(t,1H),6.27(s,2H), 6.56-6.58 (d,2H),7.11-7.13(d,2H),7.43-7.45(t,1H),7.89-7.90 (d,1H),7.93-7.95(d,1H);

(642) 2-(1,3-dimethyl-5-chloro-4-pyrazolyl)-1H-benzimidazole-4-[N-(1-methyl-2-p-chlorophenylhydroxyethyl)]amide ¹HNMR (DMSO, 400 MHz) δ: 1.12-1.15(d,3H), 2.06(s, 3H), 3.25-3.28(m,1H), 3.65-3.68(t,1H), 3.95(s,3H), 4.73-4.77(t,1H), 7.29-7.30(d,2H), 7.40-7.41(d,2H), 7.43-7.45(t, 1H), 7.89-7.91(d,1H), 7.93-7.94(d,1H);

(643) 2-(1,3-dimethyl-5-chloro-4-pyrazolyl)-1H-benzimidazole-4-(N—N'-piperidinyl)amide ¹HNMR (DMSO, 400 MHz) δ: 1.52-1.55(m,4H), 1.59-1.63(m,2H), 2.06(s,3H), 3.10-3.15(t,4H), 3.95(s,3H), 7.43-7.45(t,1H), 7.89-7.91(d,1H), 7.93-7.94(d,1H);

(644) 2-(1,3-dimethyl-5-chloro-4-pyrazolyl)-1H-benzimidazole-4-(N-2-piperazinyl)amide ¹HNMR(DMSO,400 MHz)δ:1.91-1.93(m,2H), 2.06(s, 3H), 2.62-2.63(m,1H), 2.65-2.66(m,1H), 2.69-2.70(m,1H), 2.72-2.74(m,1H), 2.77-2.80(m,1H), 3.02-3.05(m,1H), 3.95 (s,3H), 3.99-4.01(m,1H), 7.43-7.45(t,1H), 7.89-7.91(d,1H), 7.93-7.94(d,1H);

(645) 2-(1,3-dimethyl-5-chloro-4-pyrazolyl)-1H-benzimidazole-4-(N-2'-benzimidazolyl)amide ¹HNMR (DMSO, 400 MHz) δ: 2.06(s,3H), 3.95(s,3H), 7.12-7.15(d,2H), 7.22-7.24(t,2H), 7.43-7.45(t,1H), 7.89-7.91 (d,1H), 7.93-7.94(d,1H);

(646) 2-(1,3-dimethyl-5-chloro-4-pyrazolyl)-1H-benzimidazole-4-(N-o-aminophenyl)amide ¹HNMR (DMSO, 400 MHz) δ: 2.06(s,3H), 3.95(s,3H), 6.27(s,2H), 6.38-6.40(d,1H), 6.56-6.58(t,1H), 6.75-6.76(d, 1H), 7.02-7.04(t,1H), 7.43-7.45(t,1H), 7.89-7.91(d,1H), 7.93-7.94(d,1H);

(647) 2-(1,3-dimethyl-5-chloro-4-pyrazolyl)-1H-benzimidazole-4-(N-5-benzimidazolonyl)amide ¹HNMR (DMSO, 400 MHz) δ: 2.06(s,3H), 3.95(s,3H), 6.35-6.37(d,1H), 6.93(s,1H), 7.43-7.45(t,1H), 7.54-7.56(d, 1H), 7.89-7.91(d,1H), 7.93-7.94(d,1H);

(648) 2-(1,3-dimethyl-5-chloro-4-pyrazolyl)-1H-benzimidazole-4-(N-4'-carbonamido-5'-imidazolyl) amide ¹HNMR (DMSO, 400 MHz) δ: 2.06(s,3H), 3.95(s,3H), 7.43-7.45(t,1H), 7.89-7.91(d,1H), 7.93-7.94(d,1H), 8.37(s, 2H), 9.24-9.26(d,1H), 13.00-13.03(d,1H);

(649) 2-(1,3-dimethyl-5-chloro-4-pyrazolyl)-1H-benzimidazole-4-(N-4'-pyrazolyl)amide ¹HNMR (DMSO, 400 MHz) δ: 2.06(s,3H), 3.95(s,3H), 7.43-7.45(t,1H), 7.89-7.91(d,1H), 7.93-7.94(d,1H), 8.61(s, 1H), 8.63-8.65(d,1H), 13.71-13.75(d,1H);

(650) 2-(1,3-dimethyl-5-chloro-4-pyrazolyl)-1H-benzimidazole-4-(N—(N'-piperazinyl))amide ¹HNMR (DMSO, 400 MHz) δ: 1.91-1.95(m,1H), 2.06(s, 3H), 2.65-2.67(t,4H), 2.80-2.83(m,4H), 3.95(s,3H), 7.43-7.45(t,1H), 7.90-7.91(d,1H), 7.93-7.94(d,1H);

(651) 2-(1,3-dimethyl-5-chloro-4-pyrazolyl)-1H-benzimidazole-4-(N-2-pyrazinyl)amide ¹HNMR (DMSO, 400 MHz) δ: 2.06(s,3H), 3.95(s,3H), 7.43-7.45(t,1H), 7.89-7.91(d,1H), 7.93-7.94(d,1H), 8.34-8.35(d,1H), 8.36(s,1H), 8.40-8.42(d,1H);

(652) 2-(1,3-dimethyl-5-chloro-4-pyrazolyl)-1H-benzimidazole-4-(N-2-pyrimidinyl)amide $^1$HNMR (DMSO, 400 MHz) δ: 2.06(s,3H), 3.95(s,3H), 6.93-6.95(t,1H), 7.43-7.45(t,1H), 7.89-7.91(d,1H), 7.93-7.94 (d,1H), 8.45-8.46(d,2H);

(653) 2-(1,3-dimethyl-5-chloro-4-pyrazolyl)-1H-benzimidazole-4-(N-2-pyridyl)amide $^1$HNMR (DMSO, 400 MHz) δ: 2.06(s,3H), 3.95(s,3H), 6.62-6.64(t,1H), 6.70-6.72(d,1H), 7.43-7.45(t,1H), 7.55-7.57 (t,1H), 7.89-7.91(d,1H), 7.93-7.94(d,1H), 8.07-8.09(d,1H);

(654) 2-(1,3-dimethyl-5-chloro-4-pyrazolyl)-1H-benzimidazole-4-(N-4-methyl-5-thiazolyl)amide $^1$HNMR (DMSO, 400 MHz) δ: 2.06(s,3H), 2.45(s,3H), 3.95(s,3H), 7.43-7.45(t,1H), 7.89-7.91(d,1H), 7.93-7.94(d, 1H), 8.12(s,1H);

(655) 2-(1,3-dimethyl-5-chloro-4-pyrazolyl)-1H-benzimidazole-4-(N-2,4-dihydroxyl-5-pyrimidinyl)amide $^1$HNMR (DMSO, 400 MHz) δ: 2.06(s,3H), 3.95(s,3H), 7.43-7.45(t,1H), 7.89-7.91(d,1H), 7.82(s,1H), 7.93-7.94(d, 1H), 8.33(s,1H), 11.53(s,1H);

(656) 2-(1,3-dimethyl-5-chloro-4-pyrazolyl)-1H-benzimidazole-4-(N-4,6-dimethoxy-2-pyrimidinyl)amide $^1$HNMR (DMSO, 400 MHz) δ: 2.06(s,3H), 3.82(s,6H), 3.95(s,3H), 5.71(s,1H), 7.43-7.45(t,1H), 7.89-7.91(d,1H), 7.93-7.94(d,1H);

(657) 2-(1,3-dimethyl-5-chloro-4-pyrazolyl)-1H-benzimidazole-4-(N-4-chloro-6-amino-2-pyrimidinyl)amide $^1$HNMR (DMSO, 400 MHz) δ: 2.06(s,3H), 3.95(s,3H), 5.98(s,1H), 7.43-7.45(t,1H), 7.74(s,2H), 7.89-7.91(d,1H), 7.93-7.94(d,1H);

(658) 2-(1,3-dimethyl-5-chloro-4-pyrazolyl)-1H-benzimidazole-4-(N-4,6-dichloro-5-pyrimidinyl)amide $^1$HNMR (DMSO, 400 MHz) δ: 2.06(s,3H), 3.95(s,3H), 7.43-7.45(t,1H), 7.89-7.91(d,1H), 7.93-7.94(d,1H), 9.34(s,1H);

(659) 2-(1,3-dimethyl-5-chloro-4-pyrazolyl)-1H-benzimidazole-4-(N-o-fluorophenyl)amide $^1$HNMR(DMSO,400 MHz)δ:2.06(s,3H), 3.95(s,3H), 6.60-6.61(d,1H), 6.63-6.65(t,1H), 6.96-6.98(t,1H), 6.99-7.01 (d,1H), 7.43-7.45(t,1H), 7.89-7.91(d,1H), 7.93-7.94(d,1H);

(660) 2-(1,3-dimethyl-5-chloro-4-pyrazolyl)-1H-benzimidazole-4-(N-2-hydroxyl-4-pyrimidinyl)amide $^1$HNMR(DMSO,400 MHz)δ:2.06(s,3H), 3.95(s,3H), 5.46-5.48(d,1H), 7.10-7.11(d,1H), 7.43-7.45(t,1H), 7.82(s,1H), 7.89-7.91(d,1H), 7.93-7.94(d,1H);

(661) 2-(1,3-dimethyl-5-chloro-4-pyrazolyl)-1H-benzimidazole-4-(N-6-purinyl)amide $^1$HNMR(DMSO,400 MHz)δ:2.06(s,3H), 3.95(s,3H), 7.43-7.45(t,1H), 7.86-7.88(d,1H), 7.89-7.91(d,1H), 7.93-7.94(d,1H), 8.16-8.18(d,1H);

(662) 2-(1,3-dimethyl-5-chloro-4-pyrazolyl)-1H-benzimidazole-4-(N-6-hydroxyl-2-purinyl)amide $^1$HNMR (DMSO, 400 MHz) δ: 2.06(s,3H), 3.95(s,3H), 7.43-7.45(t,1H), 7.89-7.91(d,1H), 7.93-7.94(d,1H), 8.57-8.59(d,1H), 11.53(s,1H);

(663) 2-(4-hydroxyphenyl)-1H-benzimidazole-4-(N-o-fluorophenyl)amide (refer to FIG. 5)

$^1$HNMR(DMSO,400 MHz)δ:7.13-7.19(m,1H),7.23-7.27 (t,1H),7.36-7.41(t,1H),7.50-7.54(m,2H), 7.85-7.87(d,1H), 7.94-7.95(d,1H), 8.05-8.07(d,1H), 8.57-8.61(t,1H), 12.19-12.20(d,1H), 14.25(s,1H);

(664) (L)-2-(3-hydroxyphenyl)-1H-benzimidazole-4-[N-(1-hydroxymethyl-2-p-nitrophenylhydroxyethyl)]amide (Refer to FIG. 6)

$^1$HNMR(DMSO,400 MHz)δ:3.51-3.57(m,1H),3.64-3.72 (m,1H),4.22-4.26(m,1H),5.05-5.08(q,1H),5.25-5.27(d,1H), 6.16-6.18(d,1H),6.95-6.98(d,1H), 7.23-7.27(t,1H),7.30-7.34 (t,1H),7.36-7.40(m,1H),7.65-7.73(m,4H),7.80-7.84(m,1H), 8.03-8.10(m,2H), 9.76(s,1H), 10.43-10.46(d,1H), 13.31(s,1H);

(665) 2-(3-hydroxyphenyl)-1H-benzimidazole-4-(N-6-hydroxyl-2-purinyl)amide $^1$HNMR (DMSO, 400 MHz) δ: 5.35(s,1H), 6.91-6.93(d, 1H),7.04(s,1H),7.34-7.36(d,1H),7.43-7.45(t,1H),7.84-7.86 (d,1H), 7.89-7.91(d,1H), 7.93-7.94(d,1H), 8.57-8.59(d,1H), 11.53(s,1H).

EXAMPLES 666-688

1.0 g of 2,3-diaminobenzoic acid is dissolved into 20 ml of glacial acetic acid. Triethyl orthoformate (2.1 eq.) is added into the above mixture at temperature of 0° C.; and to stir it for 2 hours at temperature of 0~5° C.; and 150 ml of water is added into it, and then to isolate and filter to produce 2-ethoxy-1H-benzimidazole-4-formic acid. The yield is about 89%. 2-ethoxy-1H-benzimidzzole-4-formic acid is added into 15 ml of thionyl chloride, and to react for 60 minutes, and after end of the reaction completely, and (L)-2-amino-1-p-nitrophenyl-1,3-propylene glycol (1.1 eq) is added into the reaction mixture under stirring for 2 hours at the room temperature, and then to filter the inorganic salt, and evaporate the solvent to dry, to obtain the final product of (L)-2-ethoxy-1H-benzimidazole-4-[N-(1-hydroxymethyl-2-p-nitrophenylhydroxyethyl)amide. The yield is about 91%. Using the same process to prepare the compounds in Table 3.

TABLE 3

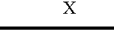

| No. | Compounds | X | Y | Field % |
|-----|-----------|---|---|---------|
| 666 | (L)-2-ethoxy-1H-benzimidazole-4-[N-(1-hydroxymethyl-2-p-nitrophenylhydroxyethyl)]amide | 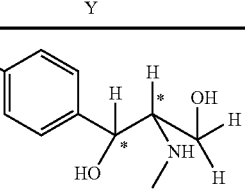 | 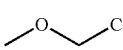 | 94 |
| 667 | (L)-2-ethoxy-1H-benzimidazole-4-[N-(1-hydroxymethyl-2-p-aminophenylhydroxyethyl)]amide | 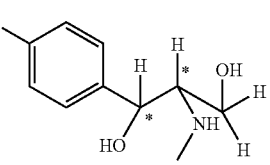 | 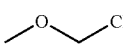 | 91 |
| 668 | 2-ethoxy-1H-benzimidazole-4-[N-(1-methyl-2-p-chlorophenylhydroxyethyl)]amide | 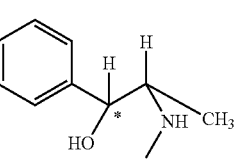 | 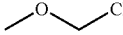 | 92 |
| 669 | 2-ethoxy-1H-benzimidazole-4-(N-N'-piperidinyl)amide | 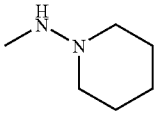 | 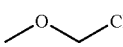 | 92 |
| 670 | 2-ethoxy-1H-benzimidazole-4-(N-2-piperazinyl))amide | 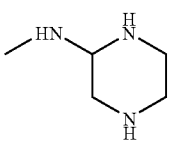 | 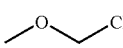 | 93 |
| 671 | 2-ethoxy-1H-benzimidazole-4-(N-2'-benzimidazolyl)amide | 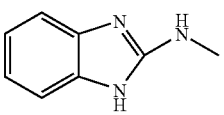 | 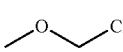 | 94 |
| 672 | 2-ethoxy-1H-benzimidazole-4-(N-o-aminophenyl)amide | 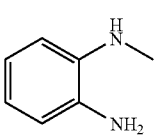 | 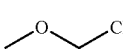 | 89 |
| 673 | 2-ethoxy-1H-benzimidazole-4-(N-5-benzimidazolonyl)amide | 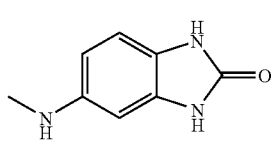 |  | 91 |
| 674 | 2-ethoxy-1H-benzimidazole-4-(N-4'-carbonamido-5'-imidazolyl)amide |  |  | 86 |

TABLE 3-continued

| No. | Compounds | X | Y | Field % |
|---|---|---|---|---|
| 675 | 2-ethoxy-1H-benzimidazole-4-(N-4'-pyrazolyl)amide | —O—CH₂CH₃ | 4-pyrazolyl-NH— | 93 |
| 676 | 2-ethoxy-1H-benzimidazole-4-(N-(N'-piperazinyl))amide | —O—CH₂CH₃ | piperazinyl-NH— | 91 |
| 677 | 2-ethoxy-1H-benzimidazole-4-(N-2-pyrazinyl)amide | —O—CH₂CH₃ | 2-pyrazinyl-NH— | 92 |
| 678 | 2-ethoxy-1H-benzimidazole-4-(N-2-pyrimidinyl)amide | —O—CH₂CH₃ | 2-pyrimidinyl-NH— | 92 |
| 679 | 2-ethoxy-1H-benzimidazole-4-(N-2-pyridyl)amide | —O—CH₂CH₃ | 2-pyridyl-NH— | 93 |
| 680 | 2-ethoxy-1H-benzimidazole-4-(N-4-methyl-5-thiazolyl)amide | —O—CH₂CH₃ | 4-methyl-5-thiazolyl-NH— | 94 |
| 681 | 2-ethoxy-1H-benzimidazole-4-(N-2,4-dihydroxyl-5-pyrimidinyl)amide | —O—CH₂CH₃ | 2,4-dihydroxy-5-pyrimidinyl-NH— | 85 |
| 682 | 2-ethoxy-1H-benzimidazole-4-(N-4,6-dimethoxy-2-pyrimidinyl)amide | —O—CH₂CH₃ | 4,6-dimethoxy-2-pyrimidinyl-NH— | 94 |
| 683 | 2-ethoxy-1H-benzimidazole-4-(N-4-chloro-6-amino-2-pyrimidinyl)amide | —O—CH₂CH₃ | 4-chloro-6-amino-2-pyrimidinyl-NH— | 89 |

TABLE 3-continued

| No. | Compounds | X | Y | Field % |
|---|---|---|---|---|
| 684 | 2-ethoxy-1H-benzimidazole-4-(N-4,6-dichloro-5-pyrimidinyl)amide | —O—CH₂CH₃ | 4,6-dichloro-5-(methylamino)pyrimidinyl | |
| 685 | 2-ethoxy-1H-benzimidazole-4-(N-o-fluorophenyl)amide | —O—CH₂CH₃ | N-methyl-2-fluorophenyl | 93 |
| 686 | 2-ethoxy-1H-benzimidazole-4-(N-2-hydroxyl-4-pyrimidinyl)amide | —O—CH₂CH₃ | 2-hydroxy-4-pyrimidinyl | 87 |
| 687 | 2-ethoxy-1H-benzimidazole-4-(N-6-purinyl)amide | —O—CH₂CH₃ | 6-purinyl | 93 |
| 688 | 2-ethoxy-1H-benzimidzzole-4-(N-6-hydroxyl-2-purinyl)amide | —O—CH₂CH₃ | 6-hydroxy-2-purinyl | 88 |

Structure Identification of Products:

(666) (L)-2-ethoxy-1H-benzimidazole-4-[N-(1-hydroxymethyl-2-p-nitrophenylhydroxyethyl)]amide ¹HNMR (DMSO, 400 MHz) δ: 1.32-1.35(t,3H), 3.17-3.18(m,1H), 3.25-3.28(m,1H), 3.50-3.52(m,1H),3.65-3.68(t,1H), 3.70-3.72(d,1H), 4.29-4.33(m,2H), 4.73-4.77(t,1H), 7.43-7.45(t,1H),7.62-7.65(d,2H), 7.89-7.90(d,1H), 7.93-7.95(d,1H), 8.17-8.20(d,2H);

(667) (L)-2-ethoxy-1H-benzimidazole-4-[N-(1-hydroxymethyl-2-p-aminophenylhydroxyethyl)]amide ¹HNMR (DMSO, 400 MHz) δ: 1.32-1.35(t,3H), 3.17-3.18(m,1H), 3.25-3.28(m,1H), 3.50-3.52(m,1H),3.65-3.68(t,1H), 3.70-3.72(d,1H), 4.29-4.33(m,2H), 4.73-4.77(t,1H), 6.27(s, 2H), 6.56-6.58(d,2H), 7.11-7.13(d,2H), 7.43-7.45(t,1H), 7.89-7.90(d,1H), 7.93-7.95(d,1H);

(668) 2-ethoxy-1H-benzimidazole-4-[N-(1-methyl-2-p-chlorophenylhydroxyethyl)]amide ¹HNMR (DMSO, 400 MHz) δ: 1.12-1.15(d,3H), 1.32-1.35(t,3H), 3.25-3.28(m,1H), 3.65-3.68(t,1H), 4.29-4.33(m,2H), 4.73-4.77(t,1H), 7.29-7.30(d,2H), 7.40-7.41(d,2H), 7.43-7.45(t,1H), 7.89-7.91(d,1H), 7.93-7.94(d,1H);

(669) 2-ethoxy-1H-benzimidazole-4-(N—N'-piperidinyl)amide

¹HNMR (DMSO, 400 MHz) δ: 1.32-1.35(t,3H), 1.52-1.55(m,4H), 1.59-1.63(m,2H), 3.10-3.15(t,4H),4.29-4.33(m,2H), 7.43-7.45(t,1H), 7.89-7.91(d,1H), 7.93-7.94(d,1H);

(670) 2-ethoxy-1H-benzimidazole-4-(N-2-piperazinyl))amide

¹HNMR (DMSO, 400 MHz) δ: 1.32-1.35(t,3H), 1.91-1.93(m,2H), 2.62-2.63(m,1H), 2.65-2.66(m,1H), 2.69-2.70(m,

1H), 2.72-2.74(m,1H), 2.77-2.80(m,1H), 3.02-3.05(m, 1H), 3.99-4.01(m,1H), 4.29-4.33(m,2H), 7.43-7.45(t,1H), 7.89-7.91(d,1H), 7.93-7.94(d,1H);

(671) 2-ethoxy-1H-benzimidazole-4-(N-2'-benzimidazolyl)amide $^1$HNMR (DMSO, 400 MHz) δ: 1.32-1.35(t,3H), 4.29-4.33 (m,2H), 7.12-7.15(d,2H), 7.22-7.24(t,2H), 7.43-7.45(t,1H), 7.89-7.91(d,1H), 7.93-7.94(d,1H);

(672) 2-ethoxy-1H-benzimidazole-4-(N-o-aminophenyl)amide $^1$HNMR (DMSO, 400 MHz) δ: 1.32-1.35(t,3H), 4.29-4.33 (m,2H), 6.27(s,2H), 6.38-6.40(d,1H), 6.56-6.58(t,1H), 6.75-6.76(d,1H), 7.02-7.04(t,1H), 7.43-7.45(t,1H), 7.89-7.91(d,1H), 7.93-7.94(d,1H);

(673) 2-ethoxy-1H-benzimidazole-4-(N-5-benzimidazolonyl)amide $^1$HNMR (DMSO, 400 MHz) δ: 1.32-1.35(t,3H), 4.29-4.33 (m,2H), 6.35-6.37(d,1H), 6.93(s,1H), 7.43-7.45(t,1H), 7.54-7.56(d,1H), 7.89-7.91(d,1H), 7.93-7.94(d,1H);

(674) 2-ethoxy-1H-benzimidazole-4-(N-4'-carbonamido-5'-imidazolyl)amide $^1$HNMR (DMSO, 400 MHz) δ: 1.32-1.35(t,3H), 4.29-4.33 (m,2H), 7.43-7.45(t,1H), 7.89-7.91(d,1H), 7.93-7.94(d,1H), 8.37(s,2H), 9.24-9.26(d,1H), 13.00-13.03(d,1H);

(675) 2-ethoxy-1H-benzimidazole-4-(N-4'-pyrazolyl)amide $^1$HNMR (DMSO, 400 MHz) δ: 1.32-1.35(t,3H), 4.29-4.33 (m,2H), 7.43-7.45(t,1H), 7.89-7.91(d,1H), 7.93-7.94(d,1H), 8.61(s,1H), 8.63-8.65(d,1H), 13.71-13.75(d,1H);

(676) 2-ethoxy-1H-benzimidazole-4-(N—(N'-piperazinyl))amide $^1$HNMR (DMSO, 400 MHz) δ: 1.32-1.35(t,3H), 1.91-1.95 (m,1H), 2.65-2.67(t,4H), 2.80-2.83(m,4H), 4.29-4.33(m,2H), 7.43-7.45(t,1H), 7.90-7.91(d,1H), 7.93-7.94(d,1H);

(677) 2-ethoxy-1H-benzimidazole-4-(N-2-pyrazinyl)amide $^1$HNMR (DMSO, 400 MHz) δ: 1.32-1.35(t,3H), 4.29-4.33 (m,2H), 7.43-7.45(t,1H), 7.89-7.91(d,1H), 7.93-7.94(d,1H), 8.34-8.35(d,1H), 8.36(s,1H), 8.40-8.42(d,1H);

(678) 2-ethoxy-1H-benzimidazole-4-(N-2-pyrimidinyl)amide $^1$HNMR (DMSO, 400 MHz) δ: 1.32-1.35(t,3H), 4.29-4.33 (m,2H), 6.93-6.95(t,1H), 7.43-7.45(t,1H), 7.89-7.91(d,1H), 7.93-7.94(d,1H), 8.45-8.46(d,2H);

(679) 2-ethoxy-1H-benzimidazole-4-(N-2-pyridyl)amide $^1$HNMR (DMSO, 400 MHz) δ: 1.32-1.35(t,3H), 4.29-4.33 (m,2H), 6.62-6.64(t,1H), 6.70-6.72(d,1H), 7.43-7.45(t,1H), 7.55-7.57(t,1H), 7.89-7.91(d,1H), 7.93-7.94(d,1H), 8.07-8.09(d,1H);

(680) 2-ethoxy-1H-benzimidazole-4-(N-4-methyl-5-thiazolyl)amide $^1$HNMR (DMSO, 400 MHz) δ: 1.32-1.35(t,3H), 2.45(s, 3H), 4.29-4.33(m,2H), 7.43-7.45(t,1H), 7.89-7.91(d,1H), 7.93-7.94(d,1H), 8.12(s,1H);

(681) 2-ethoxy-1H-benzimidazole-4-(N-2,4-dihydroxyl-5-pyrimidinyl)amide $^1$HNMR (DMSO, 400 MHz) δ: 1.32-1.35(t,3H), 4.29-4.33 (m,2H), 7.43-7.45(t,1H), 7.82(s,1H), 7.89-7.91(d,1H), 7.93-7.94(d,1H), 8.33(s,1H), 11.53(s,1H);

(682) 2-ethoxy-1H-benzimidazole-4-(N-4,6-dimethoxy-2-pyrimidinyl)amide $^1$HNMR (DMSO, 400 MHz) δ: 1.32-1.35(t,3H), 3.82(s, 6H), 4.29-4.33(m,2H), 5.71(s,1H), 7.43-7.45(t,1H), 7.89-7.91(d,1H), 7.93-7.94(d,1H);

(683) 2-ethoxy-1H-benzimidazole-4-(N-4-chloro-6-amino-2-pyrimidinyl)amide $^1$HNMR (DMSO, 400 MHz) δ: 1.32-1.35(t,3H), 4.29-4.33 (m,2H), 5.98(s,1H), 7.43-7.45(t,1H), 7.74(s,2H), 7.89-7.91 (d,1H), 7.93-7.94(d,1H);

(684) 2-ethoxy-1H-benzimidazole-4-(N-4,6-dichloro-5-pyrimidinyl)amide $^1$HNMR (DMSO, 400 MHz) δ: 1.32-1.35(t,3H), 4.29-4.33 (m,2H), 7.43-7.45(t,1H), 7.89-7.91(d,1H), 7.93-7.94(d,1H), 9.34(s,1H);

(685) 2-ethoxy-1H-benzimidazole-4-(N-o-fluorophenyl)amide $^1$HNMR (DMSO, 400 MHz) δ: 1.32-1.35(t,3H), 4.29-4.33 (m,2H), 6.60-6.61(d,1H), 6.63-6.65(t,1H), 6.96-6.98(t,1H), 6.99-7.01(d,1H), 7.43-7.45(t,1H), 7.89-7.91(d,1H), 7.93-7.94(d,1H);

(686) 2-ethoxy-1H-benzimidazole-4-(N-2-hydroxyl-4-pyrimidinyl)amide $^1$HNMR (DMSO, 400 MHz) δ: 1.32-1.35(t,3H), 4.29-4.33 (m,2H), 5.46-5.48(d,1H), 7.10-7.11(d,1H), 7.43-7.45(t,1H), 7.82(s,1H), 7.89-7.91(d,1H), 7.93-7.94(d,1H);

(687) 2-ethoxy-1H-benzimidazole-4-(N-6-purinyl)amide $^1$HNMR (DMSO, 400 MHz) δ: 1.32-1.35(t,3H), 4.29-4.33 (m,2H), 7.43-7.45(t,1H), 7.86-7.88(d,1H), 7.89-7.91(d,1H), 7.93-7.94(d,1H), 8.16-8.18(d,1H);

(688) 2-ethoxy-1H-benzimidazole-4-(N-6-hydroxyl-2-purinyl)amide $^1$HNMR (DMSO, 400 MHz) δ: 1.32-1.35(t,3H), 4.29-4.33 (m,2H), 7.43-7.45(t,1H), 7.89-7.91(d,1H), 7.93-7.94(d,1H), 8.57-8.59(d,1H), 11.53(s,1H).

Measures of Properties:

Measures of Anti-Coxsackie B3 Viruses Activity of the Compounds

The products are applied for measures of antivirus properties of Vero cells. Refer to the results of Table 3: datum of anti-coxsackie B3 viruses activities of some compounds.

TABLE 3

| NAME OF COMPOUNDS | X | Y | IC$_{50}$(μg/ml) |
|---|---|---|---|
| (L)-2-(2-pyridyl)-1H-benzimidazole-4-[N-(1-hydroxymethyl-2-p-nitrophenylhydroxyethyl)]amide | 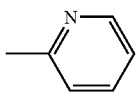 | 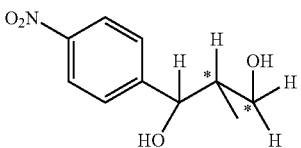 | 1.76 |
| 2-(2-pyridyl)-1H-benzimidazole-4-[N-(1-methyl-2-p-chlorophenylhydroxyethyl)]amide | 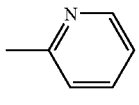 | 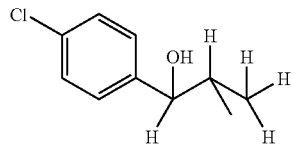 | 4.115 |
| 2-(3-pyridyl)-1H-benzimidazole-4-[N-(1-methyl-2-p-chlorophenylhydroxyethyl)]amide | 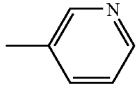 | 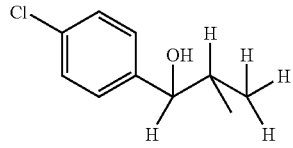 | 2.37 |
| (L)-2-(2-thienyl)-1H-benzimidazole-4-[N-(1-hydroxymethyl-2-p-nitrophenylhydroxyethyl)]amide | 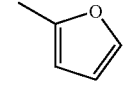 | 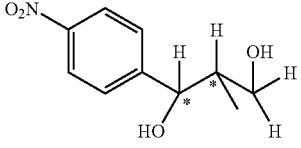 | 15.90 |
| 2-(2-thienyl)-1H-benzimidazole-4-[N-(1-methyl-2-p-chlorophenylhydroxyethyl)]amide | 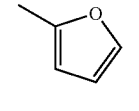 | 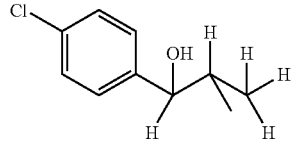 | 5.30 |
| (L)-2-(5-nitro-2-thienyl)-1H-benzimidazole-4-[N-(1-hydroxymethyl-2-p-nitrophenylhydroxyethyl)]amide | 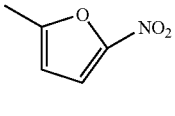 | 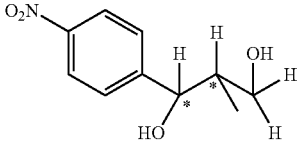 | 10.69 |
| 2-(5-nitro-2-thienyl)-1H-benzimidazole-4-(N-(1-methyl-2-p-chlorophenylhydroxyethyl))-amide | 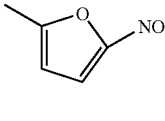 | 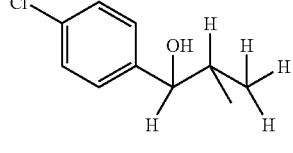 | 7.12 |
| 2-thienyl-1H-benzimidazole-4-(N-(2-fluorophenyl)-amide | 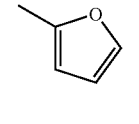 | 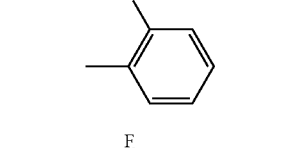 | 1.06 |
| 2-(5-nitro-2-thienyl)-1H-benzimidazole-4-(N-(2-fluorophenyl))-amide |  | 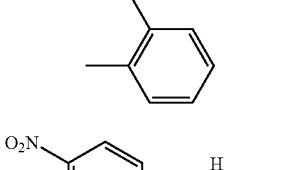 | >9.25 |
| (L)-2-(5-amino-2-thienyl)-1H-benzimidazole-4-[N-(1-hydroxymethyl-2-p-nitrophenylhydroxyethyl)]amide | 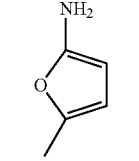 | 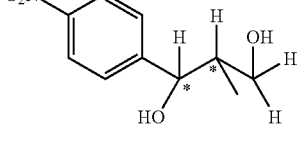 | 2.3 |

TABLE 3-continued

| NAME OF COMPOUNDS | X | Y | IC$_{50}$(μg/ml) |
|---|---|---|---|
| 2-(5-amino-2-thienyl)-1H-benzimidazole-4-(N-o-fluorophenyl)amide | 5-amino-2-thienyl (NH$_2$, O) | o-fluorophenyl | 3.5 |
| 2-(5-amino-2-thienyl)-1H-benzimidazole-4-(N-o-methylphenyl)amide | 5-amino-2-thienyl (NH$_2$, O) | o-methylphenyl (CH$_3$) | 8.7 |
| 2-(5-amino-2-thienyl)-1H-benzimidazole-4-(N-p-hydroxyphenyl)amide | 5-amino-2-thienyl (NH$_2$, O) | p-hydroxyphenyl (OH) | 6.5 |
| 2-(4-methoxypyridyl)-1H-benzimidazole-4-(N-o-fluorophenyl)amide | 4-methoxypyridyl (OCH$_3$) | o-fluorophenyl | 10.2 |
| (L)-2-(4-methoxypyridyl)-1H-benzimidazole-4-[N-(1-hydroxymethyl-2-p-nitrophenylhydroxyethyl)]amide | 4-methoxypyridyl (OCH$_3$) | O$_2$N-phenyl-CH(OH)-C*H(OH)-CH$_2$ | 6.3 |
| 2-(4-methoxypyridyl)-1H-benzimidazole-4-(N-o-hydroxyphenyl)amide | 4-methoxypyridyl (OCH$_3$) | o-hydroxyphenyl (OH) | 16.2 |
| 2-(4-methoxypyridyl)-1H-benzimidazole-4-(N-p-aminophenyl)amide | 4-methoxypyridyl (OCH$_3$) | p-aminophenyl (NH$_2$) | 13.4 |
| (L)-2-(6-methoxypyridyl)-1H-benzimidazole-4-[N-(1-hydroxymethyl-2-p-nitrophenylhydroxyethyl)]amide | 6-methoxypyridyl (OCH$_3$) | O$_2$N-phenyl-CH(OH)-C*H(OH)-CH$_2$ | 11.2 |
| 2-(6-methoxypyridyl)-1H-benzimidazole-4-(N-o-fluorophenyl)amide | 6-methoxypyridyl (OCH$_3$) | o-fluorophenyl (F) | 14.1 |

TABLE 3-continued

| NAME OF COMPOUNDS | X | Y | IC$_{50}$(μg/ml) |
|---|---|---|---|
| 2-(6-methoxypyridyl)-1H-benzimidazole-4-(N-o-hydroxyphenyl)amide | pyridyl-OCH$_3$ | o-hydroxyphenyl | 15.7 |
| 2-(6-methoxypyridyl)-1H-benzimidazole-4-(N-p-aminophenyl)amide | pyridyl-OCH$_3$ | p-aminophenyl | 16.8 |
| (L)-2-(4-dimethylaminopyridyl)-1H-benzimidazole-4-[N-(1-hydroxymethyl-2-p-nitrophenylhydroxyethyl)]amide | 4-N(CH$_3$)$_2$-pyridyl | p-O$_2$N-C$_6$H$_4$-CH(OH)-CH(CH$_3$)-CH(OH)H | 10.2 |
| 2-(4-dimethylaminopyridyl)-1H-benzimidazole-4-(N-o-fluorophenyl)amide | 4-N(CH$_3$)$_2$-pyridyl | o-fluorophenyl | 9.6 |
| 2-(4-dimethylaminopyridyl)-1H-benzimidazole-4-(N-o-hydroxyphenyl)amide | 4-N(CH$_3$)$_2$-pyridyl | o-hydroxyphenyl | 9.8 |
| 2-(4-dimethylaminopyridyl)-1H-benzimidazole-4-(N-p-aminophenyl)amide | 4-N(CH$_3$)$_2$-pyridyl | p-aminophenyl | 10.2 |
| (L)-2-(3-pyridazinyl)-1H-benzimidazole-4-[N-(1-hydroxymethyl-2-p-nitrophenylhydroxyethyl)]amide | pyridazinyl | p-O$_2$N-C$_6$H$_4$-CH(OH)-CH(CH$_3$)-CH(OH)H | 5.8 |
| 2-(3-pyridazinyl)-1H-benzimidazole-4-(N-o-fluorophenyl)amide | pyridazinyl | o-fluorophenyl | 12.3 |
| 2-(3-pyridazinyl)-1H-benzimidazole-4-(N-o-hydroxyphenyl)amide | pyridazinyl | o-hydroxyphenyl | 15.2 |

| NAME OF COMPOUNDS | X | Y | IC$_{50}$(μg/ml) |
|---|---|---|---|
| 2-(3-pyridazinyl)-1H-benzimidazole-4-(N-p-aminophenyl)amide | 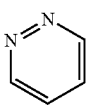 | 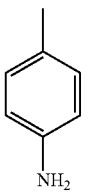 | 10.2 |
| (L)-2-(2-N-methyl-4-N-methylpiperazinyl)-1H-benzimidazole-4-[N-(1-hydroxymethyl-2-p-nitrophenylhydroxyethyl)]amide | 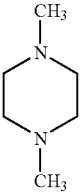 | 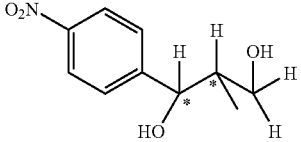 | 9.2 |
| 2-(2-N-methyl-4-N-methylpiperazinyl)-1H-benzimidazole-4-(N-o-fluorophenyl)amide | 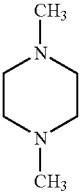 | 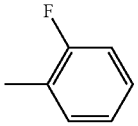 | 8.9 |
| 2-(5-methy-2-thienyl)-1H-benzimidazole-4-(N-o-hydroxyphenyl)amide | 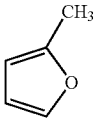 | 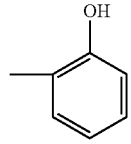 | 18.5 |
| 2-(2-N-methyl-4-N-methylpiperazinyl)-1H-benzimidazole-4-(N-p-aminophenyl)amide | 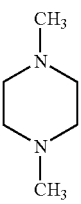 | 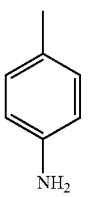 | 3.5 |
| (L)-2-(2-pyrazinyl)-1H-benzimidazole-4-[N-(1-hydroxymethyl-2-p-nitrophenylhydroxyethyl)]amide | 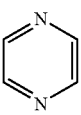 | 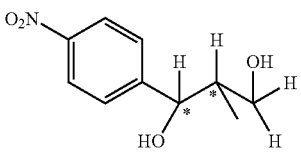 | 2.3 |
| 2-(2-pyrazinyl)-1H-benzimidazole-4-(N-o-fluorophenyl)amide | 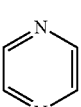 | 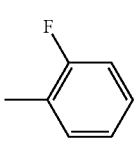 | 6.5 |
| 2-(2-pyrazinyl)-1H-benzimidazole-4-(N-o-hydroxyphenyl)amide | 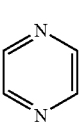 | 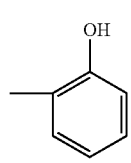 | 3.5 |

TABLE 3-continued

| NAME OF COMPOUNDS | X | Y | IC$_{50}$(μg/ml) |
|---|---|---|---|
| 2-(2-pyrazinyl)-1H-benzimidazole-4-(N-p-aminophenyl)amide |  | 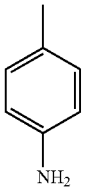 | 4.2 |
| (L)-2-N-piperazinyl-1H-benzimidazole-4-[N-(1-hydroxymethyl-2-o-nitrophenylhydroxyethyl)]amide |  | 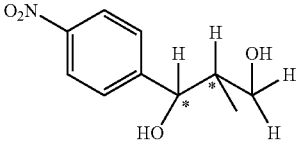 | 4.2 |
| 2-N-piperazinyl-1H-benzimidazole-4-(N-o-fluorophenyl)amide | 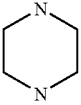 | 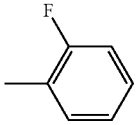 | 4.8 |
| 2-N-piperazinyl-1H-benzimidazole-4-(N-p-aminophenyl)amide |  | 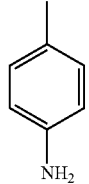 | 6.3 |
| (L)-2-(4-methyl-5-aminothiazolyl)-1H-benzimidazole-4-[N-(1-hydroxymethyl-2-p-nitrophenylhydroxyethyl)]amide | 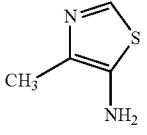 | 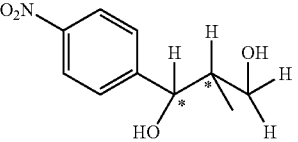 | 8.9 |
| 2-(4-methyl-5-aminothiazolyl)-1H-benzimidazole-4-(N-o-fluorophenyl)amide | 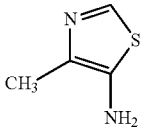 | 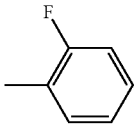 | 10.2 |
| 2-(4-methyl-5-aminothiazolyl)-1H-benzimidazole-4-(N-p-aminophenyl)amide | 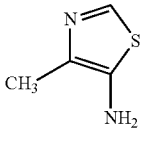 | 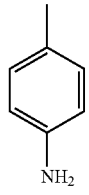 | 9.8 |
| (L)-2-thiazolyl-1H-benzimidazole-4-[N-(1-hydroxymethyl-2-p-nitrophenylhydroxyethyl)]amide |  | 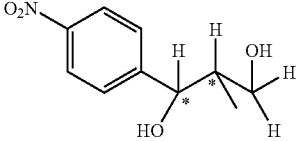 | 11.2 |
| 5-thiazolyl-1H-benzimidazole-4-(N-p-aminophenyl)amide |  | 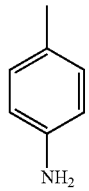 | 13.5 |

TABLE 3-continued

| NAME OF COMPOUNDS | X | Y | IC$_{50}$(μg/ml) |
|---|---|---|---|
| (L)-2-(3,4,5-trihydroxyphenyl)-1H-benzimidazole-4-[N-(1-hydroxymethyl-2-p-nitrophenylhydroxyethyl)]amide | 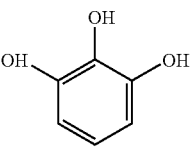 | 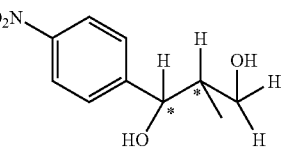 | 10.2 |
| 2-(2,3,4-trihydroxyphenyl)-1H-benzimidazole-4-(N-p-hydroxyphenyl)amide | 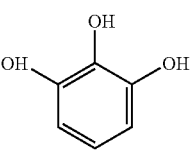 | 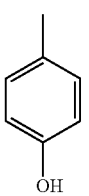 | 11.2 |
| (L)-2-(2-pyrimidinyl)-1H-benzimidazole-4-[N-(1-hydroxymethyl-2-p-nitrophenylhydroxyethyl)]amide |  | 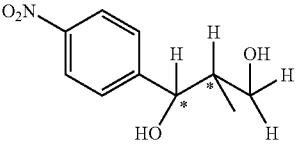 | 9.8 |
| 2-(2-pyrimidinyl)-1H-benzimidazole-4-(N-o-fluorophenyl)amide |  | 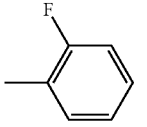 | 8.8 |
| 2-(2-pyrimidinyl)-1H-benzimidazole-4-(N-o-hydroxyphenyl)amide |  | 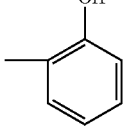 | 7.8 |
| 2-(2-pyrimidinyl)-1H-benzimidazole-4-(N-p-aminophenyl)amide |  | 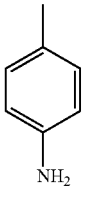 | 9.8 |
| (L)-2-(2-phenyl-5-pyrimidinyl)-1H-benzimidazole-4-[N-(1-hydroxymethyl-2-p-nitrophenylhydroxyethyl)]amide | 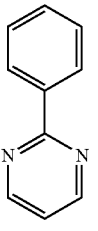 | 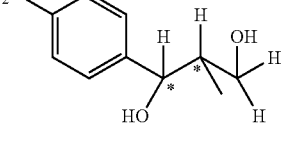 | 12.0 |
| 2-(2-phenyl-5-pyrimidinyl)-1H-benzimidazole-4-(N-o-fluorophenyl)amide | 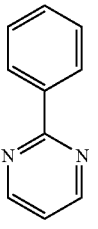 | 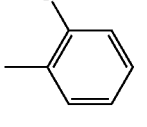 | 12.6 |

TABLE 3-continued

| NAME OF COMPOUNDS | X | Y | IC$_{50}$(μg/ml) |
|---|---|---|---|
| 2-(2-phenyl-5-pyrimidinyl)-1H-benzimidazole-4-(N-o-hydroxyphenyl)amide | 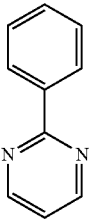 | 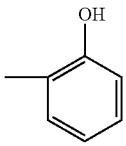 | 13.2 |
| 2-(2-phenyl-5-pyrimidinyl)-1H-benzimidazole-4-(N-p-aminophenyl)amide | 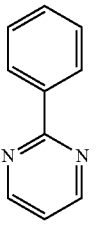 | 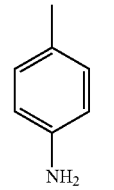 | 15.2 |
| (L)-2-(4-amino-6-chloro-5-pyrimidinyl)-1H-benzimidazole-4-[N-(1-hydroxymethyl-2-p-nitrophenylhydroxyethyl)]amide | 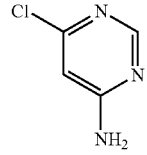 | 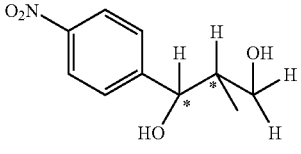 | 17.2 |
| 2-(4-amino-6-chloro-5-pyrimidinyl)-1H-benzimidazole-4-(N-o-fluorophenyl)amide | 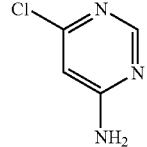 | 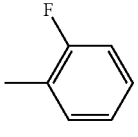 | 11.3 |
| 2-(4-amino-6-chloro-5-pyrimidinyl)-1H-benzimidazole-4-(N-o-hydroxyphenyl)amide | 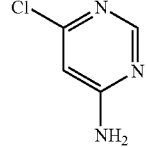 | 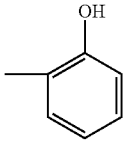 | 12.3 |
| 2-(4-amino-6-chloro-5-pyrimidinyl)-1H-benzimidazole-4-(N-p-aminophenyl)amide | 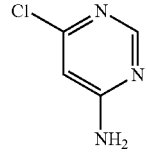 | 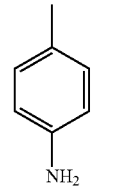 | 14.1 |
| (L)-2-(2-pyrrolyl)-1H-benzimidazole-4-[N-(1-hydroxymethyl-2-p-nitrophenylhydroxyethyl)]amide |  | 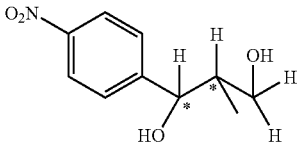 | 5.3 |
| 2-(2-pyrrolyl)-1H-benzimidazole-4-(N-o-fluorophenyl)amide |  | 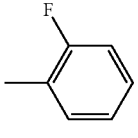 | 9.2 |

TABLE 3-continued

| NAME OF COMPOUNDS | X | Y | IC$_{50}$(μg/ml) |
|---|---|---|---|
| (L)-2-(3,5-dimethyl-2-pyrrolyl)-1H-benzimidazole-4-[N-(1-hydroxymethyl-2-p-nitrophenylhydroxyethyl)]amide | 3,5-dimethylpyrrolyl | 4-nitrophenyl-CH(OH)-C*H-CH$_2$OH | 8.6 |
| 2-(3,5-dimethyl-2-pyrrolyl)-1H-benzimidazole-4-(N-o-hydroxyphenyl)amide | 3,5-dimethylpyrrolyl | o-hydroxyphenyl | 10.2 |
| (L)-2-(N-methyl-2-pyrrolyl)-1H-benzimidazole-4-[N-(1-hydroxymethyl-2-p-nitrophenylhydroxyethyl)]amide | N-methylpyrrolyl | 4-nitrophenyl-CH(OH)-C*H-CH$_2$OH | 11.1 |
| 2-(N-methyl-2-pyrrolyl)-1H-benzimidazole-4-(N-o-fluorophenyl)amide | N-methylpyrrolyl | o-fluorophenyl | 13.2 |
| (L)-2-(2-piperidinyl)-1H-benzimidazole-4-[N-(1-hydroxymethyl-2-p-nitrophenylhydroxyethyl)]amide | piperidinyl | 4-nitrophenyl-CH(OH)-C*H-CH$_2$OH | 17.2 |
| 2-(2-quinolinyl)-1H-benzimidazole-4-(N-o-fluorophenyl)amide | quinolinyl | o-fluorophenyl | 15.3 |
| 2-(3-indolyl)-1H-benzimidazole-4-(N-p-aminophenyl)amide | indolyl | p-aminophenyl | 10.8 |
| (L-)2-(3-indolyl)-1H-benzimidazole-4-[N-(1-hydroxymethyl-2-p-nitrophenylhydroxyethyl)]amide | indolyl | 4-nitrophenyl-CH(OH)-C*H-CH$_2$OH | 9.6 |
| RBV | — | — | 353.55 |

In the above table: "-" indicates that these samples don't have anti-coxsackie B3 viruses activities at the maximum nontoxic dose.

IC$_{50}$ indicates half inhibitory concentration for viruses.

RBV indicates triazole nucleoside, is also called ribavirin, virazole.

It may be seen from the result of test, these compounds have better properties of anti-coxsackie B3 viruses. These compounds of the present invention have better effects on the coxsackie viruses of the picornaviridae and can inhibit coxsackie viruses. Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

We claim:

1. A benzimidazole-4-carboxamide derivative of Formula (I) or a pharmaceutically acceptable salt thereof,

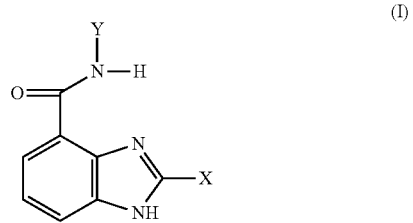

wherein X represents thienyl mono substituted by nitro or amino, or an unsubstituted thienyl;

Y represents hydroxymethyl, hydroxyethyl, aminophenyl, hydroxyphenyl, C1-C6 alkylphenyl, phenyl monosubstituted by —F, —Cl, —Br or —I, phenyl bisubstituted by hydroxyl and carboxyl, hydroxyethyl bisubstituted by hydroxylmethyl or C1-C6 alkyl and monosubstituted phenyl, piperazinyl monosubstituted or bisubstituted or trisubstituted by C1-C6 alkyl, pyridyl monosubstituted or bisubstituted or trisubstituted by C1-C6 alkyl, pyrazinyl monosubstituted or bisubstituted by C1-C6 alkyl, piperazinyl monosubstituted or bisubstituted or trisubstituted by C1-C6 alkyl, pyrrolyl monosubstituted or bisubstituted or trisubstituted by C1-C6 alkyl, thiazolyl monosubstituted by C1-C6 alkyl, pyrimidinyl monosubstituted or bisubstituted by C1-C6 alkyl, pyrimidinyl monsubstituted by C1-C6 alkyl and bisubstituted by hydroxyl, pyrimidinyl monosubstituted C1-C6 alkyl and bisubstituted or trisubstituted by —F, —Cl, —Br or —I, purinyl monosubstituted or bisubstituted by C1-C6 alkyl, purinyl monosubstituted by C1-C6 alky and substituted or trisubstituted by hydroxyl.

2. The benzimidazole-4-carboxamide derivative according to claim 1, wherein the derivative is selected from a group consisting of:

(1) (L)-2-(5-nitro-2-thienyl)-1H-benzimidazole-4-[N-(1-hydroxymethyl-2-p-nitrophenyl hydroxyethyl)] amide,
(2) (L)-2-(5-amino-2-thienyl)-1H-benzimidazole-4-[N-(1-hydroxymethyl-2-p-nitrophenyl hydroxyethyl)] amide,
(3) (L)-2-(5-amino-2-thienyl)-1H-benzimidazole-4-[N-(1-hydroxymethyl-2-p-aminophen yl hydroxyethyl)] amide,
(4) 2-(5-amino-2-thienyl)-1H-benzimidazole-4-[N-(1-methyl-2-p-chlorophenylhydroxy ethyl)]amide,
(5) 2-(5-amino-2-thienyl)-1H-benzimidazole-4-(N-o-fluorophenyl)amide,
(6) 2-(5-amino-2-thienyl)-1H-benzimidazole-4-(N-o-chlorophenyl)amide,
(7) 2-(5-amino-2-thienyl)-1H-benzimidazole-4-(N-o-bromophenyl)amide,
(8) 2-(5-amino-2-thienyl)-1H-benzimidazole-4-(N-m-fluorophenyl)amide,
(9) 2-(5-amino-2-thienyl)-1H-benzimidazole-4-(N-m-chlorophenyl)amide,
(10) 2-(5-amino-2-thienyl)-1H-benzimidazole-4-(N-m-bromophenyl)amide,
(11) 2-(5-amino-2-thienyl)-1H-benzimidazole-4-(N-p-fluorophenyl)amide,
(12) 2-(5-amino-2-thienyl)-1H-benzimidazole-4-(N-p-chlorophenyl)amide,
(13) 2-(5-amino-2-thienyl)-1H-benzimidazole-4-(N-p-bromophenyl)amide,
(14) 2-(5-amino-2-thienyl)-1H-benzimidazole-4-(N-o-methylphenyl)amide,
(15) 2-(5-amino-2-thienyl)-1H-benzimidazole-4-(N-o-hydroxylphenyl)amide,
(16) 2-(5-amino-2-thienyl)-1H-benzimidazole-4-(N-o-aminophenyl)amide,
(17) 2-(5-amino-2-thienyl)-1H-benzimidazole-4-(N-m-methylphenyl)amide,
(18) 2-(5-amino-2-thienyl)-1H-benzimidazole-4-(N-m-hydroxylphenyl)amide,
(19) 2-(5-amino-2-thienyl)-1H-benzimidazole-4-(N-m-aminophenyl)amide,
(20) 2-(5-amino-2-thienyl)-1H-benzimidazole-4-(N-p-methylphenyl)amide,
(21) 2-(5-amino-2-thienyl)-1H-benzimidazole-4-(N-p-hydroxylphenyl)amide, and
(22) 2-(5-amino-2-thienyl)-1H-benzimidazole-4-(N-p-aminophenyl)amide, or a pharmaceutically acceptable salt thereof.

3. A pharmaceutically acceptable salt of the benzimidazole-4-carboxamide derivative according to claim 1, wherein the pharmaceutically acceptable salt is an inorganic acid salt selected from sulfate, hydrochloride, nitrate, phosphate or borate, or an organic salt selected from citrate, succinate, tartrate, lactate or mesylate.

4. A pharmaceutically acceptable salt of the benzimidazole-4-carboxamide derivative according to claim 2, wherein the pharmaceutically acceptable salt is an inorganic acid salt selected from sulfate, hydrochloride, nitrate, phosphate or borate, or an organic salt selected from citrate, succinate, tartrate, lactate or mesylate.

5. A pharmaceutical composition, comprising a therapeutically effective amount of the benzimidazole-4-carboxamide derivative or the pharmaceutically acceptable salt thereof according to claim 1, and one or more pharmaceutically acceptable thinner, excipient, and/or inert carrier.

6. A pharmaceutical composition, comprising a therapeutically effective amount of the benzimidazole-4-carboxamide derivative or the pharmaceutically acceptable salt thereof according to claim 2, and one or more pharmaceutically acceptable thinner, excipient, and/or inert carrier.

7. A pharmaceutical composition, comprising a therapeutically effective amount of the pharmaceutically acceptable salt of the benzimidazole-4-carboxamide derivative according to claim 3, and one or more pharmaceutically acceptable thinner, excipient, and/or inert carrier.

* * * * *